US012788924B2

(12) United States Patent
Veliss et al.

(10) Patent No.: US 12,788,924 B2
(45) Date of Patent: Nov. 10, 2026

(54) DELIVERY OF RESPIRATORY THERAPY

(71) Applicant: ResMed Ltd Pty, Bella Vista (AU)

(72) Inventors: Lee James Veliss, Rotterdamn (NL); Scott Douglas Brackenreg, Sydney (AU); Fiona Catherine Carroll, Hawkesbury (AU); David Mark Gilliver, Black Rock (AU); Bruce David Gregory, Sydney (AU); Joshua Adam Gudiksen, Sydney (AU); Philip John Gunning, Sydney (AU); Robert Edward Henry, Sydney (AU); Philip Rodney Kwok, Sydney (AU); Gregory Robert Peake, Sydney (AU); Gerard Michael Rummery, Woodford (AU); Karthikeyan Selvarajan, Sydney (AU); Clive Solari, Sydney (AU); Jamie Graeme Wehbeh, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 903 days.

(21) Appl. No.: 17/886,635

(22) Filed: Aug. 12, 2022

(65) Prior Publication Data

US 2022/0379063 A1 Dec. 1, 2022

Related U.S. Application Data

(63) Continuation of application No. 16/193,383, filed on Nov. 16, 2018, now Pat. No. 11,446,461, which is a
(Continued)

(30) Foreign Application Priority Data

Jul. 27, 2007 (WO) ................ PCT/AU2007/001051
Jul. 27, 2007 (WO) ................ PCT/AU2007/001052
(Continued)

(51) Int. Cl.
*A61M 16/06* (2006.01)
*A61M 16/08* (2006.01)

(52) U.S. Cl.
CPC ........ *A61M 16/0683* (2013.01); *A61M 16/06* (2013.01); *A61M 16/0616* (2014.02);
(Continued)

(58) Field of Classification Search
CPC ............ A61M 16/0066; A61M 16/024; A61M 16/06; A61M 16/0605; A61M 16/0622;
(Continued)

(56) References Cited

U.S. PATENT DOCUMENTS 443,191 A 12/1890 Illing
781,516 A 1/1905 Guthrie, Jr.
(Continued)

FOREIGN PATENT DOCUMENTS

AU 199651130 10/1996
AU 712236 8/1998
(Continued)

OTHER PUBLICATIONS

Decision of Rejection with English Translation for related Japanese Application No. 2022-109724, four pages, dated Mar. 18, 2024.
(Continued)

*Primary Examiner* — Annette Dixon
(74) *Attorney, Agent, or Firm* — Nixon & Vanderhye P.C.

(57) ABSTRACT

A respiratory mask for continuous positive airway pressure treatment includes a cushion adapted to be positioned against the face of a patient. The cushion is configured in a gasket arrangement around an entrance to the airways of the patient. The cushion is constructed from a polyurethane foam and has a thickness of greater than about 5 mm.

22 Claims, 103 Drawing Sheets

Related U.S. Application Data continuation of application No. 12/448,250, filed as application No. PCT/AU2007/001936 on Dec. 14, 2007, now Pat. No. 10,166,357.

(60) Provisional application No. 60/996,485, filed on Nov. 20, 2007, provisional application No. 60/929,393, filed on Jun. 25, 2007, provisional application No. 60/924,241, filed on May 4, 2007, provisional application No. 60/874,968, filed on Dec. 15, 2006.

(30) Foreign Application Priority Data

Oct. 22, 2007 (AU) ................................ 2007905737
Nov. 6, 2007 (AU) ................................ 2007906102
Nov. 16, 2007 (AU) ................................ 2007906276

(52) U.S. Cl.
CPC .... *A61M 16/0622* (2014.02); *A61M 16/0633* (2014.02); *A61M 16/0611* (2014.02); *A61M 16/0816* (2013.01); *A61M 16/0825* (2014.02); *A61M 16/0833* (2014.02); *A61M 2205/0205* (2013.01); *A61M 2205/0216* (2013.01); *A61M 2205/0266* (2013.01); *A61M 2210/0618* (2013.01)

(58) Field of Classification Search
CPC .......... A61M 16/0633; A61M 16/0666; A61M 16/0672; A61M 16/0683; A61M 16/08; A61M 16/0816; A61M 16/0825; A61M 16/0833; A61M 16/085; A61M 16/0858; A61M 16/0875; A61M 16/0883; A61M 16/107; A61M 16/109; A61M 16/1095; A61M 16/125; A61M 16/16; A61M 16/202; A61M 16/209; A61M 2016/0021; A61M 2016/0027; A61M 2016/0039; A61M 2016/103; A61M 2202/0007; A61M 2202/0085; A61M 2202/0208; A61M 2202/0225; A61M 2205/0216; A61M 2205/15; A61M 2205/3344; A61M 2205/3368; A61M 2205/3375; A61M 2205/3592; A61M 2205/3653; A61M 2205/42; A61M 2205/505; A61M 2205/581; A61M 2205/582; A61M 2205/583; A61M 2205/584; A61M 2205/6063; A61M 2210/0618; A61M 2210/0625; A61M 2230/432; B63C 11/205; Y10S 128/26
See application file for complete search history.

(56) References Cited

U.S. PATENT DOCUMENTS 1,081,745 A 12/1913 Johnston
1,125,542 A 1/1915 Humphries
1,192,186 A 7/1916 Greene
1,229,050 A 6/1917 Donald
1,282,527 A 10/1918 Bidonde
1,362,766 A 12/1920 Mcgargill
1,445,010 A 2/1923 Feinberg
1,596,754 A 8/1926 Moschelle
1,610,793 A 12/1926 Kaufman
1,632,449 A 6/1927 McKesson
1,710,160 A 4/1929 Gibbs
1,873,160 A 8/1932 Sturtevant
2,073,335 A 3/1937 Karl
2,126,755 A 8/1938 Dreyfus
2,130,555 A 9/1938 Malcom
2,228,218 A 1/1941 Schwartz
2,353,643 A 7/1944 Bulbulian
2,376,871 A * 5/1945 Fink .................... A62B 18/025 128/206.28
2,415,846 A 2/1947 Randall
2,433,565 A 12/1947 Korman
2,578,621 A 12/1951 Yant
2,625,155 A 1/1953 Engelder
2,706,983 A 4/1955 Matheson et al.
2,763,263 A * 9/1956 Ellman ............ A61M 16/0666 128/203.22
2,931,356 A 4/1960 Schwarz
2,931,358 A * 4/1960 Sheridan .......... A61M 16/0672 128/207.18
3,013,556 A 12/1961 Galleher
3,037,251 A 6/1962 Landis
3,090,046 A 5/1963 Bowers, Sr.
3,181,532 A 5/1965 Harris
3,291,127 A 12/1966 Eimer et al.
3,330,273 A 7/1967 Bennett
3,424,633 A 1/1969 Corrigall et al.
3,508,587 A 4/1970 Mauch
3,552,778 A 1/1971 Muller
3,670,726 A 6/1972 Mahon et al.
3,682,171 A 8/1972 Dali et al.
3,739,774 A 6/1973 Gregory
3,754,552 A 8/1973 King
3,799,164 A * 3/1974 Rollins ............ A61M 16/0816 128/205.25
3,802,431 A * 4/1974 Farr ................. A61M 16/0672 128/207.18
3,831,583 A 8/1974 Edmunds, Jr.
3,850,171 A 11/1974 Ball et al.
3,861,385 A 1/1975 Carden
3,865,106 A 2/1975 Palush
3,902,486 A 9/1975 Guichard
3,905,361 A 9/1975 Hewson et al.
3,938,614 A 2/1976 Ahs
3,972,321 A 8/1976 Proctor
3,980,311 A 9/1976 Ditcher
4,006,744 A 2/1977 Steer
4,131,399 A 12/1978 Calvet
4,142,527 A 3/1979 Garcia
4,153,051 A 5/1979 Shippert
4,156,426 A 5/1979 Gold
4,245,924 A 1/1981 Fouss
4,248,218 A 2/1981 Fischer
4,258,710 A 3/1981 Reber
4,263,908 A 4/1981 Mizerak
4,264,743 A 4/1981 Maruyama et al.
4,266,540 A 5/1981 Panzik et al.
4,267,845 A 5/1981 Robertson, Jr. et al.
4,273,124 A 6/1981 Zimmerman
4,312,359 A 1/1982 Olson
4,347,205 A 8/1982 Stewart
4,367,735 A 1/1983 Dali
4,367,816 A 1/1983 Wilkes
4,406,283 A 9/1983 Bir
4,414,973 A 11/1983 Matheson et al.
4,422,456 A 12/1983 Teip
4,437,463 A 3/1984 Ackerman
4,449,526 A 5/1984 Elam
4,454,880 A 6/1984 Muto et al.
4,455,675 A 6/1984 Bose et al.
4,463,755 A 8/1984 Suzuki
4,493,614 A 1/1985 Chu et al.
4,548,200 A 10/1985 Wapner
4,549,542 A 10/1985 Chein
4,572,323 A 2/1986 Randall
4,579,113 A 4/1986 McCreadie et al.
4,587,967 A 5/1986 Chu et al.
4,601,465 A 7/1986 Roy
4,617,637 A 10/1986 Chu et al.
4,630,604 A 12/1986 Montesi
4,641,647 A 2/1987 Behan
4,648,398 A * 3/1987 Agdanowski ..... A61M 16/0666 128/207.18
4,659,869 A 4/1987 Busby
4,660,555 A 4/1987 Payton
4,671,271 A 6/1987 Bishop et al.

(56) References Cited

U.S. PATENT DOCUMENTS 4,674,134 A 6/1987 Lundin
4,676,241 A 6/1987 Webb et al.
4,677,977 A 7/1987 Wilcox
4,699,139 A 10/1987 Marshall et al.
4,706,664 A 11/1987 Snook et al.
4,711,636 A 12/1987 Bierman
4,713,844 A 12/1987 Westgate
D293,613 S 1/1988 Wingler
4,753,233 A 6/1988 Grimes
4,767,411 A 8/1988 Edmunds
4,774,946 A * 10/1988 Ackerman ........ A61M 16/0633 128/207.18
4,782,832 A 11/1988 Trimble et al.
4,790,829 A 12/1988 Bowden et al.
4,802,857 A 2/1989 Laughlin
4,803,981 A 2/1989 Vickery
4,809,692 A 3/1989 Nowacki et al.
4,811,730 A 3/1989 Milano
4,830,138 A 5/1989 Palmaer et al.
4,838,878 A 6/1989 Kalt et al.
4,878,491 A * 11/1989 McGilvray, III ..... B63C 11/205 128/201.11
4,899,740 A 2/1990 Napolitano
4,907,584 A 3/1990 McGinnis
4,915,105 A 4/1990 Lee
4,919,128 A 4/1990 Kopala et al.
4,919,654 A 4/1990 Kalt
4,944,310 A 7/1990 Sullivan
4,945,907 A 8/1990 Tayebi
4,949,733 A 8/1990 Sampson
4,960,121 A 10/1990 Nelson et al.
4,966,590 A 10/1990 Kalt
4,969,880 A 11/1990 Zamierowski
4,971,051 A 11/1990 Toffolon
4,976,698 A 12/1990 Stokley
4,989,599 A 2/1991 Carter
4,996,983 A 3/1991 Amrhein
5,000,173 A 3/1991 Zalkin et al.
5,005,571 A 4/1991 Dietz
5,018,519 A 5/1991 Brown
5,020,163 A 6/1991 Aileo et al.
5,022,900 A 6/1991 Bar-Yona et al.
5,023,955 A 6/1991 Murphy, II et al.
5,025,805 A 6/1991 Nutter
5,038,772 A 8/1991 Kolbe et al.
5,042,478 A 8/1991 Kopala et al.
5,046,491 A 9/1991 Derrick
5,062,421 A 11/1991 Burns et al.
5,065,756 A 11/1991 Rapoport
D322,318 S 12/1991 Sullivan
5,074,297 A 12/1991 Venegas
5,113,857 A 5/1992 Dickerman et al.
5,117,818 A 6/1992 Palfy
5,117,819 A 6/1992 Servidio et al.
5,121,745 A 6/1992 Israel
5,127,397 A 7/1992 Kohnke
5,137,017 A 8/1992 Salter
5,138,722 A 8/1992 Urella et al.
5,148,802 A 9/1992 Sanders et al.
5,155,863 A 10/1992 Roberts
5,160,325 A 11/1992 Nichols
D333,015 S 2/1993 Farmer et al.
5,188,101 A 2/1993 Tumolo
5,207,665 A 5/1993 Davis et al.
5,217,391 A 6/1993 Fisher, Jr.
5,220,699 A 6/1993 Farris
5,233,978 A 8/1993 Callaway
5,243,709 A 9/1993 Sheehan et al.
5,243,971 A 9/1993 Sullivan et al.
5,245,995 A 9/1993 Sullivan et al.
5,261,893 A 11/1993 Zamierowski
5,263,939 A 11/1993 Wortrich
5,265,592 A 11/1993 Beaussant
5,265,595 A 11/1993 Rudolph
5,267,557 A 12/1993 Her-Mou
5,269,296 A 12/1993 Landis
5,271,391 A 12/1993 Graves
5,299,599 A 4/1994 Farmer et al.
5,304,146 A 4/1994 Johnson et al.
5,335,656 A 8/1994 Bowe et al.
5,349,949 A 9/1994 Schegerin
5,355,878 A 10/1994 Griffiths et al.
5,355,893 A 10/1994 Mick et al.
5,364,367 A 11/1994 Banks et al.
5,372,130 A 12/1994 Stem et al.
5,372,388 A 12/1994 Gargiulo
5,372,389 A 12/1994 Tam et al.
5,372,390 A 12/1994 Conway et al.
5,372,391 A 12/1994 Bast et al.
5,375,593 A 12/1994 Press
5,385,141 A 1/1995 Granatiero
5,394,568 A 3/1995 Brostrom et al.
5,396,885 A 3/1995 Nelson
5,398,676 A 3/1995 Press et al.
5,400,776 A 3/1995 Bartholomew
5,419,318 A 5/1995 Tayebi
5,425,359 A 6/1995 Liou
5,429,683 A 7/1995 Le Mitouard
5,437,267 A 8/1995 Weinstein et al.
5,441,046 A 8/1995 Starr et al.
5,462,528 A 10/1995 Roewer
5,477,852 A 12/1995 Landis et al.
5,488,948 A 2/1996 Dubruille et al.
5,509,409 A 4/1996 Weatherholt
5,513,634 A 5/1996 Jackson
5,513,635 A 5/1996 Bedi
5,526,806 A 6/1996 Sansoni
5,533,506 A 7/1996 Wood
5,538,000 A 7/1996 Rudolph
5,538,001 A 7/1996 Bridges
5,556,390 A 9/1996 Hicks
5,560,354 A 10/1996 Berthon-Jones et al.
5,570,684 A 11/1996 Behr
5,592,938 A 1/1997 Scarberry et al.
5,623,923 A 4/1997 Bertheau et al.
5,647,357 A 7/1997 Barnett et al.
5,647,358 A 7/1997 Vilasi
5,653,228 A 8/1997 Byrd
5,655,527 A 8/1997 Scarberry et al.
5,657,752 A 8/1997 Landis et al.
5,662,101 A 9/1997 Ogden et al.
5,682,881 A 11/1997 Winthrop et al.
5,704,345 A 1/1998 Berthon-Jones et al.
5,707,342 A 1/1998 Tanaka
5,724,965 A 3/1998 Handke et al.
5,735,272 A 4/1998 Dillon et al.
5,740,799 A 4/1998 Nielson
5,746,201 A 5/1998 Kidd
5,752,510 A 5/1998 Goldstein
5,752,511 A 5/1998 Simmons et al.
5,765,557 A 6/1998 Warters
5,794,619 A 8/1998 Edeiman et al.
5,807,341 A 9/1998 Heim
5,842,469 A 12/1998 Rapp et al.
5,842,470 A 12/1998 Ruben
5,884,336 A 3/1999 Stout
5,906,203 A 5/1999 Klockseth et al.
5,918,598 A 7/1999 Belfer et al.
5,921,239 A 7/1999 McCall et al.
5,937,851 A 8/1999 Serowski et al.
5,954,049 A 9/1999 Foley et al.
5,966,745 A 10/1999 Schwartz et al.
5,975,079 A 11/1999 Hellings et al.
6,012,455 A 1/2000 Goldstein
6,016,804 A 1/2000 Gleason et al.
6,019,101 A 2/2000 Cotner et al.
6,026,811 A 2/2000 Settle
6,044,844 A 4/2000 Kwok et al.
6,082,360 A 7/2000 Rudolph et al.
6,086,118 A 7/2000 McNaughton et al.
6,095,996 A 8/2000 Steer et al.
6,098,205 A 8/2000 Schwartz et al.
6,109,263 A 8/2000 Feuchtgruber
6,112,746 A 9/2000 Kwok et al.

(56) References Cited

U.S. PATENT DOCUMENTS 6,119,693 A 9/2000 Kwok et al.
6,119,694 A 9/2000 Correa et al.
6,123,071 A 9/2000 Berthon-Jones et al.
6,123,082 A 9/2000 Berthon-Jones
6,139,787 A 10/2000 Harrison
6,152,137 A 11/2000 Schwartz et al.
6,192,886 B1 2/2001 Rudolph
6,193,914 B1 2/2001 Harrison
6,196,223 B1 3/2001 Belfer et al.
6,211,263 B1 4/2001 Cinelli et al.
6,231,548 B1 5/2001 Bassett
6,241,930 B1 6/2001 Harrison
6,247,470 B1 6/2001 Ketchedjian
6,258,066 B1 7/2001 Urich
6,295,366 B1 9/2001 Haller et al.
6,328,038 B1 12/2001 Kessler et al.
6,341,606 B1 1/2002 Bordewick et al.
6,347,631 B1 2/2002 Hansen et al.
6,354,293 B1 3/2002 Madison
6,357,440 B1 3/2002 Hansen et al.
6,357,441 B1 3/2002 Kwok et al.
6,358,279 B1 3/2002 Tahi et al.
6,374,826 B1 4/2002 Gunaratnam et al.
6,397,847 B1 6/2002 Scarberry
6,412,487 B1 7/2002 Gunaratnam et al.
6,412,488 B1 7/2002 Barnett et al.
6,412,593 B1 7/2002 Jones
6,419,660 B1 7/2002 Russo
6,422,238 B1 7/2002 Lithgow
6,423,036 B1 7/2002 Van Huizen
6,431,172 B1 8/2002 Bordewick
6,434,796 B1 8/2002 Speirs
6,435,181 B1 8/2002 Jones, Jr. et al.
6,439,234 B1 8/2002 Curti et al.
6,448,303 B1 9/2002 Paul
6,457,473 B1 10/2002 Brostrom et al.
6,467,482 B1 10/2002 Boussignac
6,467,483 B1 10/2002 Kopacko et al.
6,470,887 B1 10/2002 Martinez
6,478,026 B1 11/2002 Wood
6,482,178 B1 11/2002 Andrews et al.
6,491,034 B1 12/2002 Gunaratnam et al.
6,513,526 B2 2/2003 Kwok et al.
6,530,373 B1 3/2003 Patron et al.
6,532,961 B1 3/2003 Kwok et al.
6,536,435 B1 3/2003 Fecteau et al.
6,558,247 B1 5/2003 Peak
6,561,188 B1 5/2003 Ellis
6,561,190 B1 5/2003 Kwok et al.
6,561,191 B1 5/2003 Kwok
6,561,192 B2 5/2003 Palmer
6,561,193 B1 5/2003 Noble
6,571,798 B1 6/2003 Thornton
6,579,267 B2 6/2003 Lynch et al.
6,581,594 B1 6/2003 Drew et al.
6,581,601 B2 6/2003 Ziaee
6,581,602 B2 6/2003 Kwok et al.
6,584,975 B1 7/2003 Taylor
6,584,976 B2 7/2003 Japuntich et al.
6,595,214 B1 7/2003 Hecker et al.
6,595,215 B2 7/2003 Wood
6,607,516 B2 8/2003 Cinelli et al.
6,615,832 B1 9/2003 Chen
6,627,289 B1 9/2003 Dilnik et al.
6,631,718 B1 10/2003 Lovell
6,634,358 B2 10/2003 Kwok et al.
6,637,434 B2 10/2003 Noble
6,644,315 B2 11/2003 Ziaee
6,651,663 B2 11/2003 Barnett
6,655,385 B1 12/2003 Curti et al.
6,663,600 B2 12/2003 Bierman et al.
6,668,882 B1 12/2003 Cazes
6,669,712 B1 12/2003 Cardoso
D485,905 S 1/2004 Moore et al.
6,679,257 B1 1/2004 Robertson et al.
6,679,265 B2 1/2004 Strickland et al.
6,691,707 B1 2/2004 Gunaratnam et al.
6,698,427 B1 3/2004 Clowers
6,701,927 B2 3/2004 Kwok et al.
6,710,099 B2 3/2004 Cinelli et al.
6,766,800 B2 7/2004 Chu et al.
6,766,817 B2 7/2004 da Silva
6,776,162 B2 8/2004 Wood
6,776,163 B2 8/2004 Dougill et al.
6,789,543 B2 9/2004 Cannon
6,796,308 B2 9/2004 Gunaratnam et al.
6,805,117 B1 10/2004 Ho et al.
6,807,967 B2 10/2004 Wood
6,817,362 B2 11/2004 Gelinas et al.
6,820,617 B2 11/2004 Robertson et al.
6,823,865 B2 11/2004 Drew et al.
6,823,869 B2 11/2004 Raje et al.
6,834,650 B1 12/2004 Fini
6,851,425 B2 2/2005 Jaffre et al.
6,860,270 B2 3/2005 Sniadach
D505,489 S 5/2005 Sleeper
6,889,689 B1 * 5/2005 Neuman ........... A61M 16/0683
128/207.18
6,895,965 B2 5/2005 Scarberry et al.
6,907,882 B2 6/2005 Ging et al.
6,918,404 B2 7/2005 Dias da Silva
6,926,004 B2 8/2005 Schumacher
6,938,620 B2 9/2005 Payne, Jr.
6,968,844 B2 11/2005 Liland
6,972,003 B2 12/2005 Bierman et al.
6,981,503 B1 1/2006 Shapiro
6,986,352 B2 1/2006 Frater et al.
6,997,177 B2 2/2006 Wood
7,007,696 B2 3/2006 Palkon et al.
7,011,090 B2 3/2006 Drew et al.
7,018,362 B2 3/2006 Bierman et al.
7,036,157 B1 5/2006 Andersson
7,052,127 B2 5/2006 Harrison
7,066,586 B2 6/2006 da Silva
7,076,282 B2 7/2006 Munro et al.
7,080,645 B2 7/2006 Genger et al.
7,086,422 B2 8/2006 Huber et al.
7,101,359 B2 9/2006 Kline et al.
7,104,491 B2 9/2006 Vinding
7,107,989 B2 9/2006 Frater et al.
7,146,976 B2 12/2006 McKown
7,152,599 B2 12/2006 Thomas
7,152,601 B2 12/2006 Barakat et al.
7,152,602 B2 12/2006 Bateman et al.
7,178,525 B2 2/2007 Matula, Jr. et al.
7,178,528 B2 2/2007 Lau et al.
7,191,781 B2 3/2007 Wood
7,207,328 B1 4/2007 Altemus
7,210,481 B1 5/2007 Lovell et al.
7,237,551 B2 7/2007 Ho et al.
7,243,723 B2 7/2007 Surjaatmadja
D550,836 S 9/2007 Chandran et al.
D552,733 S 10/2007 Criscuolo et al.
7,285,255 B2 10/2007 Kadlec et al.
7,318,437 B2 1/2008 Gunaratnam et al.
7,353,827 B2 4/2008 Geist
7,357,136 B2 4/2008 Ho et al.
7,481,220 B2 1/2009 Meyer et al.
7,523,754 B2 4/2009 Lithgow
7,658,189 B2 2/2010 Davidson
7,827,990 B1 11/2010 Melidis et al.
7,856,982 B2 12/2010 Matula, Jr. et al.
7,942,148 B2 5/2011 Davidson et al.
7,958,893 B2 6/2011 Lithgow et al.
8,025,058 B2 * 9/2011 Chandran ......... A61M 16/0683
128/207.18
8,225,553 B1 7/2012 Redfern
8,291,906 B2 10/2012 Kooij et al.
8,297,285 B2 10/2012 Henry et al.
8,443,807 B2 5/2013 McAuley et al.
8,479,741 B2 7/2013 McAuley et al.
8,701,667 B1 4/2014 Ho et al.
8,714,157 B2 5/2014 McAuley et al.
8,944,061 B2 2/2015 D'Souza et al.

(56) References Cited

U.S. PATENT DOCUMENTS 8,950,404 B2 2/2015 Formica et al.
8,960,196 B2 2/2015 Henry
9,027,556 B2 5/2015 Ng et al.
9,119,931 B2 9/2015 D'Souza et al.
9,162,034 B2 10/2015 Veliss
9,242,062 B2 1/2016 Melidis et al.
9,333,315 B2 5/2016 McAuley et al.
9,381,316 B2 7/2016 Ng et al.
9,517,317 B2 12/2016 McAuley et al.
9,539,405 B2 1/2017 McAuley et al.
9,827,391 B2 11/2017 Kwok
9,907,922 B2 3/2018 Stephenson et al.
9,907,923 B2 3/2018 Stephenson et al.
9,974,914 B2 5/2018 McAuley et al.
10,166,357 B2 1/2019 Veliss et al.
11,040,165 B2 * 6/2021 Kooij .................... A61M 16/06
11,305,087 B2 * 4/2022 Kwok ................ A61M 16/0611
11,666,724 B2 * 6/2023 Wagner ............. A61M 16/0816 128/206.24
12,214,136 B2 * 2/2025 Wagner ............. A61M 16/0683
2001/0015204 A1 8/2001 Hansen et al.
2001/0020474 A1 9/2001 Hecker et al.
2001/0042547 A1 11/2001 McDonald et al.
2002/0005198 A1 1/2002 Kwok et al.
2002/0020416 A1 2/2002 Namey
2002/0023647 A1 2/2002 Hansen et al.
2002/0029780 A1 3/2002 Frater et al.
2002/0046755 A1 4/2002 Devoss
2002/0053347 A1 5/2002 Ziaee
2002/0059935 A1 5/2002 Wood
2002/0066452 A1 6/2002 Kessler et al.
2002/0069872 A1 6/2002 Gradon et al.
2002/0096172 A1 7/2002 Gell
2002/0096173 A1 7/2002 Berthon-Jones
2002/0096178 A1 7/2002 Ziaee
2002/0117177 A1 8/2002 Kwok
2002/0124849 A1 9/2002 Billette De Villemeur
2002/0143296 A1 10/2002 Russo
2002/0157673 A1 10/2002 Kessler et al.
2002/0162556 A1 11/2002 Smith et al.
2002/0174868 A1 11/2002 Kwok et al.
2002/0185134 A1 12/2002 Bishop
2003/0000526 A1 1/2003 Goebel
2003/0019495 A1 1/2003 Palkon et al.
2003/0029454 A1 2/2003 Gelinas et al.
2003/0075176 A1 4/2003 Fukunaga
2003/0079749 A1 5/2003 Strickland et al.
2003/0089373 A1 5/2003 Gradon et al.
2003/0111080 A1 6/2003 Olsen et al.
2003/0145857 A1 8/2003 Sullivan
2003/0154980 A1 8/2003 Berton-Jones et al.
2003/0164170 A1 9/2003 Drew et al.
2003/0168063 A1 9/2003 Gambone et al.
2003/0196655 A1 10/2003 Ging et al.
2003/0196656 A1 10/2003 Moore et al.
2003/0196658 A1 10/2003 Ging et al.
2003/0205231 A1 11/2003 Shigematsu
2004/0025882 A1 2/2004 Madaus et al.
2004/0025885 A1 2/2004 Payne, Jr.
2004/0041342 A1 3/2004 Frieman
2004/0045551 A1 3/2004 Eaton et al.
2004/0065328 A1 4/2004 Amarasinghe et al.
2004/0067333 A1 4/2004 Amarasinghe
2004/0079374 A1 4/2004 Thornton
2004/0106891 A1 6/2004 Langan et al.
2004/0111104 A1 6/2004 Schein et al.
2004/0112384 A1 6/2004 Lithgow et al.
2004/0118406 A1 6/2004 Lithgow et al.
2004/0127856 A1 7/2004 Johnson
2004/0134497 A1 7/2004 Gunaratnam
2004/0149280 A1 8/2004 Semeniuk
2004/0182398 A1 9/2004 Semeniuk
2004/0211428 A1 10/2004 Jones
2004/0221850 A1 11/2004 Ging
2004/0226564 A1 11/2004 Persson
2004/0226566 A1 11/2004 Gunaratnam et al.
2004/0255949 A1 12/2004 Lang et al.
2005/0001152 A1 1/2005 Stewart et al.
2005/0011523 A1 1/2005 Aylsworth et al.
2005/0011524 A1 1/2005 Thomlinson et al.
2005/0025816 A1 2/2005 Tanaka
2005/0028822 A1 2/2005 Sleeper et al.
2005/0033247 A1 2/2005 Thompson
2005/0039757 A1 2/2005 Wood
2005/0039810 A1 2/2005 Toliver
2005/0051171 A1 3/2005 Booth
2005/0051176 A1 3/2005 Riggins
2005/0056286 A1 3/2005 Huddart et al.
2005/0061326 A1 3/2005 Payne
2005/0066976 A1 3/2005 Wondka
2005/0092326 A1 5/2005 Drew et al.
2005/0092329 A1 5/2005 St-Maria
2005/0101933 A1 5/2005 Marrs et al.
2005/0121030 A1 6/2005 Bateman et al.
2005/0121033 A1 * 6/2005 Starr ..................... A61M 16/06 128/204.23
2005/0139221 A1 * 6/2005 Duncan ................. A61M 16/16 128/207.18
2005/0150495 A1 7/2005 Rittner et al.
2005/0150498 A1 7/2005 McDonald
2005/0150499 A1 7/2005 Bordewick et al.
2005/0155604 A1 7/2005 Ging et al.
2005/0188990 A1 9/2005 Fukunaga
2005/0199239 A1 9/2005 Lang et al.
2005/0199242 A1 9/2005 Matula, Jr. et al.
2005/0205096 A1 9/2005 Matula
2005/0211252 A1 9/2005 Lang et al.
2005/0235999 A1 10/2005 Wood et al.
2005/0241644 A1 11/2005 Gunaratnam et al.
2005/0284481 A1 12/2005 Meyer
2006/0017489 A1 1/2006 Negishi et al.
2006/0042629 A1 3/2006 Geist
2006/0060200 A1 3/2006 Ho et al.
2006/0081250 A1 4/2006 Bordewick et al.
2006/0095008 A1 5/2006 Lampropoulos et al.
2006/0095009 A1 5/2006 Lampropoulos et al.
2006/0118117 A1 6/2006 Berthon-Jones et al.
2006/0122285 A1 6/2006 Falloon et al.
2006/0124131 A1 6/2006 Chandran et al.
2006/0137690 A1 6/2006 Gunaratnam et al.
2006/0174887 A1 8/2006 Chandran et al.
2006/0180151 A1 8/2006 Rinaldi
2006/0201514 A1 9/2006 Jones
2006/0207597 A1 9/2006 Wright
2006/0231103 A1 10/2006 Matula, Jr. et al.
2006/0237017 A1 10/2006 Davidson et al.
2006/0249159 A1 11/2006 Ho
2006/0260838 A1 11/2006 Ariel
2006/0272646 A1 12/2006 Ho et al.
2006/0283460 A1 12/2006 Brown
2006/0283461 A1 12/2006 Lubke et al.
2007/0023044 A1 2/2007 Kwok et al.
2007/0044804 A1 3/2007 Matula, Jr. et al.
2007/0045152 A1 3/2007 Kwok et al.
2007/0074723 A1 4/2007 Coury et al.
2007/0107733 A1 5/2007 Ho
2007/0125387 A1 6/2007 Zollinger et al.
2007/0130663 A1 6/2007 Lang et al.
2007/0144525 A1 6/2007 Davidson et al.
2007/0175479 A1 8/2007 Groll
2007/0175480 A1 8/2007 Gradon et al.
2007/0186930 A1 8/2007 Davidson et al.
2007/0215161 A1 9/2007 Frater
2007/0246043 A1 10/2007 Kwok et al.
2007/0251527 A1 11/2007 Sleeper
2007/0272249 A1 11/2007 Chandran et al.
2007/0282272 A1 12/2007 Bannon et al.
2008/0000477 A1 1/2008 Huster et al.
2008/0004573 A1 1/2008 Kaufmann et al.
2008/0006277 A1 1/2008 Worboys et al.
2008/0047560 A1 2/2008 Veliss et al.
2008/0060649 A1 3/2008 Veliss et al.
2008/0065022 A1 3/2008 Kyvik et al.
2008/0106056 A1 5/2008 Kleckner

(56) References Cited

U.S. PATENT DOCUMENTS

| | | | | |
|---|---|---|---|---|
| 2008/0110464 | A1 | 5/2008 | Davidson et al. | |
| 2008/0110469 | A1 | 5/2008 | Weinberg | |
| 2008/0200880 | A1 | 8/2008 | Kyvik et al. | |
| 2008/0257354 | A1 | 10/2008 | Kooij et al. | |
| 2009/0014007 | A1 | 1/2009 | Brambilla | |
| 2009/0044808 | A1 | 2/2009 | Guney et al. | |
| 2009/0217929 | A1 | 9/2009 | Kwok et al. | |
| 2010/0000534 | A1 | 1/2010 | Kooij et al. | |
| 2010/0000545 | A1* | 1/2010 | Lee | A61M 16/0683 128/207.18 |
| 2010/0018534 | A1 | 1/2010 | Veliss | |
| 2010/0224196 | A1* | 9/2010 | Jablons | A61M 16/0666 128/207.18 |
| 2010/0236552 | A1 | 9/2010 | Kwok et al. | |
| 2011/0072553 | A1 | 3/2011 | Ho | |
| 2012/0325219 | A1* | 12/2012 | Smith | A61M 16/0875 128/205.25 |
| 2014/0083430 | A1 | 3/2014 | Matula, Jr. et al. | |
| 2019/0111227 | A1 | 4/2019 | Veliss et al. | |
| 2019/0134332 | A1 | 5/2019 | Kwok et al. | |
| 2019/0134333 | A1 | 5/2019 | Kwok et al. | |
| 2019/0134334 | A1 | 5/2019 | Kwok et al. | |
| 2019/0151589 | A1 | 5/2019 | Kwok et al. | |
| 2020/0330712 | A1 | 10/2020 | Henry | |
| 2020/0398011 | A1 | 12/2020 | Henry | |
| 2021/0030987 | A1 | 2/2021 | Henry et al. | |

FOREIGN PATENT DOCUMENTS

| | | | |
|---|---|---|---|
| AU | 2004308536 | | 12/2004 |
| AU | 2005 232 337 | | 10/2005 |
| AU | 2005100738 | | 11/2005 |
| CN | 1688269 | | 10/2005 |
| CN | 1750854 | | 3/2006 |
| DE | 185017 | | 5/1907 |
| DE | 30 11 900 | | 10/1980 |
| DE | 146 688 | | 2/1981 |
| DE | 37 19 009 | | 12/1988 |
| DE | 39 27 038 | | 2/1991 |
| DE | 297 23 101 | | 7/1998 |
| DE | 197 03 526 | | 8/1998 |
| DE | 199 44 242 | | 3/2001 |
| DE | 100 02 571 | | 7/2001 |
| DE | 102 13 905 | | 10/2002 |
| DE | 10 2004 055 433.1 | | 11/2004 |
| EP | 0288937 | | 11/1988 |
| EP | 0427474 | | 5/1991 |
| EP | 0 466 960 | | 1/1992 |
| EP | 0 303 090 | | 4/1992 |
| EP | 0 658 356 | | 6/1995 |
| EP | 0697225 | | 2/1996 |
| EP | 0 747 078 | | 12/1996 |
| EP | 0 776 679 | | 6/1997 |
| EP | 1027905 | | 8/2000 |
| EP | 1 099 452 | | 5/2001 |
| EP | 1149603 | | 10/2001 |
| EP | 1 258 266 | | 11/2002 |
| EP | 1314445 | | 5/2003 |
| EP | 1396277 | | 3/2004 |
| EP | 1 481 702 | | 12/2004 |
| EP | 1 529 505 | | 5/2005 |
| EP | 1637175 | | 3/2006 |
| EP | 1696989 | | 9/2006 |
| FR | 2 720 280 | | 12/1995 |
| GB | 532214 | | 1/1941 |
| GB | 2 176 404 | | 12/1986 |
| GB | 2 368 533 | | 5/2002 |
| GB | 2 385 533 | | 8/2003 |
| JP | 52-47455 | | 4/1977 |
| JP | UM-A-1-120860 | | 8/1989 |
| JP | 1997-10311 | | 1/1997 |
| JP | H10-508786 | | 9/1998 |
| JP | 11-332391 | | 12/1999 |
| JP | 2001-327615 | | 11/2001 |
| JP | 2002-102352 | | 4/2002 |
| JP | 2002-525179 | | 8/2002 |
| JP | 2002-540859 | | 12/2002 |
| JP | 1688269 | | 12/2002 |
| JP | 2003-502119 | | 1/2003 |
| JP | 2003501220 | | 1/2003 |
| JP | 2003-135600 | | 6/2003 |
| JP | 2003-175121 | | 6/2003 |
| JP | 2003-325629 | | 11/2003 |
| JP | 2004-570 | | 1/2004 |
| JP | 3102973 | | 5/2004 |
| JP | 2005-13492 | | 1/2005 |
| JP | 2005-503869 | A | 2/2005 |
| JP | 2005-529687 | | 10/2005 |
| JP | 2006-518231 | | 8/2006 |
| JP | 2007-532205 | A | 11/2007 |
| JP | 2008-136826 | | 6/2008 |
| WO | WO 1982/003548 | | 10/1982 |
| WO | WO 1987/001950 | | 4/1987 |
| WO | WO 1992/020392 | | 11/1992 |
| WO | WO 1992/20395 | | 11/1992 |
| WO | WO 1996/028207 | | 9/1996 |
| WO | WO 1997/009090 | | 3/1997 |
| WO | WO 1998/004310 | | 2/1998 |
| WO | WO 1998/012965 | | 4/1998 |
| WO | WO 1998/023305 | | 6/1998 |
| WO | WO 1998/024499 | | 6/1998 |
| WO | WO 1999/016327 | | 4/1999 |
| WO | WO 1999/025410 | | 5/1999 |
| WO | WO 1999/043375 | | 9/1999 |
| WO | WO 1999/061088 | | 12/1999 |
| WO | WO 00/18457 | | 4/2000 |
| WO | WO 2000/018457 | | 4/2000 |
| WO | WO 2000/020072 | | 4/2000 |
| WO | WO 2000/038772 | | 7/2000 |
| WO | WO 00/50122 | | 8/2000 |
| WO | WO 2000/050121 | | 8/2000 |
| WO | WO 2000/059567 | | 10/2000 |
| WO | WO 2000/069521 | | 11/2000 |
| WO | WO 00/74758 | | 12/2000 |
| WO | WO 00/76568 | | 12/2000 |
| WO | WO 00/76568 | A1 | 12/2000 |
| WO | WO 2000/072905 | | 12/2000 |
| WO | WO 2000/076568 | | 12/2000 |
| WO | WO 2000/078384 | | 12/2000 |
| WO | WO 01/32250 | | 5/2001 |
| WO | WO 2001/062326 | | 8/2001 |
| WO | WO 2001/095965 | | 12/2001 |
| WO | WO 2001/097892 | | 12/2001 |
| WO | WO 2001/097893 | | 12/2001 |
| WO | WO 2002/013884 | | 2/2002 |
| WO | WO 2002/038221 | | 5/2002 |
| WO | WO 2002/045784 | | 6/2002 |
| WO | WO 2002/047749 | | 6/2002 |
| WO | PCT/AU2003/000458 | | 4/2003 |
| WO | WO 2003/105921 | | 12/2003 |
| WO | WO 2004/022146 | | 3/2004 |
| WO | WO 2004/022147 | | 3/2004 |
| WO | WO 2004/041341 | | 5/2004 |
| WO | WO 2004/041342 | | 5/2004 |
| WO | WO 2004/073778 | | 9/2004 |
| WO | WO 2004/078230 | | 9/2004 |
| WO | WO 2005/018524 | | 3/2005 |
| WO | WO 2005/021075 | | 3/2005 |
| WO | WO 2005/051468 | | 6/2005 |
| WO | WO 2005/053781 | | 6/2005 |
| WO | WO 2005/063328 | | 7/2005 |
| WO | WO 2005/076874 | | 8/2005 |
| WO | WO 2005/079726 | | 9/2005 |
| WO | WO 2005/086943 | | 9/2005 |
| WO | WO/2005/099801 | | 10/2005 |
| WO | PCT/AU2005/000704 | | 11/2005 |
| WO | WO 2005/118040 | | 12/2005 |
| WO | WO 2005/123166 | | 12/2005 |
| WO | PCT/AU2006/000031 | | 1/2006 |
| WO | WO 2006/000046 | | 1/2006 |
| WO | PCT/AU2006/000417 | | 3/2006 |
| WO | PCT/AU2006/000770 | | 6/2006 |
| WO | PCT/AU05/01941 | | 7/2006 |

(56) References Cited

FOREIGN PATENT DOCUMENTS

| | | | |
|---|---|---|---|
| WO | WO 2006/069415 | | 7/2006 |
| WO | WO 2006/074513 | | 7/2006 |
| WO | WO 2006/074516 | | 7/2006 |
| WO | WO 2006/074517 | | 7/2006 |
| WO | WO 2006/074517 | A1 | 7/2006 |
| WO | PCT/AU06/000321 | | 9/2006 |
| WO | WO 2006/130903 | | 12/2006 |
| WO | WO 2007 /006089 | | 1/2007 |
| WO | WO 2007/009182 | | 1/2007 |
| WO | WO 2007/014088 | | 2/2007 |
| WO | WO 2007/041751 | | 4/2007 |
| WO | WO 2007/041786 | | 4/2007 |
| WO | WO 2007 /045008 | | 4/2007 |
| WO | WO 2007/048174 | | 5/2007 |
| WO | WO 2007/053878 | | 5/2007 |
| WO | WO 2007/104042 | | 9/2007 |
| WO | PCT/AU2007/001936 | | 12/2007 |
| WO | WO 2007/143772 | | 12/2007 |
| WO | WO 2007/145534 | | 12/2007 |
| WO | WO 2007/147088 | | 12/2007 |
| WO | WO 2008/007985 | | 1/2008 |
| WO | WO 2008/011682 | | 1/2008 |
| WO | WO 2008/011683 | | 1/2008 |
| WO | WO 2008/030831 | | 3/2008 |
| WO | WO 2008/040050 | | 4/2008 |
| WO | WO 2008/068966 | | 6/2008 |
| WO | WO 2009/026627 | | 3/2009 |
| WO | WO 2009/052560 | | 4/2009 |
| WO | WO 2009/059353 | | 5/2009 |
| WO | WO 2009/108994 | | 9/2009 |
| WO | WO 2009/109004 | | 9/2009 |
| WO | WO 2010/028425 | | 3/2010 |
| WO | WO 2010/066004 | | 6/2010 |

OTHER PUBLICATIONS

Office Action for related U.S. Appl. No. 16/432,976, 12 pages, dated Apr. 4, 2024.
Office Action mailed Oct. 20, 2021 in related U.S. Appl. No. 17/010,393.
JP Notice of Reasons for Rejection and English translation thereof dated Jul. 19, 2021 in related JP Application 2020-128274 (8 pages).
JP Notice of Reasons for Rejection and English translation thereof dated Sep. 6, 2021 in related JP Application 2018-112701 (5 pages).
U.S. Office Action dated Jul. 6, 2021 in related U.S. Appl. No. 16/414,012 (66 pages).
U.S. Office Action dated Apr. 22, 2021 in related U.S. Appl. No. 17/010,393 (32 pages).
NZ First Examination Report dated Jun. 3, 2021 in related NZ Application 776317 (3 pages).
NZ First Examination Report dated May 14, 2021 in related NZ Application 774989 (3 pages).
U.S. Office Action dated Feb. 3, 2021 in related U.S. Appl. No. 17/072,316 (33 pages).
NZ First Examination Report dated Dec. 24, 2020 in related NZ Application 770201 (3 pages).
NZ Proceedings Correspondence dated Jul. 27, 2020 in related NZ Application 702644.
EP Search Report dated Jun. 16, 2020 in related EP Application 19208684.1.
Japanese Notice of Reasons for Rejection and English translation thereof dated Mar. 9, 2020 in related JP Application P2018-112701.
Japanese Final Rejection and English translation thereof dated Mar. 30, 2020 in related JP Application P2018-154578.
NZ First Examination Report dated Dec. 12, 2019 in related NZ application 759228.
NZ Further Examination Report dated Jan. 16, 2020 in related NZ application 759228.
NZ First Examination Report dated Dec. 12, 2019 in related NZ application 759229.
NZ Further Examination Report dated Jan. 16, 2020 in related NZ application 759229.
EP Extended Search Report and Opinion dated Feb. 7, 2020 in related EP application 19203143.3.
JP Notice of Reasons for Rejection and English translation thereof dated Sep. 9, 2019 in related JP Application P2016-181474
NZ First Examination Report dated May 31, 2019 in a related NZ application 753520.
NV First Examination Report dated Jun. 10, 2019 in a related NZ application 753803.
JP Notice of Reasons for Rejection and English translation thereof dated Jul. 8, 2019 in a related JP Application P2018-154578.
JP Notice of Reasons for Rejection and English translation thereof dated Jul. 8, 2019 in a related JP application P2018-112701.
U.S. Appl. No. 10/298,845, filed Nov. 2002, Kwok et al.
U.S. Appl. No. 10/364,358, filed Feb. 2003, Kwok et al.
U.S. Appl. No. 11/417,234, filed May 2006, Huber et al.
U.S. Appl. No. 11/645,582, filed Dec. 2006, Kwok et al.
U.S. Appl. No. 11/878,932, filed Jul. 2007, Veliss et al.
U.S. Appl. No. 11/878,933, filed Jul. 2007, Veliss et al.
U.S. Appl. No. 12/309,696, filed Jan. 2009, Kwok et al.
U.S. Appl. No. 60/833,841, filed Jul. 2006, Veliss et al.
JP Notice of Allowance mailed Nov. 9, 2020 in related JP Application 2018-154578.
U.S. Office Action dated Sep. 15, 2020 in related U.S. Appl. No. 15/809,475.
U.S. Office Action dated Aug. 19, 2020 in related U.S. Appl. No. 16/922,391.
JP Pre-Appeal Examination Report, and English translation thereof dated Dec. 14, 2020 in related JP Application 2018-112701.
U.S. Office Action dated Jan. 13, 2021 in related U.S. Appl. No. 17/010,393.
ACP Composites—Large Stock of Ready to Use Composite Plate, Tube, Sheet, Fabrics and Core Materials, https://www.acpsakes.com/Core-Materials-nd-Foam.html. dated Oct. 5, 2015, 4 pages.
Flexifit instructions, http://web.archive.org/web/1 9970126045828/http:/www.aichive.org/ dated Jan. 26, 1997, Affidavit of Christopher Butler dated Sep. 6, 2016, 23 pages.
Guidelines for Sandwich Core Materials, http://fibreglast.com/product/guidelinesfor-sandwich-core-materials/Learning Center, dated Oct. 5, 2015, 3 pages.
Malloy, Plastic Part Design for Injection Molding, New York: Hanser Publishers, 1994, 14 pages.
Opus Brochure, Fisher & Paykel Healthcare, www.fphcare.com, 2 pages.
ResMed Mask Frames, Nasal Cushions and Headgear, http://web.archive.org/web/19970 126045828/http://www.archive.org/ dated Jan. 26, 1997, Affidavit of Christopher Butler dated Jul. 6, 2017, 8 pages.
ResMed Mirage Swift Nasal Pillows System, www.resmed.com, 2004, 6 pages.
ResMed Mirage Vista Nasal Mask-Component Cards, www.resmed.com Reference No. 1010279/30502, dated 2005, 1 page.
ResMed Origins Brochure dated Apr. 17, 2016, 64 pages.
Ultra Mirage Full Face Mask brochure, http://web.archive.org/web/199701 26045828/http://www.archive.org/ dated Jan. 26, 1997, Affidavit of Christopher Butler dated Sep. 6, 2016, 9 pages.
Users Guide ResMed Mirage Swift Nasal Pillows System, www.myresmed.com dated May 6, 2004, 11 pages.
Final Office Action dated Feb. 21, 2019 in related U.S. Appl. No. 15/650,577.
NZ Amended Statement of Case dated Feb. 7, 2019 in related NZ Patent Application 702644.
A Pre-Appeal Examination Report issued in related Japanese Application No. 2016-181474 dated Nov. 20, 2018, and English translation thereof, (7 pages).
U.S. Appl. No. 10/385,701 (U.S. Pat. No. 7,302,950), filed Mar. 2003 (Dec. 2007), Berthon-Jones et al.
U.S. Appl. No. 10/781,929 (U.S. Pat. No. 7,318,437), filed Feb. 2004 (Jan. 2008), Gunaratnam et al.
U.S. Appl. No. 60/935,179, filed Jul. 2007, Guney et al.
International Search Report for PCT/AU2007/001936, dated Mar. 4, 2008.
“Ear Loop Face Mask”.

(56) References Cited

OTHER PUBLICATIONS

Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
U.S. Appl. No. 12/085,191, filed Apr. 16, 2009.
European Search Report issued in EP 07845378.4, dated Dec. 1, 2009.
Supplementary European Search Report dated Sep. 8, 2009 in European Appln. No. 04802133.1.
Supplementary Search Report issued in European Appln. 05746824.1, dated Dec. 17, 2009.
Supplementary European Search Report dated Dec. 18, 2009 in European Application No. 03810331.3.
U.S. Appl. No. 10/533,928 (2006-0118117), filed Jun. 2006, Berthon-Jones et al.
U.S. Appl. No. 11/080,446 (2005-0155604), filed Jul. 2005, Ging et al.
U.S. Appl. No. 11/491,016 (2007-0023044), filed Feb. 2007, Kwok et al.
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
European Examination Report issued in EP 07845378.4 (dated Sep. 16, 2010).
New Zealand Examination Report issued in NZ Appln. No. 575405 (dated Jan. 17, 2011).
Office Action issued in Chinese Appln. No. 200780046385.3 (dated Jun. 30, 2011) w/English translation.
Examination Report issued in European Appln. No. 07845378.4 (dated Jul. 21, 2011).
Office Action issued in Chinese Application No. 200780046385.3 (dated Mar. 22, 2012) with English translation.
Examination Report issued in a related New Zealand Patent Appl. No. 575405 (dated May 7, 2012).
Extended European Search Report issued in a corresponding Patent Appl. No. 12 16 5191.3, dated Aug. 2, 2012.
Extended European Search Repot issued in a corresponding Patent Appl. No. 12 16 5188.9, dated Aug. 3, 2012.
Office Action issued in a corresponding Chinese Application No. 200780046385.3 (dated Jan. 4, 2013) with English translation thereof.
Final Office Action issued in a related U.S. Appl. No. 12/085,191, dated Feb. 12, 2013.
Communication issued in a related European Application No. 11 191 110.3, dated Feb. 15, 2013.
Communication issued in a related European Application No. 11 191 107.9, dated Feb. 28, 2013.
U.S. Appl. No. 10/584,711, filed Dec. 2004, Davidson.
U.S. Appl. No. 10/655,622, filed Sep. 2003, Lithgow.
U.S. Appl. No. 10/871,929, filed Feb. 2004, Surjaatmadja.
U.S. Appl. No. 11/447,295, filed Jun. 2006, Lubke et al.
U.S. Appl. No. 11/474,415, filed Jun. 2006, Davidson et al.
U.S. Appl. No. 11/597,909, filed Jul. 2007, Worboys.
U.S. Appl. No. 11/703,082, filed Feb. 2007, Davidson.
U.S. Appl. No. 12/081,696, filed Apr. 2008, Davidson et al.
U.S. Appl. No. 12/219,852, filed Jul. 2008, Guney et al.
U.S. Appl. No. 12/382,517, filed Mar. 2009, Lithgow.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Pro®," www.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
Examination Report filed in New Zealand Application 539836, dated Aug. 25, 2005.
Examiner's Report No. 3 mailed Nov. 18, 2009 in New Zealand Application No. 2003275762.
Extended European Search Report dated Mar. 19, 2009 in European Application No. EP 08161249.
Extended European Search Report Mailed Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphkc.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action mailed Dec. 22, 2009 in European Appln. No. 04802133.1.
ResMed Co.—Mask Products—http://resmed.com/portal/site/RedMedUS/index.jsp?. . . .
Respironics Co.—Mask Family—http://masksfamily.respironics.com/.

(56) References Cited

OTHER PUBLICATIONS

Snapp Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.
Office Action issued in a corresponding Japanese Application No. 2009-540550 with English translation thereof (Feb. 12, 2013).
Decision of Rejection issued in a related Japanese Appl. No. 2009-521069 with English translation thereof (Apr. 2, 2013).
Non-final Office Action issued in related U.S. Appl. No. 12/085,191 dated Jul. 2, 2013.
Communication pursuant to Article 94(3) EPC issued in a related European Patent Application No. 07 784 696.2-1662 on Jul. 17, 2013.
First Examination Report issued in corresponding New Zealand Patent Application No. 615330 on Sep. 30, 2013.
Final Office Action issued in related U.S. Appl. No. 12/085,191 on Jan. 3, 2014, including PTO-892 listing US 2006/0042629 (Geist) and U.S. Pat. No. 6,615,832 (Chen).
Decision of Rejection issued Mar. 3, 2014 in corresponding Japanese Patent Application No. 2009-540550 (English language version only).
Non-final Office Action issued Jun. 6, 2014 in related U.S. Appl. No. 12/085,191, including PTO-892 listing US 2005/0205096 A1 (Matula, Jr et al.), WO 2005/053781 A1 (McAuley et al.) and WO 2007/104042 A2 (Ho).
Office Action issued Jun. 30, 2014 in related Japanese Application No. 2013-157403 with English-language translation thereof, listing JP 2003-502119 (of which WO 00/78384 is a corresponding English language document).
Office Action issued Jun. 30, 2014 in corresponding Japanese Application No. 2013-166104 with English-language translation thereof.
Further Examination Report dated Sep. 23, 2014 issued in corresponding New Zealand Application No. 610755 (2 pages).
Communication dated Nov. 12, 2014 issued in corresponding European Application No. 12 165 188.9 (7 pages).
Communication dated Nov. 4, 2014 issued in corresponding European Application No. 12 165 191.3 (5 pages).
Summons to Attend Oral Proceedings pursuant to Rule 115(1) EPC issued Dec. 9, 2014 in related European Patent Application Publication No. 11 191 110.3.
First Examination Report issued Dec. 19, 2014 in related New Zealand Patent Application No. 702644.
Patent Examination Report No. 1 dated Dec. 22, 2014 issued in related Australian Application No. 2014201200 6 pages).
Office Action dated Jan. 13, 2015 issued in related U.S. Appl. No. 12/085,191 (30 pages).
Further Examination Report issued Dec. 18, 2014 in related New Zealand Application No. 610755.
Decision of Rejection dated Mar. 2, 2015 issued in related Japanese Application No. 2013-157403 with English translation (4 pages).
Notification of the First Office Action dated Apr. 20, 2015 issued in a corresponding Chinese application No. 2013103088382 with English translation (14 pages).
Decision of Rejection issued Apr. 27, 2015 in a corresponding Japanese Patent Application No. 2013-166104, with English Translation thereof (8 pages).
First Office Action issued May 18, 2015 in a corresponding Japanese application No. 2014-13753, and English translation thereof (11 pages).
Non-Final Office Action issued in related U.S. Appl. No. 12/085,191 on Jun. 3, 2015, including PTO-892 listing WO 2004/041342 (19 pages).
Office Action issued Sep. 14, 2015 in a related Japanese Application No. 2014-198231 (4 pages) and English translation thereof (5 pages).
A Second Office Action issued Sep. 21, 2015 in a related Chinese Application No. 201310138927.7 (9 pages), and an English translation thereof (12 pages).
Third Office Action issued Oct. 5, 2015 in a corresponding Japanese Patent Application No. 2009-540550 (4 pages), and an English Translation thereof (4 pages).
Fourth Office Action issued Nov. 18, 2015, in a related Chinese Application No. 201210210669.4 (8 pages) and an English translation thereof (13 pages).
Final Office Action issued Dec. 14, 2014, in a related U.S. Appl. No. 12/085,191 (44 pages), citing U.S. Pat. No. 8,701,667, U.S. Patent Publication No. 2006/0231103 and U.S. Patent Publication No. 2005/0066976.
Second Office Action issued Nov. 30, 2015 in a corresponding Japanese Application No. 2013-166104 (2 pages) and an English translation thereof (2 pages).
Second Office Action issued Jan. 7, 2016 in a corresponding Chinese Application No. 201310308838.2 (6 pages) and an English translation thereof (8 pages).
Third Office Action dated Mar. 25, 2016 in a related Chinese Application No. 201310138927.7 (10 pages), and an English translation thereof (12 pages).
Notice of Opposition filed Oct. 25, 2016 in a related New Zealand Application No. 702644 (3 pages), citing U.S. Patent Publication No. 2004/0149280.
Communication enclosing an Extended European Search Report dated Jun. 28, 2016 in a related European Application No. 16155760.8-1662 (10 pages), citing U.S. Pat. Nos. 6,698,427, 4,579,113 and 5,155,863, and U.S. Patent Publication No. US 2002/0162556.
A Third Office Action dated Jul. 4, 2016 in a corresponding Chinese Application No. 201310308838.2 (3 pages), and an English translation thereof (6 pages).
First Examination Report dated Jun. 30, 2016 in a related New Zealand Application No. 721025 (2 pages).
Second Office Action dated Nov. 28, 2016 in a related Japanese Application No. 2013-218972 (4 pages), and an English translation thereof (7 pages).
Non-Final Office Action dated Dec. 14, 2016 in a related U.S. Appl. No. 12/085,191 (38 pages), citing U.S. Pat. Nos. 4,809,692, 5,966,745, 6,012,455 and 7,152,602, and U.S. Patent Publication No. 2005/012030.
Deadline for Counterstatement issued Feb. 1, 2017 in a related New Zealand Application No. 702644 (2 pages), forwarding an Amended Notice of Opposition to Grant of Patent (Section 21) (2 pages) and a Statement of Case (13 pages).
Communication enclosing an Extended European Search Report dated Jun. 28, 2016 in a related European Application No. 16155760.8-1662 (10 pages)
Notice of Opposition filed Oct. 25, 2016, in a related New Zealand Application No. 702644 (3 pages).
Non-Final Office Action dated Dec. 14, 2016 in a related U.S. Appl. No. 12/085,191 (38 pages).
Communication enclosing the Extended European Search Report dated Jan. 17, 2017 in a related European Application No. EP 161659008 (7 pages).
A Third Office Action dated Mar. 27, 2017, in a related Japanese Application No. 2013-157403 (2 pages), and an English translation thereof (2 pages).
A Final Office Action dated Jun. 12, 2017, in a related U.S. Appl. No. 12/085,191 (38 pages).
Further Examination Report dated Jun. 30, 2017, in a related New Zealand Application No. 721025 (3 pages).
A Non-Final Office Action dated Sep. 19, 2017, in a related U.S. Appl. No. 12/085,191, citing U.S. Pat. No. 3,552,778 (Muller), U.S. Pat. No. 3,799,164 (Rollins) and U.S. Pat. No. 4,878,491 (McGilvray ) (45 pages).
A Second Office Action dated Dec. 5, 2016 in a related Japanese Application No. 2013-157403 (4 pages), and an English translation thereof (6 pages).
A First Examination Report dated Dec. 4, 2017, in a related New Zealand Patent Application No. 736962 (4 pages).
A Final Office Action dated Mar. 30, 2018, in a related U.S. Appl. No. 15/650,577 (34 pages).

(56) References Cited

OTHER PUBLICATIONS

Non-Final Office Action issued in U.S. Appl. No. 15/650,577, dated Aug. 9, 2018 (33 pages), citing U.S. Pat. No. 6,684,882 (Morine) and US 2006/0174889 (Noble).

* cited by examiner

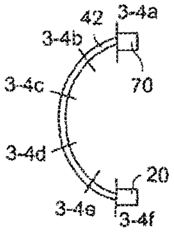
Fig. 3-4
Fig. 3-4a
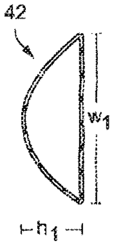
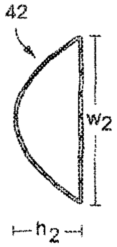
Fig. 3-4b
Fig. 3-4c
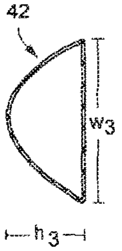
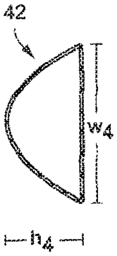
Fig. 3-4d
Fig. 3-4e
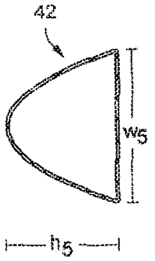
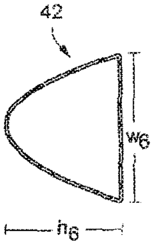
Fig. 3-4f
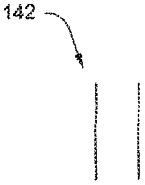
Fig. 3-5a
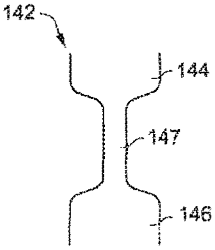
Fig. 3-5b
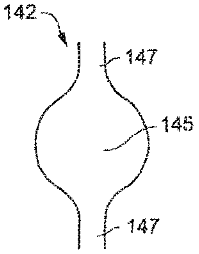
Fig. 3-5c
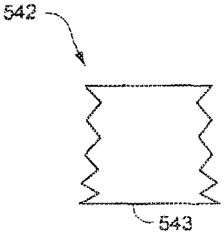
Fig. 3-6a
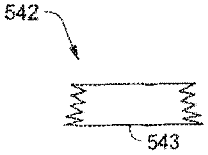
Fig. 3-6b

| PROPERTY | UNITS | 1st EXEMPLARY RANGE | 2nd EXEMPLARY RANGES | TEST STANDARD |
|---|---|---|---|---|
| Density | (kg/m^3) | 40-70 | <60 30 - 60<br>~55 30 - 100<br>30-90 50 - 60 | DIN EN ISO 845 |
| Compression Set | (%) | < 10 | 2 - 50 | ISO 1856 |
| Tear Strength | (N/mm) | > 0.30 | 0.1 - 1 | DIN 53515 |
| Tensile Strength | (kPa) | > 150 | 30 - 180 | DIN EN ISO 1798 |
| Elongation @ Break | (%) | > 200 | 50 - 400 | DIN EN ISO 1798 |
| Hardness CLD @ 40% | (kPa) | 0.4 - 1.5 | 0.2 - 5 | ISO 3386 - 1/2 |
| Hardness ILD @ 40% | (N) | 25 - 80 | 50 - 100 20 -80<br><100 40 -60<br><80 10-100 | ISO 2439 |
| Hysteresis | (%) | 25 - 35 | 2 - 50 10 - 35<br>5 - 40 15 - 35 | ISO 3386 - 1/2 |
| Resilience (% Rebound) | (%) | < 10 | < 80 < 40<br>< 15 | N/A |
| Cell Count | (Cells/cm) | 60 - 120 | 5 - 120 | N/A |
| Cell Structure | Homo/Heterogeneous (Cell size - μm) | Heterogeneous (20 - 1000) | Homogeneous - Heterogeneous (20 - 4000) | N/A |
| Air Permeability | (L/m^2/s) | 0 - 50 | 0 - 500 < 10<br>10 - 50 < 5 | DIN EN ISO 9237 |

Fig. 14-1

DELIVERY OF RESPIRATORY THERAPY

CROSS-REFERENCE TO APPLICATION

This application is a continuation of U.S. application Ser. No. 16/193,383, filed Nov. 16, 2018, which is a continuation of U.S. application Ser. No. 12/448,250, filed Jun. 15, 2009, now U.S. Pat. No. 10,166,357, which is the U.S. national phase of International Application No. PCT/AU2007/001936, filed Dec. 14, 2007, which designated the U.S. and claims the benefit of U.S. Provisional Application Nos. 60/874,968, filed Dec. 15, 2006, 60/924,241, filed May 4, 2007, 60/929,393, filed Jun. 25, 2007, and 60/996,485, filed Nov. 20, 2007, and claims the benefit of International Application Nos. PCT/AU2007/001051, filed Jul. 27, 2007, and PCT/AU2007/001052, filed Jul. 27, 2007, and claims the benefit of Australian Application Nos. 2007905737, filed Oct. 22, 2007, 2007906102, filed Nov. 6, 2007, and 2007906276, filed Nov. 16, 2007, each of which is hereby incorporated herein by reference in its entirety.

FIELD OF THE INVENTION

The invention relates to the delivery of respiratory therapy to a patient. Examples of such therapies are Continuous Positive Airway Pressure (CPAP) treatment, Non-Invasive Positive Pressure Ventilation (NIPPY), and Variable Positive Airway Pressure (VPAP). The therapy is used for treatment of various respiratory conditions including Sleep Disordered Breathing (SDB) and more particularly Obstructive Sleep Apnea (OSA).

BACKGROUND OF THE INVENTION

Typically, respiratory therapy is delivered in the form of a mask system positioned between a patient and apparatus providing a supply of pressurized air or breathing gas. Mask systems in the field of the invention differ from mask systems used in other applications such as aviation and safety in particular because of their emphasis on comfort. This high level of comfort is desired because patients must sleep wearing the masks for hours, possibly every night for the rest of their lives. In addition, therapy compliance can be improved if the patient's bed partner is not adversely affected by the patient's therapy and wearing of the mask generally.

Mask systems typically have a highly clinical aesthetic (as will be described below). This can lead to patients becoming embarrassed about their therapy since the clinical aesthetic serves as a blatant reminder that they are ill and consequently can leave a negative perception of the patient in the mind of an observer.

Mask systems typically, although not always, comprise (i) a rigid or semi-rigid portion often referred to as a shell or frame, (ii) a soft, patient contacting portion often referred to as a cushion, and (iii) some form of headgear to hold the frame and cushion in position. If the mask system does in fact include multiple components, at least some assembly and adjustment may be required, which can be difficult for patients who may suffer from lack of dexterity, etc. Further, mask systems often include a mechanism for connecting an air delivery conduit. The air delivery conduit is usually connected to a blower or flow generator.

Patient contacting portions, e.g., cushions, are typically constructed of a silicone material, but patient contacting portions including foam are known. For example, U.S. Pat. No. 5,429,683 discloses a lining for a mask made of a polyurethane foam covered with skin (e.g., latex or silicone). However, skinned foam does not allow the portion in contact with the face to breathe, which can lead to skin irritation, and the sealing portion may be subject to creasing which may cause discomfort and lead to leak. The skin can also feel too hard for some patients, depending on the thickness and support structure. The skin also does not allow a high degree of local deformation and may be subject to tension transfer across its surface, which can result in shifting of the mask on the face and loss of seal/comfort.

A range of mask systems are known including nasal masks, nose & mouth masks, full face masks and nasal prongs, pillows, nozzles & cannulae. Masks typically cover more of the face than nasal prongs, pillows, nozzles and cannulae. Nasal prongs, nasal pillows, nozzles and cannulae all will be collectively referred to as nasal prongs.

There is a continuous need in the art to provide mask systems with a high level of comfort and usability and a newly perceived need to provide mask systems having improved aesthetics (i.e., less clinical and bulky).

SUMMARY OF THE INVENTION

One aspect of the present invention is to provide a therapy compliance-enhancing patient interface.

Another aspect of the present invention is to provide a comfortable patient interface.

Another aspect of the invention is to provide a patient interface having a non-medical appearance. In one form, this may be achieved by creating a soft, comfortable, flexible patient interface that has the appearance of an article of clothing.

Another aspect of the invention relates to a comfortable, stable mask to administer a supply of air at positive pressure to the entrance of a patient's airways.

In an embodiment, the mask includes a gasket-type cushion including a pair of side stabilizing portions.

Another aspect of the invention relates to a cushion constructed from a low permeability foam.

In an embodiment, the cushion may be constructed from a slow recovery foam.

In an embodiment, the foam cushion may have a thickness of greater than about 5 mm.

In an embodiment, the cushion may be die cut from a slab of foam.

In an embodiment, the cushion may be attached to a structure to impart a curve in the cushion in one or more directions.

Another aspect of the invention relates to a comfortable, unobtrusive, easy to use, stable system for delivering a supply of air at positive pressure to the entrance to the patient's airways such as may be used in nasal CPAP treatment of sleep disordered breathing. This system is compatible with a range of interfaces and/or sealing structures, including nasal masks, nasal cushions, mouth masks, etc. The system has been particularly designed so that a patient may comfortably sleep in a range of different positions, including rolling onto the side of their face, without experiencing discomfort and while maintaining adequate therapy. This system offers a number of improvements over the prior art.

Another aspect of the invention relates to an interfacing structure that provides improved comfort, enhanced interfacing performance, and ease of use over prior sealing structures. Aspects of the improved interfacing structure are that it requires less precise fitting than prior sealing structures and does so with a more comfortable and even pressure distribution on the patient's face. The interfacing structure has a more natural feel against the skin than prior sealing structures and also features controlled air permeability so that the skin is allowed to breathe. Another aspect of the improved interfacing structure is that it is less prone to disruption by movement than prior sealing structures.

Another aspect of the invention relates to a respiratory mask for continuous positive airway pressure treatment. The respiratory mask includes a cushion adapted to be positioned against the face of a patient. The cushion is configured in a gasket arrangement around an entrance to the airways of the patient. The cushion is constructed from a polyurethane foam and having a thickness of greater than about 5 mm.

Another aspect of the invention relates to a respiratory mask for continuous positive airway pressure treatment. The respiratory mask includes a cushion. The cushion is configured in a gasket arrangement around an entrance to the airways of the patient. The cushion is constructed from an unskinned polyurethane foam having a permeability less than about 10 L/s/m$^2$. The cushion is adapted to be positioned against the face of a patient.

Another aspect of the invention relates to a respiratory mask for continuous positive airway pressure treatment. The respiratory mask includes a cushioning component constructed from a polyurethane foam having a thickness of greater than about 5 mm, an ILD hardness @40% of less than about 200 N and a density of less than about 200 kg/m$^3$.

Another aspect of the invention relates to a respiratory mask for continuous positive airway pressure treatment. The respiratory mask includes a cushioning component constructed from a polyurethane foam having a thickness of greater than about 5 mm, an ILD hardness @40% of less than about 100 N and a resiliency of less than about 15%.

In one form, the cushioning component is constructed from a polyurethane foam having an ILD hardness @40% of less than about 200N.

In one form the cushioning component is constructed from a polyurethane foam having a density of less than about 200 kg/m$^3$.

In one form the cushioning component includes a layer of a polyurethane foam having a thickness in the range of 5 mm to 15 mm, preferably about 10 mm.

Another aspect of the invention relates to a respiratory mask for continuous positive airway pressure treatment. The respiratory mask includes a cushion. The cushion is configured in a gasket arrangement around an entrance to the airways of the patient. The cushion is constructed from an unskinned foam having a thickness of greater than about 5 mm, and a hardness of less than about 100 N at 40%. The cushion is adapted to be positioned against the face of a patient.

Another aspect of the invention relates to a respiratory mask for continuous positive airway pressure treatment. The respiratory mask includes a cushion. The cushion is configured in a gasket arrangement around an entrance to the airways of the patient. The cushion is constructed from an unskinned fine-celled foam with an heterogeneous cell structure having a thickness of greater than about 5 mm and is arranged to be in contact with the skin.

Another aspect of the invention relates to a respiratory mask for continuous positive airway pressure treatment. The respiratory mask includes a cushioning component constructed from a polyurethane foam having a thickness of greater than about 5 mm, an ILD hardness @40% of less than about 200 N, a resiliency of less than about 40%, density of less than about 200 kg/m$^3$, permeability less than about 10 L/s/m$^2$, and hysteresis in the range of 5-40%.

Another aspect of the invention relates to a respiratory mask assembly including an interfacing structure adapted to provide an interface with the patient's face, a pair of tubes adapted to deliver breathable gas to the interfacing structure and support the mask assembly in position on the patient's head, the tubes being arranged to define a generally ring shape, and an adjustment mechanism structured to allow lengthwise adjustment of the ring shape.

Another aspect of the invention relates to a respiratory mask for continuous positive airway pressure treatment. The respiratory mask includes a cushion adapted to be positioned against the face of a patient. The cushion is configured in a gasket arrangement around an entrance to the airways of the patient. The cushion is constructed from foam and having a general chevron, delta, boomerang or circumflex shape.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of various embodiments of this invention. In such drawings:

FIGS. 2-1 to 2-2 are schematic views illustrating assembly of a patient interface according to an embodiment of the present invention;

FIG. 2-3 is a schematic view illustrating attachment of a patient interface to a PAP device according to an embodiment of the present invention;

FIGS. 2-4*a* to 2-4*b* illustrate attachment of a patient interface to a PAP device according to another embodiment of the present invention;

FIGS. 3-1, 3-2*a*, and 3-2*b* illustrate a tube of a patient interface in open and collapsed phases according to an embodiment of the present invention;

FIG. 3-3 is a schematic view of a tube and rigidizing element of a patient interface according to an embodiment of the present invention;

FIGS. 3-4 and 3-4*a* to 3-4*f* illustrate various cross-sections of a tube along its length according to an embodiment of the present invention;

FIGS. 3-5*a* to 3-5*c* are schematic views of a tube of a patient interface in open and collapsed or partially collapsed phases according to another embodiment of the present invention;

FIGS. 3-6*a* to 3-6*b* illustrate a tube having a concertina configuration according to another embodiment of the present invention;

FIGS. 4-1 to 4-5 illustrate tubing for a patient interface according to an embodiment of the present invention;

FIGS. 4-6 to 4-9 illustrate tubes and a rigidizing element according to an embodiment of the present invention;

FIGS. 5-1 to 5-3 illustrate tubes of a patient interface according to alternative embodiments of the present invention;

FIGS. 6-1 to 6-4 illustrate a back strap of a patient interface according to an embodiment of the present invention;

FIG. 6-5 illustrates a back strap of a patient interface according to another embodiment of the present invention;

FIGS. 7-1 to 7-2 illustrate manifolds of a patient interface according to alternative embodiments of the present invention;

FIGS. 8-1 to 8-5 illustrate a tube configuration according to an embodiment of the present invention;

FIG. 8-6 is a schematic view that illustrates a region where tubing may pass according to an embodiment of the present invention;

FIG. 8-7 illustrates an adjustable tube configuration according to another embodiment of the present invention;

FIG. 8-8-1 illustrates a mask assembly incorporating an adjustment mechanism in accordance with an embodiment of the invention;

FIG. 8-8-2 illustrates another view of the mask assembly shown in FIG. 8-8-1;

FIGS. 8-8-3*a* to 8-8-3*e* show various views of the adjustment mechanism shown in FIG. 8-8-1;

FIGS. 8-8-4*a* to 8-8-4*f* show various views of a first rack of the adjustment mechanism shown in FIG. 8-8-1;

FIGS. 8-8-5*a* to 8-8-5*e* show various views of a second rack of the adjustment mechanism shown in FIG. 8-8-1;

FIGS. 8-8-6*a* to 8-8-6*f* show various views of a pinion of the adjustment mechanism shown in FIG. 8-8-1;

FIGS. 8-8-7*a* to 8-8-7*f* show various views of a dial of the adjustment mechanism shown in FIG. 8-8-1;

FIGS. 8-8-8*a* to 8-8-8*f* show various views of a first housing portion of the adjustment mechanism shown in FIG. 8-8-1;

FIGS. 8-8-9*a* to 8-8-9*f* show various views of a second housing portion of the adjustment mechanism shown in FIG. 8-8-1;

FIGS. 9-1 to 9-3 illustrate a method for fitting a patient interface according to an embodiment of the present invention;

FIGS. 10-1 to 10-6 are various views of a patient interface including a cover according to an embodiment of the present invention;

FIG. 11-1 illustrates a valve of a patient interface according to an embodiment of the present invention;

FIGS. 12-1 to 12-3 illustrate clips of a patient interface according to alternative embodiments of the present invention;

FIGS. 13-1 to 13-2 are various views of a foam interface and support according to an embodiment of the present invention;

FIGS. 13-3 and 13-4 are top and side views of a foam interface having a cut, unskinned surface according to an embodiment of the present invention;

FIG. 13-5 is a top view of a foam interface having a skinned surface according to an embodiment of the present invention;

FIG. 13-6 is an enlarged, schematic cross-section of a portion of the foam interface shown in FIG. 13-5;

FIGS. 13-7*a* to 13-7*c* illustrate foams according to alternative embodiments of the present invention;

FIG. 13-8 is a schematic cross-section of a portion of a foam interface having a skinned surface and a vent according to an embodiment of the present invention;

FIG. 14-1 is a table of mechanical properties of a foam interface according to an embodiment of the present invention;

FIG. 14-2 is a graph illustrating properties of a foam interface according to an embodiment of the present invention;

FIG. 14-3 is a schematic view of a dispenser adapted to dispense individual packages containing a foam interface according to an embodiment of the present invention;

FIGS. 15-1 to 15-2 illustrate front and side cross-sectional views, respectively, of a foam interface according to an embodiment of the present invention;

FIG. 15-3-1 shows a front view of a mask assembly in accordance with an embodiment of the invention;

FIG. 15-3-2 shows a side view of the mask assembly shown in FIG. 15-3-1;

FIG. 15-3-3 shows a top detail view of the mask assembly shown in FIG. 15-3-1;

FIG. 15-3-4 shows a front perspective view of the mask assembly shown in FIG. 15-3-1;

FIGS. 15-3-5-1 to 15-3-5-3 show three forms of cushions in accordance with an embodiment of the invention including side portions, one of the forms is a flat cushion and the other two forms are curved;

FIG. 15-3-6 shows a flat cushion embodiment that has been adhered to a curved surface;

FIG. 15-3-7 shows a perspective view of the cushion embodiment shown in FIG. 15-3-6;

FIG. 15-3-8 shows a mounting arrangement for a flat cushion that is configured to provide a curved shape to the flat cushion;

FIGS. 15-3-9-1 to 15-3-9-3 show an alternative embodiment of the invention wherein headgear connectors are located close to the nares in between a foam cushion and a decoupling joint;

FIG. 16-1 is a schematic view of a patient interface according to an embodiment of the present invention;

FIGS. 16-2 to 16-3 are schematic views of a frame and force vector according to an embodiment of the present invention;

FIG. 17-1 schematically illustrates layers of an interfacing structure according to an embodiment of the present invention;

FIG. 17-2 illustrates a method of joining an interface to a frame according to an embodiment of the present invention;

FIGS. 17-3A to 17-3C illustrate a mechanical interference type attachment mechanism to removably attach an interfacing structure to a patient interface according to an embodiment of the present invention;

FIGS. 17-4A to 17-4C illustrate a hook and loop type attachment mechanism to removably attach an interfacing structure to a patient interface according to an embodiment of the present invention;

FIGS. 18-1 to 18-3 illustrate a method of joining an under-the-nose interface to a frame according to an embodiment of the present invention;

FIGS. 19-1 to 19-3 are sequential views illustrating a manufacturing process for applying a pressure sensitive adhesive to the back of an under-the-nose interface according to an embodiment of the present invention;

FIGS. 20-1 to 20-3 illustrate a method of joining an under-the-nose interface to a frame according to an embodiment of the present invention;

FIGS. 20-4 to 20-7 are sequential views illustrating a manufacturing process for forming a composite under-the-nose interface according to an embodiment of the present invention;

FIGS. 21-1 to 21-3 illustrate a flexible frame according to an embodiment of the present invention;

FIG. 22-1 illustrate a flexible frame according to another embodiment of the present invention;

FIG. 23-1 illustrates a flexible frame with a spring element according to an embodiment of the present invention;

FIG. 23-2 is a graph for a variable spring element with k values that vary across its length according to an embodiment of the present invention;

FIG. 23-3 illustrates a flexible frame with a spring element according to another embodiment of the present invention;

FIG. 24-1 illustrates a foam interface including a rigidizer that provides venting according to an embodiment of the present invention;

FIG. 25-1 illustrates a patient interface including an under-the-nose interface and a mouth interface according to an embodiment of the present invention;

FIG. 26-1 is a perspective view of a known mask commercially sold by Respironics under the name of ComfortCurve™;

FIGS. 26-2 to 26-10 illustrate improvements and/or alternative arrangements of Respironics' ComfortCurve™ mask according to embodiments of the present invention;

FIG. 27-1 is a perspective view of a known mask commercially sold by Respironics under the name of OptiLife™;

FIGS. 27-2 to 27-7 illustrate improvements and/or alternative arrangements of Respironics' OptiLife™ mask according to embodiments of the present invention;

FIG. 28-2A illustrates an improvement and/or alternative arrangement of Respironics' ComfortLite™ mask according to an embodiment of the present invention;

FIG. 28-1B is a perspective view of a known mask commercially sold by Respironics' under the name of ComfortLite™ 2;

FIG. 28-2B illustrates an improvement and/or alternative arrangement of Respironics' ComfortLite™ 2 mask according to an embodiment of the present invention;

FIGS. 29-1 to 29-2 illustrate a known mask commercially sold by Fisher & Paykel under the name of Opus™;

FIGS. 29-3 to 29-9 illustrate improvements and/or alternative arrangements of Fisher & Paykel's Opus™ mask according to embodiments of the present invention;

FIGS. 30-1 to 30-2 are perspective views of a known mask commercially sold by Puritan Bennett under the name of Breeze® SleepGear® DreamSeal®;

FIGS. 30-3 to 30-5 illustrate improvements and/or alternative arrangements of Puritan Bennett's Breeze® SleepGear® DreamSeal® mask according to embodiments of the present invention;

FIGS. 31-1 to 31-2 illustrate a known mask commercially sold by InnoMed Technologies under the name of NasalAire™; and FIGS. 31-3 to 31-4 illustrate improvements and/or alternative arrangements of InnoMed Technologies' NasalAire™ mask according to embodiments of the present invention.

DETAILED DESCRIPTION OF ILLUSTRATED EMBODIMENTS

Figure 1:
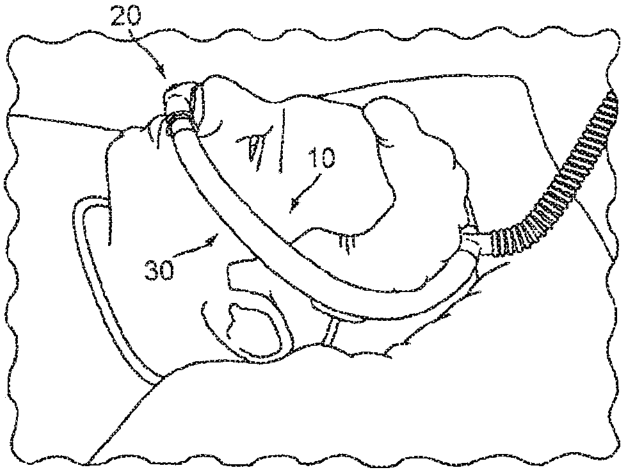
FIGS. 1-1 to 1-16 are various views of a patient interface according to an embodiment of the present invention.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

While the patient interfaces below are described as including under-the-nose interface types, the patient interfaces may be adapted for use with other suitable interface types. That is, the interface type is merely exemplary, and aspects of the present invention may be adapted to include other interface types, e.g., nasal cushions, nasal prongs, full-face masks, mouth masks, etc.

Embodiments of the invention are directed towards moving from uncomfortable, unattractive mask systems to sleek and elegant patient interfaces that are soft, comfortable, lightweight, functional, therapy enhancing, fashionable, easy and intuitive to fit and adjust with little or no adjustment, shape holding, low impact, low profile, continuity of form, individualized or customized, and/or are more appealing and much less objectionable by patients and bed partners alike. The subject patient interfaces are less obstructive, less obtrusive, anatomically coherent and appear like an organic extension of and/or blends with the patient, rather than a bulky, mechanical extension affixed to the patient which can appear to be ungainly or unattractive. This can help the patient and the patient's bed partner more readily relax and/or sleep during treatment. Moreover, the patient interface can improve the overall perception such that the patient is simply wearing a garment like a night cap or bed clothes, etc. rather than being treated for a respiratory illness. This improved perception can help increase the chances that the patient will actually wear the patient interface and comply or better comply with therapy, therefore increasing the likelihood of effective therapy for the user of the device. There is also the possibility that the bed partner will more readily accept and participate in the patient's therapy by encouraging the use of a sleep-enhancing device that is easy to use/adjust, more attractive and/or appealing interface.

Patient Interface

FIGS. 1-1 to 1-16 illustrate a patient interface or mask system 10 according to an embodiment of the present invention. As illustrated, the patient interface 10 includes an interfacing structure 20 (also referred to as a cushioning structure or conforming structure) adapted to provide an effective interface with the patient's face and an air delivery and stabilizing system 30 (also referred to as conduit headgear or inlet conduit arrangement) adapted to deliver breathable gas to the interfacing structure 20 and support the patient interface 10 in a desired position on the patient's head. A cover (also referred to as a sock or covering) may be optionally provided to substantially enclose one or more portions of the interfacing structure 20 and/or the air delivery and stabilizing system 30.

1. Air Delivery and Stabilizing System

1.1 Background and Summary

Known patient interfaces typically include separate headgear and air delivery components that are used to locate and supply breathable gas to a mask or the like. Known headgear typically includes an assembly of elastic (or inelastic) straps, buckles, locks, and/or clips. Known air delivery components typically include 15-22 mm diameter spiral reinforced tubing and swivel connectors. These known arrangements of headgear and air delivery components can be difficult to use for those who are less dexterous and/or unfamiliar with them. These known arrangements of headgear and air delivery components can also be uncomfortable or impractical to lie on.

One aspect of the present invention relates to air delivery and interfacing structure stability provided by one combined system. In the illustrated embodiment, the air delivery and stabilizing system 30 includes four main components, i.e., tubing 40, a rigidizer 50, a back strap 60, and a manifold 70 (e.g., see FIG. 1-6). In use, a supply of air is directed to the manifold 70, e.g., located on or in front of the crown of the patient's head. The supply of air passes from the manifold 70 to the tubing 50, e.g., at least one and preferably two tubes, towards the patient's nose and/or mouth. The tubing 40 has the property of being collapsible to lie on, yet sufficiently rigid in other directions so as to maintain sufficient stability of the interface.

1.2 Tubing

In the illustrated embodiment, the tubing 40 includes two tubes or inlet conduits 42 (also referred to as gas passages or gas conduits) communicated with the interfacing structure 20 to deliver breathable gas to the interfacing structure 20 (e.g., see FIG. 1-6). In one embodiment, a single tube may be used. However, it is preferred that two tubes be used, so that a sufficient supply of breathable gas can still be delivered to the interfacing structure 20 when one of the tubes 42 is fully collapsed, e.g., due to the patient lying on his/her side. That is, when two tubes 42 are used, one or both of the tubes 42 may be open in use. In an alternative embodiment, more than two tubes may be used, e.g., three or more tubes. For example, the tubing may provide a four tube arrangement including two upper tubes along upper sides of the patient's face and two lower tubes along lower sides of the patient's face.

Figures 1, 2:
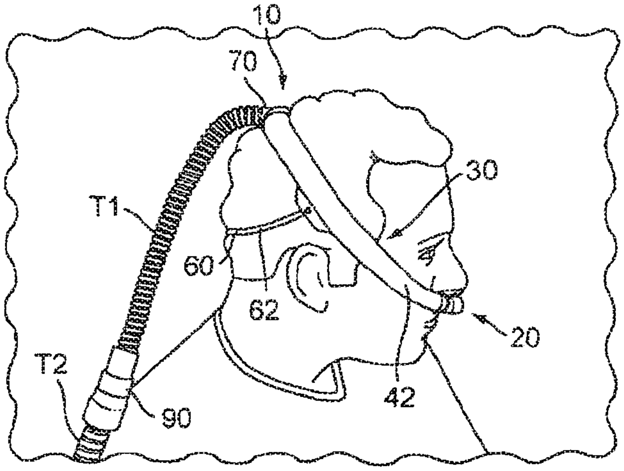

Each tube 42 includes a first end 42.1 adapted to engage a respective end of a frame 22 of the interfacing structure 20 and second end 42.2 adapted to engage a respective end of the manifold 70, as shown in FIGS. 2-1 and 2-2. In an embodiment, the frame 22 and manifold 70 may each include tube portions 25 adapted to engage respective ends of the tubes 42, e.g., via friction fit. In use, the tubes 42 are supplied with pressurized breathable gas from the manifold 70, and the pressurized breathable gas is delivered into opposing ends of the interfacing structure 20.

In the illustrated embodiment, the tube portions 25 of the frame 22 and manifold 70 (e.g., see FIGS. 2-1 and 2-2) each have a stepped configuration so that when the respective tube is attached thereto the joint has a smooth, almost seamless form, e.g., no visible step changes in the overall form. For example, the boundary between each tube portion 25 and the main body of the frame or manifold may have a step height substantially equal to the wall thickness of the respective end 42.1, 42.2 of the tube, and mating the tube portion and respective end of the tube will result in a smooth, almost seamless form at the joint. The smooth joint improves aesthetics and may have a functional benefit in reducing drag forces picked up on pillows, bedclothes, etc. as the patient rolls around in bed in use.

Figures 1, 2, 3:
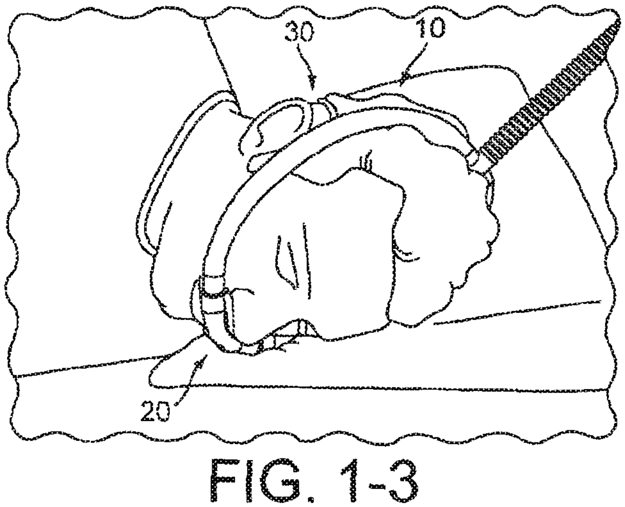

In an alternative embodiment, the two tubes may be independently connected to the supply of gas (e.g., positive airway pressure (PAP) device or flow generator). For example, as schematically shown in FIG. 2-3, one tube 42 may extend from one end of the interfacing structure 20 to a first outlet O1 of the PAP device and the other tube 42 may extend from the other end of the interfacing structure 20 to a second outlet O2 of the PAP device. In such an arrangement, the manifold may be eliminated or the manifold may be incorporated into the PAP device itself.

In another embodiment, the two tubes may be joined together at an outlet of the PAP device (e.g., both tubes adapted to be coupled to a single outlet of the PAP device), and then the tubes bifurcate (i.e., split or divide into separated tubes) towards the interfacing structure. For example, as shown in FIG. 2-4*a*, tube 42(1) may be coupled to a single outlet O of the PAP device and then split into separate tubes 42(2) towards respective ends of the interfacing structure 20. As shown in FIG. 2-4*b*, the tube 42(1) may include an internal dividing wall W to divide the tube into two conduits associated with a respective one of the tubes 42(2).

1.2.1 Collapsible and Thin

Figures 1, 3:
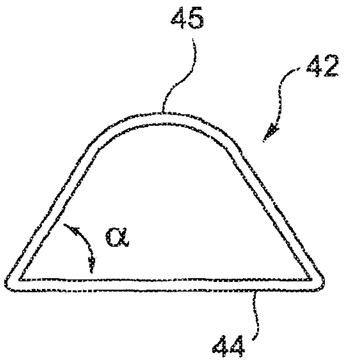
Figures 2A, 3:
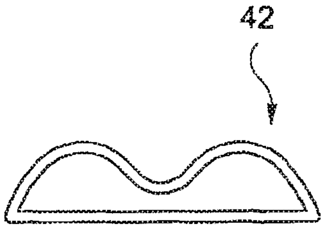
Figures 2B, 3:
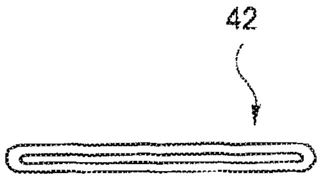
Figure 3:
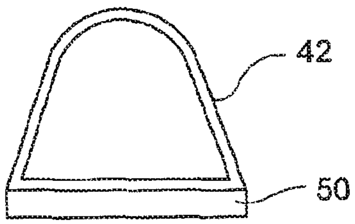
Figures 1, 4:
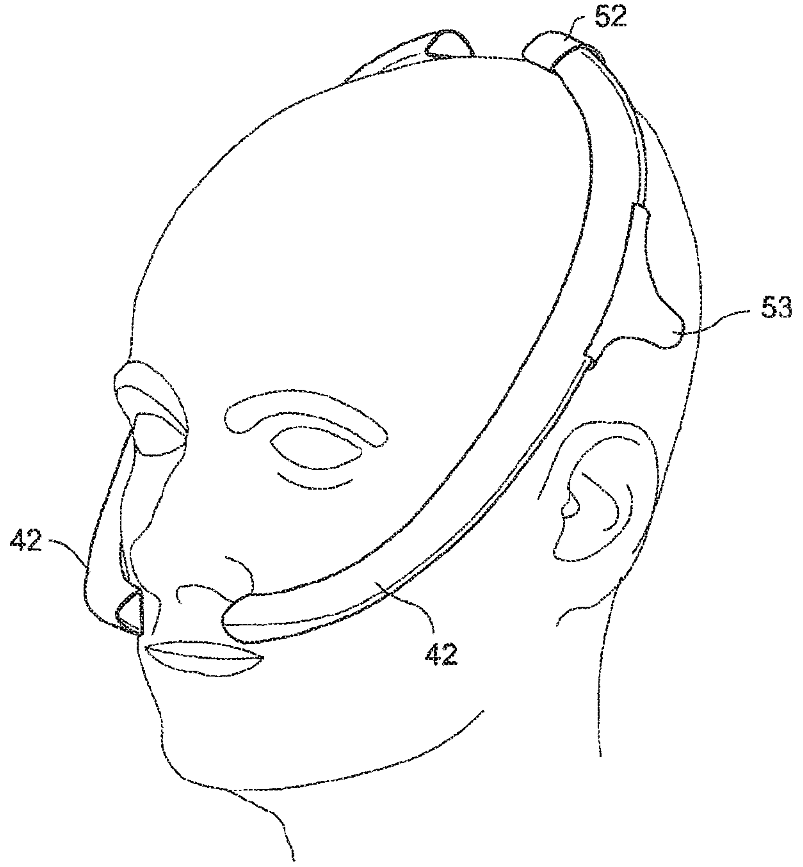
Figures 2, 4:
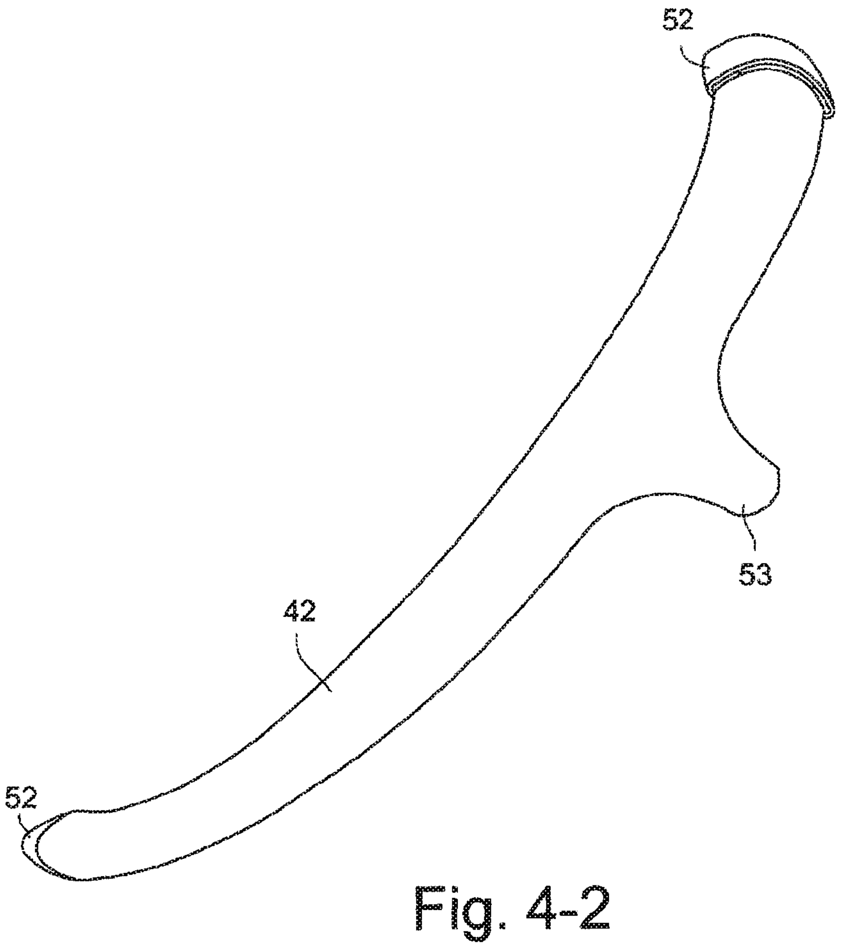
Figures 3, 4:
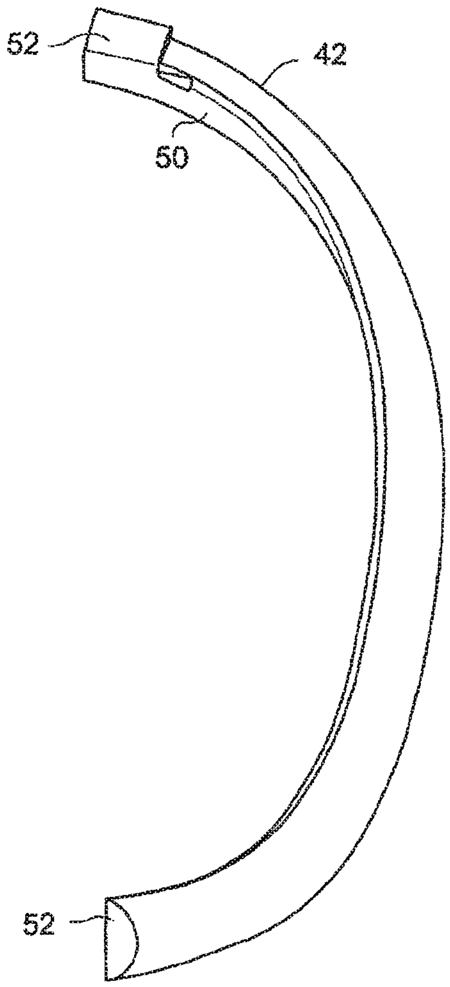
Figure 4:
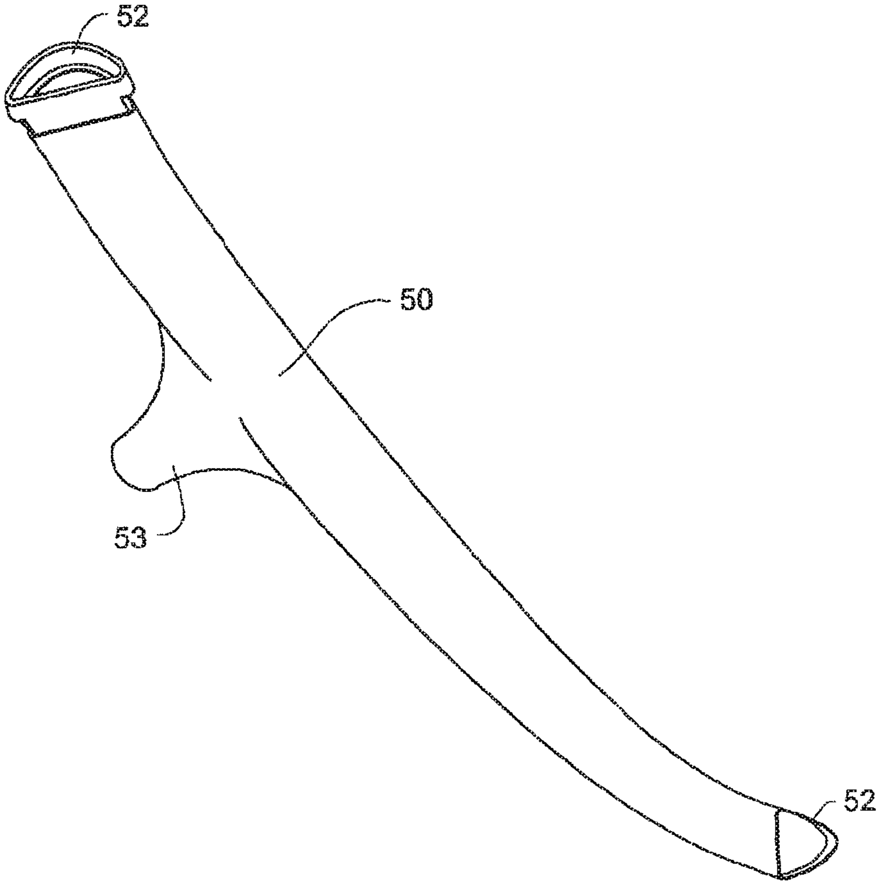
Figures 4, 5:
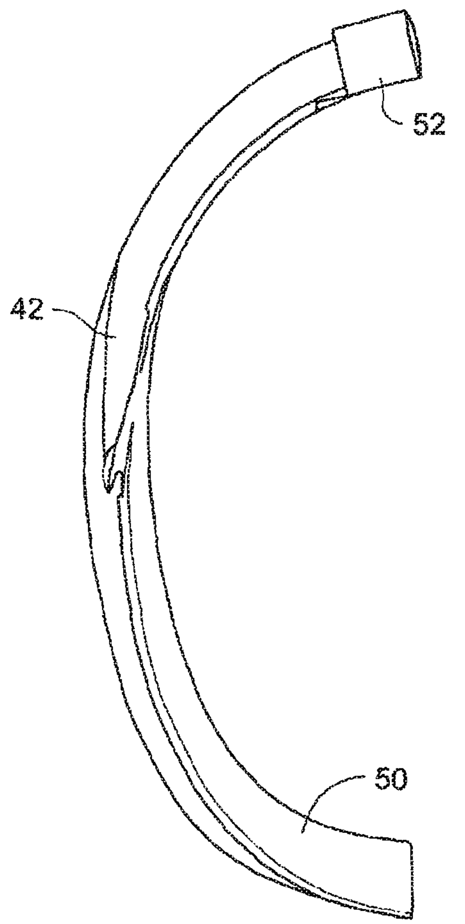
Figures 4, 5, 6:
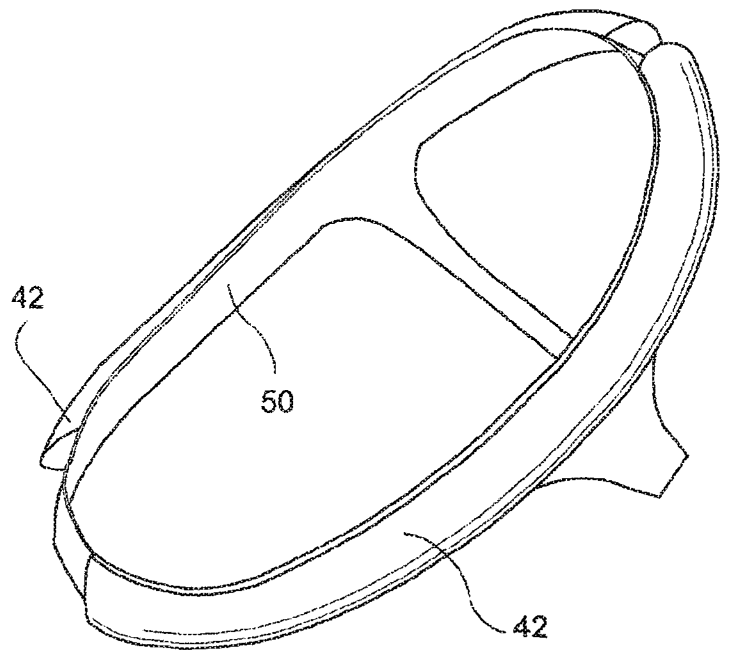
Figures 4, 5, 6, 7:
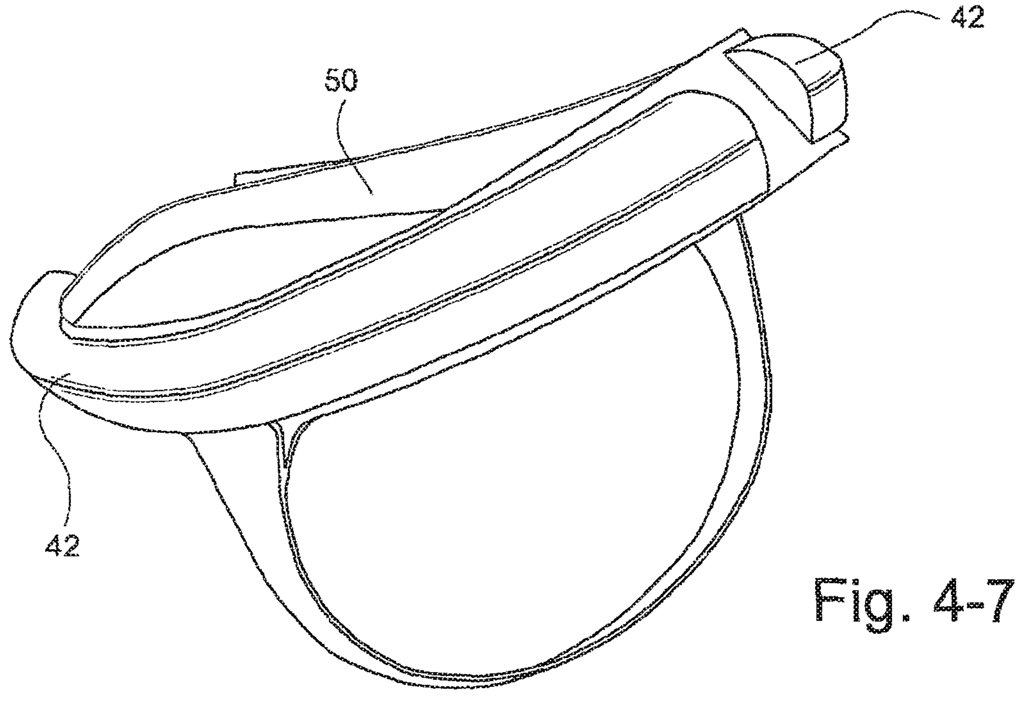
Figures 4, 5, 6, 7, 8:
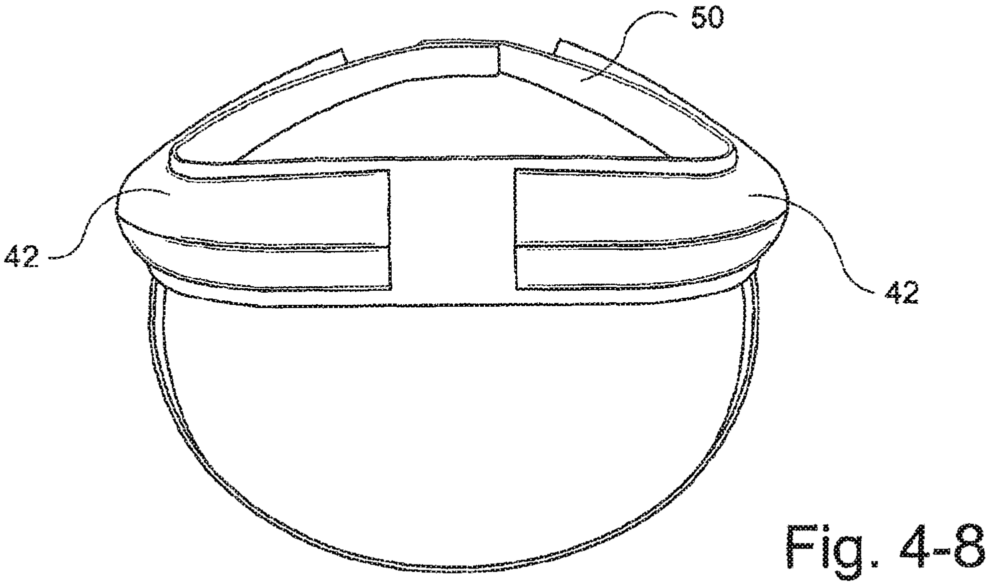
Figures 4, 5, 6, 7, 8, 9:
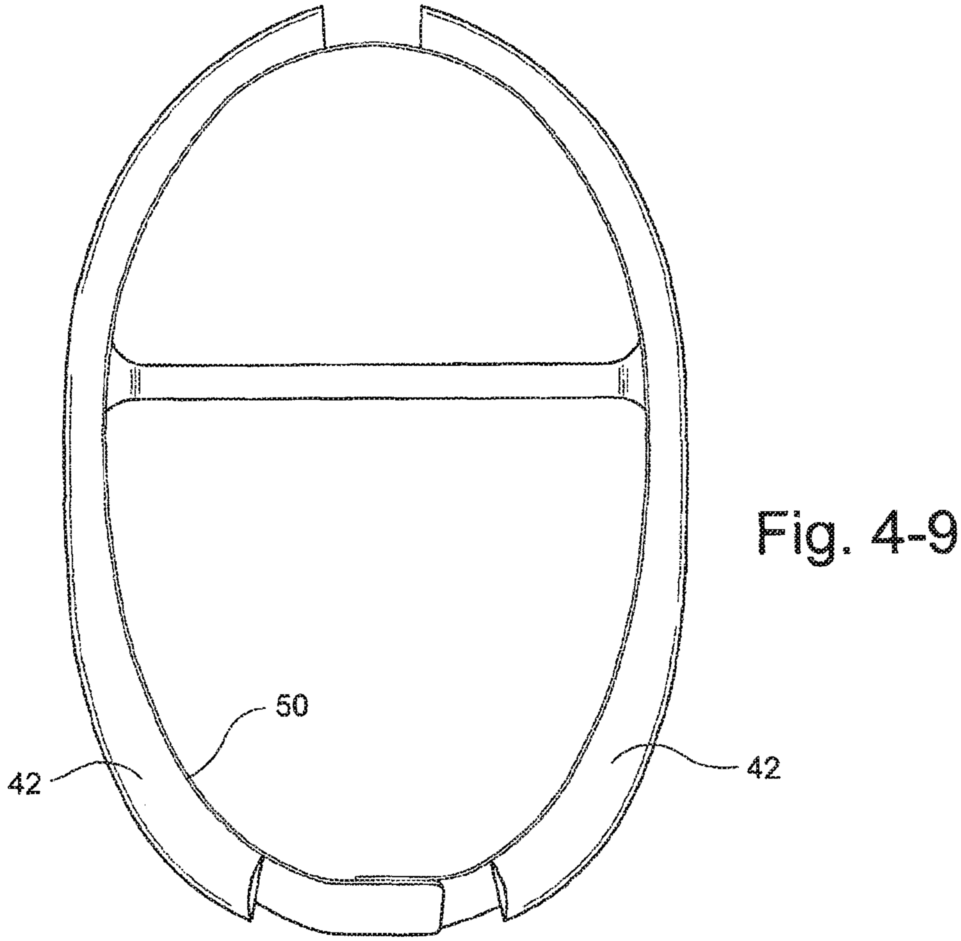
Figures 1, 5:
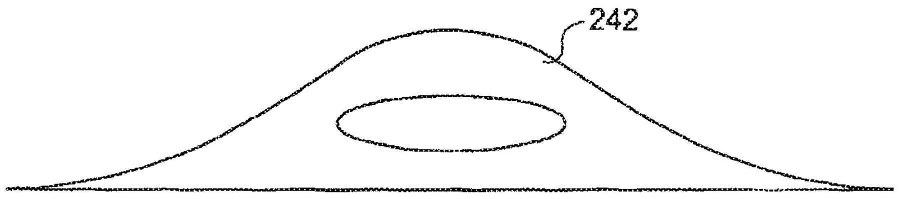
Figures 2, 5:
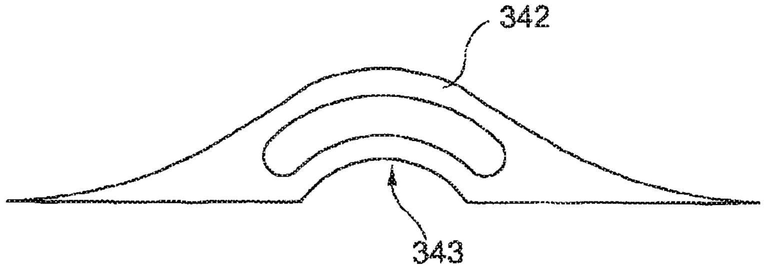
Figures 3, 5:
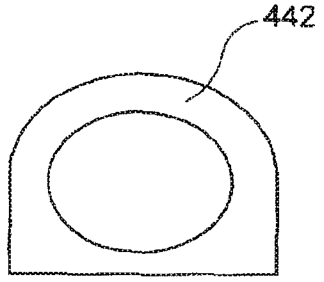
Figures 1, 6:
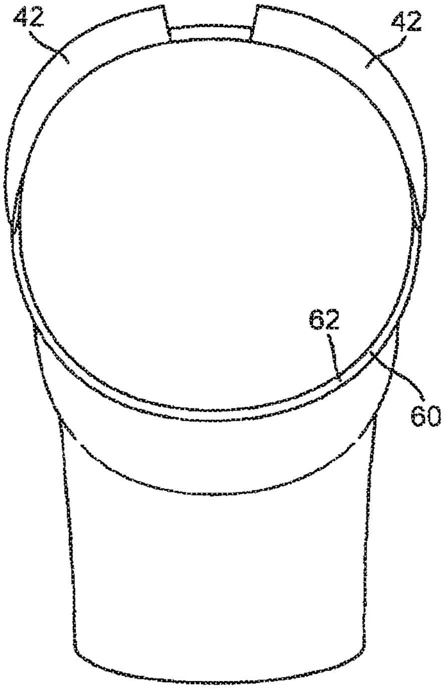
Figures 2, 6:
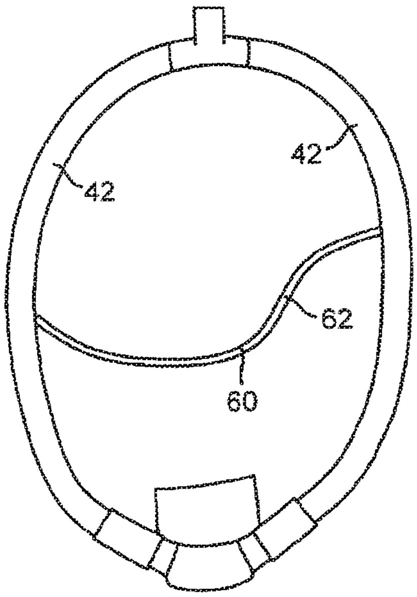
Figures 3, 6:
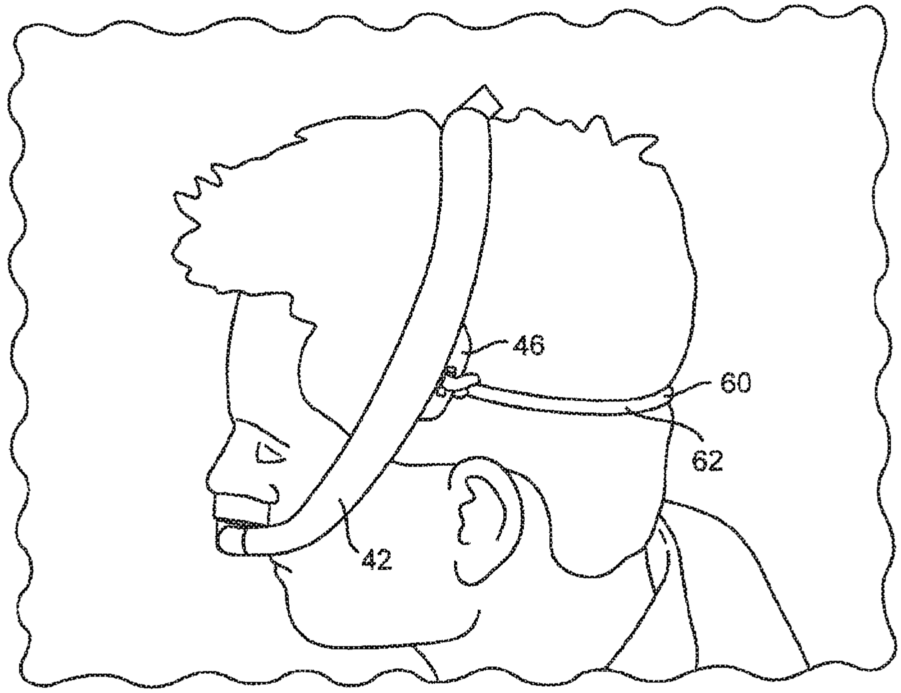
Figures 4, 6:
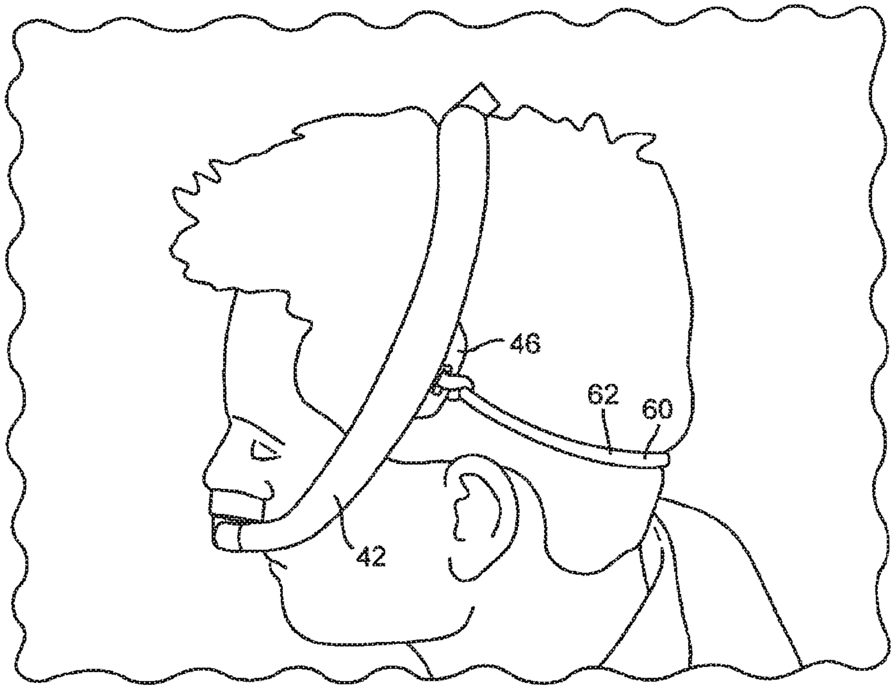
Figures 5, 6:
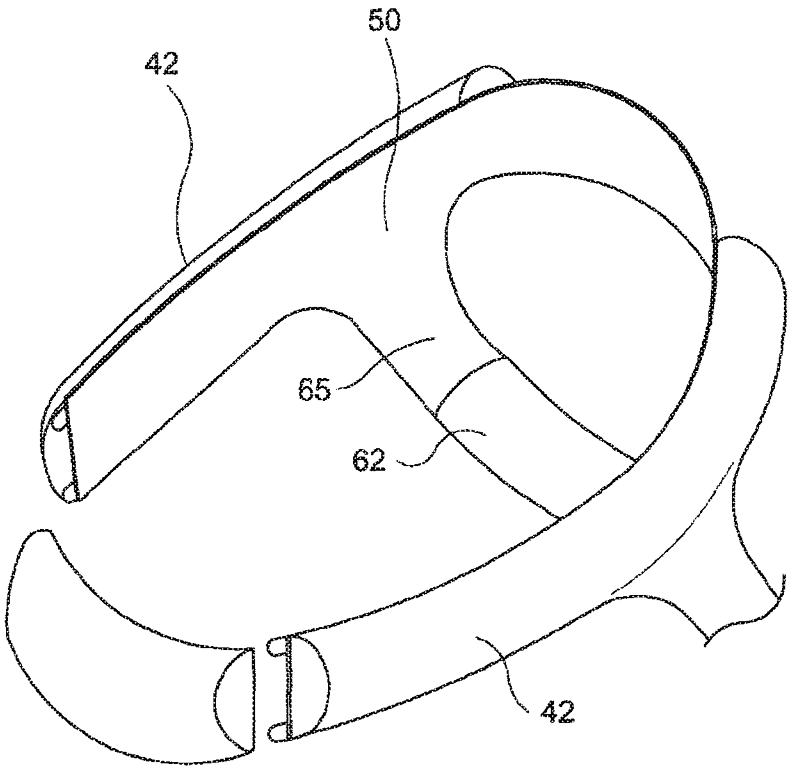
Figures 1, 7:
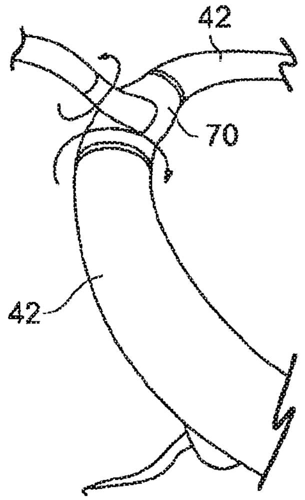
Figures 2, 7:
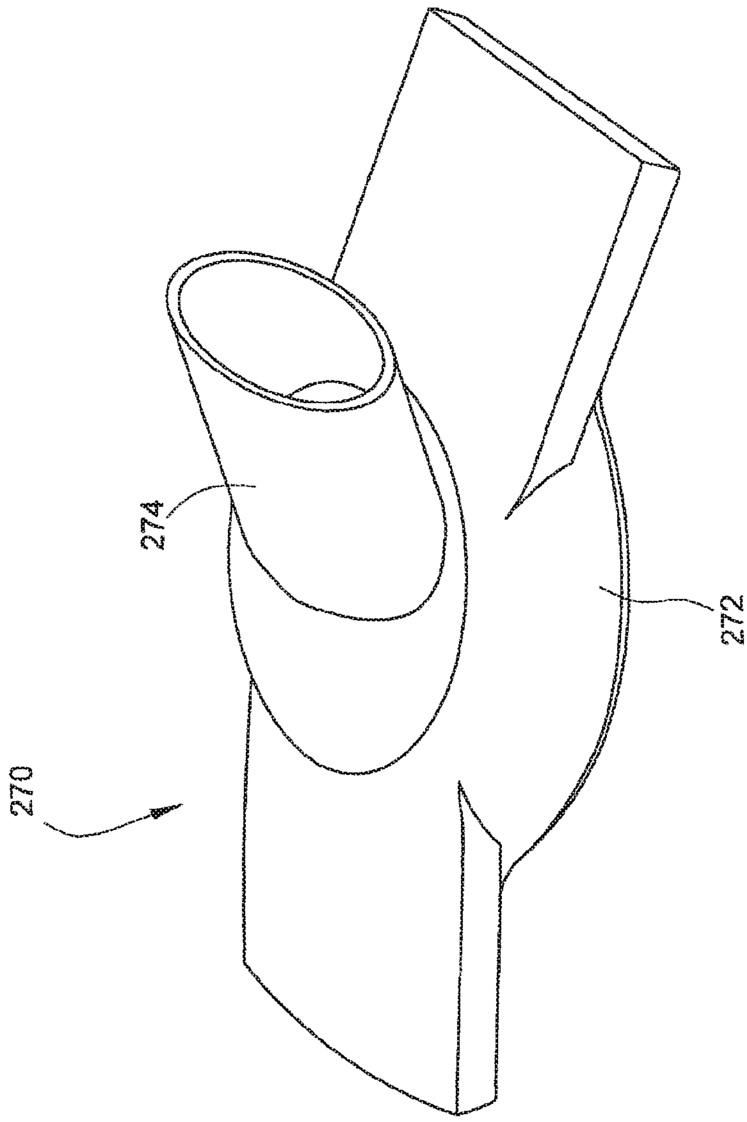

In the illustrated embodiment, each tube 42 is structured such that it may move between two phases, i.e., a first open phase in which the tube 42 allows the passage of air (e.g., see FIG. 3-1) and a second collapsed phase in which the tube 42 is fully collapsed and comfortable to lie on (e.g., see FIG. 3-2*b*). Each tube 42 is structured such that the weight of any patient's head (e.g., adult or infant/child) resting on the tube 42 is sufficient to collapse the tube 42 so the patient may comfortably lie on his/her side (e.g., see FIGS. 1-3, 1-5, and 1-14). However, because the tubes have a consistency similar to that of a tubular balloon inflated under low pressure, each tube 42 may collapse under much less weight than a typical patient's head.

In the open phase, the tube is open or at least partially open so that the tube allows the passage of air, e.g., without undue resistance to flow, sufficient to provide treatment. In the collapsed phase, the tube is collapsed to substantially prevent the passage or conductance of air.

It should be appreciated that each tube need not collapse fully or entirely to provide improved comfort. For example, each tube may be structured such that it may move between a first open phase in which the tube 42 allows the passage of air and a second partially or substantially collapsed phase (e.g., see FIG. 3-2*a*) in which the tube 42 is at least partially or substantially collapsed to restrict and/or at least partially prevent the passage of air.

In a partially or substantially collapsed phase, opposing inner walls of the tube may engage one another at one or more points or surfaces along their length such that conductance through the partially or substantially collapsed tube is minimized or even reduced to negligible amounts. Also, in the partially or substantially collapsed phase, the tube may be open enough to maintain a small degree of conductance of pressurized gas. A small degree of patency can be accomplished using wall thicknesses of a certain gauge (such that opposed walls will not contact or fully contact one another upon application of loads normally encountered during therapy) and/or one or more short anti-crush ribs provided to an inside surface of the tube.

Each tube 42 is sufficiently air tight and structured to deliver air from the top of the patient's head to the patient's nose without discomfort to the patient, e.g., see FIGS. 1-4 and 4-2. Impedance provided by the tube will be appropriate for the blower in use, regardless of whether one or both tubes are in the open phase. That is, the tube 42 provides a wide open cross-section with low impedance when in the open phase and provides a low profile when in the collapsed phase. Moreover, the tubes essentially provide a linear tubing system with a parallel line which can be switched on or off (i.e., open phase or collapsed phase), and the switching of either side of the parallel line off will have negligible effect on the total impedance of the tubing system. That is, the impedance "felt" by the PAP device is substantially independent of whether one or both tubes are open. The tubes may also be adapted to control pressure swings, e.g., deep breath by the patient.

In an embodiment, each tube 42 may have sufficient strength to maintain patency or an open, unblocked state without being pressurized. That is, the tube 42 may be structured such that it only collapses when it is "actively" compressed, otherwise the tube 42 remains in its open phase. In an alternative embodiment, the supply of gas may help to inflate each tube.

Each tube 42 may collapse anywhere along its length and may collapse to a substantially flat configuration so the tube 42 is substantially flat against the patient's face for comfort.

However, the tube 42 may be structured to collapse along selected portions thereof, e.g., middle only, central only, etc.

In another embodiment, at least one tube may have at least one laterally ballooning feature. In such a tube (also referred to as a "bubble" tube), a portion of the tube is collapsed or partially collapsed and a portion of the tube is open, e.g., the tube is "pinched" in the middle to provide a general figure-8 shape. In another embodiment, at least one tube may have a relatively wide, flat shape to provide a stretched-out tube adapted to cover more of the patient's cheeks. For example, FIG. 3-5*a* is a schematic view of a tube 142 in its initial configuration, FIG. 3-5*b* illustrates the tube 142 when end portions 144, 146 are collapsed or partially collapsed into a flat configuration, and FIG. 3-5*c* illustrates the tube 142 when a middle portion 145 is collapsed or partially collapsed into a flat configuration. In yet another variant, the tube could be preformed to have one or more relatively flatter portions 144, 145, 146 and one or more rounded conduit portions 147 as shown in FIGS. 3-5*b* and 3-5*c*.

It should be appreciated that the patient interface preferably does not collapse at the manifold and in an area at the front of the patient's nose, e.g., at the interfacing structure 20. That is, the manifold may be constructed of a substantially rigid material and the interfacing structure 20 may include a substantially rigid frame (e.g., frame 22 shown in FIG. 2-1) that prevents collapse in use. This arrangement ensures that an air flow path is provided from at least one of the tubes 42 to the patient's nose.

In an embodiment, each tube 42 may be molded from a silicone material, e.g., liquid silicone rubber (LSR), having a thin wall thickness of about 0.5 mm. However, each tube may have a wall thickness in the range of about 0.3 mm to 5 mm. The tubes may have varying colors, and the tubes may be formed in a mold with a polished surface to provide the tubes with smooth exterior surfaces. However, each tube may be constructed from other soft, flexible materials, e.g., thermoplastic elastomers (e.g., Santoprene), foam, foam laminate, closed cell impermeable foam, dipped and knitted textiles including cotton or silk. In an embodiment, each tube may be constructed from two sheets of material, e.g., laminate, that are attached to one another, e.g., heat welded, to form a tube. In an alternative embodiment, each tube may be constructed of a plurality of elements, e.g., relatively rigid elements, arranged in a concertina configuration so as to allow the tube to move between open and collapsed phases. In an embodiment, each tube may have a concertina configuration that allows each tube to collapse from one volume to another smaller volume. For example, FIG. 3-6*a* illustrates a cross-section of a concertina-type tube 542 in a first phase that provides a first volume, and FIG. 3-6*b* illustrates the concertina-type tube 542 in a second phase that provides a second volume smaller than the first volume. In this example, one side 543 of the tube 542 is placed adjacent the patient's face.

The tube arrangement according to an embodiment of the present invention contrasts with prior arrangements such as InnoMed's Nasal Aire and other forms of nasal cannula that are designed to resist crushing (i.e., breathable gas is able to be delivered through both tubes all the time) and thus present an uncomfortable structure for a patient to lie on. Furthermore, unlike prior arrangements, the tube arrangements according to embodiments of the present invention are capable of providing a sufficient supply of pressurized gas when one of the pair of tubes is fully collapsed. Because of the particular arrangement of the pair of tubes in accordance with an embodiment of the present invention, both tubes are not crushed at one time during normal use. This allows the patient to assume any sleeping position (e.g., total freedom of sleeping position) without compromising the supply of pressurized gas (e.g., see FIGS. 1-1, 1-3, 1-5, 1-7, 1-8, and 1-14). That is, the tube arrangement according to an embodiment of the present invention provides two or more tubes that cooperate to maintain sufficient conductance of gas (e.g., sufficient flow of gas at therapeutic pressure) and comfort to the patient without introducing unnecessarily high impedance. For example, when a two tube arrangement is provided, each tube has sufficiently low impedance (e.g., large enough hydraulic diameter) which facilitates the adequate supply of gas when one of the tubes is occluded, e.g., lain on.

1.2.2 Cross-Sectional Profile

In the illustrated embodiment, each tube 42 has a non-cylindrical cross-sectional shape which provides a blending contour to blend with the patient's face (e.g., see FIGS. 3-1 and 4-1 to 4-5). That is, each tube 42 provides a blending contour or free form with few or no sharp edges or straight lines. The blending contour is smooth, streamlined, sleek, and blends or tapers the tubes 42 with or into the contours of the patient's head, e.g., anatomically coherent, less obtrusive and more aesthetically appealing. In addition, the blending contour has no sharp edges that could cause discomfort, e.g., skin irritations or abrasions.

The contour or cross-section of each tube 42 may vary along its length, e.g., vary non-uniformly with location around the patient's head. In an embodiment, each tube may have a cross-sectional area that changes along its length with an approximately constant hydraulic diameter. For example, each tube 42 may provide flatter regions in certain areas, e.g., where the patient rests on the tube during sleep. In this way, the tubes can be said to be an organic extension of the patient's facial contours.

FIG. 3-1 illustrates an exemplary cross-section of a tube 42. As illustrated, the tube 42 has a generally D-shaped cross-section and includes an internal or inwardly facing surface 44 and an external or outwardly facing surface 45.

The internal surface 44 is relatively flat and adapted to sit substantially flush against the patient's face in use. The internal surface 44 may have a tapered configuration form an inner edge to an outer edge to provide a comfortable fit for a wide range of patients. The internal surface 44 provides a relatively large surface area which results in a more even load distribution. This arrangement is less likely to create pressure points in use. Also, the internal surface 44 may have grip-like material to help stabilize the patient interface on the patient's face. As described below, a rigidizing element may be provided to the internal surface to add rigidity to the tube.

The external surface 45 has a smooth contour that blends with the patient's face. That is, the external surface 45 has a profile or organic form with edges that blend into the patient's face, e.g., in a tangential manner, to prevent any edges from catching on bedclothes, pillows, etc., during sleep (e.g., when the patient rolls over).

Figures 1, 2, 3, 4:
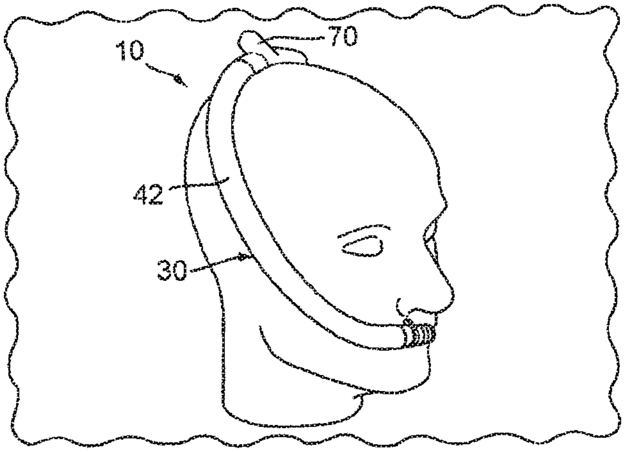
Figures 1, 2:
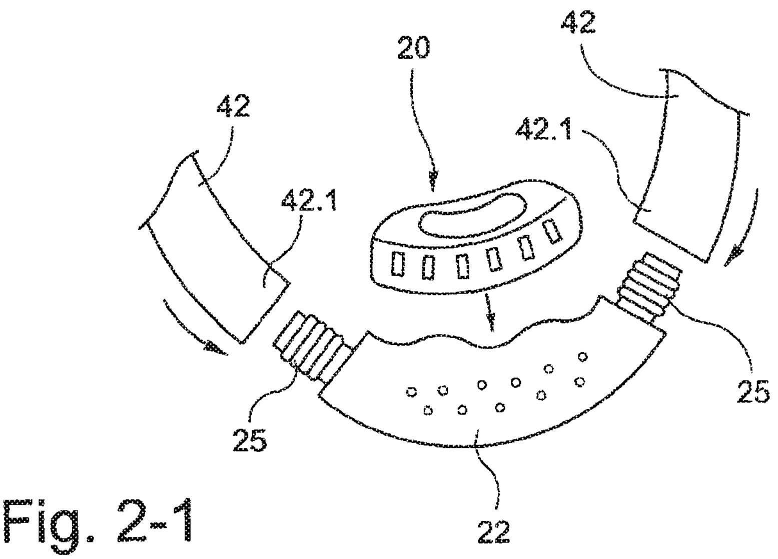
Figure 2:
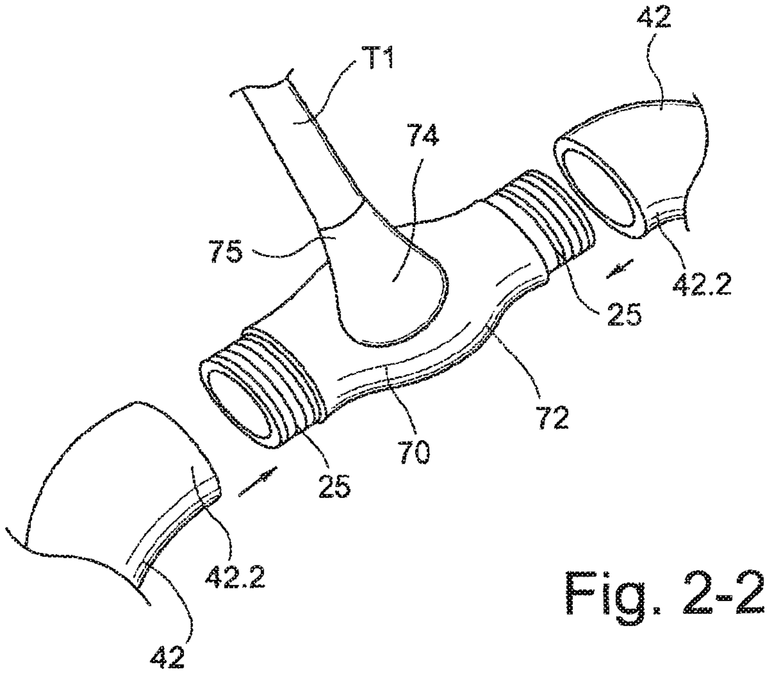
Figures 2, 3:
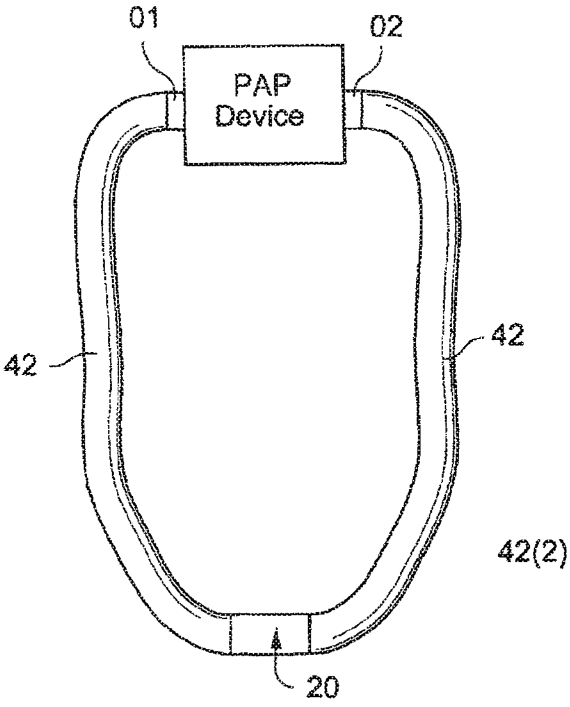
Figures 2, 3, 4, 4A:
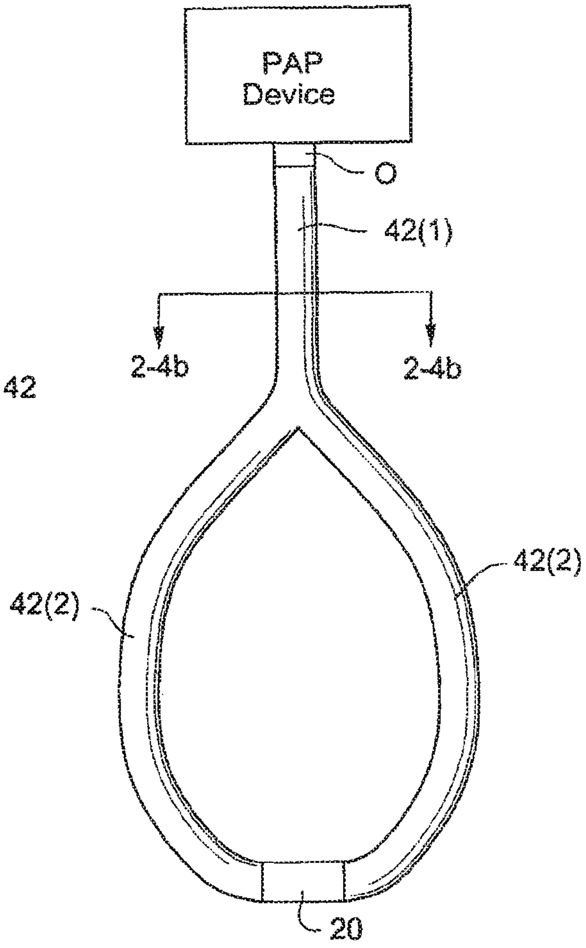
Figures 2, 3, 4, 4B:
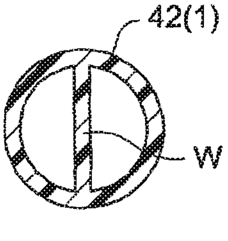

As noted above, the generally D-shaped cross-section may vary along its length, e.g., tall, thin D-shaped cross-section near the patient's nose and wide, shallow D-shaped cross-section along cheek and near the top of the patient's head. For example, FIGS. 3-4 and 3-4*a* to 3-4*f* illustrate various cross-sections of a tube 42 along its length according to an embodiment of the present invention. Specifically, FIG. 3-4*a* illustrates a cross-section of the tube 42 at the end adapted to engage the manifold 70, FIG. 3-4*b* illustrates a cross-section of the tube 42 that is 20% of the tube length from the manifold end, FIG. 3-4*c* illustrates a cross-section of the tube 42 that is 40% of the tube length from the manifold end, FIG. 3-4*d* illustrates a cross-section of the tube 42 that is 60% of the tube length from the manifold end, FIG. 3-4*e* illustrates a cross-section of the tube 42 that is 80% of the tube length from the manifold end, and FIG. 3-4*f* illustrates a cross-section of the tube 42 at the end adapted to engage the interfacing structure 20. As illustrated, the D-shape of the cross-section varies along its length. Specifically, each cross-section has a width w and a height h, and the width and height of the various cross-sections varies along the length of the tube, e.g., a relatively long width and short height at the manifold end and a relatively short width and tall height at the interfacing structure end. Also, all of the cross-sections have a very similar or common hydraulic diameter, e.g., about 10-15 mm or about 13 mm. The shape may be configured based on aesthetic and/or impedance requirements. In addition, the shape may be configured to provide low profile, comfort, and/or stabilization.

However, the tubes 42 may have other suitable cross-sectional shapes, e.g., trapezoidal, semi-circular, cylindrical, oval, elliptical, flatter section, etc. Also, the tubes may have a flat configuration with anti-crush ribs. This arrangement is disclosed in U.S. patent Ser. No. 10/385,701, the entirety of which is incorporated herein by reference.

Figures 1, 2, 3, 4, 5:
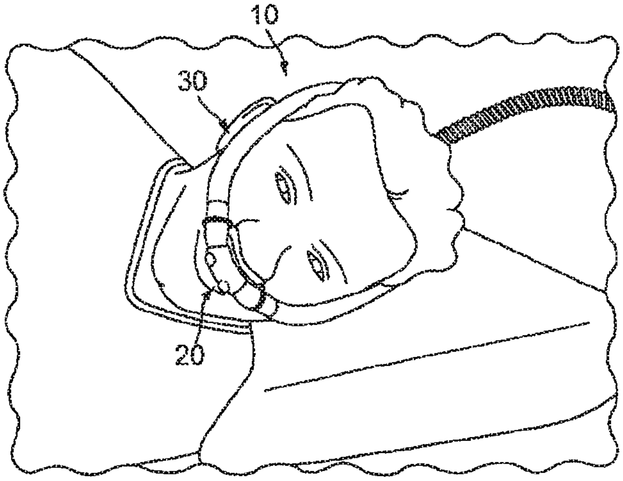

FIGS. 5-1 to 5-3 illustrate alternative cross-sections of the tube. FIG. 5-1 illustrates a tube 242 that more gradually blends into the patient's face. As shown in FIG. 5-2, the tube 342 may provide a gap 343 in the internal surface, e.g., to allow air flow or breathing. While less preferred than the cross-sections shown in FIGS. 3-1, 5-1, and 5-2, the cross-section of tube 442 in FIG. 5-3 would be more preferable than a normal cylindrical tube for its blending contour.

It is noted that a D-shaped or generally trapezoidal-shaped tube does not produce as pronounced pressure regions along bottom edges thereof as a semi-circular-shaped tube would. The reason for this is that the side walls of the D-shaped or generally trapezoidal-shaped tube meet the base at an acute angle $\alpha$, i.e., less than 90°, as shown in FIG. 3-1. The side walls of the semi-circular-shaped tube meet the base at approximately 90°, and if the tube were pressed against the patient's face, the region where the side walls meet the base would be quite rigid and may lead to pressure points. In addition, a semi-circular-shaped tube may provide a discontinuity of form when viewed in relation to the patient's facial contours.

1.3 Air Delivery Rigidizing Element

In the illustrated embodiment, a rigidizing element or rigidizer 50 is provided to each tube 42 to add rigidity to the tube 42 (e.g., see FIGS. 1-6, 3-3, and 4-3 to 4-5). A rigidizing element 50 in accordance with an embodiment of the present invention is preferably thin and conforming when a patient lies upon it, yet has sufficient stiffness to resist out-of-plane bending. That is, the rigidizing element 50 is structured to allow bending in some planes and resist bending in other planes, e.g., allow bending towards and away from the patient's face. The rigidizing element 50 also makes the tube 42 inextensible or not stretchy so that the tube 42 is strong in tension and maintains its size.

In an embodiment, the rigidizing element 50 may provide structural integrity or self-holding form to the patient interface 10 so that the patient interface 10 can hold its shape and not fall into a heap, e.g., shape memory, whether the patient interface 10 is on or off the patient's head. The shape holding arrangement maintains the tubes in a desired position and may facilitate donning of the patient interface in use.

The rigidizing element 50 may be provided to an interior and/or exterior portion of the tube 42. For example, FIGS. 1-6 and 4-1 to 4-5 illustrate a rigidizing element 50 provided to an exterior portion of the tube 42 (e.g., along internal surface 44) that is adapted to engage the patient's head in use. As illustrated, the rigidizing element 50 may include tubular end portions 52 to facilitate connection of the tubes 42 to the manifold 70 and/or interfacing structure 20. The tube/rigidizer sub-assembly may also provide an extension 53 for supporting the back strap 60, e.g., see FIGS. 4-1, 4-2, and 4-4.

FIGS. 4-6 to 4-9 illustrate another embodiment of a rigidizing element 50 with the tubes 42 attached thereto. As illustrated, the rigidizing element 50 may be structured to extend under the interfacing structure, the manifold, and/or the back strap in use.

The rigidizing element 50 may have a varying thickness along its length, e.g., to vary the stiffness or rigidity of the tube 42 along its length. For example, the rigidizing element 50 may be thinner at the patient's cheeks and thicker at the top of the patient's head. In an embodiment, the rigidizing element 50 and/or tube 42 may be structured to accommodate a respective arm of patient eyeglasses.

In an embodiment, the rigidizing element 50 may be cut and/or formed from thin plastic sheet, e.g., 0.5 mm high impact polystyrene (or EPP foam). However, other suitable materials are possible, e.g., textile, nylon, polypropylene, high duro silicones, elastomers, etc., and the rigidizing element may have other suitable wall thicknesses, e.g., in the range of about 0.3 mm to 5 mm.

In an embodiment, each tubing/rigidizer sub-assembly may have a total thickness (e.g., thickness of collapsed tubing/rigidizer) of about 1.5 mm, e.g., 0.5 mm rigidizing element, 0.5 mm tube wall on one side, and 0.5 mm tube wall on opposite side. However, the total thickness may be more or less depending on application, e.g., 1-10 mm, 1-5 mm, less than 5 mm, about 10 mm, about 5 mm, and/or about 3 mm. It should be appreciated that the wall thickness of the tube and/or rigidizer may be adjusted for comfort and/or robustness, e.g., wall thicknesses thickened. The wall thickness of the tube and rigidizer is preferably as thin as possible, but may be thickened so as to be more shape-holding, self-supporting, and/or robust.

In an embodiment, a separate rigidizing element 50 may be employed. For example, see International Patent Application PCT/AU03/00458 (published as WO 03/090827), which is incorporated herein by reference in its entirety.

In an embodiment, a separate rigidizing element 50 may be formed, and then attached to the respective tube 42, e.g., by an adhesive or by a mechanical interlocking arrangement.

In another embodiment, the rigidizing element 50 may be co-molded or co-extruded with the respective tube 42. That is, the tube 42 and rigidizing element 50 may form an integral, one-piece structure.

In another embodiment, the rigidizing element may made of polypropylene and the tube may be made of a thermoplastic elastomer of a grade suitable for welding/co-molding to the polypropylene rigidizing element.

In an alternative embodiment, the rigidizing element may include multiple components that are adjustable or movable with respect to one another, e.g., slidable, to adjust the position and/or rigidity provided by the rigidizing element.

1.4 Back Strap

In the illustrated embodiment, a back strap 60 is provided to the tubing/rigidizer sub-assembly (e.g., see FIGS. 1-2, 1-6, and 6-1 to 6-4). The back strap 60 is adapted to be positioned generally on the patient's occipital bone in use to facilitate stabilizing the patient interface on the patient's head. The back strap 60 may also assist in providing an interfacing force against the interfacing surface, e.g., under the patient's nose.

Figures 1, 2, 3, 4, 5, 6:
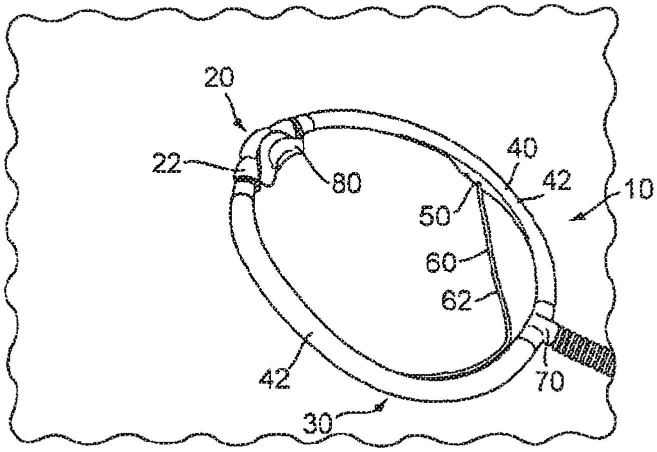

In an embodiment, the back strap 60 (also referred to as an elasto-stabilizer or elastic stabilizer) includes a length of elastic strap 62. The two ends of the elastic strap 62 are attached to the tubing/rigidizer sub-assembly, e.g., via eyes 46 provided to respective tubes 42 as shown in FIGS. 6-3 and 6-4.

In use, the back strap 60 may sit in a range of positions on the patient's head and still effect an adequate interfacing force in both magnitude and direction. This arrangement allows some variation in fit size, and aids the patient's comfort in moving the back strap 60 to the most comfortable of locations, e.g., higher or lower positions at the back of the patient's head as shown in FIGS. 6-3 and 6-4. The elasticity of the back strap allows the patient interface to fit a broad range of the population, e.g., 80-90% of the population.

The back strap 60 is primarily used to maintain the patient interface on the patient's head, rather than provide an interfacing force. That is, the interfacing structure 20 does not require high tension for interface (as described below), and therefore the back strap 60 does not need to be relied on for tension for an interfacing force.

In an embodiment, the strap 62 may have selected elastic properties, e.g., from zero extension to a relatively small extension, the tension rises and plateaus. The tension may remain generally similar over a relatively large further extension until it reaches the fully extended elastic limit.

A range of alternative straps 62 may be provided with the patient interface for use with different size heads, e.g., different elasticity, thickness, length, etc.

The back strap 60 may have other suitable configurations with selectively adjustable lengths, e.g., baseball cap adjuster (e.g., see FIG. 10-4), hook and loop material, ladder lock, adjustable elastic. In an embodiment, as shown in FIG. 6-5, the back strap may include side rigid portions 65 (e.g., integrally formed with the rigidizing element 50) and an elastic strap 62 joining the free ends of the rigid portions 65.

In yet another alternative embodiment, the back strap may be constructed of the same material as the tubes, e.g., tube and back strap co-molded to a rigidizing element. In an embodiment, the two sides of the patient interface may be molded at once, e.g., two rigidizing elements held together by the back strap which blends into both rigidizing elements. To complete the patient interface, the tubes would be engaged with a manifold and an interfacing structure.

In an alternative embodiment, the back strap may be replaced by ear anchors adapted to engage the patient's ears and support the patient interface on the patient's face.

In another embodiment, the back strap may only extend across part of the occiput (e.g., the back strap comprises resilient fingers that extend inwards from each side and press against the occiput to provide a rearwardly directed force).

1.5 Manifold

The manifold 70 is provided to interconnect the two tubes 42 and direct air flowing from a suitable source, e.g., a blower, into the two tubes 42 (e.g., see FIGS. 1-2, 1-4, and 1-6). As best shown in FIG. 2-2, the manifold 70 is generally T-shaped and includes a base portion 72 and an inlet tube portion 74 that is coupled (e.g., movably coupled via a ball joint, hinge, general flexibility, etc.) to the base portion 72. In an embodiment, the manifold 70 is designed to be sleek and to have a form continuous with the shape of the patient's head and the patient interface, e.g., unobtrusive. For example, the manifold may have a relatively flat form or low profile to minimize the height or angle of air delivery.

The manifold provides a transition from the air delivery tubing leading from the PAP device to the inlet tubing leading to the interfacing structure. Thus, the manifold transitions non-crushable tubing of the air delivery tubing to crushable tubing of the inlet tubing. Also, the manifold transitions tubing profile, e.g., relatively round tubing of the air delivery tubing to relatively flat tubing of the inlet tubing.

The base portion 72 includes opposing tube portions 25 adapted to engage respective tubes 42, e.g., with a friction fit. The cross-sectional shape of the tube portions 25 may be non-circular and correspond to the cross-sectional shape of the tubes 42. The base portion 72 may be curved to match the shape of the patient's head and is otherwise suitably contoured such that it can rest and sit substantially flush with the top of the patient's head in use. However, the base portion may include other suitable connections or air holding bonds with the tubes.

The inlet tube portion 74 may be fixed to the base portion 72, or the inlet tube portion 74 may be movably coupled, e.g., swivel, to the base portion 72 so that the inlet tube portion 74 may be angled with respect to the base portion 72 in use. The swivel arrangement may provide 360° rotation or any other suitable angle range. The inlet tube portion 74 has an inlet tube 75, e.g., 15 mm diameter, adapted to connect to an air delivery tube T1 (e.g., see FIGS. 1-2, 1-7, and 2-2) connected to a suitable air delivery source, e.g., a blower.

In an embodiment, the manifold 70 and tubes 42 may be integrally formed as a one-piece structure, e.g., to reduce the number of parts.

In an embodiment, the manifold may be structured to control dynamic flow and/or reduce noise.

1.5.1 Location

The manifold 70 is positioned in a region on the top of the patient's head that does not interfere with a pillow when the patient interface is used (e.g., see FIGS. 1-2, 1-4, and 1-7). That is, the manifold 70 directs the air delivery tube T1 out of the bed so it does not interfere with the pillow and does not pass along the patient's body. In an embodiment, the manifold 70 may be positioned on the crown of the patient's head, e.g., generally in the plane of the patient's ears. For example, the manifold 70 may be positioned generally in the region of the Bregma in use.

An advantage of this approach is that tube drag does not directly affect the interface in use. For example, by placing the manifold 70 near the crown of the head, it is positioned furthest from the interfacing structure 20, so if the air delivery tube is yanked or moved, the movement has less affect on the interface, e.g., by changing the load distribution in the interfacing region, and therefore increases the stability of the interface. Also, the positioning of the manifold enables the tube connection to the mask to be less obtrusive by avoiding the patient's field of vision.

The manifold may provide multiple functions or utilities. For example, the manifold may provide a point of reference or anchor point for the patient interface. That is, the manifold may act as a head support or stabilizer, an air delivery conduit, and an inlet tubing attachment point. In addition, the manifold resists tube drag as described above.

1.5.2 Swiveling Features

In an embodiment, the manifold 70 is generally T-shaped and defines two generally perpendicular axes, i.e., the base portion 72 along a first axis and the inlet tube portion 74 along a second axis that is perpendicular to the first axis.

Figures 1, 2, 3, 4, 5, 6, 7:
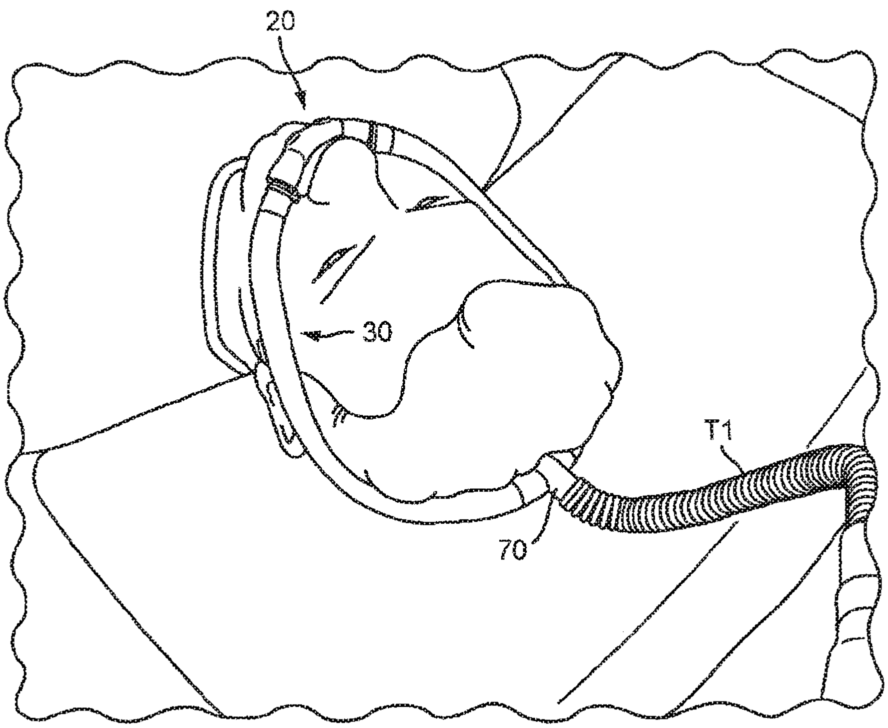

The manifold 70 may incorporate swiveling features that allow the manifold 70 to swivel or hinge about one or both axes (e.g., see FIG. 7-1). FIG. 7-2 illustrates a manifold 270 having a ball and socket arrangement that allows the inlet tube portion 274 to rotate or swivel with respect to the base portion 272. The base portion and/or inlet tube portion may incorporate one or more stops to limit swiveling in use. The swiveling feature allows the air delivery tube to be suitably angled with respect to the patient interface, e.g., so the air delivery tube does not extend into the wall or bed headboard.

1.5.3 Offset Attachment

In the illustrated embodiment, the manifold 70 is positioned at the top of the patient's head, e.g., see FIGS. 1-2, 1-4, and 1-7. In alternative embodiments, the manifold 70 may be offset from the top of the patient's head, e.g., positioned at a side of the patient's head. This offset arrangement may provide more comfort as there may be less drag (particularly if the patient sleeps on the opposite side of their head). This arrangement may also facilitate an alternative tube attachment and routing, e.g., a snorkel-like side tube routing.

The length of the tubes 42 may be selected to adjust the manifold 70 to a position where the patient can view and more easily manipulate air delivery tube connections.

In an embodiment, the manifold 70 may have an adjustable connection, e.g., sliding or translating coupling, so that two or more positions of the manifold (e.g., along a back-strap of the headgear) may be selected.

1.6 Location on Head

In the illustrated embodiment, the air delivery and stabilizing system 30 includes two alternative, complementary air delivery pathways located on different parts of the patient's head (e.g., preferably either side of the patient's face) so that a patient may roll through almost a complete circle without occluding both pathways.

Figures 1, 2, 3, 4, 5, 6, 7, 8:
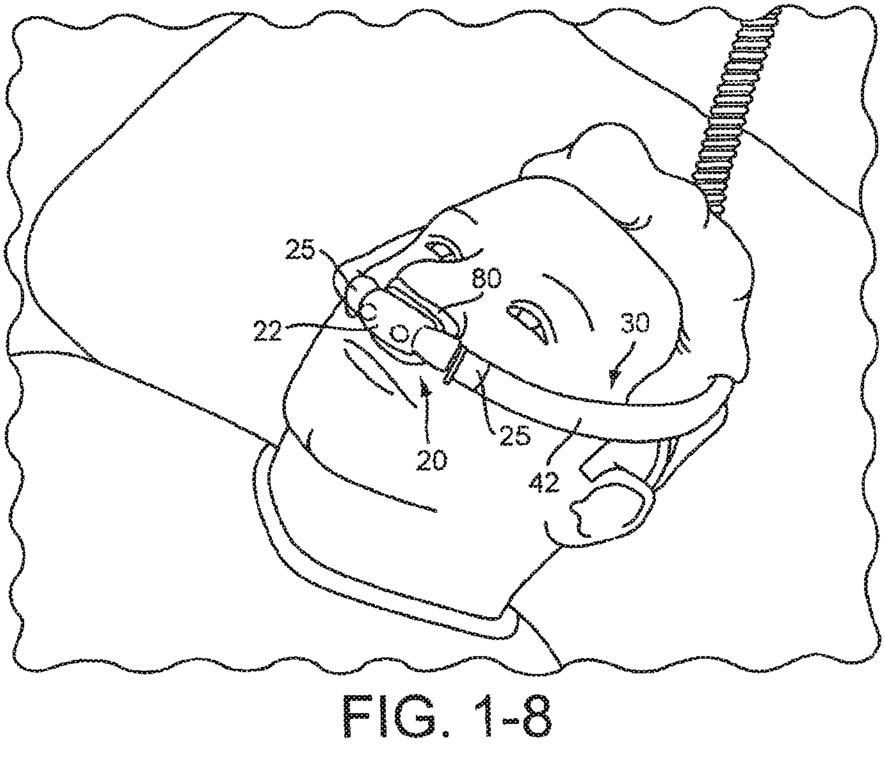

In an embodiment, the air delivery and stabilizing system 30 has a generally oval or ring-shaped configuration (e.g., see FIGS. 8-1 to 8-4). In use, each tube 42 of the system has one end that passes generally over the crown of the patient's head and the other end passes under the patient's nose, as shown in FIG. 8-5. In this way, the air delivery and stabilizing system 30 is outside the patient's eyes and does not interfere with the patient's vision or field of view and may be simply donned as one does a cap. In an alternative embodiment, the ring-shaped configuration may incorporate a divider to split the ring shape, e.g., ring shape divided at manifold or under nose.

Each tube 42 of the air delivery and stabilizing system 30 passes along a respective side of the patient's face between the patient's eye and ear to provide an arrangement that does not obstruct the patient's vision. That is, each tube 42 is sufficiently spaced from the ear to reduce noise and sufficiently spaced from the eye so it does not affect the field of view. In an embodiment, the tube 42 passes in a direct line from the patient's nose to the crown of the patient's head. However, the tube 42 is not limited to any specific path.

For example, as shown in FIG. 8-6, each tube 42 may pass within a region defined between a first boundary curve P1 and a second boundary curve P2. The first and second boundary curves P1, P1 are represented by two identical curves, one curve rotated with respect to the other curve. The curves are positioned so that they are both on the extremes of the region. As illustrated, the first boundary curve P1 is adjacent to the eye at a position where it would impinge upon the patient's field of view, and the second boundary curve P2 is adjacent the patient's ear. The second boundary curve P2 may be described as a position adjacent a top forward location on the patient's auricle where the auricle joins the patient's temple. Dimension B shows a head height. As illustrated, curve P2 stops on the crown of the patient's head. That is, if the curve represented tubing, it would be substantially snug against the top of the patient's head. When the curve or tubing is rotated forward, dimension A shows the head height of a patient that this would fit. As illustrated, a fit range delta AB is achievable using the same non-adjustable tubing.

In an embodiment, the air delivery and stabilizing system 30 may pass along the upper jaw bone of the patient, e.g., avoid cheek and follow fleshy areas of the patient's face. Also, in an embodiment, the air delivery and stabilizing system 30 may reside over the mid-point of the patient's temple in use. However, the air delivery and stabilizing system 30 may be sufficiently soft so that sensitive areas do not need to be avoided for comfort.

It should be appreciated that positioning of the air delivery and stabilizing system 30 on the patient's head does not critically depend on exact alignment with certain facial features as do prior art systems. That is, a satisfactory interface may be formed and retained by the air delivery and stabilizing system 30 despite movement.

1.7 Other Aspects of System 1.7.1 Assembly

In a preferred embodiment, the patient interface 10 is structured such that little or no adjustment is needed to fit the patient interface to the patient's head. Thus, the patient interface is relatively self-locating, intuitive, auto-adjusting, easy fitting. In an embodiment, the patient interface may be assembled one handed, e.g., slip on like a hat.

As noted above, the air delivery and stabilizing system 30 has a generally oval or ring-shaped configuration, e.g., a generally truncated elliptical cone or funnel. A tapering surface or conical-elliptical ring may be provided between the inner and outer edges to define a contact surface that engages the patient's head. Depending on the size of the patient's head, the tapered contact surface will engage the patient's head in different positions. For example, if the patient has a larger head, the patient interface may sit higher up on the patient's head. If the patient has a smaller head, the patient interface may sit more towards a rear portion of the patient's head. Once fit, the patient may adjust the back strap 60 as necessary. Thus, the patient may require a single adjustment to fit the patient interface to his/her head. Further details of such an arrangement are disclosed in U.S. Provisional Application No. 60/833,841, filed Jul. 28, 2006, which is incorporated herein by reference in its entirety.

In an embodiment, the oval or ring-shape configuration of the air delivery and stabilizing system 30 may be adjustable, e.g., depending on patient fit and/or preference. For example, as shown in FIG. 8-7 top and/or bottom portions of the "ring" may include an adjustment mechanism 55 to allow adjustment of the ring size, e.g., depending on patient's head size.

FIGS. 8-8-1 to 8-8-9*f* illustrate a mask assembly 2110 including a headgear adjustment mechanism 2155 according to an embodiment of the present invention. Such mask assembly is disclosed in U.S. Provisional Application No. 60/996,485, filed Nov. 20, 2007 and entitled "A Respiratory Mask Headgear Adjustment Apparatus", which is incorporated herein by reference in its entirety.

In this mask assembly 2110, a pair of soft flexible tubes 2142 are routed from a foam interface 2120 positioned under the nose to a manifold 2170 located near the crown of the head, as shown in FIGS. 8-8-1 and 8-8-2. Such arrangement forms an oval or ring-shaped "headgear" to support the mask assembly in a desired position on the patient's head.

A headgear adjustment mechanism 2155 in accordance with an embodiment of the invention allows lengthwise adjustment of a portion of the headgear, enabling it to be better fitted on a range of different head sizes.

In one form, the headgear adjustment mechanism 2155 incorporates a rack and pinion, whereby rotational motion of a dial 2156 is arranged to provide lengthwise adjustment of a headgear configuration. As shown in FIGS. 8-8-1 and 8-8-2, this allows adjustment of the headgear length so that points A and B may be moved closer together, or farther apart.

In the illustrated embodiment, the adjustment mechanism 2155 includes a first rack 2157(1) (FIGS. 8-8-4*a* to 8-8-41), a second rack 2157(2) (FIGS. 8-8-5*a* to 8-8-5*e*), a pinion 2158 (FIGS. 8-8-6*a* to 8-8-61), and a dial 2156 (FIGS. 8-8-7*a* to 8-8-71) connected to the pinion 2158. A first housing portion 2159 (FIGS. 8-8-8*a* to 8-8-81) and a second housing portion 2161 (FIGS. 8-8-9*a* to 8-8-91) support the pinion 2158 and dial 2156 with respect to the racks 2157(1), 2157(2). The racks 2157(1), 2157(2) are connected to or form part of the headgear. FIGS. 8-8-3*a* to 8-8-3*e* illustrate the adjustment mechanism 2155 isolated from the mask assembly.

As shown in FIGS. 8-8-4*a* to 8-8-4*f* and 8-8-5*a* to 8-8-5*e*, each rack 2157(1), 2157(2) includes a tube connector portion 2163 and a rack portion 2164 that provides a slot 2164.1 and a series of teeth 2164.2 along one side of the slot. Each tube connector portion 2163 is connected between a respective tube 2142 and a conduit 2143 provided to the manifold 2170 (see FIGS. 8-8-1 and 8-8-2). As illustrated, the ends of the tube connector portion may have different cross-sectional configurations, e.g., to accommodate different cross-sectional configurations of the tube 2142 and conduit 2143. In an embodiment, each tube connector portion 2163 may be rotatably or otherwise movably mounted to the rack portion 2164 to allow adjustment of the tube connector portion 2163 with respect to the rack portion 2164, e.g., to adjust routing of the tube 2142 and conduit 2143. In another embodiment, each tube connector portion may be include a bellows-type structure to allow flexibility, slack pick-up, etc.

Figures 1, 8:
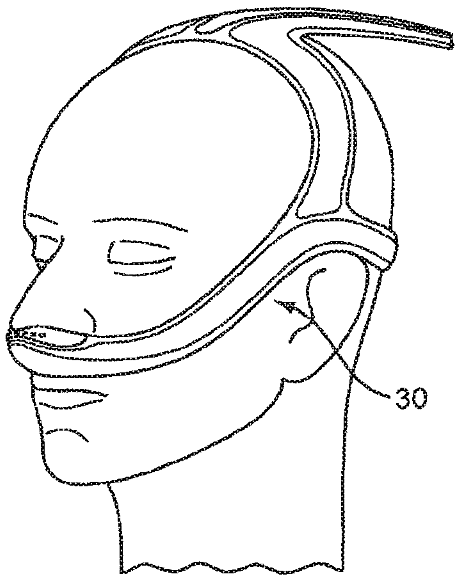
Figures 2, 8:
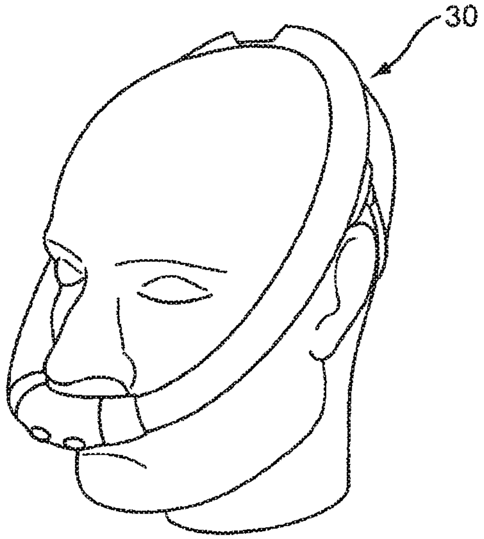
Figures 3, 8:
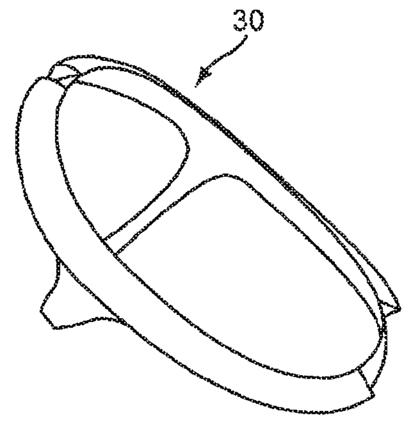
Figures 4, 8:
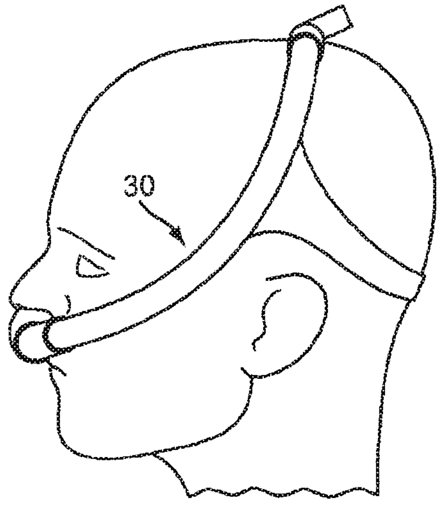
Figures 5, 8:
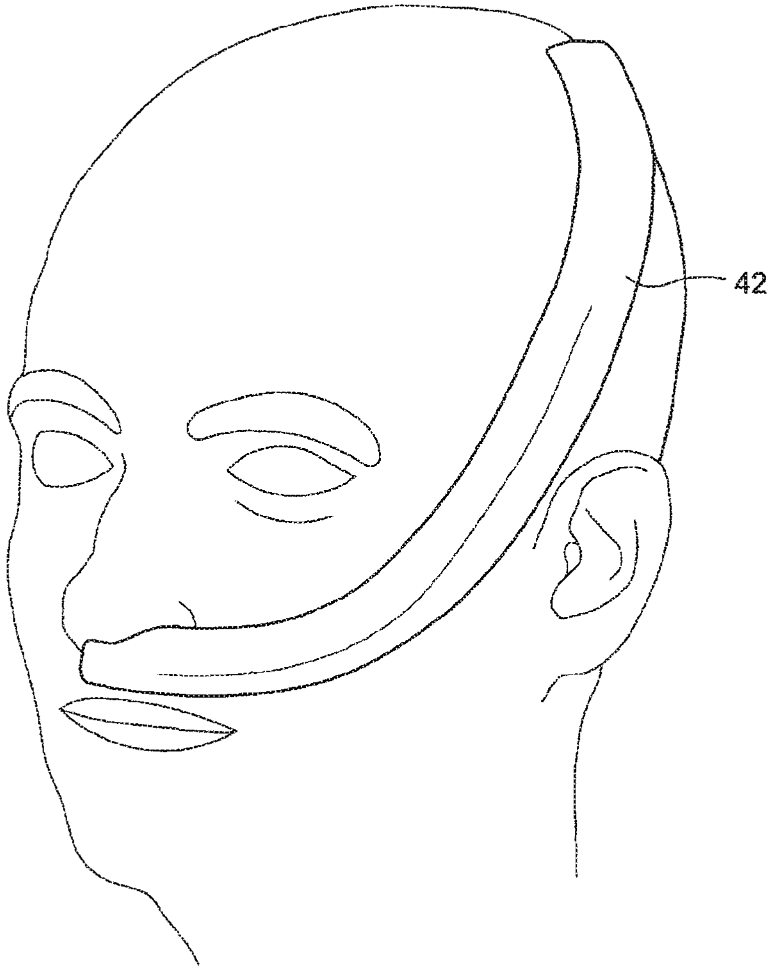
Figures 6, 8:
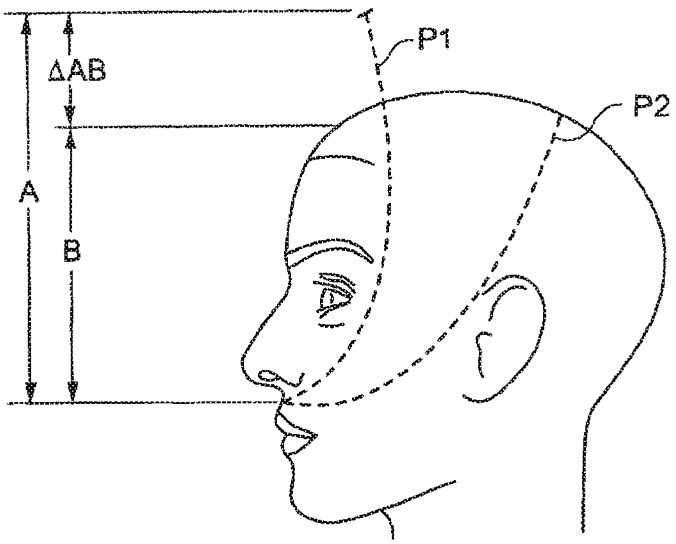
Figures 7, 8:
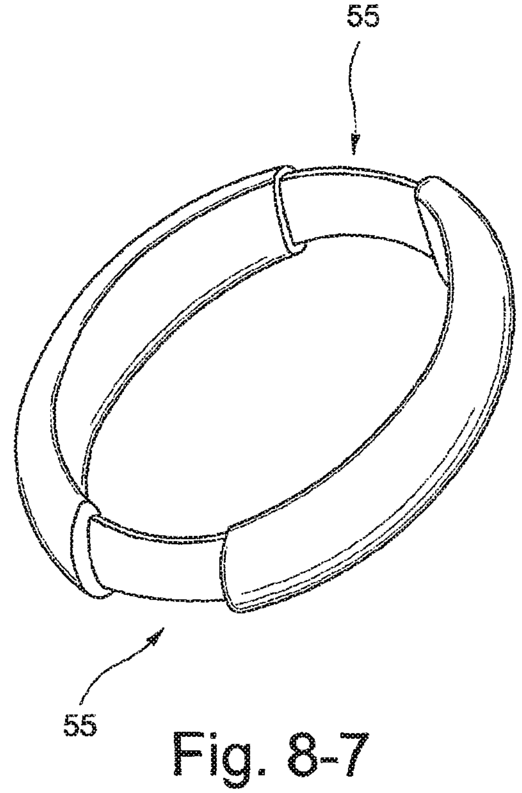
Figures 1, 8:
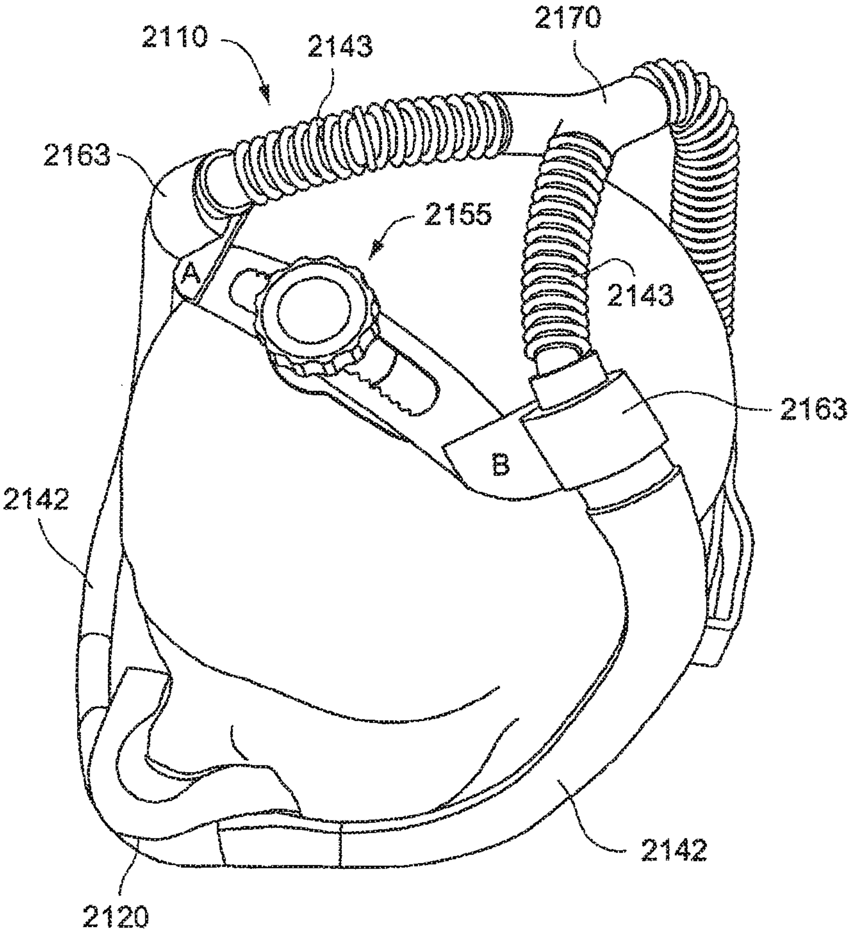
Figures 2, 8:
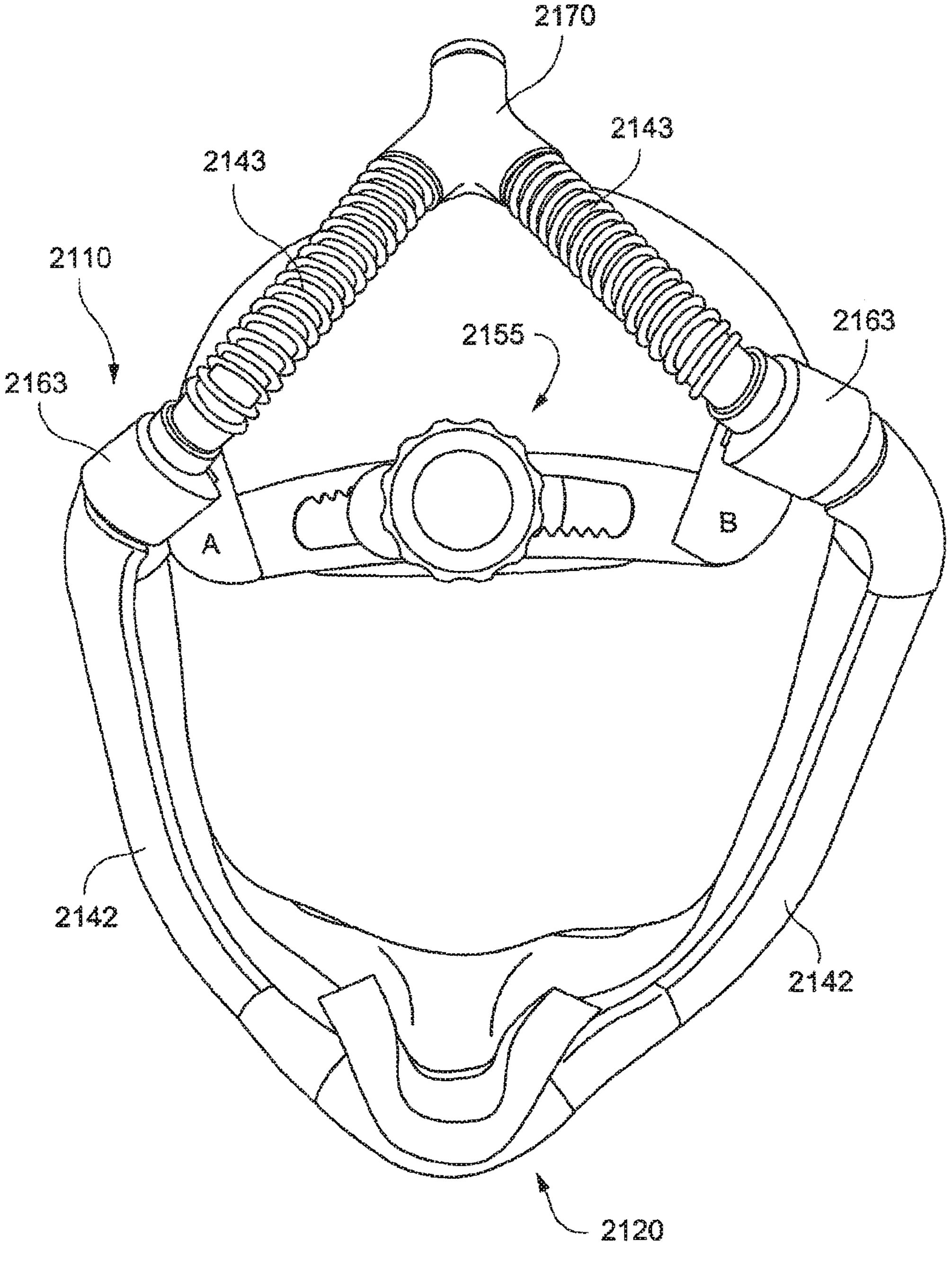
Figures 3B, 8:
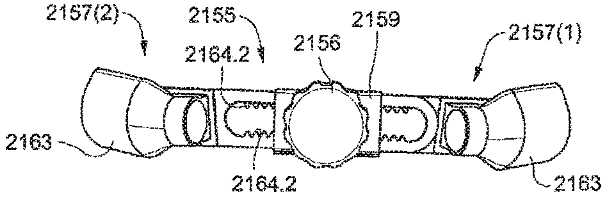
Figures 3A, 8:
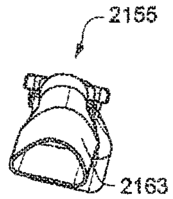
Figures 3C, 8:
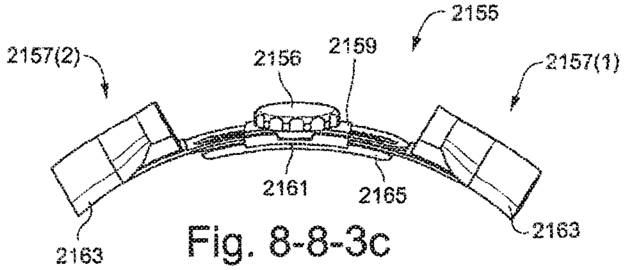
Figures 3E, 8:
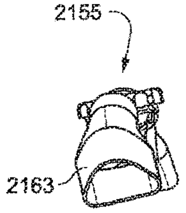
Figures 3D, 8:
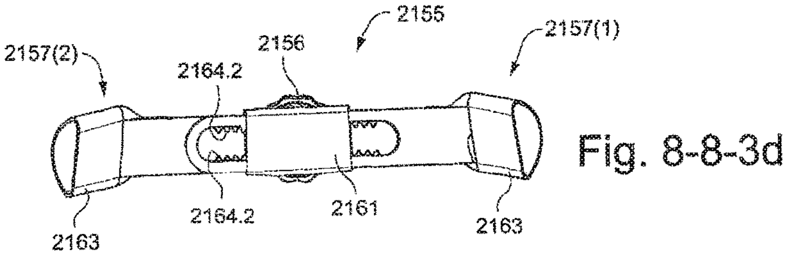
Figures 4B, 8:
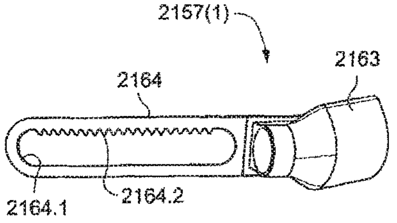
Figures 4F, 8:
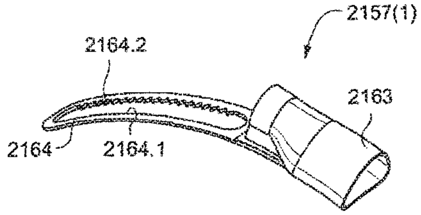
Figures 4A, 8:
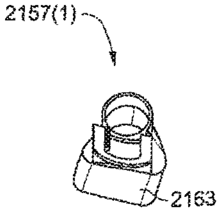
Figures 4C, 8:
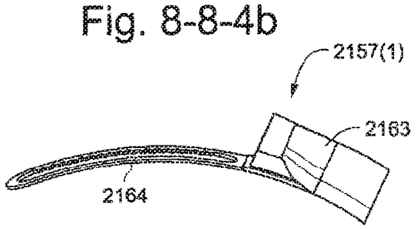
Figures 4E, 8:
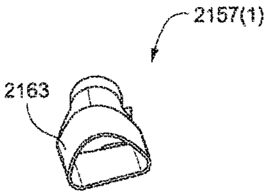
Figures 4D, 8:
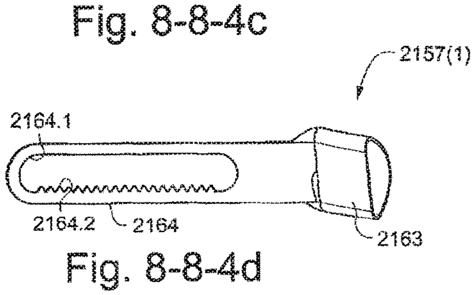
Figures 5A, 8:
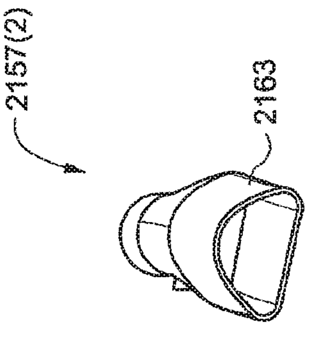
Figures 5B, 8:
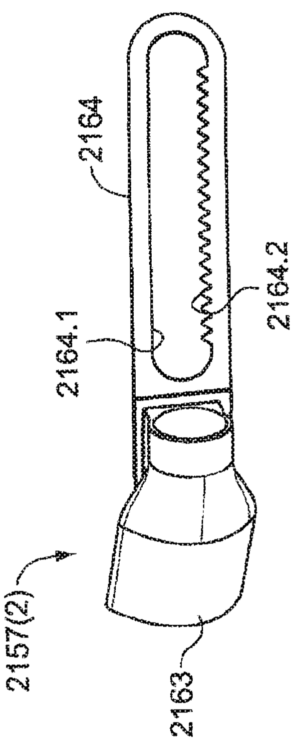
Figures 5C, 8:
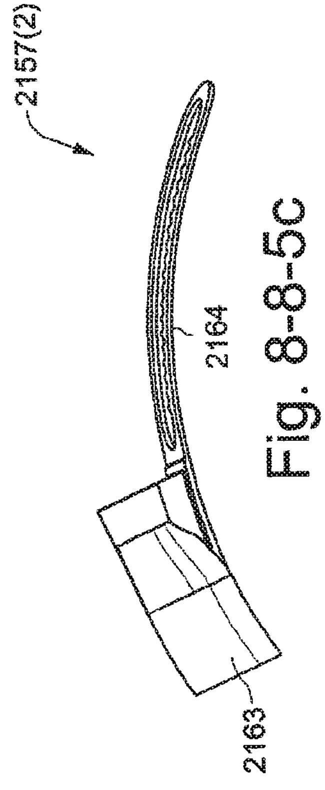
Figures 5D, 8:
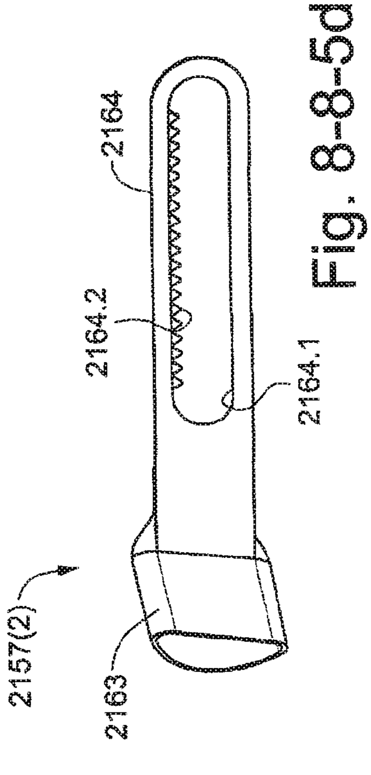
Figures 5E, 8:
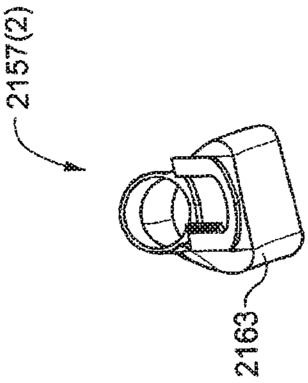
Figures 6A, 8:
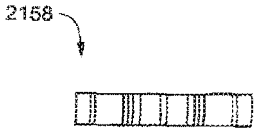
Figures 6B, 8:
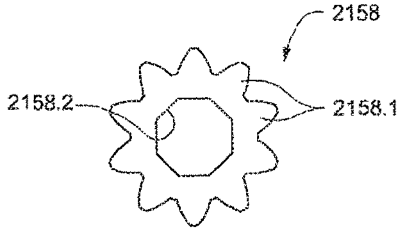
Figures 6C, 8:
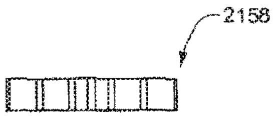
Figures 6D, 8:
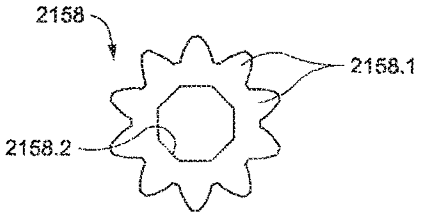
Figures 6E, 8:
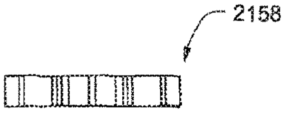
Figures 6F, 8:
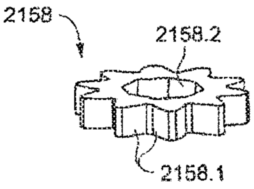

The rack portions 2164 of the first and second racks 2157(1), 2157(2) are overlapped with one another to align the slots 2164.1 and provide opposed teeth 2164.2 (e.g., see FIGS. 8-8-3*b* and 8-8-3*d*). The pinion 2158 is positioned within the aligned slots and the pinion teeth 2158.1 are engaged with opposed teeth 2164.2.

The first and second housing portions 2159, 2161 are provided on opposing sides of the rack portions 2164 to enclose the pinion 2158 and maintain the pinion 2158 in an operative position. The first and second housing portions 2159, 2161 are coupled to one another, e.g., with a snap-fit interlock.

The dial 2156 includes a dial portion 2156.1 and a shaft portion 2156.2 extending from the dial portion. The dial 2156 is supported by the first housing portion 2159 and the shaft portion 2156.2 extends through an opening 2159.1 in the first housing portion 2159 and is interlocked with an correspondingly shaped opening 2158.2 provided in the pinion 2158. Accordingly, rotation of the dial 2156 causes corresponding rotation of the pinion 2158, which provides lengthening or shortening of the headgear via the pinion's toothed engagement with the first and second racks 2157(1), 2157(2).

In the illustrated embodiment, the adjustment mechanism 2155 includes a detent assembly to provide tactile feedback with the motion of the dial 2156. Specifically, the first housing portion 2159 includes spring-biased projections 2159.2 that interact with recesses 2156.3 provided on the underside of the dial portion 2156.1 (see FIG. 8-8-7*d*). As the dial 2156 is rotated, the spring-biased projections 2159.2 will move into and out of engagement with the recesses 2156.3. Also, the spring-biased projections 2159.2 will be seated within respective recesses 2156.3 to assist in restraining the dial 2156 at the desired position.

In another example, the racks can simply be coupled with the ends of one or more headgear straps, such that adjustment of the knob changes the length of the headgear. In addition, each rack can be associated with another part of the mask, e.g., the conduits 2143 shown in FIGS. 8-8-1 and 8-8-2. For example, each rack is structured to accommodate the end of one of the air delivery conduits 2143 which pass over the top of the user's head. Moreover, the racks (e.g., the ends of the tube connector portions) may form a junction where the air delivery conduits (of relatively smaller circular cross section) join with the tubes (of relatively larger, non circular (e.g., D-shaped cross section)) which extend across the cheeks from the patient interface.

Preferably, the adjustment mechanism is configured to be positioned on the crown of the patient's head, although in other configurations, it may be positioned on different parts of the patient's head, or for adjustment of the lengths of different sections of headgear. In an embodiment, padding may be provided to the underside of the adjustment mechanism and adapted to engage the patient's head in use (e.g., exemplary padding 2165 illustrated in FIG. 8-8-3*b*).

The adjustment mechanism may include alternative configurations for size adjustment. For example, the adjustment mechanism may include a baseball-cap type adjustment, a belt-loop type adjustment, friction lock type adjustment, etc.

1.7.1.1 Method to Fit Patient

Figures 1, 2, 3, 4, 5, 6, 7, 8, 9:
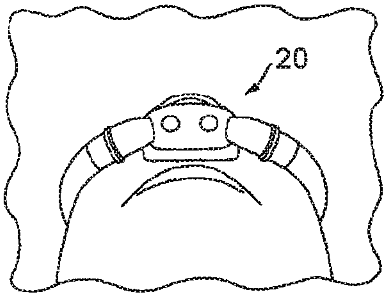

FIGS. 9-1 to 9-3 illustrate an exemplary method for fitting the patient interface to a patient. As shown in FIG. 9-1, the interfacing structure 20 may first be located under the patient's nose. Then, as shown in FIG. 9-2, the air delivery and stabilizing system 30 may be rotated about the interfacing structure 20 onto the patient's head. The patient interface is rotated, e.g., for X°, until the air delivery and stabilizing system 30 engages the patient's head and prevents further movement. Finally, as shown in FIG. 9-3, the back strap 60 may be adjusted as necessary to comfortably secure the patient interface on the patient's head.

Figures 1, 30:
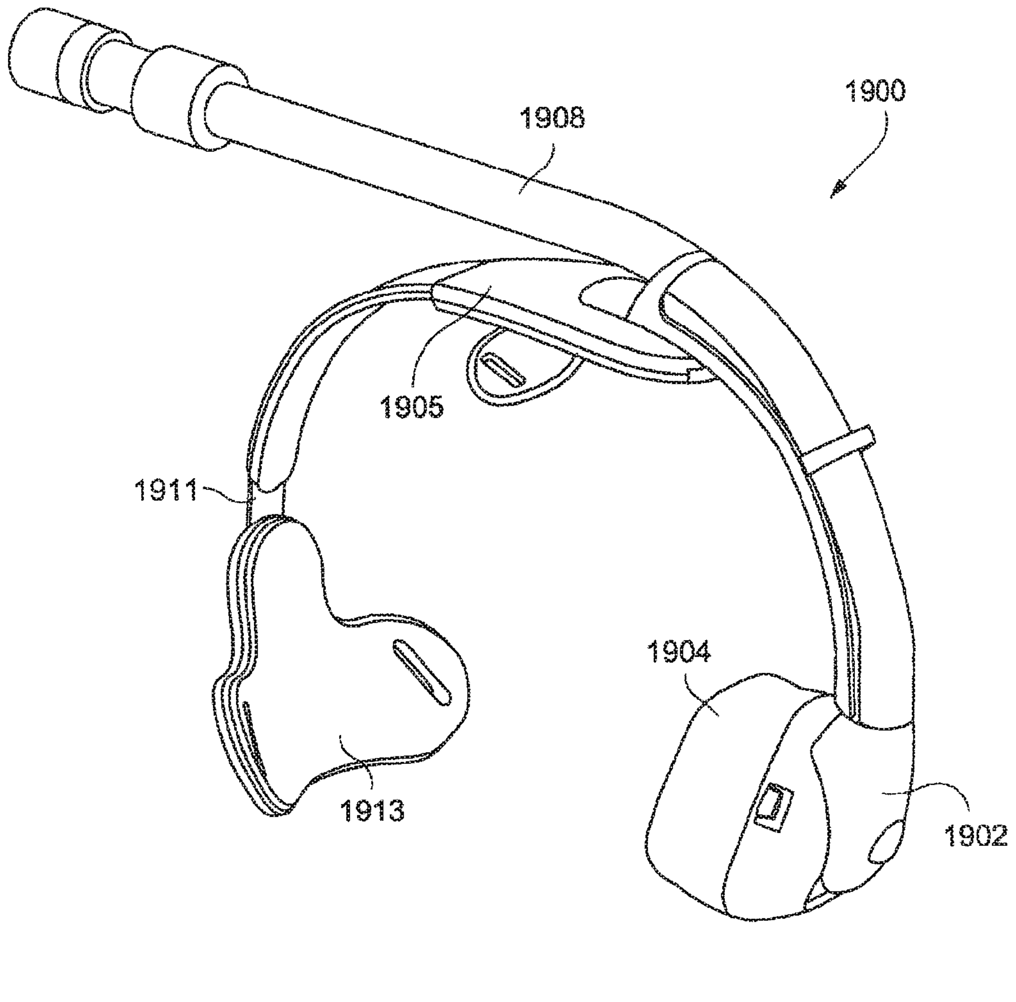
Fig. 30-1 (PRIOR ART)
Figures 2, 30:
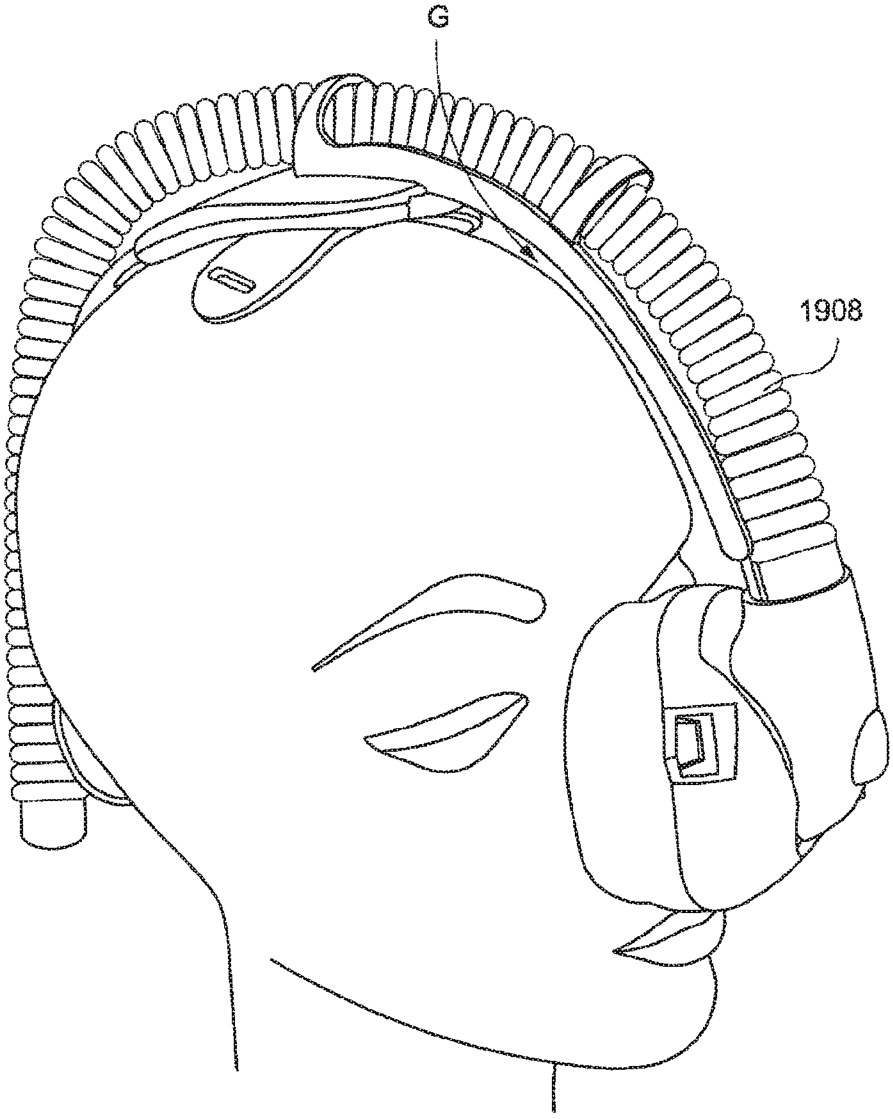
Fig. 30-2 (PRIOR ART)
Figures 3, 30:
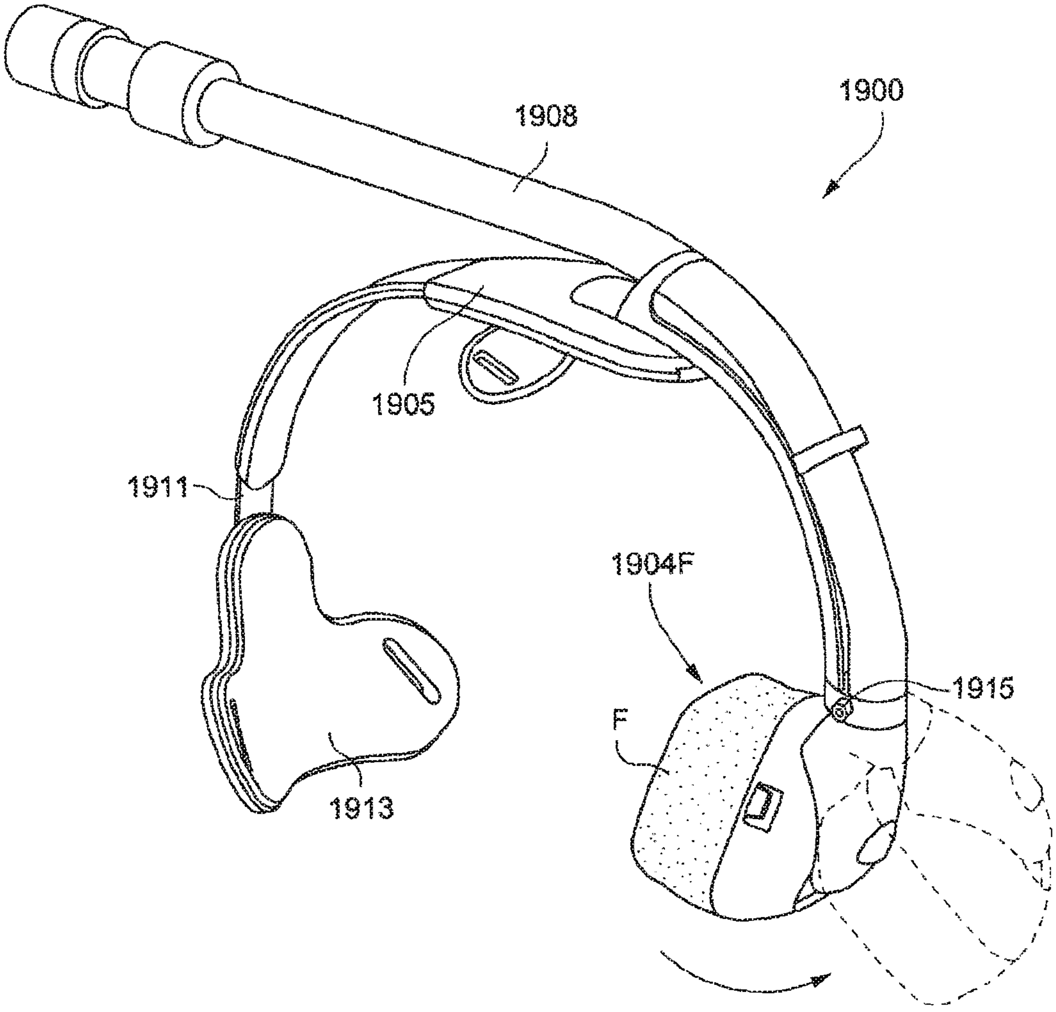
Figures 4, 30:
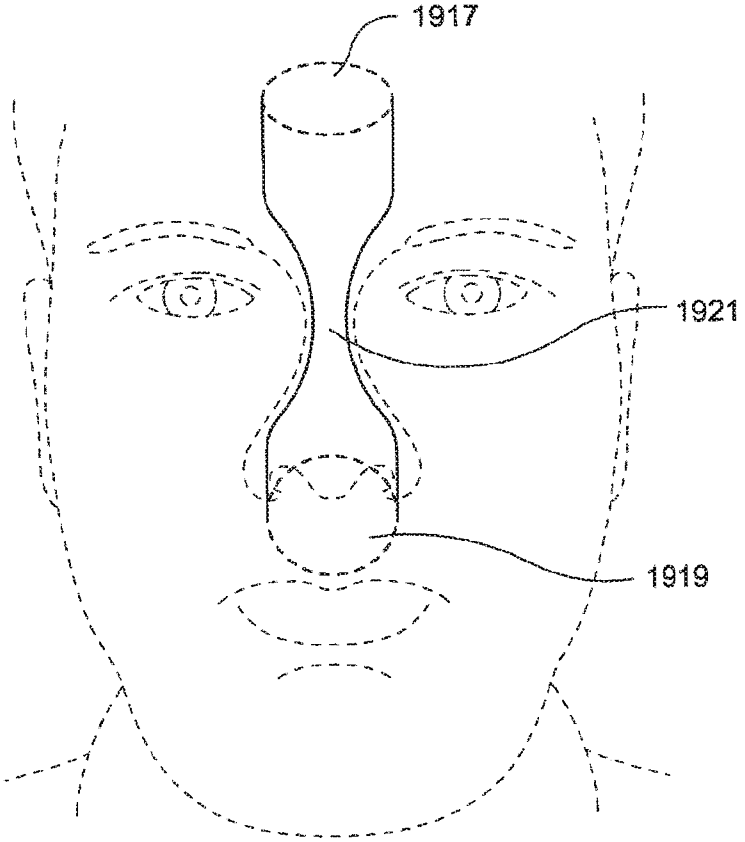
Figures 5, 30:
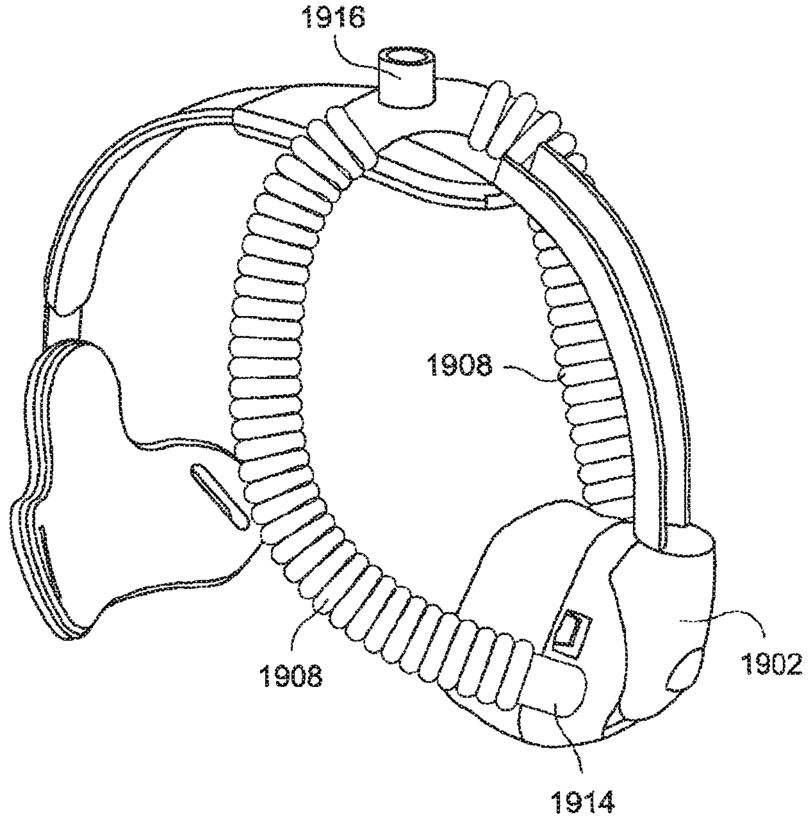

In an alternative embodiment, the patient interface may be structured to provide "staged fitting" of the patient interface. In such embodiment, one part of the patient interface (e.g., air delivery and stabilizing system) may be engaged with the patient and another part of the patient interface (e.g., interfacing structure) may be subsequently engaged when the patient is ready for therapy to begin. This arrangement allows the air delivery and stabilizing system to be engaged with the patient's head, while the interfacing structure is out of engagement. For example, in the case of an Adam's circuit (e.g., such as that shown in FIGS. 30-1 to 30-4), the interfacing structure may be adapted to pivot upwards or laterally into a "standby" position that is out of the patient's field of view and/or not engaged with the patient's face or nose. The interfacing structure may be moved from the "standby" position to a fully operable/engaged position at the last minute just before the patient is ready for therapy (e.g., before sleep). In one example, the tube or the joint between the tube and the mask may be pivotable/bendable/movable to move the mask away from the face while still maintaining the headgear in place. For example, FIG. 30-3 illustrates an exemplary pivot 1915 at the joint between the tube and the mask that allows the mask to move away from the face (e.g., to a position shown in dashed lines).

1.7.1.2 Sizing

In the illustrated embodiment, the patient interface includes a single adjustment point. The adjustment mechanism may be either passive (e.g., elastic back strap) or require active adjustment (e.g., baseball cap fitting) to provide a one-size fits all arrangement. In an embodiment, the adjustment point may be tailored or modified to fit the patient at the point of sale, and then altered to prevent further adjustment, e.g., tear off.

In an alternative embodiment, the patient interface may have a non-adjustable slip-on shape, e.g., like a shoe, with little or no elasticity. In this arrangement, the patient interface may be provided in many different sizes, e.g., up to 20 different sizes, 5, 10, 15, or any other number of sizes (e.g., small, medium, and large). This arrangement may be aided by high mechanical compliance of the sealing interface to provide ample fit-range.

In another alternative embodiment, the patient interface may include a method for adjusting the size (e.g., length) of the headgear in either or both of the upper and rear sections of the headgear.

1.7.1.3 Surface Properties

In embodiments, the air delivery and stabilizing system may be textured, colored, foamed, and/or flocked (e.g., lots of little bits of yarn or fluff adhered to it) to give a fabric-like feel or softness for aesthetics and/or comfort. For example, the tubing, rigidizing elements, back strap, and/or manifold may be textured, colored, foamed, and/or flocked.

Figures 1, 2, 3, 4, 5, 6, 7, 8, 9, 10:
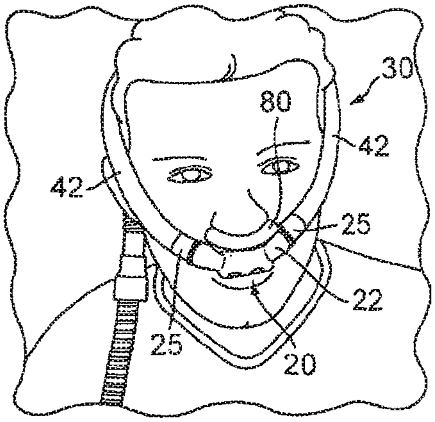

In an alternative embodiment, a sock S may be provided to substantially enclose one or more portions of the tubing, rigidizing elements, back strap, and/or manifold (e.g., see FIGS. 10-1 to 10-6). Such an arrangement is disclosed in U.S. Provisional Application No. 60/833,841, filed Jul. 28, 2006, which is incorporated herein by reference in its entirety.

In another embodiment, different materials may be co-molded in the same mold to provide a one-piece, integrated structure. For example, instead of providing a cover or sock to tubing, a fabric or cloth material may be co-molded with silicone tubing to provide a one-piece, integrated tube with a fabric/cloth exterior surface and a silicone interior surface. In such embodiment, the fabric/cloth material may be placed in a mold and then silicone may be injected into the same mold so that it bonds with the fabric/cloth material and forms a one-piece, integrated tube.

In another embodiment, multiple portions of the patient interface may be co-molded in the same mold with different materials to provide a one-piece, integrated structure. For example, a fabric/cloth material may be co-molded with tubing constructed of a first material, a manifold constructed of a second material, and a frame constructed of a third material to provide a one-piece, integrated structure. In an embodiment, the first, second, and third materials may include the same material with different durometers or hardnesses, e.g., tubing constructed of relatively soft silicone and manifold and frame constructed of relatively hard silicone. Alternatively, the first, second, and third materials may include different polymers or materials. Further, each portion of the patient interface may include regions with different properties, e.g., end portions of the tubing may be harder than an intermediate portion of the tubing. In such embodiment, the fabric/cloth material may be placed in a mold and then the first, second, and third materials may be injected into the same mold so that all the materials bond and form a one-piece, integrated structure, e.g., integrally formed tubing, manifold, frame with fabric/cloth cover.

In another embodiment, the tubing, rigidizing elements, manifold, and/or back strap may include silicone or other elastic beading for grip. This arrangement may be particularly useful for patient's with bald heads as the beading is adapted to grip the bald head and prevent sliding or movement of the patient interface with respect to the patient's head in use. In an embodiment, the patient interface may be reversible so that the beading may be selectively used, e.g., depending on whether the patient is bald. For example, fabric may be provided on one side and beading may be provided on the opposite side so that the patient may use one or the other depending on preference, e.g., beading oriented towards the patient's head for bald heads and fabric oriented towards the patient's head for hairy heads.

1.7.1.4 Manufacture

In an embodiment, each tube 42 may be manufactured as a bifurcated tube having a co-molded thickened section that forms a rigidizer.

In another embodiment, each tube 42 may be constructed of two pieces, i.e., a top half and a bottom half attached to the top half. In an exemplary embodiment, the top half may be constructed of textile or foam (e.g., with a sealing layer), and the bottom half may constitute a rigidizer with a skin-contacting portion.

1.7.2 Low Visual Obstruction

The patient interface may incorporate one or more regions having different colors (color contrast), patterns, and/or surface textures to reduce visual impact or distraction to the user. Such coloring, patterning, and/or surface texturing may be incorporated into the tubing, rigidizing elements, manifold, back strap, and/or interfacing structure. Alternatively, a sock having coloring, patterning, and/or surface texturing may be provided to the patient interface.

For example, FIGS. 10-1 to 10-10-6 illustrate a patient interface including a cover or sock S having a two-tone color scheme, e.g., a dark color D and a light color L. Such a patient interface is described in U.S. Provisional Application No. 60/833,841, filed Jul. 28, 2006, which is incorporated herein by reference in its entirety. As illustrated, the dark color D is positioned adjacent the field of vision. This arrangement provides a low impact, unobtrusive, sleek look that is less visually obtrusive to the patient and others.

Specifically, bright colors are more easily picked up by the patient and should be avoided in the field of view as they are more likely to cause a distraction than darker colors, e.g., bright colors reflect light into patient's eyes. Thus, the dark color D is positioned adjacent the field of vision to minimize visual obstruction or obtrusiveness. In an embodiment, the patient interface may only be visible to the patient at the very outer limits of their field of view, e.g., only the section of the patient interface which rests lower than the patient's eye level may be visible. Further, the dark color D may seem to disappear at the extremities of the field of view resulting in the patient undergoing very little visual obstruction.

Also, the two-tone textile cover S may slim the perception of the size of the patient interface on the patient's face. That is, this arrangement has the functional advantage that lighter colors, e.g., white, can be incorporated into the cover that make the relevant region look smaller, slimmer, or less bulky. Thus, the patient interface has a lower visual impact (e.g., less aesthetically obtrusive). In addition, the patient interface may be more fashionable like clothing. In alternative embodiments, one or more light colored lines, e.g., white lines, may be incorporated into the cover. Also, in an embodiment, the interface of the interfacing structure may include a darker color to reduce its visual obstruction.

It should be appreciated that different colors, patterns, and/or surface texture may be selected for different users. In an embodiment, the cover may be transparent or selected to blend in with the patient's skin, e.g., camouflaged or skin color. For example, if the patient has relatively darker skin, the cover could be black or dark brown to blend with the patient's skin. In an alternative embodiment, the color and/or texture of the cover may be selected to match the patient's hair.

1.7.3 Valve

Figures 1, 2, 3, 4, 5, 6, 7, 8, 9, 10, 11:
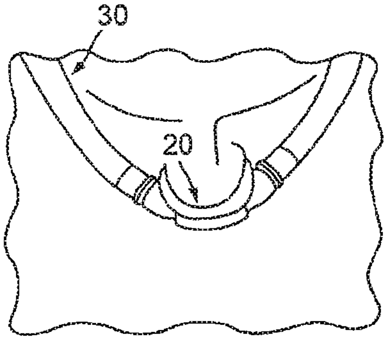

In an embodiment, as shown in FIG. 11-1, a valve V, e.g., mechanical gate, may be provided to the patient interface that is adapted to open when both tubes 42 are occluded. For example, the valve V may remain closed if the interior pressure $P_{int}$ is over 2 $cmH_2O$, and the valve may open if the interior pressure $P_{int}$ is less than 2 $cmH_2O$ thereby allowing the patient to breathe if both tubes 42 are occluded.

1.7.4 Connection to a Blower

In an embodiment, the patient interface 10 may be connected to the blower by a pair of air delivery tubes, i.e., a 15 mm tube and a 22 mm tube. As shown in FIG. 1-2, a 15 mm tube T1 connects the manifold 70 to a 22 mm tube T2, and the 22 mm tube T2 connects the 15 mm tube T1 to the blower. A quick-release connector 90 is provided at the transition between the 15 mm and 22 mm tubes T1, T2 to allow quick release of the 15 mm and 22 mm tubes T1, T2, and hence quick release of the patient interface 10 from the blower. In an alternative embodiment, a quick-release connector may be provided to the manifold 70 positioned adjacent the top of the patient's head. The quick-release connector may have any suitable structure to facilitate tubing assembly/disassembly, e.g., mechanical interlock, friction fit, screw-type arrangement, etc. The various connection points facilitates assembly/disassembly of the patient interface system which facilitates cleaning, adjustment, etc.

The 15 mm tube T1 has a suitable length to allow easy patient access to the quick-release connector 90, e.g., quick-release connector 90 in patient's field of view. Also, the 15 mm tube T1 has a suitable length so that the quick-release connector 90 may be positioned sufficiently away from the patient interface so the weight of the quick-release connector may be supported by the bed mattress or other support system.

Impedance in the system is as little as possible so that therapy does not vary significantly whether one or both tubes 42 are open. Therefore, the system is designed such that the hydraulic restriction or bottleneck is provided upstream of the patient interface including the case in which only one of the tubes 42 is open, i.e., the hydraulic bottleneck is provided in the manifold 70 or anywhere upstream of the manifold 70 (e.g., in the 15 mm tube and/or in the 22 mm tube).

Impedance is at least partially based on tube length. In the illustrated embodiment, the tubing is designed such that the tubes 42 are shorter than each of the 15 mm tube and the 22 mm tube, e.g., 15 mm and 22 mm tubes at least 40-50 cm long. In an embodiment, the 22 mm inlet tube may be about 2 m long and the 15 mm inlet tube may be about 70-75 cm long, with the bottleneck in the 22 mm inlet tube due to its length. However, other suitable lengths are possible.

In an embodiment, the air delivery tubing that leads to the manifold may have a look and feel similar to the inlet tubes 42. The air delivery tubing may have a smooth, noiseless outer portion, e.g., outer portion constructed of a material that is soft to the touch and provides sound insulation. The air delivery tubing may provide continuity of form from the PAP device or blower to the manifold of the patient interface.

1.7.5.1 Clip to Isolate Tube Drag

A clip or clamp may be provided to either air delivery tube T1, T2 and/or quick release connector 90 that is adapted to attach to a bed headboard or other support system. The clip or clamp supports the air delivery tube and/or quick release connector on the bed headboard or other support system to isolate tube drag from the patient interface. In an embodiment, the clip or clamp may be magnetic to allow magnetic attachment.

Figures 1, 2, 3, 4, 5, 6, 7, 8, 9, 10, 11, 12:
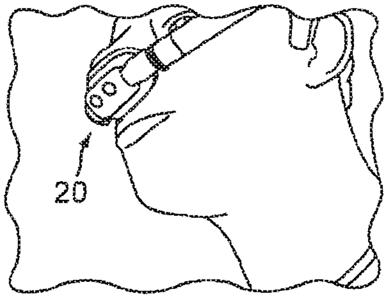

For example, FIG. 12-1 illustrates the quick release connector 90 magnetically attached to a headboard, FIG. 12-2 illustrates a clip 92 adapted to attach the tube T1 to a headboard, and FIG. 12-3 illustrates the tube T1 clipped to the patient interface.

1.7.5.2 Switch to Turn CPAP Therapy on/Off

A switch may be provided along any suitable portion of the patient interface that is adapted to turn the blower providing CPAP therapy on and/or off. For example, the switch may be provided on the air delivery tube or quick release connector. In an embodiment, the switch may be wirelessly communicated with the blower.

1.7.6 Inflatable Headgear

In an alternative embodiment, inflatable tubes may be provided around a relatively more rigid air delivery tube to insulate the air delivery tube from the patient's face.

1.7.7 Moveable Tubes

In an alternative embodiment, tubes may be provided that are adapted to move out of the way when the patient's head is turned.

2. Interfacing Structure 2.1 Background and Summary

Known patient interfaces typically include a silicone seal that is adapted to seal around and/or within the patient's nose and/or mouth. Sealing mechanisms may be categorized as: (1) a flap-type seal, (2) a bulk compression or gasket-type seal, or (3) a combination of (1) & (2). A flap-type seal may utilize the mechanics of a flexible membrane to achieve a reliably sealing interface. Compared to a flap-type seal that works by deflection of the flap, a bulk material seal works by compression of the material. A preferred interfacing structure of the present invention utilizes foam in the form of a bulk compression type seal although the foam may take other forms. The foam interface may be formed by die cutting from a block of foam. Preferably, the cut piece of foam is configured into a gasket or compression-type seal.

One aspect of the present invention relates to an interfacing structure 20 in the form of an under-the-nose interface 80 made of foam (e.g., see FIGS. 1-6, 1-8, 1-10, 13-1, 13-2) that provides an effective and superiorly comfortable engagement with the underside of the patient's nose in use. In embodiments, the under-the-nose interface may be in the form of a cupping portion, prongs, or pillows. The foam interface 80 may be supported by a support and/or frame or shell adapted to communicate with respective tubes 42 of the air delivery and stabilizing system 30 described above.

For example, as shown in FIGS. 1-6, 1-8, and 1-10, the foam interface 80 may be provided to a relatively stiff shell or frame 22, e.g., formed of silicone, including tube portions 25 adapted to engage respective ends of the tubes 42, e.g., via friction fit.

Figures 1, 2, 3, 4, 5, 6, 7, 8, 9, 10, 11, 12, 13:
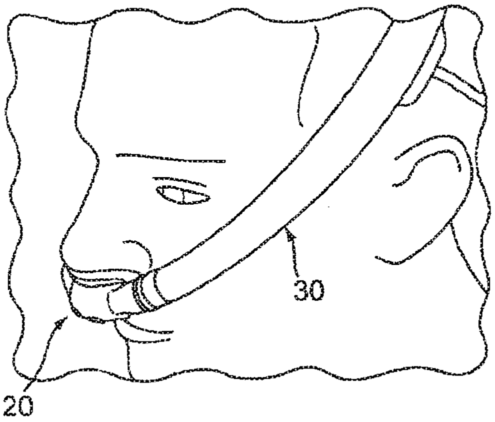

In another embodiment, as shown in FIGS. 13-1 to 13-2, the foam interface 80 may be provided to a cylindrical support or base 82, e.g., constructed of silicone, and the cylindrical support 82 is adapted to be attached to a relatively rigid frame (not shown) adapted to engage respective ends of the tubes 42. The cylindrical support 82 may have a substantially similar structure to the base portion of a nozzle assembly (with the nozzles removed) as disclosed in U.S. patent application Ser. No. 10/781,929, the entirety of which is incorporated herein by reference. The flexibility of the cylindrical support 82 adds compliance to the interface. The cylindrical support 82 may have a split base to be connected with a channel in the frame. In an embodiment, the interface, cylindrical support, and/or frame may be adapted to rotate to add further compliance and/or adjustment to the interface. In an embodiment, the rotational adjustment and positioning may be maintained through the use of friction, indexing, and locking mechanisms.

In the illustrated embodiment, the foam interface 80 is constructed of a very soft foam that is compliant enough to gently cradle the patient's nose and provide an unobtrusive and comfortable nasal interface, e.g., under-the-nose foam interface. The under-the-nose foam interface provides the visual freedom and unobtrusiveness of nasal prongs, without the intrusiveness and potential discomfort of silicone prongs inside the patient' nose.

One issue that has emerged with the prevalence of nasal prong interfaces is a recognizable decrease in breathing comfort where a cold, frictional or burning sensation may be felt inside the nose from air rushing through the nose, particularly upon inhalation and higher pressures when the air travels at higher speeds through the nose. This sensation has been dubbed the 'jetting effect'. This jetting effect is thought to be partially due to the air entering the nose in a channeled manner through the narrow prong orifices and impinging on sensitive nasal mucosa. It may also be attributed to air temperature and humidity. Thus, another advantage of the under-the-nose foam interface is the elimination or minimization of the jetting effect that nasal prongs are known to produce. This is because the air is not being forced through narrow orifices inside the nostrils, but through a larger orifice that covers both nostril openings. The exit of the foam interface remaining entirely or predominantly outside of the nose allows for the impedance of the orifice to be matched to, or lower than, the nostril openings so that flow is not restricted and formed into a jet stream inside the nose. The foam also has a diffusing effect at the boundary of the flow as it enters the nose. The irregular surface of the foam may add turbulence to the boundary layer of the flow entering the nostrils and as such navigates the nostril cavity with less concentrated force on the sensitive anatomy inside the nose. This diffusing effect also allows for the alignment of the interface with the nostril to be less critical with respect to the generation of the jetting effect. The foam being slightly air permeable also has the advantage of minimizing the aspects of the jetting effect that are attributable to humidity and temperature. Cold air and temperature variable air entering and exiting the nose can cause an irritating sensation inside the nose with known interfaces. Upon exhalation, the foam may be infused with warm exhaled air, and upon subsequent inhalation this small amount of warm air may reenter and/or heat the air stream that enters the nose therefore reducing the jetting effect. Yet another advantage of the foam in relation to the jetting effect is its ability to retain moisture (e.g., moist air), again due to the permeable nature of the foam. Upon inhalation, the stored moisture may add to the humidity of the inhaled air and reduce the jetting effect.

In another embodiment, the under-the-nose interface may have a central portion that divides the singular orifice into two. In this embodiment, the two resulting orifices may be size-matched, smaller than, or larger than the nostrils.

In both of the aforementioned embodiments (single and double orifice), alignment of the orifices with the nostrils can be relaxed compared to nasal prong designs. This is a result of not having positively intruding features inside the nostrils. The interface allows for greater movement along the surface of the skin without compromising the interface and/or seal. As a result of the very low hardness of the foam (e.g., particularly the very soft viscoelastic grades), the foam may intrude slightly inside the nostrils as it takes the shape of the anatomy it is interfacing with.

In a preferred embodiment, the interface may be made from a very soft, viscoelastic polyurethane foam grade. One method of quantifying the viscoelastic nature of foam is to measure the rate of deformation or recovery of the foam after it has been compressed. In an embodiment, the rate of recovery is designed so that the interface remains comfortably and sealingly engaged with the user's face while wearing the mask. The viscoelastic nature has particular benefits for maintaining comfort and seal during movement while wearing the mask. In other embodiments, the range of viscoelasticity may range from a foam that has a very slow rate of recovery to a very fast rate of recovery.

Another aspect of an interfacing structure in accordance with a preferred embodiment of the present invention is its relatively slow rate of return compared to known interfacing structures. A silicone or other rigid elastomer cushion has a relatively fast rate of return in the order of 5 to 10 cm/sec or higher. In one embodiment of the invention, the interfacing structure has a rate of return of less than about 5 cm/sec. In a preferred embodiment, the rate of return is about 1 cm/sec.

Rate of return can be measured by sandwiching a sample of bulk material between a bottom flat, rigid plate and a top flat, rigid, light plate. The top plate is moved downwards by a predetermined distance, compressing the bulk material and then is released. The time it takes the bulk material to raise the top plate to the original position is measured. The measure will be relative only, because the time taken to return to the original position will be dependent on the weight of the plate. The rate of return is equal to the thickness of the foam divided by the time to return. A relatively fast rate of return will take place in under a second.

The preferred type of foam was measured using the above mentioned rate of return test and a very light top plate (of rigid foam) was used such that the weight of the top plate was negligible. The block of foam sandwiched between the two plates was 5 cm thick and was manually sandwiched down until it was about 1 cm thick. It took 3.5 sec to return. This corresponds to a rate of return of about 1 cm/sec. By comparison, a typical prior art silicone membrane would return in under half a second.

Figures 1, 2, 3, 4, 5, 6, 7, 8, 9, 10, 11, 12, 13, 14:
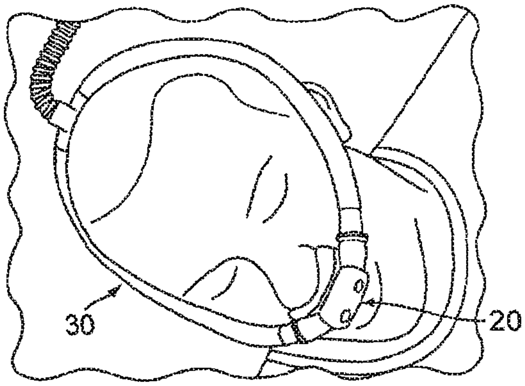

A related material property is hysteresis. With reference to FIG. 14-1, another aspect of a preferred embodiment of the invention is a material exhibiting hysteresis in the range of 25 to 35 percent. However, hysteresis of the foam may include other exemplary ranges. For example, the foam may exhibit hysteresis in the range of approximately 2 to 50%. In another embodiment, the foam may exhibit hysteresis in the range of approximately 5 to 40%. In another embodiment, the foam may exhibit hysteresis in the range of approximately 10 to 35%. In another embodiment, the foam may exhibit hysteresis in the range of approximately 15 to 35%.

Preferably, the foam interface has a permanent low resilience. In an embodiment, the foam has a resilience of less than about 40%. In another embodiment, the foam has a resilience of less than about 15%. Resilience is one measure of visco-elasticity. Low resilience foam has a high visco-elasticity, giving the foam a characteristic of slow deformation (slow recovery). The foam deforming at a slow rate enables the foam to conform gently to the wearer's face and gives a unique perception of comfort. Preferably, the cushion includes an antimicrobial agent.

It should be appreciated that the under-the-nose interface may be constructed of other materials that form a cellular polymeric structure, e.g., polyethylene, polypropylene, silicone, latex rubber.

It should also be appreciated that the under-the-nose interface may be constructed of other suitable material types and configurations, e.g., textile covered foam, textile, textile strata, silicone (e.g., dual wall silicone under-the-nose interface with membrane and undercushion), silicone foam.

In yet another embodiment, the foam interface features the foam acting as a HCH (Hygroscopic Condenser Humidifier) or HME (Heat and Moisture Exchanger). This allows heat and moisture to be captured and returned to the user's airway to increase breathing comfort as described above in relation to the jetting effect.

In another embodiment, the foam interface may be structured to provide acoustical properties, e.g., dampen noise, vibrations.

The porous moisture absorbing and moisture retaining properties of the foam allow for the addition of scented vaporous liquids to the interface before or during the wearing of the interface. Such scents may or may not be therapeutic in nature. The mechanical properties of the foam may be modified (e.g., pore size, surface tension) to adjust the rate of evaporation of the scented liquid. Similarly, the drying performance of the foam may be adjusted.

2.2 Bulk Material Properties

In the illustrated embodiment, the foam interface 80 is a very soft, flexible, visco-elastic foam (e.g., converted slab-stock) that has a soft, comfortable feel against the patient's skin and a hardness or stiffness that resembles the soft fleshy anatomy of the patient's face with properties as defined in FIG. 14-1. If sufficient stability and sealing reaction force is afforded by the patient interface design, the hardness will ideally be softer than the fleshy anatomy of the face. The hardness of the interface being softer than the anatomy it is interfacing with maximizes comfort by allowing for minimal pressure to be applied to the face to achieve an interface or pressure increase to the user's airway (i.e., low hardness and high visco-elasticity allows low contact pressure and maximal conformance to the contours of the patient's face (shape forming ability)). The interfacing dynamics are also improved whereby the interface conforms around the facial anatomy more so than the interface deforming the face, e.g., interface can accommodate relatively small features on the patient's face (e.g., facial creases and features which are the size of dimples on a golf ball, undulations, etc.).

The foam interface provides a static seal that may allow lower strap tension from headgear to create a sealing force and a dynamic seal that allows the interface to withstand macro-movement from a patient rolling around in bed and maintain an interface. Such interface properties are described in greater detail below.

The visco-elastic foam has a much more natural feeling against the patient's skin compared to conventional silicone interfaces, which may have a sweaty, plastic feel. The foam may include a moisture content, e.g., slightly moist or damp after usage or washing, which may provide a cooling effect or a refreshing feel when air flows through the foam in use.

A preferred form of interface in accordance with an embodiment of the invention is cut from a block of polyurethane foam. In a preferred embodiment, the foam interface 80 may be an unskinned, low hardness, low density, low porosity, soft, low odor, low air-permeability, low resiliency, low isocyanate index polyether polyurethane foam with a very fine heterogeneous cell structure and visco-elastic behavior. The foam also features color and colorfastness to a pantone reference. In addition, the foam may provide moisture wicking ability to wick moisture or sweat from the patient's skin. In an embodiment, properties of the foam interface may vary along its thickness, e.g., density, porosity, or hardness of the foam may vary in different layers, and/or properties of the foam interface may vary along its perimeter, e.g., breathability may vary in different regions of the interface's perimeter. Visco-elasticity is the range of recovery of the foam interface from compression. While it is preferable that a foam have all of these properties, in different forms of the invention, the foam may not have all of these properties, or may have various subcombinations of them. Also, the foam cushion may be constructed of another suitable material (e.g., non-foam material) that mimics one or more of the foam properties/characteristics as described above, e.g., micro cellular polyurethane.

Figures 7A, 8:
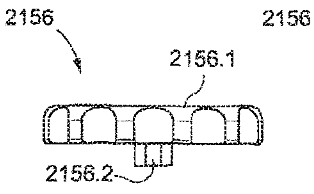
Figures 7B, 8:
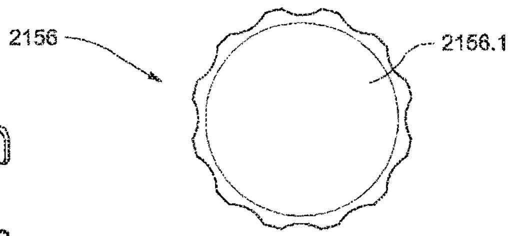

For example, FIGS. 13-3 to 13-4 illustrate foam with a mixed heterogeneous cell structure and FIGS. 13-7*a* and 13-7*b* illustrate foam with a layered heterogeneous cell structure. FIGS. 13-7*a* and 13-7*b* also illustrate how properties of foam may vary in different layers. As shown in FIGS. 13-7*a* and 13-7*b*, the foam may include three layers, i.e., small, medium, and large cell layers. In FIG. 13-7*a*, small cell layers are near the surface and the cell layers get gradually larger towards the interior, and in FIG. 13-7*b*, large cell layers are near the surface and the cell layers get gradually smaller towards the interior. However, the layers may have any suitable arrangement, e.g., medium layer near surface, then small and large layers towards interior. Such cell structure arrangements may be achieved depending on the choice of manufacturing methods.

Figures 7C, 8:
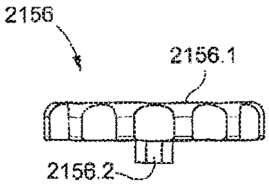
Figures 7D, 8:
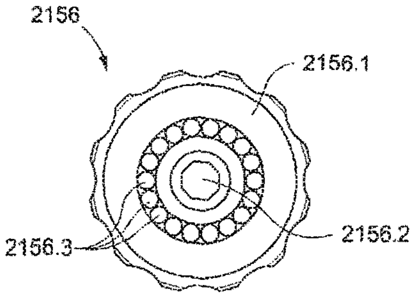
Figures 7E, 8:
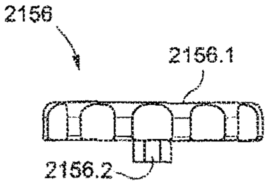
Figures 7F, 8:
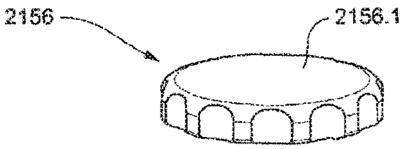
Figures 8, 8A:
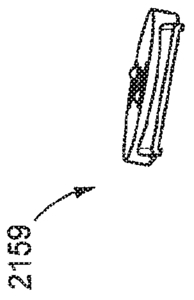
Figures 8, 8B:
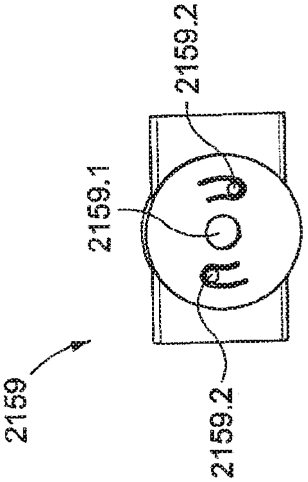
Figures 8, 8C:
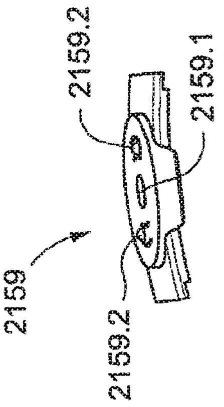
Figures 8, 8D:
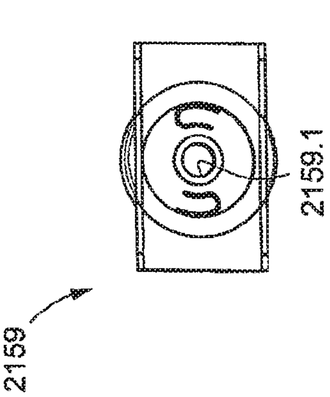
Figures 8, 8E:
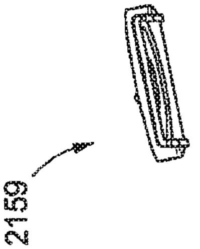
Figures 8, 8F:
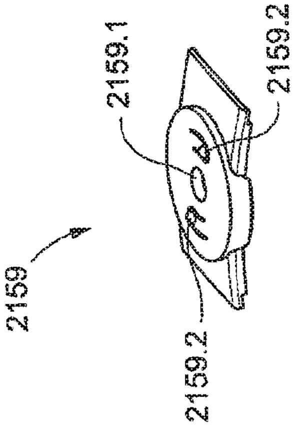
Figures 8, 9A:
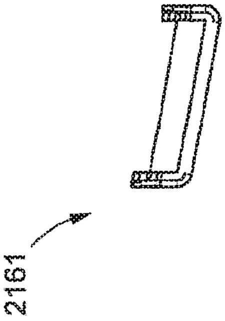
Figures 8, 9B:
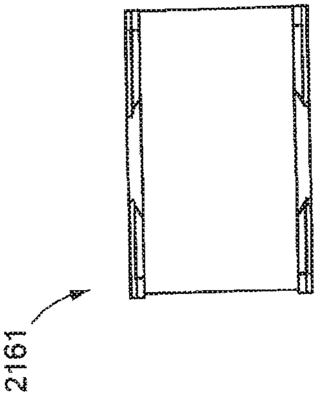
Figures 8, 9C:
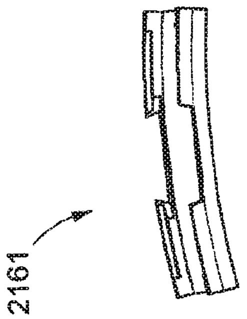
Figures 8, 9D:
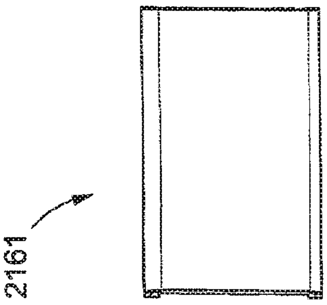
Figures 8, 9E:
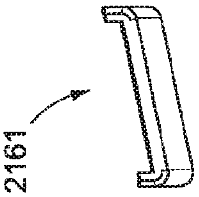
Figures 8, 9F:
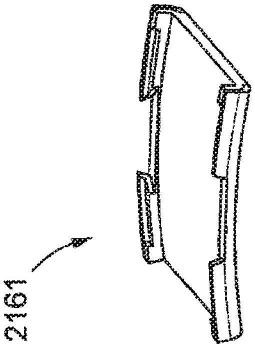
Figures 3, 9:
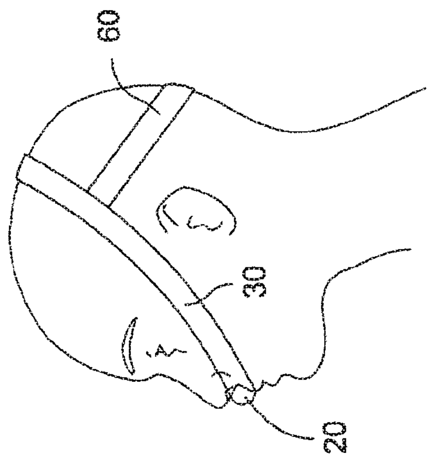
Figures 2, 9:
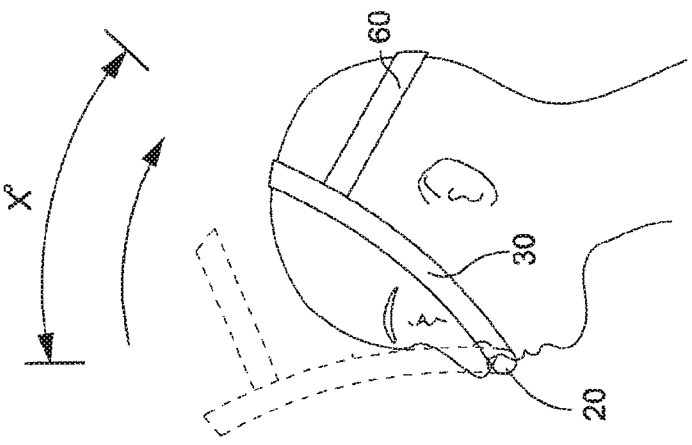
Figures 1, 9:
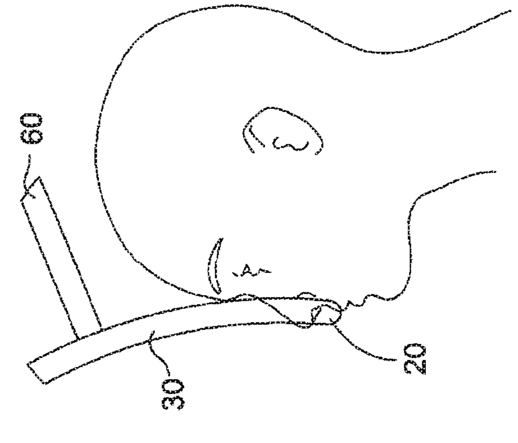
Figures 1, 10:
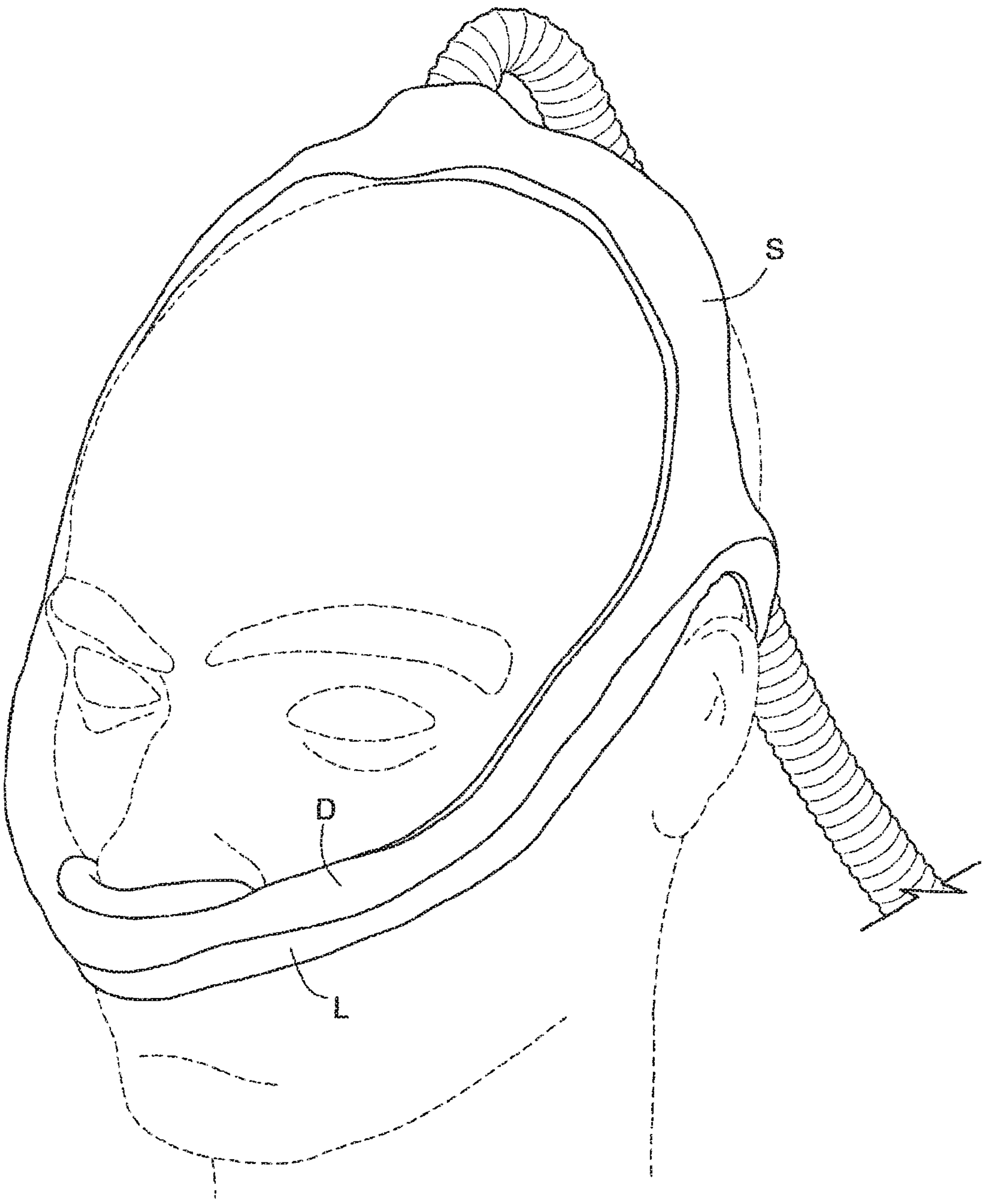
Figures 2, 10:
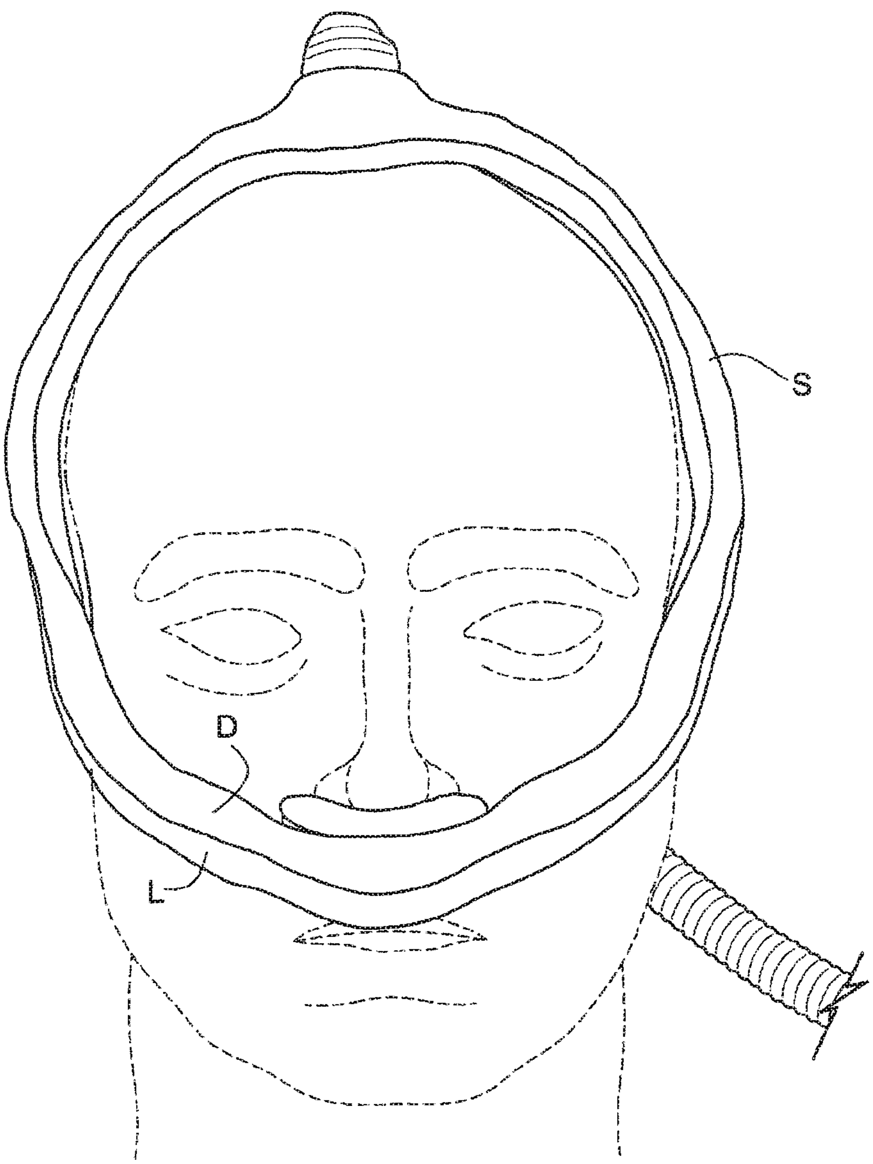
Figures 3, 10:
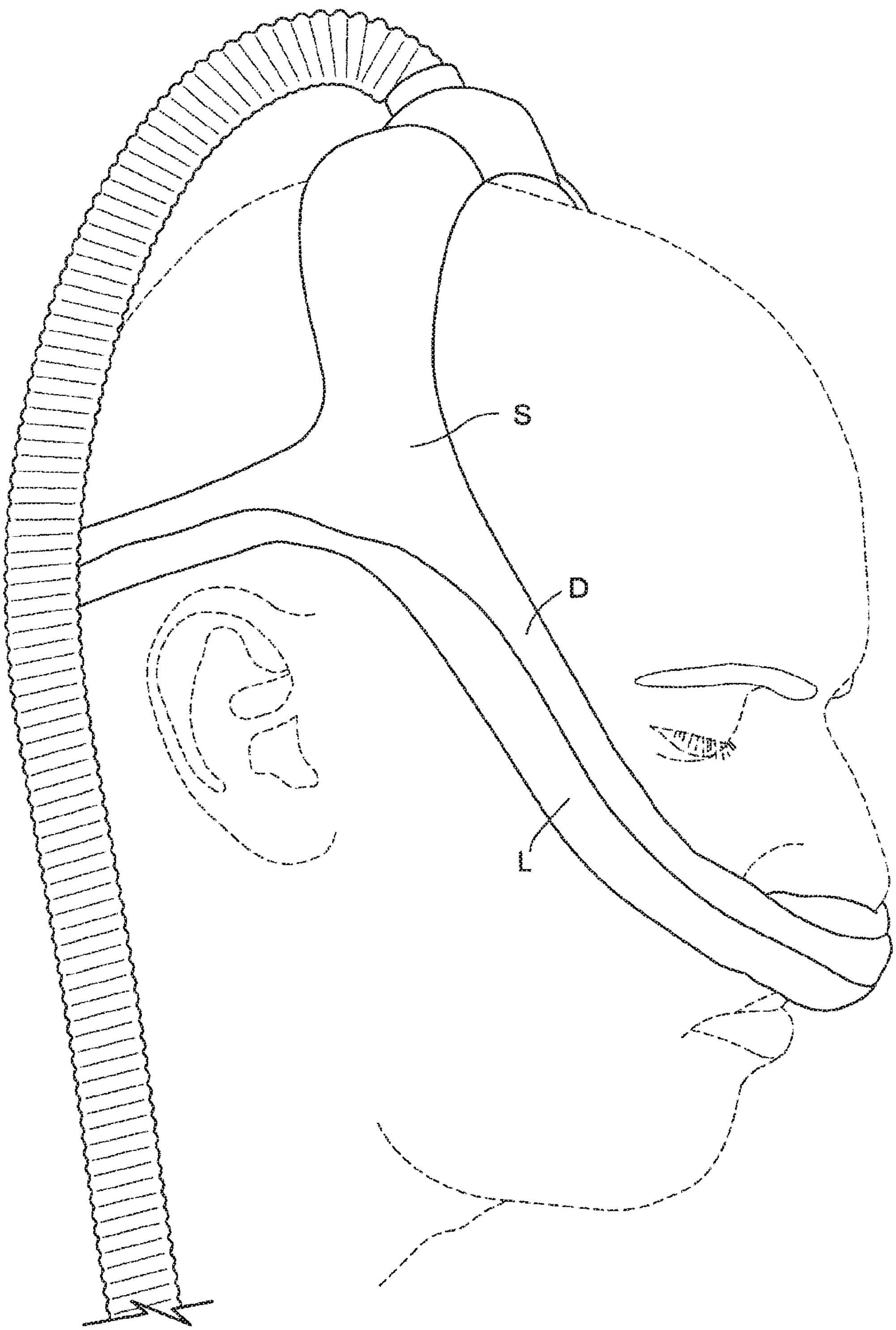
Figures 4, 10:
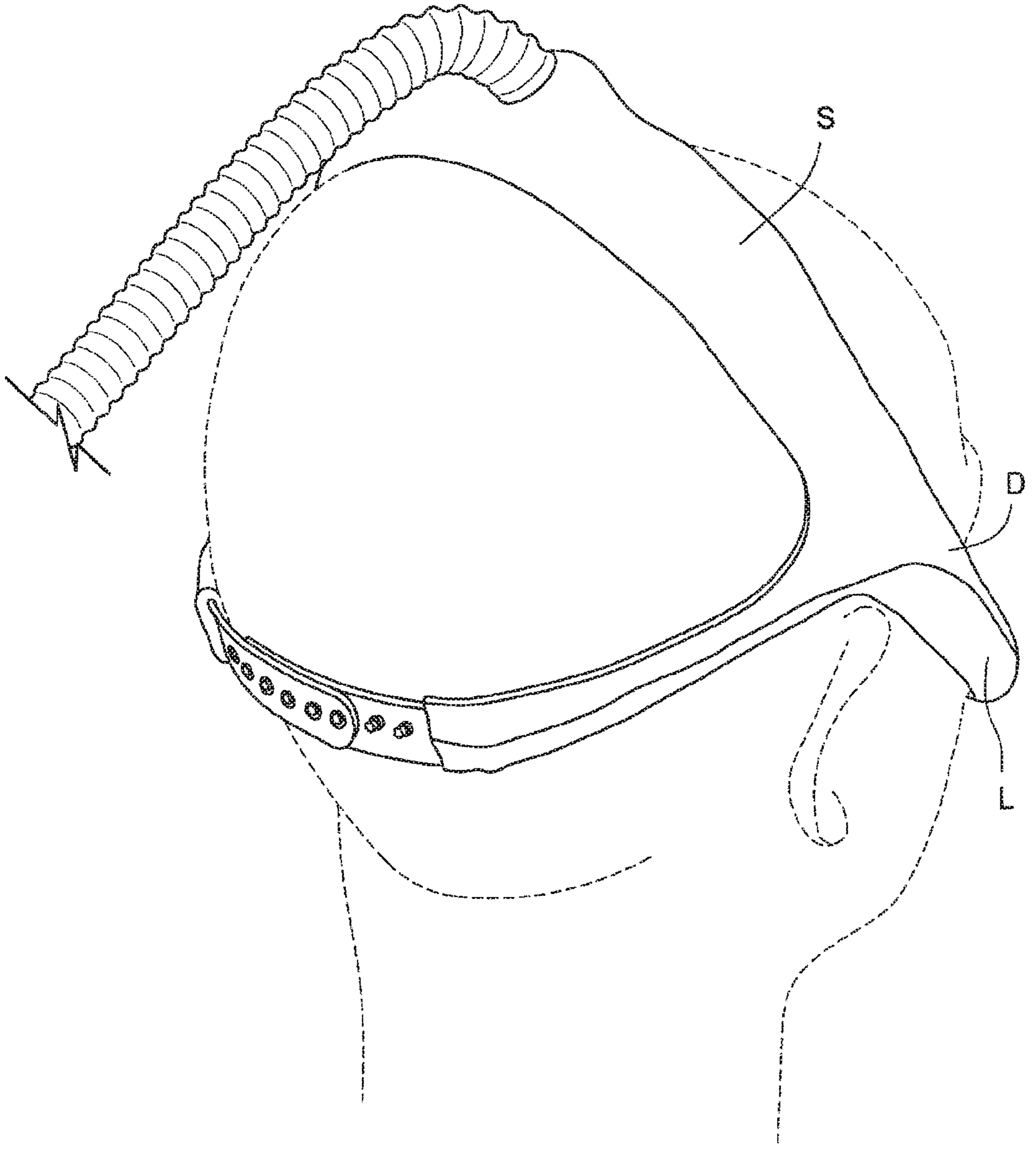
Figures 5, 10:
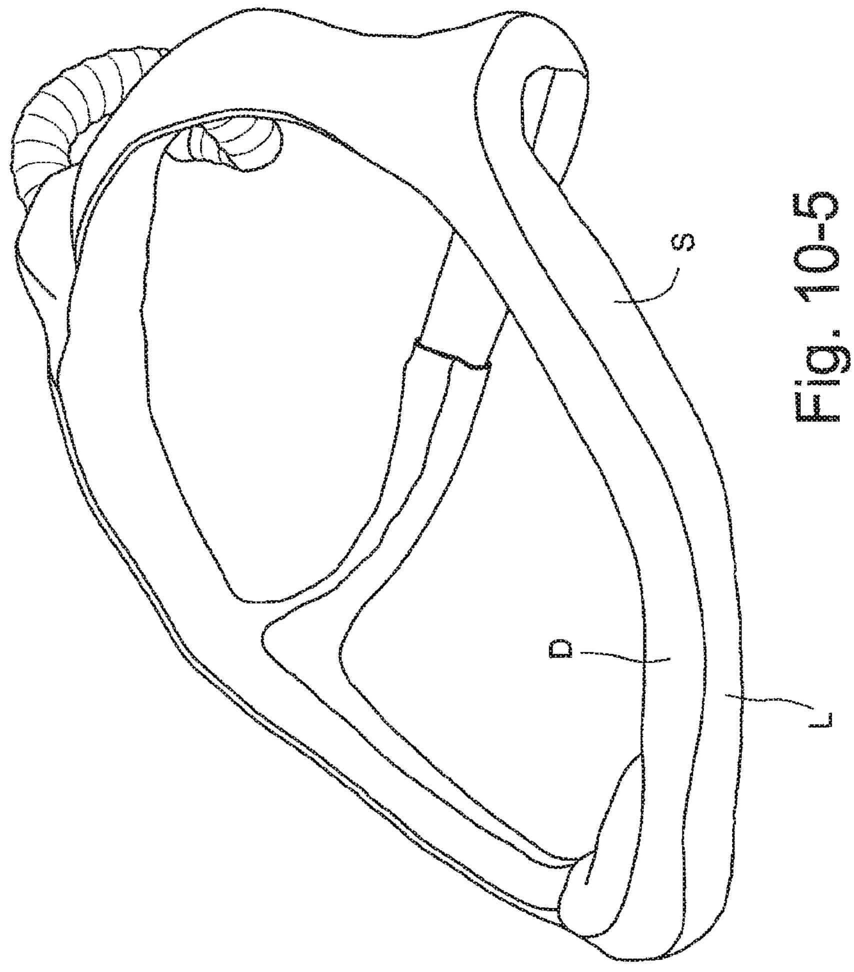
Figures 6, 10:
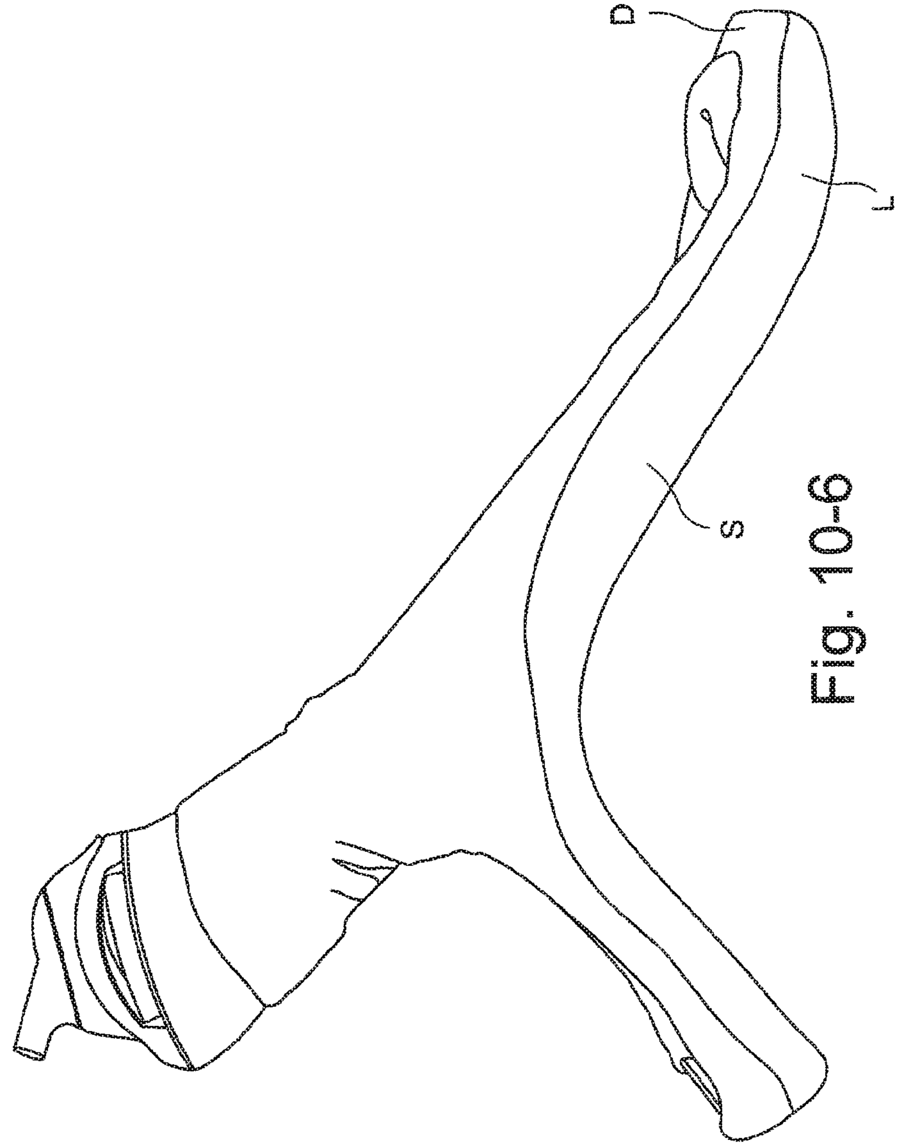
Figures 1, 11:
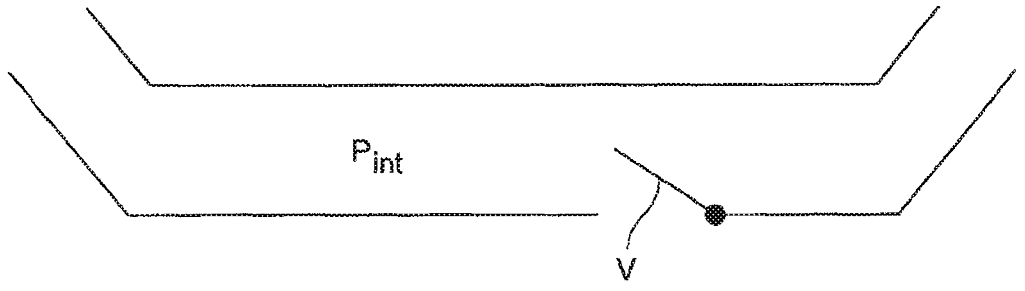
Figures 1, 12:
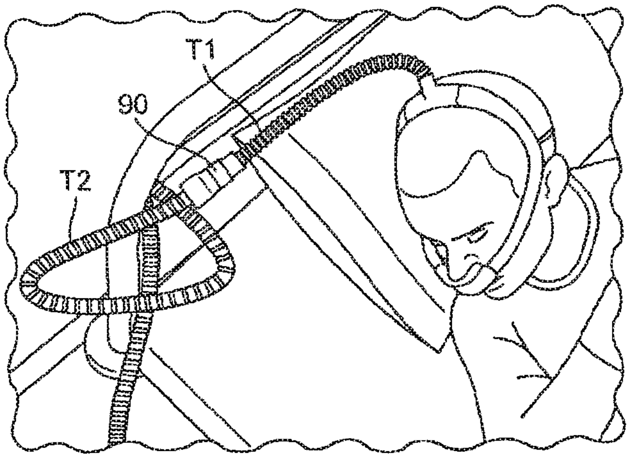
Figures 2, 12:
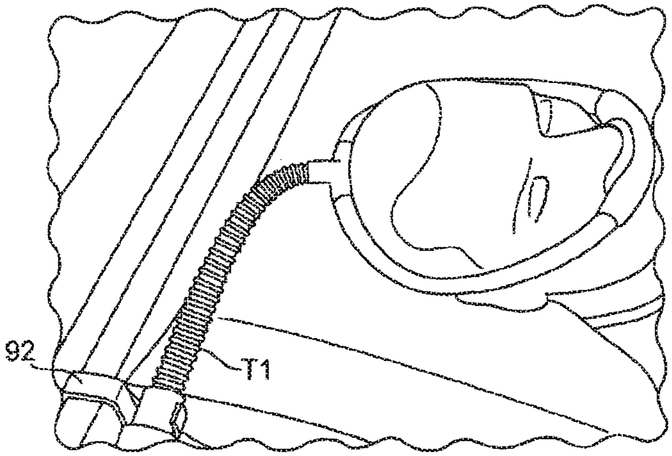
Figures 3, 12:
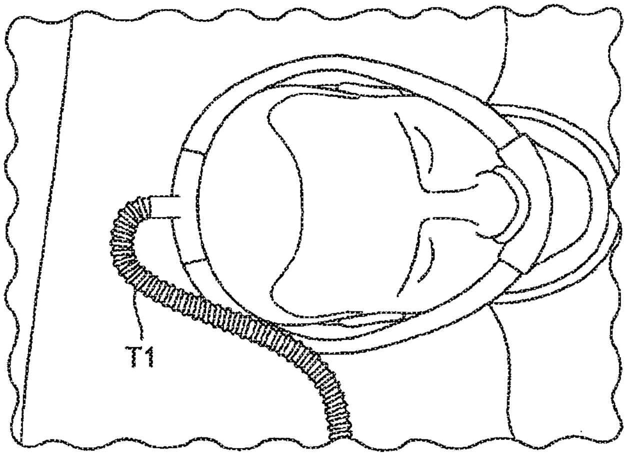
Figures 1, 13:
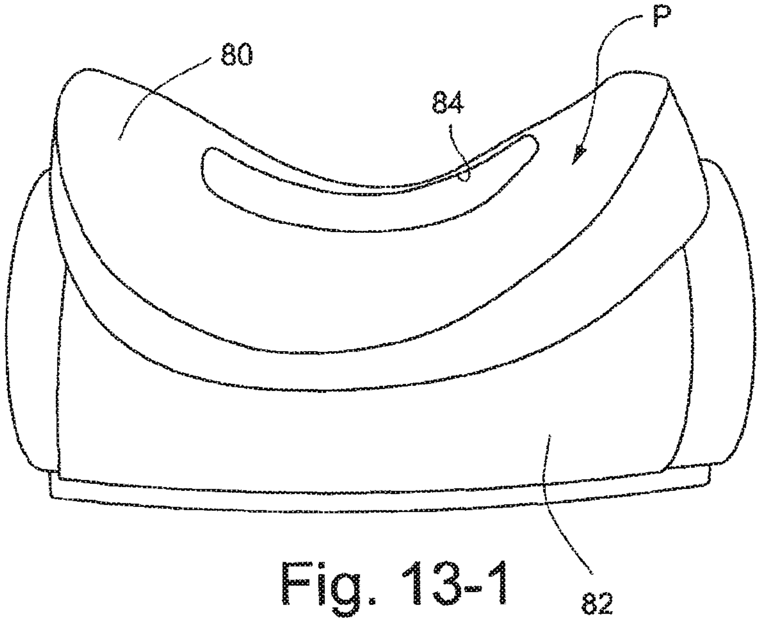
Figures 2, 13:
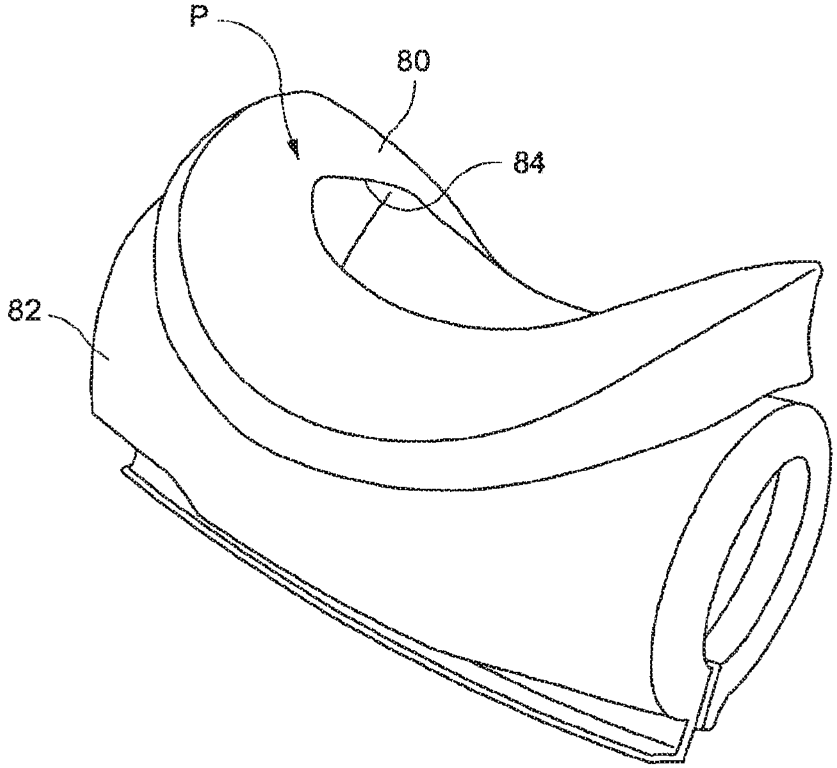
Figures 3, 13:
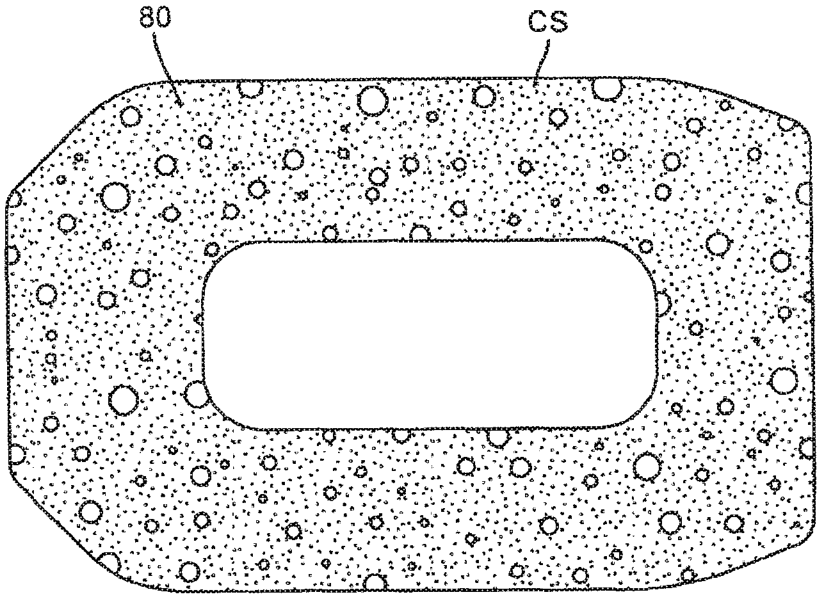
Figures 4, 13:
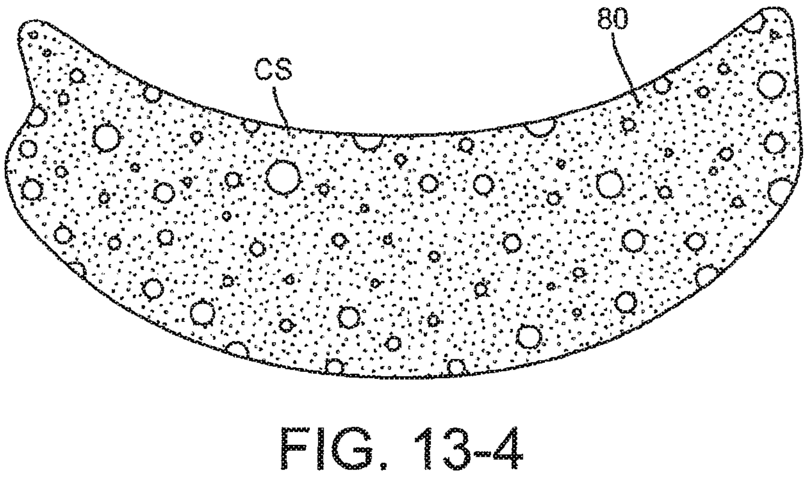
Figures 5, 13:
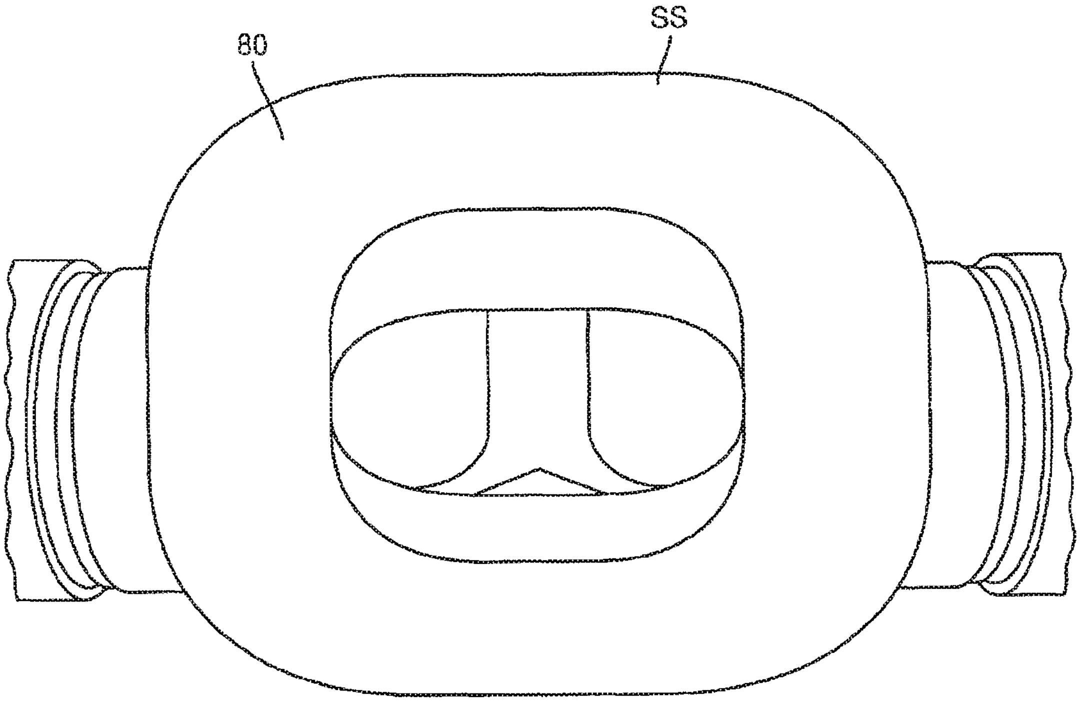
Figures 6, 13:
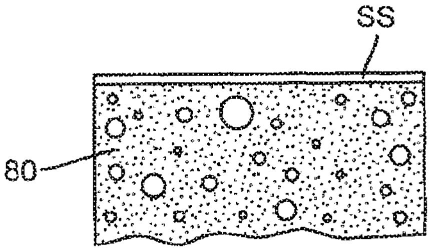
Figures 8, 13:
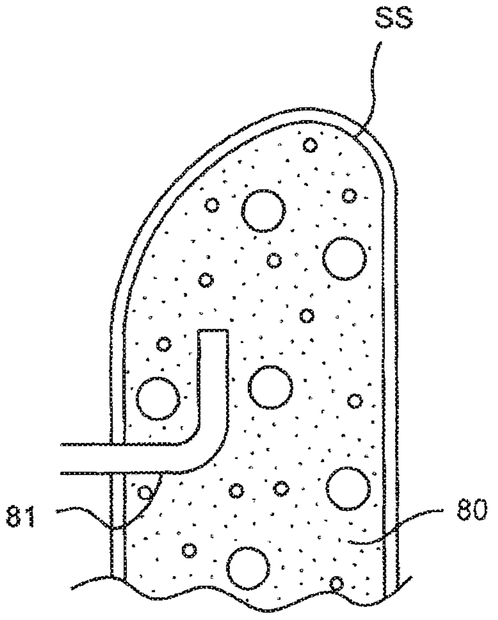
Figures 7A, 13:
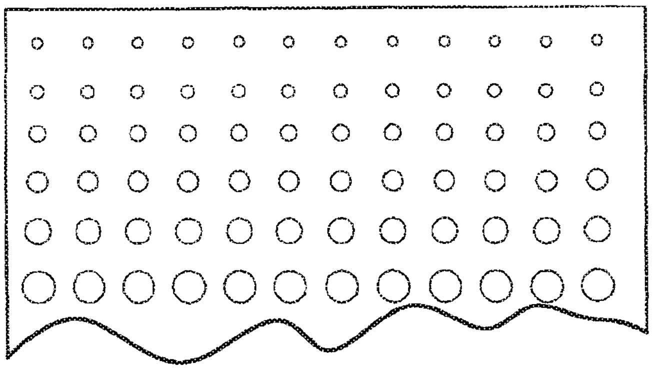
Figures 7B, 13:
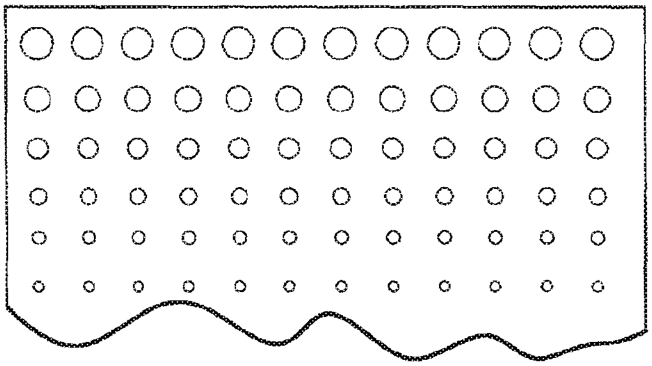
Figures 7C, 13:
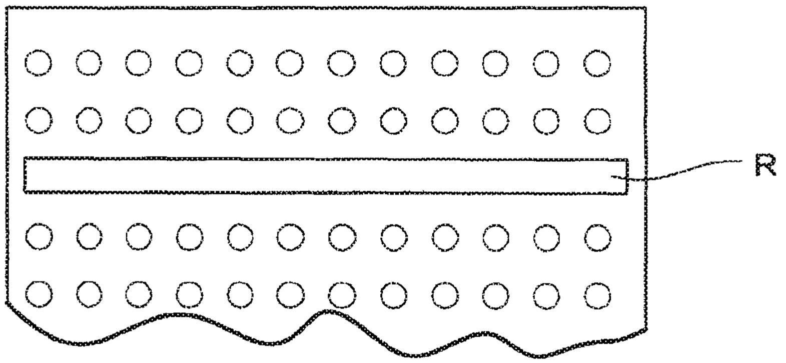
Figures 2, 14:
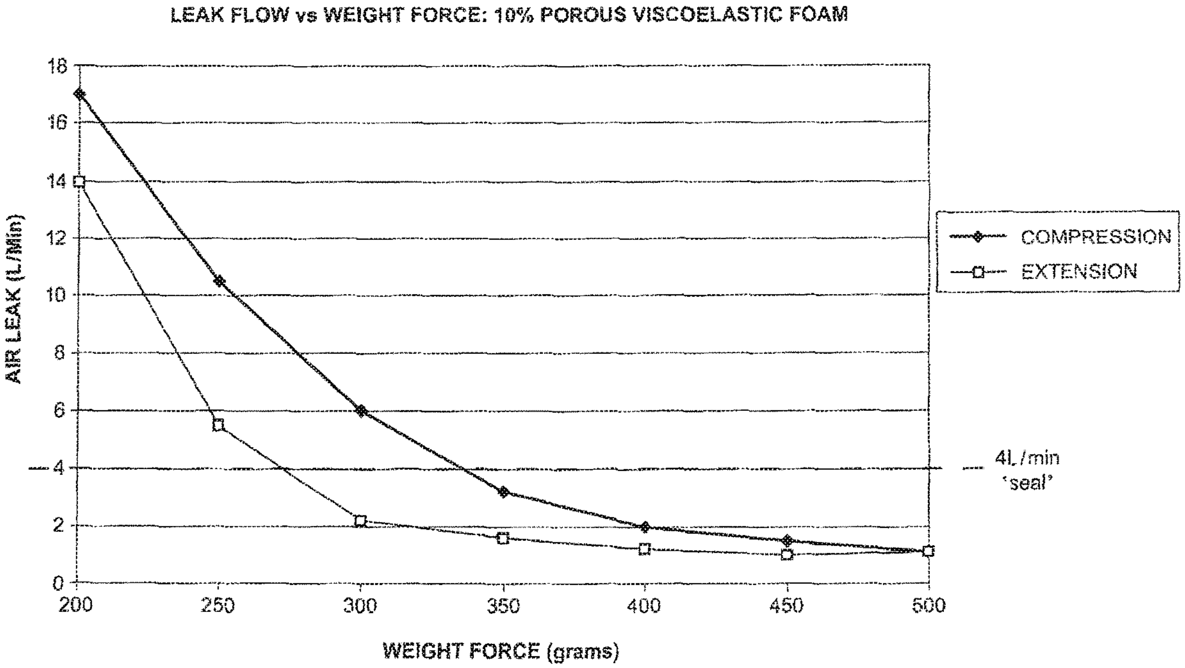
Figures 3, 14:
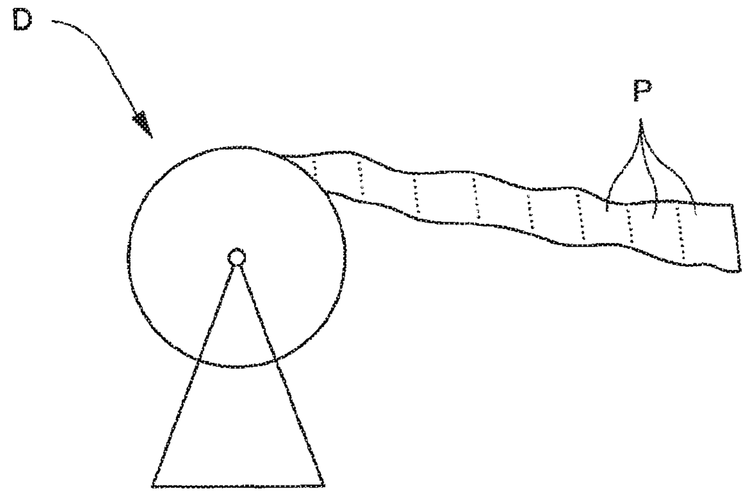
Figures 1, 15:
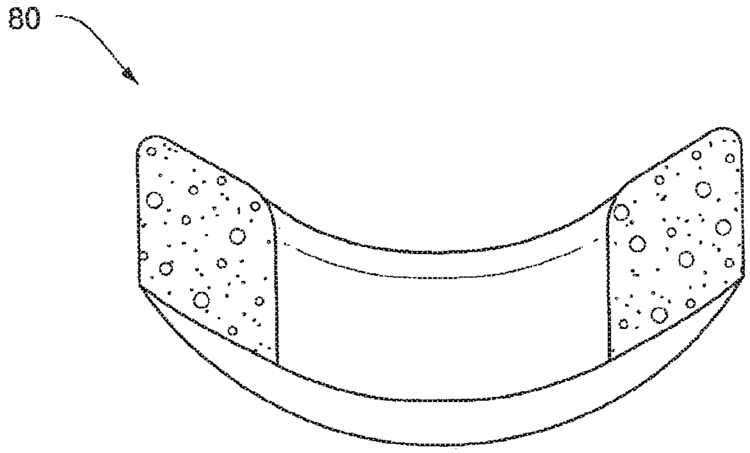
Figures 2, 15:
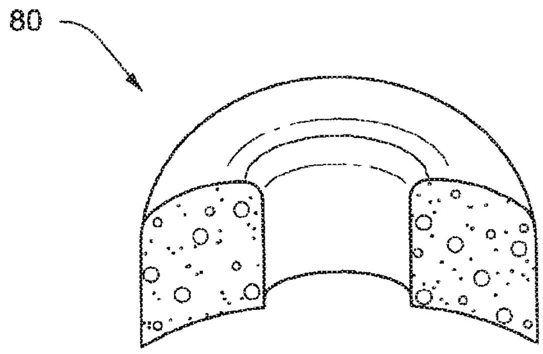
Figures 1, 3, 15:
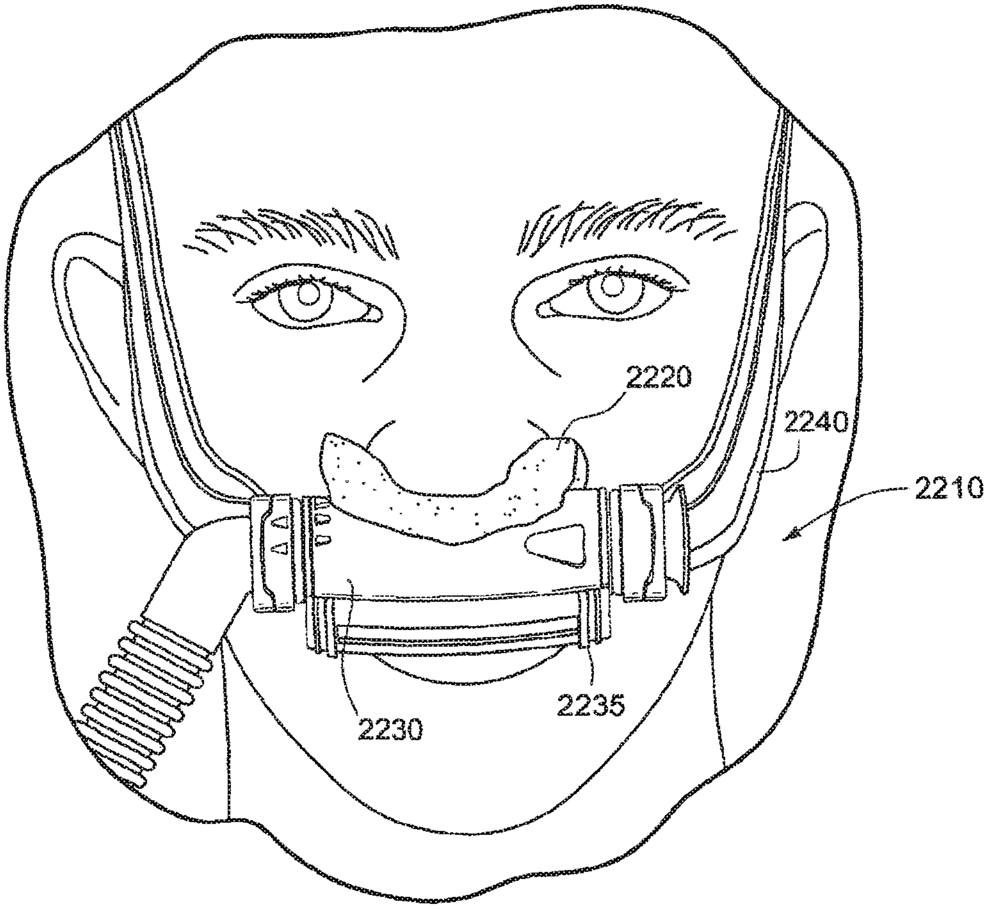
Figures 2, 3, 15:
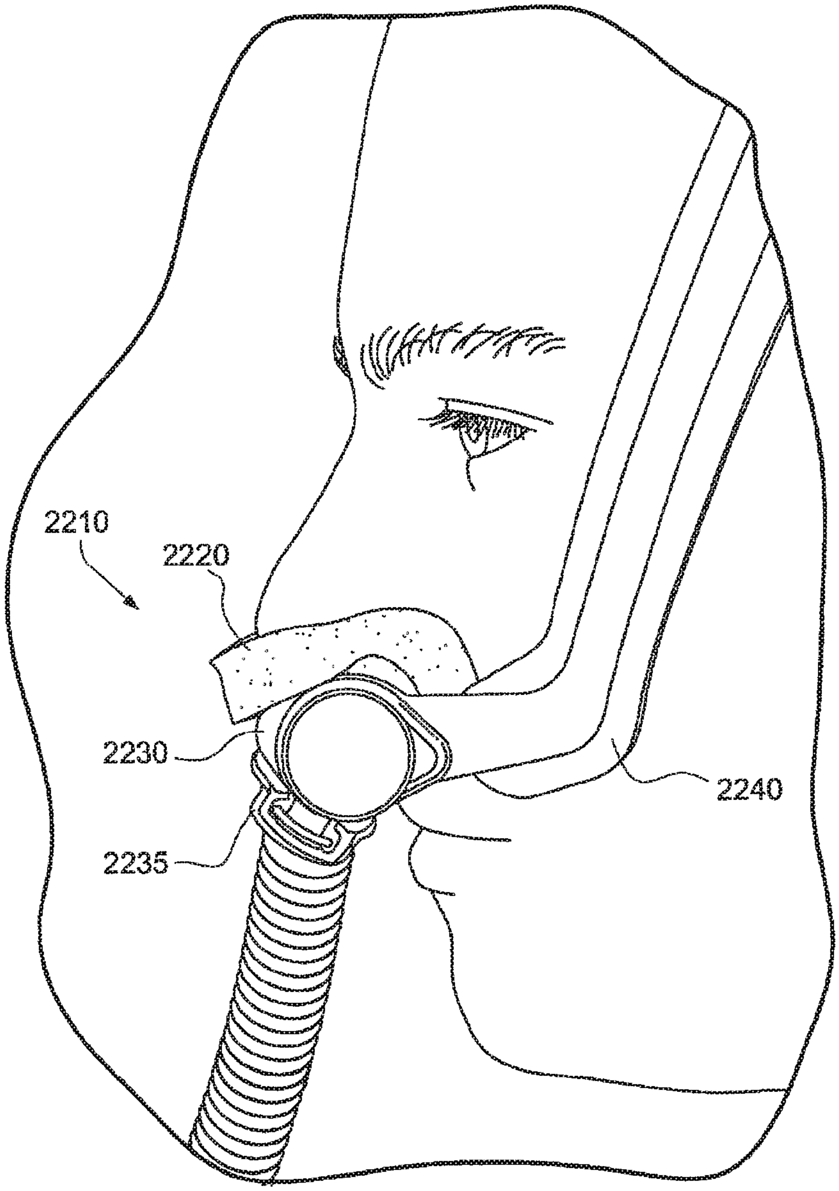
Figures 3, 15:
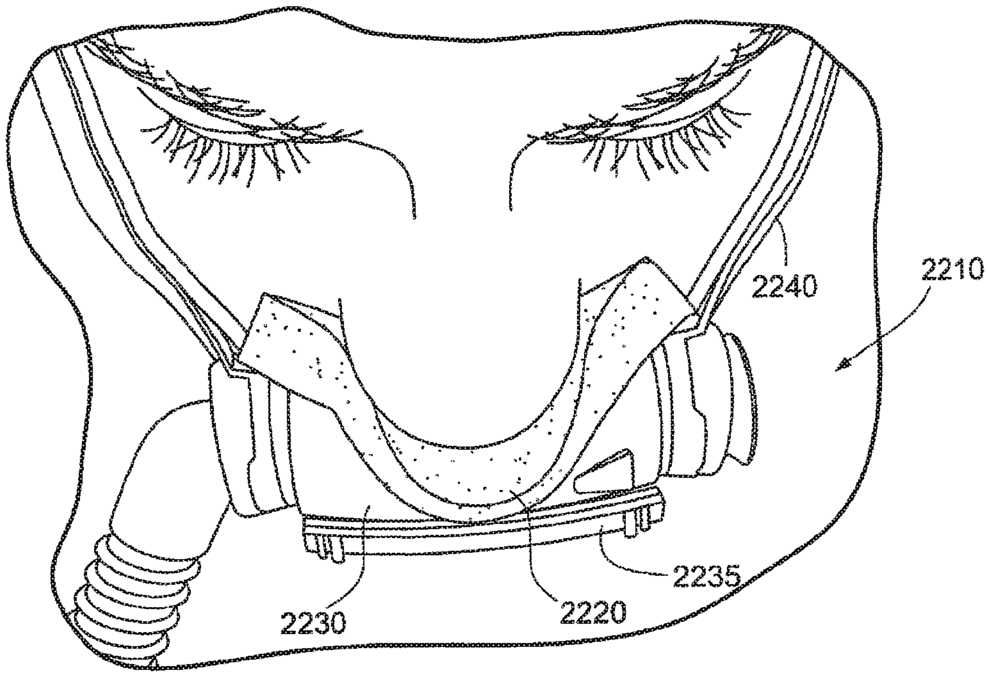
Figures 3, 4, 15:
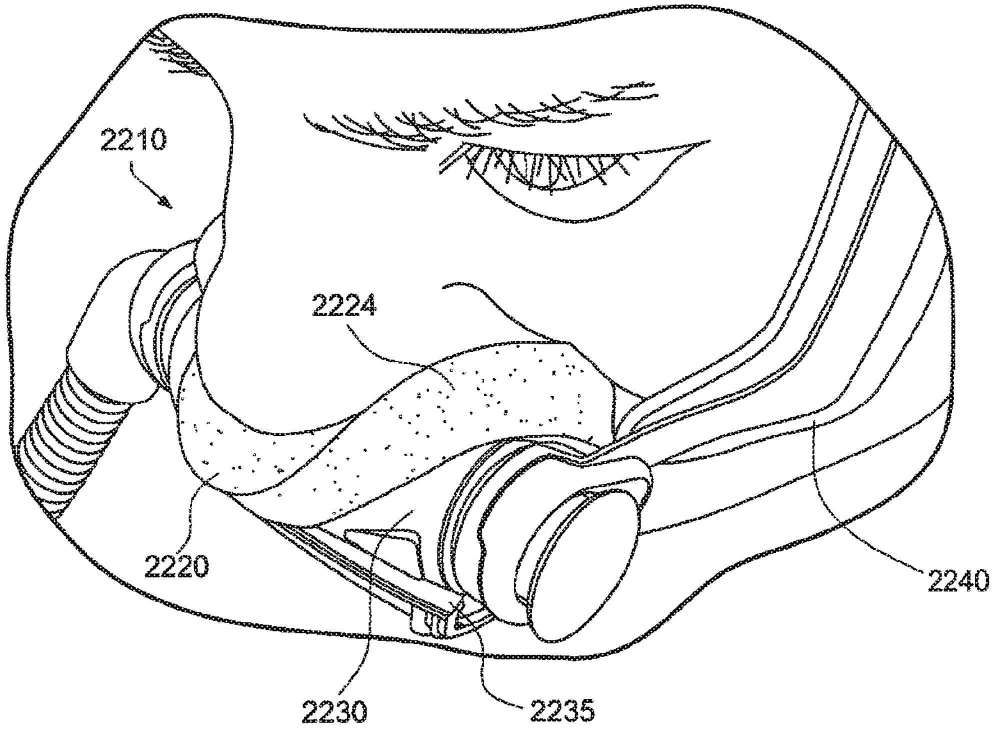
Figures 1, 3, 5, 15:
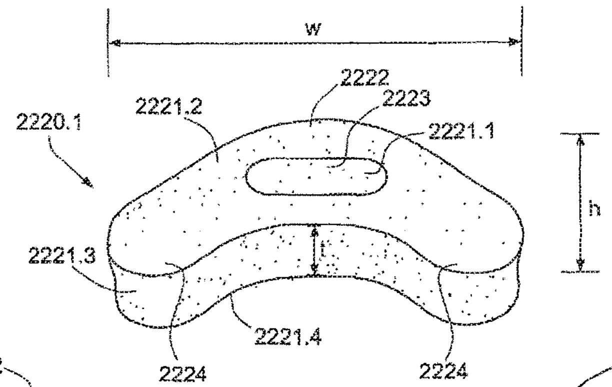
Figures 2, 3, 5, 15:
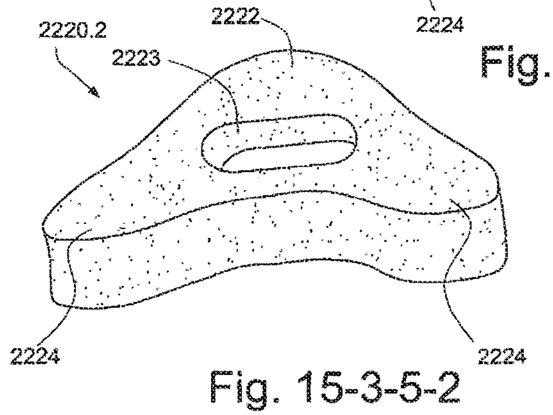
Figures 3, 5, 15:
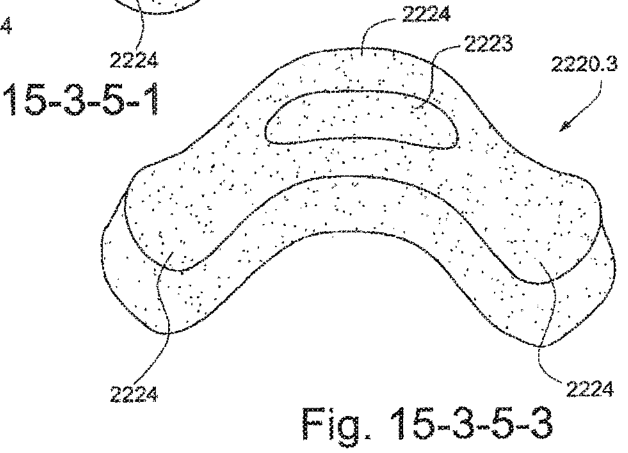
Figures 3, 6, 15:
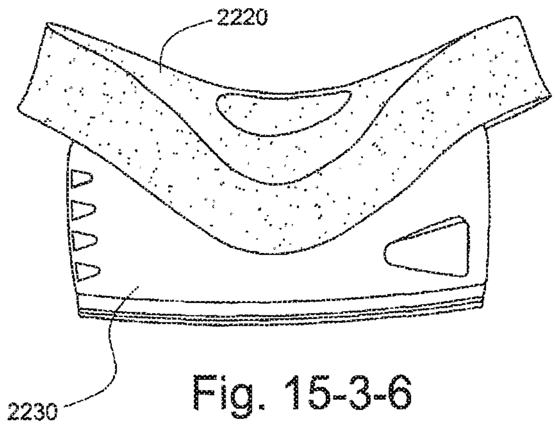
Figures 3, 7, 15:
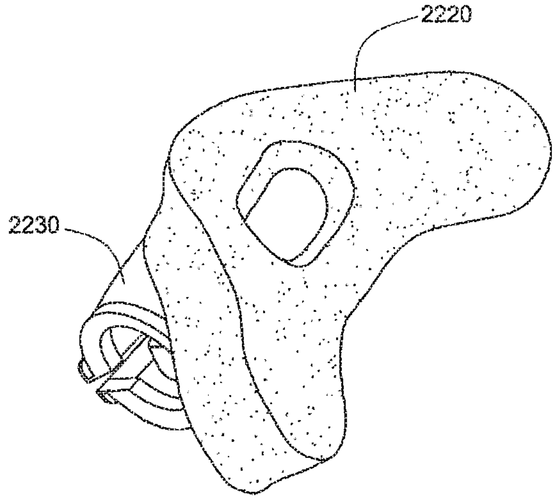
Figures 3, 8, 15:
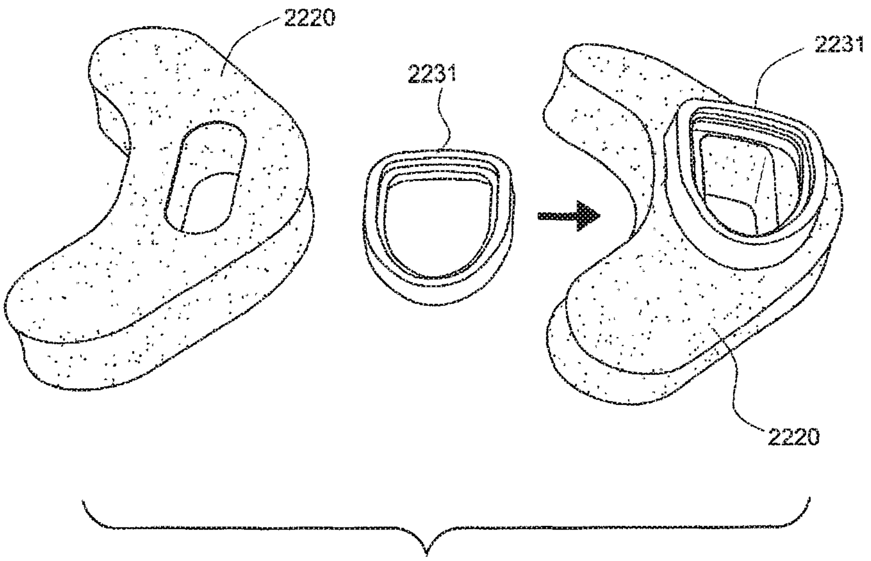
Figures 1, 3, 9, 15:
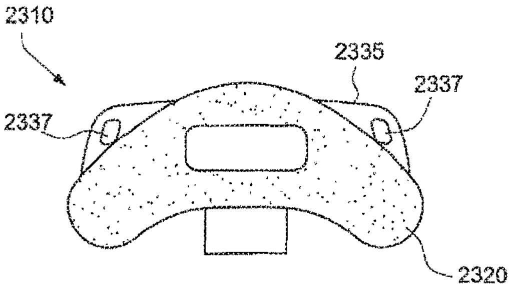
Figures 2, 3, 9, 15:
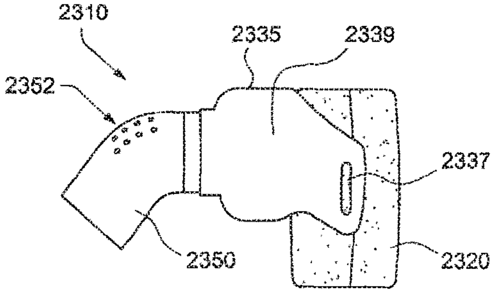
Figures 3, 9, 15:
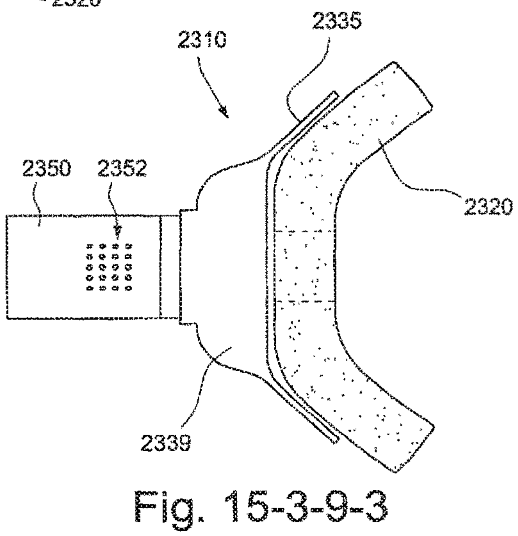
Figures 1, 16:
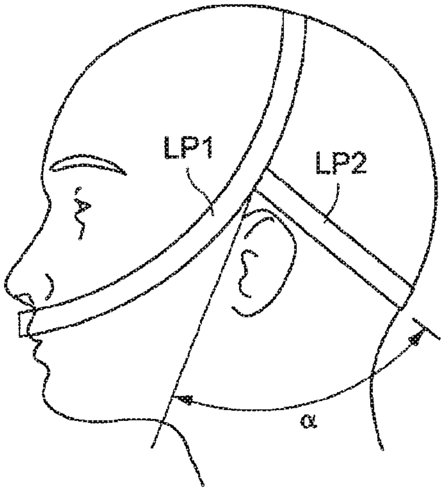
Figures 2, 16:
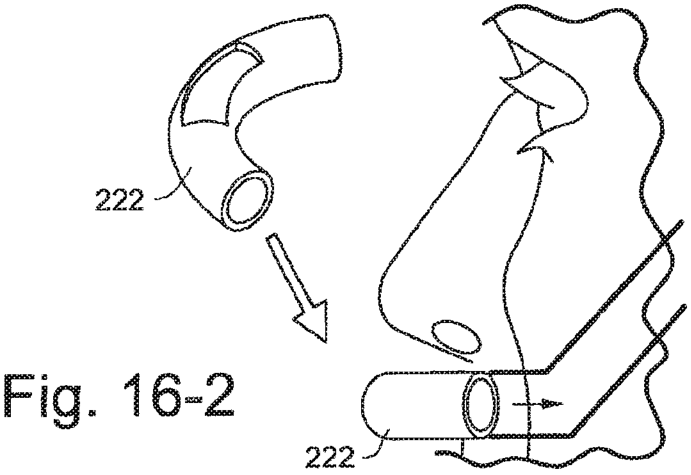
Figures 3, 16:
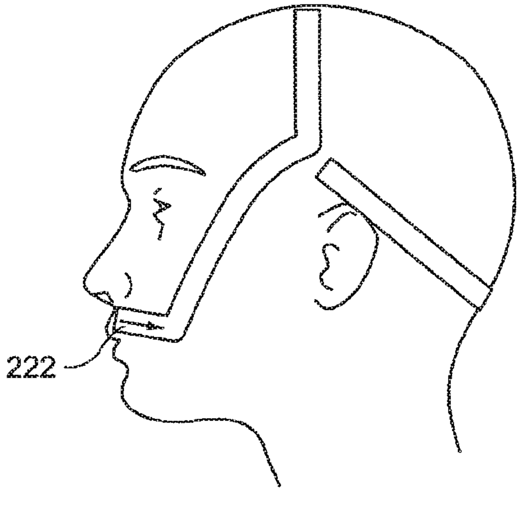

FIG. 13-7*c* illustrates a foam including a reinforcement element R, e.g., constructed of a laminate of stiffer foam, plastic, or metal, at an interior portion thereof. The reinforcement element R is structured to add rigidity to the foam in use. The foam portions on each side of the reinforcement element may include a homogeneous structure (as shown in FIG. 13-7*c*) and/or a heterogeneous structure (layered or mixed). In a preferred embodiment, the reinforcement element R may be situated on one side of the foam interface, e.g., the bottom/non-facial contacting surface. In this way, the reinforcement may provide dual functionality, i.e., providing both reinforcement and a method for attachment to the mask (e.g., mechanical interference fit, Velcro, pressure-sensitive adhesive).

FIG. 14-1 illustrates a table of mechanical properties of a foam interface according to an embodiment of the present invention.

One aspect of a preferred embodiment of the present invention is the low hardness of the foam (or other soft material) of the sealing structure. Hardness can be defined in terms of both indentation and compression hardness. An exemplary ILD hardness @ 40% is in the range of 25 to 80 N while an exemplary CLD hardness @ 40% is in the range of 0.4 to 1.5 kPa.

However, the foam hardness may include other exemplary ranges. For example, a preferred ILD hardness @ 40% may be in the range of 50-200N. In another embodiment, the foam may have an ILD hardness @ 40% generally less than about 100 N. In another embodiment, the foam may have an ILD hardness in the range of less than about 80 N. In another embodiment, the foam may have an ILD hardness in the range of about 20 N to about 80 N. In another embodiment, the foam may have an ILD hardness in the range of about 25 to 80 N. In another embodiment, the foam may have an ILD hardness of approximately 40 N to 60 N. If the foam is too hard, it will not conform to the wearer's face and seal. Subsequently, this can lead to pressure points, or sores on the patient's face. Similarly, if the foam is too soft it will not provide sufficient force to seal against the skin, potentially "bottoming-out" and also causing discomfort. A thinner layer of foam (e.g. 5 mm to 10 mm) may be constructed using a harder foam (e.g. ILD hardness at 40% between 100N to 200N)

In an embodiment, the foam has a density of less than about 60 $kg/m^3$. In another embodiment, the foam has a density of about 55 $kg/m^3$. In another embodiment, the foam has a density in the range of about 30-60 $kg/m^3$. In another embodiment, the foam has a density in the range of about 30-200 $kg/m^3$, or 50-150 $kg/m^3$, or 75-125 $kg/m^3$. In another embodiment, the foam has a density in the range of about 50-60 $kg/m^3$, or 60-100 $kg/m^3$. A suitable foam density balances stability, comfort and ease of use. If the density is too low, a foam interface may lack stability.

Preferably, the foam has an internal cell structure that is permeable. Having the foam permeable has the advantage of allowing transport of air and moisture through the foam, which can also moderate the temperature at the foam-skin interface, all of which improves the comfort for the wearer. In a preferred embodiment, the foam may have a low permeability. This strikes a balance between having sufficient air flow to be comfortable, but low enough air flow so as to not be disturbing to the wearer, as well as maintaining sufficient therapeutic positive pressure at the airway (if the foam is too permeable pressure is lost at the airway). Preferably, the foam has a permeability in the range of 10 to 50 $L/s/m^2$, although in some forms, an impermeable foam may be used. Hence, it may not be necessary for the foam to form a complete seal provided an adequate supply of air can be provided at appropriate pressures and flow rates for effective therapy.

In another embodiment, the foam has a preferred permeability of less than about 10 L/min @ 125 Pa, more preferably less than about 5 L/min @ 125 Pa. However, the foam permeability may include other exemplary ranges. For example, where a layered foam structure is used, the different layers of foam may have different permeabilities.

Figures 1, 2, 3, 4, 5, 6, 7, 8, 9, 10, 11, 12, 13, 14, 15:
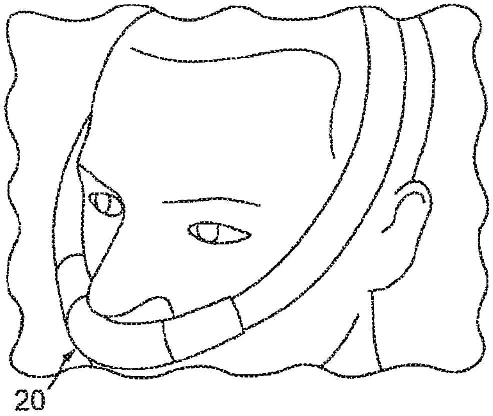

As shown in FIG. 15-3-1 which is described in greater detail below, the foam interface includes four generic surfaces. As illustrated, the interface includes an air path (inside) surface 2221.1, a skin contact (sealing) surface 2221.2, an atmospheric (outside) surface 2221.3, and an attachment (mask attachment) surface 2221.4. Each of these surfaces may be permeable, impermeable, or a combination thereof. Accordingly, it should be appreciated that the interface may have multiple degrees or ranges of permeability.

The foam interface according to an embodiment of the present invention may also include a degree of one or more of the following characteristics:

Cellular foam type—flexible polyurethane;

Polyurethane type—polyether based;

Cell structure—control of the cell structure of the foam is desirable to control the feel (also known as the "hand") and look of the foam. The cell structure may be controlled to have a more heterogeneous or more homogeneous distribution of cell sizes, and this can affect the feel and look of the foam in various ways. The foam can also be produced to have a cell structure with varying degrees of open and closed cell content, which can affect several aspects of the foam's properties, e.g., air and moisture permeability.

Sealing—foam with a high closed cell content may have sufficiently low permeability so that a positive pressure seal may be created inside the interface upon compression against the skin. In an embodiment, the foam may include significantly more closed cells than open cells, e.g., 90% closed and 10% open. The compressive force provided by the foam to seal is therefore a function of the mechanical stiffness of the foam, and also the compressive stiffness added by having pressurized air inside the foam's cellular structure (e.g., air spring/air pressure stiffness). In this manner, the sealing function is provided while still allowing a small deliberate flow of air to escape along the surface and through the body of the foam structure. In embodiments, the foam has a cut, open cellular structure against the skin, however other embodiments may include foam that has a permeable skin. Another embodiment may have foam that is skinned (both permeable and impermeable skin) only on the skin contacting surfaces of the interface, leaving flow to pass through the body of the foam structure rather than along the skin-contacting surface.

Air permeability—the foam can be produced to have a controlled range of air permeability. Typically, for a sealing application, foam would be produced to have the highest closed cell content possible to prevent air or moisture from passing through the foam. In an embodiment, it may be desirable that there is allowed a relatively small amount of air permeability. This has several distinct advantages in relation to both the comfort and sealing performance of the interface when it is worn, e.g., allowing a small, diffuse flow to pass through the foam gives the skin in contact with the interface the ability to breathe, and for excess moisture to be removed from the interface during use;

Air permeability durability—maintenance of the desired level of air permeability throughout the component usage life is desirable because the flow through all elements of the mask system may be required to meet a given specification. Changes in air permeability can occur with cyclic mechanical compression loading therefore measures that are taken to improve the durability of the foam structure in relation to its permeability are an advantage. In a preferred embodiment, a polyurethane formulation that uses an MDI (Methylene-Bis-Di-Isocyanate) type isocyanate may be chosen to give the foam a durable closed cell content;

Odor/Volatiles—As the foam is intended to be used in close proximity to a person's nose, any measure that can be taken to minimize or preferentially modify the odor is an advantage. In a preferred embodiment, a polyurethane formulation that uses an MDI (Methylene-Bis-Di-Isocyanate) type isocyanate (e.g., a refined MDI) is a preferred choice to minimize odor. In other forms, a toluene di-isocyanate (TDI) may be used, although such a foam may have higher odors. In an embodiment, the foam cushion may be structured to provide an aromatic scent;

Particulates—The chemistry and processing of the foam is chosen such that the foam component will not produce small particles that may be inhaled during use;

Feel/Hand—There are aesthetic advantages to producing the foam to have a feel that is silky and soft. In a preferred embodiment, the foam is produced to have a fine cell heterogeneous cell structure to maximize the smooth feel of the foam, and this can also aid in minimizing the potential for skin abrasion and irritation. Another aspect of the foam's mechanical properties that may aid its aesthetic appeal is for it to be produced with a high level of visco-elasticity, which gives the foam an intriguing interactive property;

Durability—The foam chemistry may be chosen so that it maintains its desired mechanical properties for the required shelf life and usage life of the component (e.g., foam structure may be manipulated to have predetermined life span, ranging from single use to long term use). This affords the advantage of providing a renewable product to the user on suitable replacement frequencies whereby the foam component may be replaced on a daily, weekly, monthly or other basis. Components that are packaged in predetermined multiples may then be supplied to the user, e.g., on a 3, 6, or 12 monthly or other suitable basis;

Thermal stability—the foam may be designed to withstand the thermal conditions of storage and transportation. It may also be designed to withstand the temperatures of disinfection and sterilization processes (e.g., autoclaving temperatures and potentially temperatures up to 180 degrees);

UV stability/Light fastness—the foam material will not breakdown easily with light exposure;

Swelling resistance—the foam component may be designed to have given swelling characteristics when saturated with water or other liquids. It may be designed to minimize or maximize its change in geometry depending on the desired characteristics of the foam under saturated conditions (e.g., swelling may be desirable to open the pores of the foam for cleaning, swelling may be undesirable to preserve the functional geometry under saturated conditions);

Dryability—the foam component may be designed to become dry under specific time constraints and environmental conditions, e.g., the component may be moist after usage or cleaning procedures so it may be desirable for the component to dry as quickly as possible prior to further usage, e.g., moisture in the interface may be desirable under certain usage conditions (cool feeling against the skin in hot conditions), so it may be advantageous for the component to retain moisture for longer periods of time, e.g., the component may be designed to dry during use by the air flowing through the material under the pressurized conditions during CPAP therapy (self drying);

Hydrolytic stability—the chemical formulation of the polyurethane foam may be chosen to give the foam a desired level of hydrolytic stability. The choice of a polyether type polyol over a polyester type polyol may give the foam improved resistance to hydrolysis (mechanical breakdown in the presence of moisture);

Color—the foam component may be colored to a defined Pantone reference (e.g. PC287);

Color fastness—A key challenge with respect to the use of foams is discoloration, both from natural aging and environmental factors during use. This is particularly an issue with natural and light colored foams. One method of countering discoloration is to deliberately color the foam with colors that change less obviously with age and usage (e.g., darker and more intense colors may discolor less). That is to say that the coloring of the foam has a functional attribute in preserving the perceived utility and cleanliness of the component during its usage life. Another issue that may occur is the running of any dye or pigment that is removably included in the foam structure. In a preferred embodiment, a reactive colorant is incorporated so that color reacts into the foam chemical structure so that it becomes part of the polyurethane chemical background, e.g., Reactint™ Colorants from Milliken Chemical. This gives the foam a significant advantage in its intended application to resist discoloration such that the product presents well upon initial usage and remains presentable with ongoing use;

Slabstock packaging—slabstock foam may be wrapped and sealed in plastic for shipment and storage;

Component packaging and distribution methods—The foam interface components may be designed to have a predetermined usage life. In this case, the component may need to be replaced on a more frequent basis than that which is currently known in the industry. For convenience of replacement, the component may be packaged to include multiple components in one package (e.g., box or carton). For example, one box or carton of components may include 50 components, 100 components, monthly supply of components, yearly supply of components, or other suitable basis. Components may be individually packaged and manufactured as part of a continuous perforated strip and provided in one package (e.g., single foam interface in one package similar to a condom wrapper having two side walls sealed about their perimeter). The components may be in grouped or solitary component cells. In an embodiment, a significant advantage is afforded by vacuum packaging the components. This form of packaging offers protection against aging from environmental factors (e.g., oxygen, humidity), as well as the ability to provide the component in a customized micro-environment (e.g., inert gases to prevent aging, scented gases for therapeutic and non-therapeutic purposes, color, flavor). Vacuum packaging also offers a significant advantage in reducing the physical volume of the product for shipping efficiency and logistical convenience. The foam can be compressed for extended periods of time—weeks or months—and still return to its uncompressed shape when the package is opened. FIG. 14-3 is a schematic view of a rotatable dispenser or reel D adapted to dispense individual packages P containing a foam interface, e.g., continuous stream of individual packages separated by perforations to allow perforated tear-off. However, the components may be separated by other suitable frangible or breakable connections.

Machinability—foam may be produced to be sufficiently dense and hard so that it can be machined into intricate 3D geometries;

Biocompatibility—Biological safety (biocompatibility) is paramount in the main intended applications for the foam. It must therefore not emit any harmful volatiles or have any harmful or irritating interactions with the human body. The chemistry and processing of foam is chosen to produce a foam that is in compliance with ISO 10993 biocompatibility standards;

Microbial growth—The foam structure may provide an environment that houses potential microbial (e.g., bacterial, fungal) growth, particularly in the presence of warmth and humidity and in close proximity to the nose. Any measures that can be inhibitory to the growth of fungus and bacteria may be desirable to preserve the cleanliness and/or prolong the usage life of the component. Typically, this is achieved by using non-porous materials or skinned porous materials that are minimally absorbent and easily cleanable for components that are in intimate contact with the user. However, due to the significant advantages for comfort and sealing performance in using a revealed, cut or open cellular structure (e.g., cut foam) against the face (as outlined in this disclosure), other methods must be pursued to address cleanliness and longevity of the component. In embodiments, the foam interface component is configured to be replaced at suitable frequencies (e.g., daily, weekly, monthly or other suitable regime). Suitable cleaning and maintenance regimes may also be recommended for the component (e.g., washing, drying, cleaning solutions (e.g., isopropyl alcohol), steaming, microwave sterilization). Another method to inhibit microbial growth is to include an antibacterial or antimicrobial agent (e.g., AEGIS brand antimicrobial for polyurethane foams) into the foam chemistry; and Recyclable/Biodegradable—As the foam interface may be a frequently replaced component, the foam grade may be selected to be degradable within a chosen timeframe for minimal environmental impact. This may be expressed as a half life for the material to break down in landfill. In an embodiment, the foam is designed to break down in a time frame that is much less than materials known in the industry (e.g., silicone, skinned porous structures, gels). This may be achieved by augmenting the chemistry of the foam and porous structure of the foam to allow the ingress of landfill and microorganisms that aid the breakdown of the foam. Another significant advantage of the foam that minimizes environmental impact is that the material is much softer and of much lower densities than typical materials known in the industry, meaning that the material may be easily compressed and take up far less space in landfill.

As noted above, the foam interface components may be available individually and/or in box sets or cartons. This arrangement provides the possibility of a broad range of distribution channels, e.g., available via home-healthcare dealer, chemist, internet, etc.

In an embodiment, when the interface component wears out or needs replacement, the patient may order a box when needed or a replacement box (e.g., including daily-use interface components) may be periodically sent out to a patient, e.g., patient signs up for 1 year supply with monthly delivery.

This arrangement provides repeat business for a home-healthcare dealer. Also, this arrangement creates assembly line efficiencies because an assembly step (i.e., attachment of interface component to frame) is transferred to the patient. This arrangement may be adapted to reduce shipping by setting up manufacturing locally. In addition, this arrangement may provide an advantage to sleep labs because they do not need to sterilize, but just use disposable interface components.

In an embodiment, the packaging of the component may reflect replacement or reordering requirements. For example, the last items in a box may be packaged differently to indicate "end of supply". In another example, the packaging may include different colors to indicate different days, weeks, months, etc.

As noted above, the foam structure may have a certain usage life or life span. According to an embodiment of the present invention, the foam structure may include an end-of-life indicator to indicate that this usage life has been reached.

For example, the end-of-life indicator may include one or more of the following: pH based color change (microbes produce acid to cause color change at replacement frequency); dirt/color changes; environmental aging (take environmental gases out of packaging); adhesive deteriorates with time (provides single assembly so patient cannot remove component without destroying it—cohesive strength of glue greater than adhesive); and/or packaging include color guides that you match the component to see whether it needs replacement.

2.3 Surface Properties

The foam interface 80 may be manufactured (e.g., from free rise slab stock) to have a skinned surface or a cut, unskinned surface. Because foam has a cellular internal structure, when the foam is cut (e.g., die cut), an open cellular structure is exposed. The cut, open cellular structure on the surface of the interface in contact with the skin has different performance characteristics compared to a skinned foam, particularly when used as a patient interface. For example, FIGS. 13-3 and 13-4 illustrate a foam interface 80 having a cut, unskinned surface CS, and FIGS. 13-5 and 13-6 illustrates a foam interface 80 having a skinned surface SS. As illustrated, the cut surface CS in FIGS. 13-3 and 13-4 exposes the cellular structure of the foam, e.g., air bubbles and pin holes exposed. In contrast, the skinned surface SS in FIGS. 13-5 and 13-6 conceals the cellular structure of the foam, e.g., smooth exterior surface with no air bubbles or pin-holes exposed.

Preferably, the foam is unskinned. However in some forms, a skinned foam may be used. A partially skinned foam may also be used, e.g., to control air permeability. An unskinned foam has the advantage of allowing the air permeability of the foam (so-called "breathability" of the foam) to be utilized, improving the comfort for the wearer by controlling moisture buildup and temperature gradients at the cushion-skin interface. In addition, the airflow through the foam benefits the sealing characteristics at the cushion-skin interface. For example, the foam cushion provides "a leaky" interface that helps to create air circulation to keep the contact surfaces relatively dry and comfortable (e.g., about 5-10% leak).

2.3.1 Comfort

Preferably, the foam cushion is arranged to be skin contacting. Preferably, the foam cushion does not have a layer of silicone between it and the patient's skin. Specifically, a foam including a cut cellular structure (e.g., see FIGS. 13-3 and 13-4) on surfaces that interface or contact with the patient's skin has a different feel against the skin particularly compared to silicone material, which is used almost without exception in the industry. Also, the foam may be designed to have a very pleasing, comfortable tactile property that is not sticky or plastic in feel as with silicone. A relationship exists between the cellular structure of the foam and its comfort against the patient's skin. Foam can be produced to have a coarse to very fine-celled structure, and a homogeneous or heterogeneous distribution of cell sizes. These properties may be controlled through the manufacturing process. In a preferred embodiment, to maximize comfort against the patient's skin, a heterogeneous cell structure with a high content of fine sized cells may be preferred.

2.3.2 Sealing and/or Gripping Function

The cut cellular surface (e.g., see FIGS. 13-3 and 13-4) of the foam provides seal and/or grip. The foam may mechanically deform and engage the patient's face, e.g., to provide seal, and may also grip the skin sufficiently so as to not dislodge (e.g., and lose seal) under micro-movement (i.e., less than 1 mm). A cut cellular surface provides this grip (e.g., friction grip) and may be improved in combination with a "wetter" feeling foam grade and a high degree of softness and visco-elasticity in the foam grade. If the seal and/or grip is dislodged, it should regain its sealing and/or gripping properties easily, ideally without the need to reseat the patient interface on the patient's face. An example of a preferred foam may be a very soft, low (isocyanate) index foam having a wet, sticky, and/or moist feeling to touch. The "stickiness" or "wetness" of the foam may allow sliding movement of the foam along the patient's face without substantially breaking the seal, e.g., "crawling" seal. That is, the location of the seal may be shifted without losing contact with the patient's face and without losing substantial therapeutic pressure. The degree of grip or stickiness may be determined at least in part by surface tension (e.g., coefficient of static friction) and/or the geometry of the cut surface (e.g., roughness).

2.4 Geometry

The foam interface 80 may have a geometry that is generally cradle shaped (i.e., curvature in one direction) or saddle shaped (i.e., curvature in two directions). The interface may also have more than two directions of curvature and complex curvature arrangements to address, match, or deliberately mismatch certain anatomical regions, depending on the intended function of the geometry.

In the illustrated embodiment, the top surface of the foam interface 80 provides a saddle shape that includes curvature in two directions that aids engagement of the patient's nose and its orifices. For example, curvature in a first direction (e.g., see front view of FIG. 15-1) is structured to accommodate the anatomy that forms the alar angle of the patient's nose, and curvature in a second direction (e.g., see side view of FIG. 15-2) is structured to accommodate the anatomy that forms the naso-labial angle of the patient's nose. The degree of curvature in both first and second directions may be traded for extra compliance in the interface mechanical properties in combination with extra interface thickness (pile), e.g., the first and second curvature directions may be omitted for an interface that has sufficient softness and thickness to comfortably and effectively hug engage and seal against the interfacing (e.g., nasal and facial) anatomy.

In an alternative embodiment, the mechanical properties of the foam may be adjusted (e.g., softer) so that the interface will seal effectively using a geometry that has a flat top surface (without curvature in the first and second directions described above).

In another embodiment, the curvature and shape of the foam may be provided by the frame, backing, or other support structure that the foam is attached to.

Most sealing interfaces known in the art (especially silicone interfaces) are membranous. They are long, thin and flexible. The cross section of the membrane has a high aspect ratio (length divided by width or thickness) and hence, in combination with the softness of the membrane's material, it buckles easily along its length and bends easily across its width. Membranes typically do not compress along their length because they buckle easily and cannot support a compressive load in the direction of its length (the material buckles before it compresses). This ability to buckle and bend gives a membrane type seal its ability to conform and adapt to the varying anatomy of the face, particularly when presented (typically) tangentially to the face. Air pressure inside the mask is known to provide a supporting reaction force to the membrane against the face.

The under-the-nose interface according to an aspect of the present invention is not a membrane and does not behave as such. Its cross sectional shape has a low aspect ratio and may be approximately square, rhomboid, rectangular or diamond in shape, as illustrated in FIGS. 15-1 to 15-2. In other embodiments, the cross-section may be round, elliptical, or other more organic shapes depending on the possibilities afforded by the manufacturing process. Because the interface cross-section is not long and thin, it does not behave as a membrane, but as a compression seal. So rather than relying primarily upon its ability to buckle to conform (tangentially) to the face like conventional membrane seals, it relies upon its softness and compliance in a direction normal to the face to conform to the facial anatomy that it is interfacing with. The subject interface is also not as reliant upon air pressure to support the interfacing structure and/or form a seal. The substantial thickness of the cross section in combination with its circular or annular profile means that it is predominantly self-supporting, and as described previously the compressive force is incrementally a function of the pressurized air (air spring stiffness) where the foam sealing structure is air-permeable. The interface may deform outwardly by the positive air pressure inside the mask chamber, but this deformation is a feature that may encourage the interface to engage the anatomy that it is interfacing with, e.g., the shape of the interface may change under pressure to more closely approximate the shape of the patient's face.

2.4.1 Foam Interface with Wings

FIGS. 15-3-1 to 15-3-4 illustrate a patient interface 2210 including a foam interface 2220 according to an embodiment of the present invention. In this embodiment, the foam interface 2220 is incorporated into an existing nasal assembly such as that disclosed in U.S. patent application Ser. No. 10/781,929, the entirety of which is incorporated herein by reference. For example, the nozzles may be removed from the existing assembly, and the remaining base portion or cylindrical support (e.g., constructed of silicone) may be modified to incorporate the foam cushion. FIGS. 15-3-1 to 15-3-4 illustrate the foam interface 2220 on base portion 2230, and the base portion 2230 is provided to a relatively rigid frame 2235 and maintained on the patient's face by headgear 2240.

2.4.2 "Wings"

As shown in FIGS. 15-3-5-1 to 15-3-5-3, the foam interface cut from the block of foam may have a general chevron, delta, boomerang or circumflex shape. The overall width w (from left to right as viewed in FIG. 15-3-5-1) of the chevron may be approximately 6 cm to 9 cm, preferably 8 cm. The height h (from top to bottom as viewed in FIG. 15-3-5-1) of the chevron may be approximately 3 cm to 5 cm. The thickness t (as viewed in FIG. 15-3-5-1) of the interface may be approximately 15 mm.

The foam interface may include lateral portions or "wings" to provide stability, particularly lateral stability of the interface in use. FIGS. 15-3-5-1 to 15-3-5-3 illustrate three foam interfaces 2220.1, 2220.2, 2220.3 including wings in accordance with an embodiment of the invention. As illustrated, each interface 2220.1, 2220.2, 2220.3 includes a main body 2222 with an orifice 2223 and wings 2224 extending from the main body 2222. In FIG. 15-3-5-1 the interface 2220.1 is relatively flat, and in FIGS. 15-3-5-2 and 15-3-5-3 the interfaces 2220.2, 2220.3 are curved or contoured, e.g., wings 2224 curved or contoured with respect to the main body 2222.

In an embodiment, the wings 2224 are sufficiently wide (e.g., 8 cm) so that the wings are wider than nose widths for a large range of patients. Moreover, in use, the wings 2224 are adapted to provide a wrapping or hugging effect around the patient's nose, e.g., see FIGS. 15-3-1 to 15-3-4. For example, the wings may extend laterally beyond lateral flanks of the patient's nose and/or vertically above the lateral flanks, possibly including the tip of the patient's nose.

The wings may be constructed and arranged to engage the facial groove on each side of the patient's nose—crease formed between lower cheek and upper lip area. For example, FIG. 15-3-4 illustrates the wings 2224 engaged with such facial groove or crease on each side of the patient's nose.

In other forms of the invention, side stabilizing portions may be separate from a main interface. For example, cheek pads may be formed of a foam in accordance with an embodiment of the invention.

2.4.3 Curvature

While the interface may be cut into a flat shape, preferably it is either cut or held so as to impart curvature in one or two directions. When the interface has curvature in two direction, it has a geometric "saddle" shape.

In an embodiment, the foam may be cut to have the desired curvature. In another embodiment, the desired curvature may be achieved by cutting an interface into a flat shape, and then gluing (or otherwise adhering) the interface to a support structure, such as a surface having the desired curvature. Because the foam is so conforming, it readily takes up the shape of the surface to which it is adhered. For example, FIGS. 15-3-6 and 15-3-7 illustrate the foam interface 2220 on base portion 2230, such as described in reference to FIGS. 15-3-1 to 15-3-4. The upper surface of the base portion 2230 provides a contoured surface which shapes the desired curvature of the foam interface 2220. FIG. 15-3-8 illustrates a foam interface 2220 provided to a support ring 2231. One side of the support ring 2231 provides a contoured surface which shapes the desired curvature of the foam interface 2220, and the opposite side of the support ring 2231 provides structure to mount the foam interface to the mask frame. An advantage of having a generally flat shape is that it facilitates automated manufacture.

The width can be supported at the back of the foam (i.e., non patient-contacting side) by some rigid or semi-rigid material or laminate material.

The surface to which the foam is adhered can be used to mount the foam into the mask frame.

In one form, a ResMed SWIFT mask is adapted and a foam interface is adhered directly to the silicone barrel of the cushion, such as described above in reference to FIGS. 15-3-1 to 15-3-4.

In each embodiment, the projecting end portions or wings may remain unattached or floppy to facilitate conformance to the patient's face in use.

2.4.4 Alternative Patient Interface

FIGS. 15-3-9-1 to 15-3-9-3 show an alternative patient interface 2310 in accordance with an embodiment of the invention. The mask assembly of this configuration is generally described in Australian Provisional Patent application 2007905737, filed 22 Oct. 2007, the entire contents of which are hereby expressly incorporated by cross-reference. As illustrated, the mask assembly 2310 includes a support structure or frame 2335, a foam interface 2320 provided to one side of the frame 2335, and an elbow 2350 including a plurality of vents 2352 provided to the other side of the frame 2335. Each lateral side of the frame 2335 includes a headgear connector 2337 in the form of a slot adapted to attach a headgear strap. In addition, the frame 2335 includes a decoupling joint 2339 to removably couple the foam cushion 2320. As illustrated, the lateral sides of the frame 2335 are curved to shape the desired curvature of the foam interface 2320.

2.5 Thickness

In an embodiment, the foam may have a thickness of about 5-20 mm, e.g., 15 mm, depending on the hardness and visco-elasticity of the foam, so that the foam can deform with a hugging or wrapping effect under and around the bottom of the patient's nose. In other embodiments, depending on the number of layers of foam that make up the sealing interface and the mechanical properties (e.g., hardness) of each layer, the thicknesses may vary accordingly, e.g., 5-50 mm, 10-30 mm, 14-20 mm. For example, the thickness of the skin-contacting layer of foam may be very soft and very thin (e.g., 1-3 mm), and the conforming layer harder and thicker (5-20 mm). A harder and similarly thin or thinner (e.g., <1 mm) layer of foam may serve as a layer acting as an attachment mechanism.

The thickness of the foam may determine the mechanical compliance of the interface in combination with the hardness of the foam. A softer foam in combination with a greater thickness can provide additional mechanical compliance and fit range, specifically when compared to silicone seals known in the art. The density, hardness, and thickness of the foam can be controlled to achieve an interface that delivers a therapeutic pressure and a comfortable fit without fully compressing the provided foam thickness. Due to the forgiving and compliant nature of the foam, a distinct advantage over other interfaces known in the art is that of sizing consolidation, and even the possibility of providing a one-size-fits-all interface. That is, the softness and compliance of the material used in the interface may allow the interface component to fit a much broader percentage of the population with the same or a reduced number of sizes.

A suitable thickness for foam in accordance with an embodiment of the invention is greater than about 5 mm, e.g., preferably about 10-15 mm. If the cushion is too thin, it may not provide adequate cushioning effect in use and may compress flat when subject to the forces used in stabilizing and retaining a mask on a face. In other forms, it may have a thickness of approximately 5 mm, approximately 10 mm, approximately 20 mm, approximately 25 mm, or approximately 30 mm, or greater, depending on the combination of other features. In another embodiment, the thickness may be greater than about 10 mm. For example, a softer cushion might require a greater thickness. In use, the cushion is adapted to compress and form a seal with the patient's face without high headgear strap forces, i.e., less reliant on strap tension from headgear to create a sealing force.

2.6 Orifice

In a preferred embodiment, the foam interface 80 includes a single orifice 84 adapted to interface with both of the patient's nostrils (e.g., see FIGS. 13-1 to 13-2). Specifically, the interface compresses around the openings of both left and right nostrils, e.g., either surrounding or partially occluding the nostrils, such that the orifice 84 is in airpath communication with the nasal airways. In alternative embodiments, the airpath communication may be via two or more orifices (e.g., two orifices with one for use with each nostril). In embodiments, the profile of the orifice 84 may have a generally round, rectangular, rounded rectangular, triangular, elliptical, or oval shape. However, other suitable orifice shapes are possible, e.g., rounded triangular shape, rounded trapezoidal shape, rhomboid shape. In a preferred embodiment, the orifice matches the shape of the external profile of the component, however the orifice profile and external profile may differ in shape considerably (e.g., the external profile may be elliptical and the internal profile may be triangular). In an alternative embodiment, the foam interface may include a block of foam with no orifice and the permeability of the foam adjacent the airway openings may be sufficiently high so as to allow sufficient airflow to the patient's nose.

2.7 Interfacing Path

In the illustrated embodiment, an external upper perimeter of the foam interface 80 forms an interfacing path P (e.g., see FIGS. 13-1 to 13-2) that encompasses the inferior width of the nose, e.g., interfaces outside of nose or external nares.

For example, the foam interface may be designed to engage the underside of the nose. The geometry of the interface may be described generically as annular, having an inner and outer perimeter when observed in top view. The inner perimeter of the interface (which defines the orifice) may encompass the nostrils or partially occlude the nostrils making alignment of the interface with the nostrils less critical. The area between the inner and outer perimeter may engage a broader area of the face in comparison to other interfaces known in the art (e.g., nasal prongs) to provide a more evenly distributed pressure and low force on the face. The outer perimeter may sit within the inferior outline of the nose or give a close geometrical match to the width of the nose itself. In a preferred embodiment, the outer perimeter lies outside of the inferior outline of the nose to enhance the stability and snugness of fit by allowing the interface to have a wrapping or cradling effect around the width of the nose. This can aid the unobtrusive visual perception of the product when viewed from other than a first person perspective. Alternatively, the outer perimeter of the interface can be designed to lie outside the inferior outline of the nose, having a hugging or wrapping effect around the width of the nose. In the case where the outer perimeter of the interface is wider than the nose, this arrangement may provide enhanced stability and snugness of the interface. It may also allow for increased intuitiveness of fitting the interface, especially in combination with a first direction curvature or V-shape (looking front-on at the face). The interface then features a self-alignment mechanism and intuitive location for the nose to be snuggly received.

In an embodiment, the foam interface is structured to sit under the nostrils and the angle of the interface or interfacing vector is more diagonally upward towards the crown of the head as opposed to directly backwards and into the plane of the face, as is typical of the conventional over-the-nose interfaces.

Figures 1, 2, 3, 4, 5, 6, 7, 8, 9, 10, 11, 12, 13, 14, 15, 16:
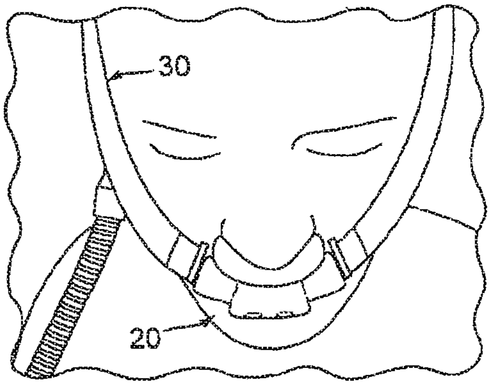

For example, as shown in FIG. 16-1, the patient interface may include a first loop LP1 (e.g., air delivery tubes) and a second loop LP2 (e.g., back strap) connected to the first loop LP1 in use. As illustrated, the first loop LP1 passes along an underside of the patient's nose, along the cheek region, above the ears, and over the crown of the patient's head to define a sealing force against the underside of the patient's nose. The second loop LP2 passes generally over the occipital bone to define a headgear vector at an angle $\alpha$ between 40°-80° (e.g., 60°) with the first loop LP1.

Another embodiment is shown in FIGS. 16-2 to 16-3 which schematically illustrate a frame 222 for supporting the foam interface that is adapted to angle the interfacing vector more backwards. In combination with tubing having a rigidizing element, this allows the separation of sealing forces and forces that stabilize the patient interface on the head. More distinct control and adjustment of these forces is therefore provided as more of the stabilizing forces are supported above the top lip and on the cheek region of the patient. Thus, the interfacing vector is less forcibly directed into the patient's nose, improving the comfort for the patient. In another embodiment, the stabilizing forces may be relieved off the top lip and born more on the cheek region by providing load-bearing features on the headgear adjacent to the interface. This provides greater stability of the mask system on the head without the need to pull the very soft interface too tightly into the nose. The load bearing features may form an integral part of the foam interface component and extend along the (e.g., inner) facial contacting surfaces of the headgear. They may also be permanently or removably fixed to the headgear separate to the interface.

Further, the surface area provided by the frame may be smaller (e.g., narrower width across the face, narrower diameter), which may provide a smaller reaction force into the patient's face to achieve an effective interface.

2.8 Breathability

According to an embodiment of the present invention, the foam interface may include a breathable or permeable foam (e.g., based on a cut surface and/or the elimination of skin) that allows a deliberate amount of airflow both through the interface material (e.g., foam bulk structure) and between the interface and the patient's skin (e.g., cut surface of foam). Patient comfort and compliance is enhanced by decreasing the accumulation of sweat around the face, keeping the skin drier, and moderating the temperature of the skin in contact with and around the interface. Ideally, the airflow is designed to be less than an amount that causes excessive drying of the skin and cooling of the anatomy around the interface when worn on the face.

That is, the foam's construction provides a breathable interface such that condensation buildup and associated irritation can be avoided at the contact interface between the patient and interface. The foam provides "a leaky" interface (e.g., measured by a percentage of vent flow) with intentional/controllable leak through the foam structure/matrix that helps to create air circulation to keep the contact surfaces relatively dry and comfortable (e.g., about 10% of vent flow, 30-40% of vent flow). The amount of leak provided by the foam may depend on comfort, drying skin, and/or annoyance, for example.

In an embodiment, the foam interface may be constructed to leak within predictable and predetermined limits and physical locations, e.g., vary air flow permeability or breathability around the outer perimeter of the interface. Also, the material of the foam may be selected to manage moisture, e.g., avoid moisture buildup in some regions and encourage moisture in other regions, e.g., near nose for humidification. Hydrophobic and hydrophilic (e.g., moisture wicking) materials (or treatments resulting in similar properties) are some options. Moisture wicking foam adapted to "pull" moisture or sweat from the patient's skin may decrease skin breakdown, pressure sores, and/or ulceration.

The foam may be designed to feature different degrees of air permeability through the bulk of the foam and through the surface of the foam. The foam may be impermeable through its body and permeable just at its interfacing surface. Conversely, the foam may be permeable through its body and impermeable at its interfacing surface, though resulting in different sealing characteristics. For example, this could allow breathability to be achieved while achieving alternative interfacing and/or sealing characteristics to the cut-cellular structured foam interface described herein. The foam may also be structured to be impermeable throughout, or impermeable in specific locations where airflow permeability is to be avoided, e.g., into the eyes.

The breathable interface may improve the dynamic interfacing performance (i.e., the ability to withstand macro-movement from a patient rolling around in bed and maintain an interface) over conventional interfacing materials. This is achieved because a small amount of airflow is already flowing between the interface surface and the patient's skin and there is less consequence to the interfacing mechanism when it is subjected to macro-movement compared to a conventional silicone seal. Silicone relies partially on its ability to "stick" to the patient's skin to provide a stable dynamic seal. Thus, when the silicone seal is moved tangentially along the skin surface, it is forced to buckle and completely detach from the skin and be reseated normally to the face to regain its geometrical form that it was designed to sit in to seal. That is, the silicone seal will provide an abrupt leak upon shifting or macro-movement that requires reseating of the interface, whereas the breathable foam interface provides an interface that can regain its interfacing properties easily without the need to reseat the foam interface on the patient's face to recover from its buckled geometry (e.g., from movement of the face relative to the interface). This is also an effect of having an interface that does not rely on membrane mechanics to interface and/or seal. The width of the cross-section of the interface may typically be an order of magnitude larger than a membrane thickness (preferably 5-12 mm and even more preferably 8-10 mm, as compared to 0.35-1.0 mm). The larger width may allow for the interface to engage with the patient's face over a larger area, and as such may not be as sensitive to a local disruption in the interfacing mechanism due to movement or surface irregularity on the patient's face. In addition, the cut surface of the foam interface provides lower tension transfer across the surface when it is compressed into the face, which is an improvement in dynamic sealing performance over silicone membrane seals which are susceptible to leakage due to creasing when they move on the face.

In an alternative embodiment, the foam interface may have a skinned surface, and the skinned surface may be permeable to provide similar effects as a foam interface having a cut, unskinned surface. For example, the skinned surface may be in the form of a breathable polyurethane skin, a membrane that allows permeability, a textured surface, a spray-on porous coating, a perforated skin, and/or a textile. In another example, as shown in FIG. 13-8, the foam interface 80 may have a skinned surface SS, and a vent 81 may extend from the foam interior to atmosphere to allow permeability.

FIG. 14-2 is a graph that illustrates properties of a foam interface according to an embodiment of the present invention. As illustrated, the foam interface may be structured such that leak decreases as force applied to the interface (both in compression and extension) is increased. Also, the disruption to leak flow with movement away from the patient's face is minimal.

2.9 Compliance

The foam interface has a (mechanically) compliant nature that allows it to accommodate a much larger range of facial geometry compared to interfaces made of silicone and other materials known in the art. This arrangement allows for the possibility of consolidating the number of sizes required to fit a patient population, e.g., potentially a one-size-fits-all interface.

Because of the mechanical compliance of the bulk material, the foam seal conforms readily to a larger range of facial shapes as compared to a non-foam seal.

One way that compliance can be quantified is by measuring to what extent the bulk material wraps around a cylinder of a given diameter. More specifically, the angle the bulk material wraps around the cylinder can be measured with respect to the longitudinal axis of the cylinder.

A preferred foam according to an embodiment of the present invention has a cut or unskinned patient contacting surface and a thickness of between 8 and 14 mm and has a density of between 40 and 70 kg/cubic meter.

That is, the foam interface may provide superior mechanical compliance, and this combined with the fact that the region of interfacing is less complex and has less magnitude of anthropometric variation (e.g., compared to conventional nasal and full face interfaces) gives the interface superior fitting qualities. The foam can deform to the appropriate size and shape (e.g., localized deformation) without compromising the interface (e.g., buckling, creasing) and without adding discomfort to the patient (e.g., lower and more even pressure on the face). In addition, the highly compliant foam fits and interfaces with a broader range of population for a given geometry (e.g., size), especially compared to silicone interfaces. Further, the mechanical compliance of the foam interface can make the patient interface design less reliant on strap tension from headgear. In an embodiment, the patient interface may be fitted to the patient's face by fitting the air delivery and stabilizing system (e.g., headgear) and then allowing the interface to find its way to the patient's nose without the need for refined adjustments. That is, the foam interface better accommodates imprecise fitting.

The compliant nature of the foam also allows the foam to quickly adapt to the patient's face, (e.g., upon initial fitting or when the patient moves or rolls around during sleep), without compromising the interface and without adding discomfort to the patient. That is, the foam provides greater tolerance to misalignment.

2.10 Warming

The foam interface may provide a warming sensation to the patient's nares upon exhalation, e.g., similar to breathing into a blanket on a cold night. This arrangement reduces the "frozen nose" effect experienced by some users of nasal prong or nasal pillow interfaces. In an embodiment, the foam interface may include extended side portions that extend along sides of the patient's face, e.g., along upper cheek regions between the air delivery tubes and the patient's cheeks near or extending from the mouth, to provide the warming sensation to other areas of the patient's face.

2.11 Layers

In an embodiment, the interfacing structure may include a soft foam attached to a stiffer structure, e.g., 40 Shore A silicone shell with a wall thickness of approximately 1.5 mm such as the cylindrical support described in U.S. patent application Ser. No. 10/781,929, the entirety of which is incorporated herein by reference.

Figures 1, 17:
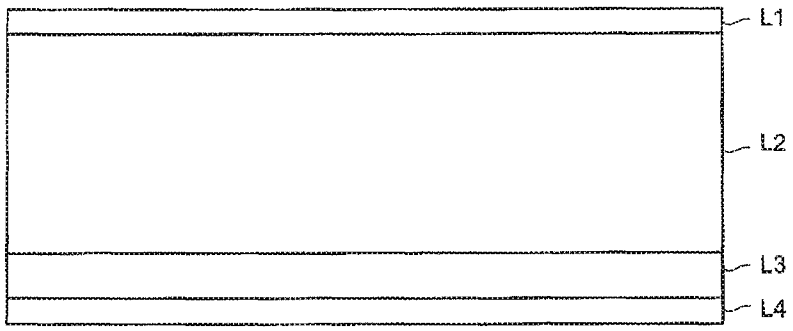
Figures 2, 17:
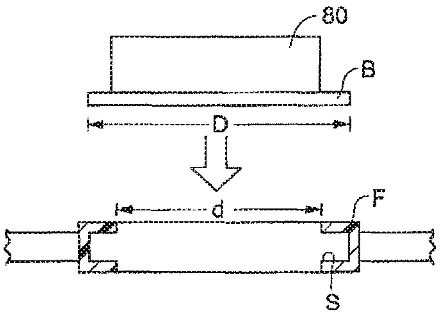
Figures 3A, 17:
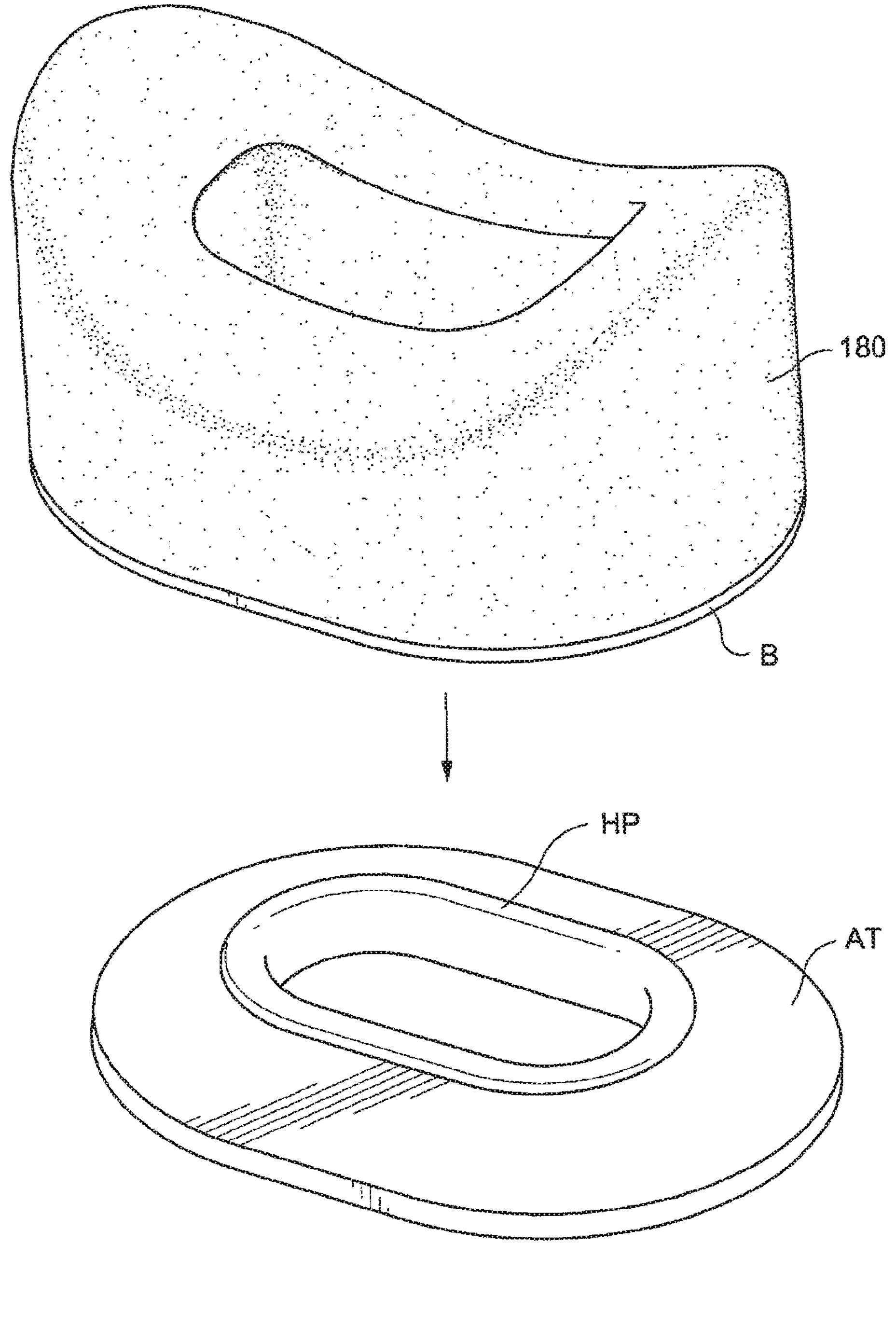
Figures 3B, 17:
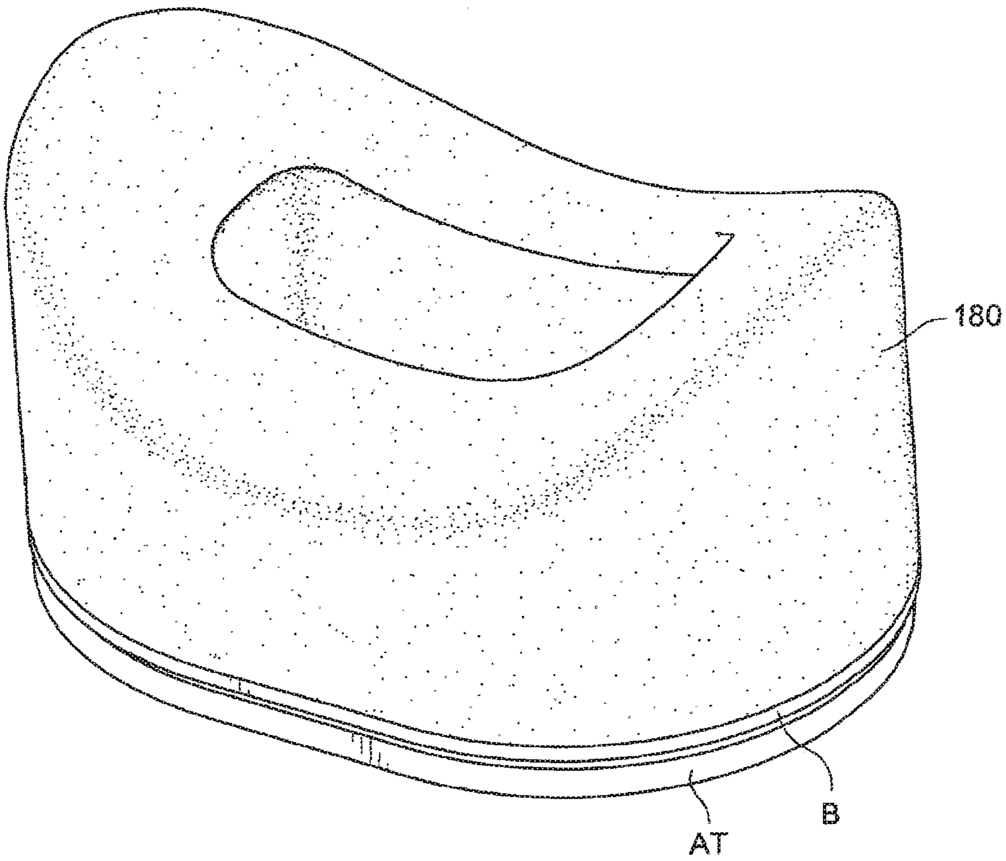
Figures 3C, 17:
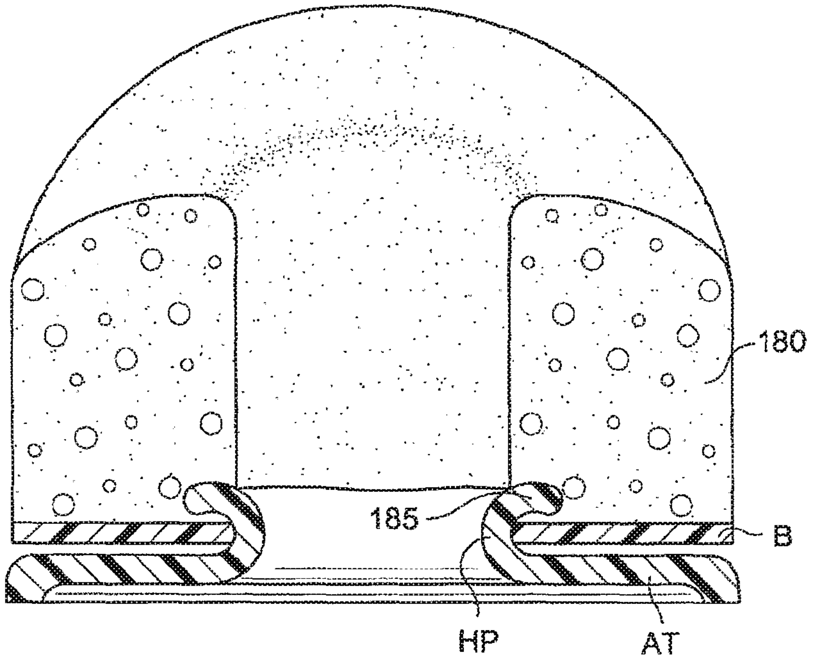
Figures 4A, 17:
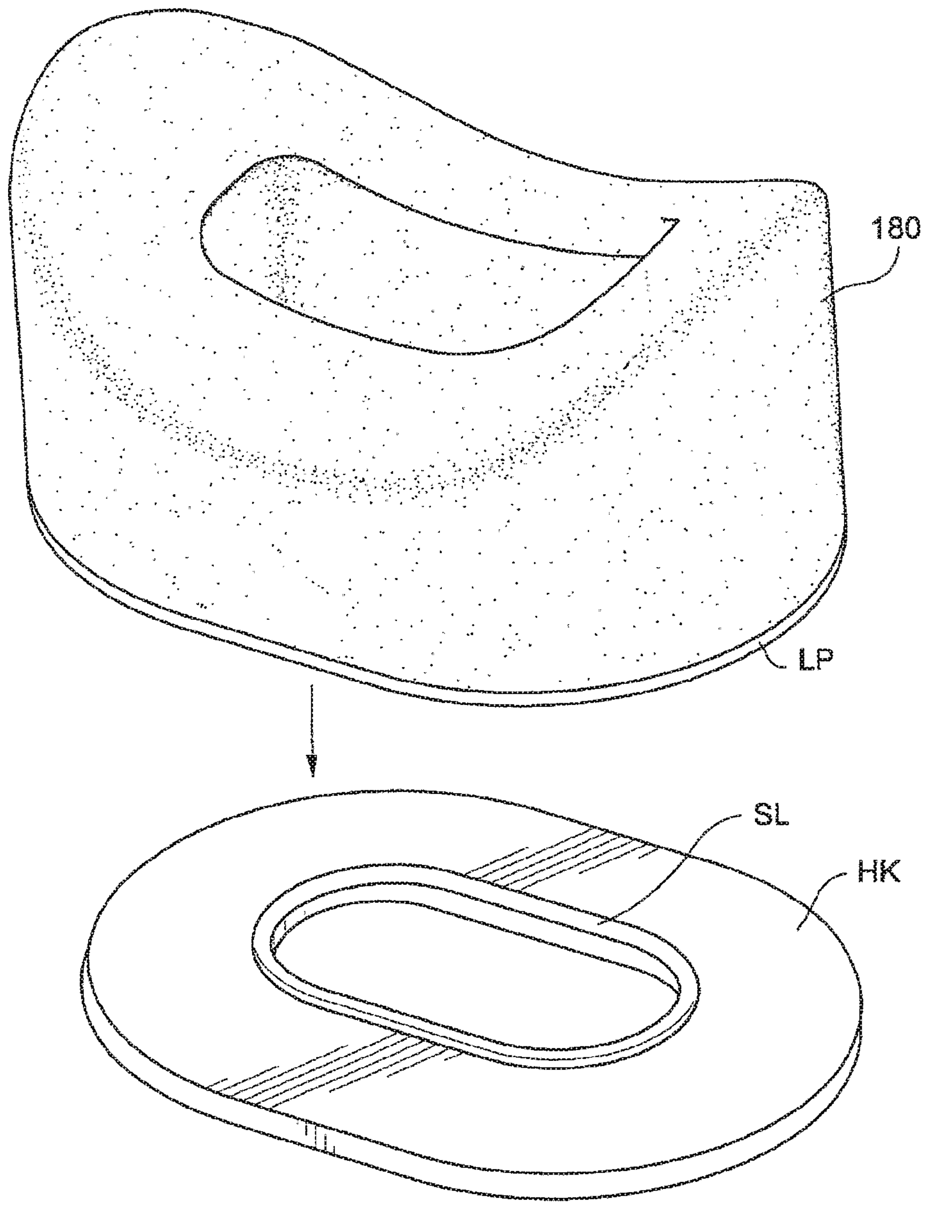
Figures 4B, 17:
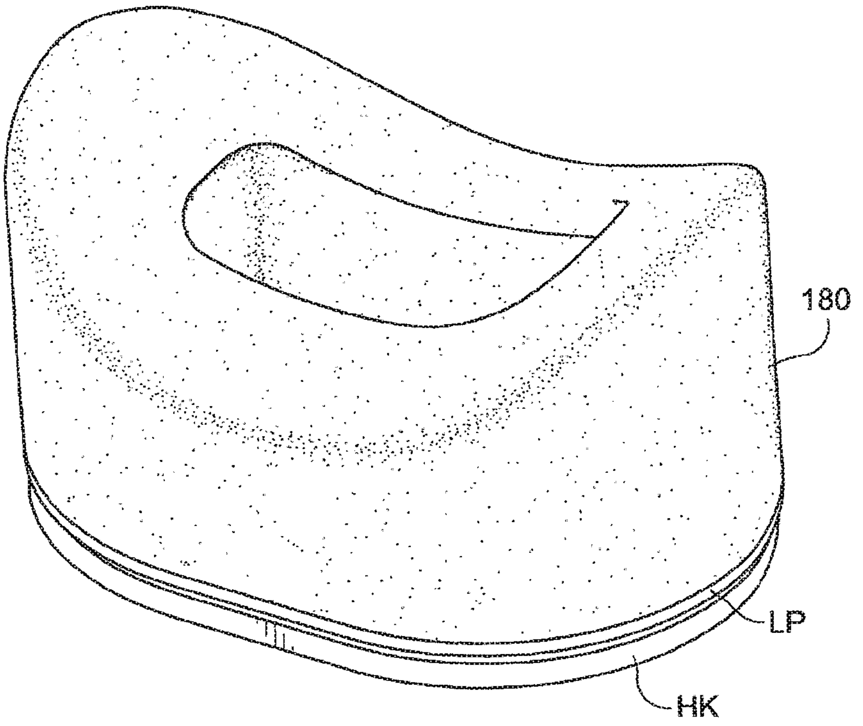
Figures 4C, 17:
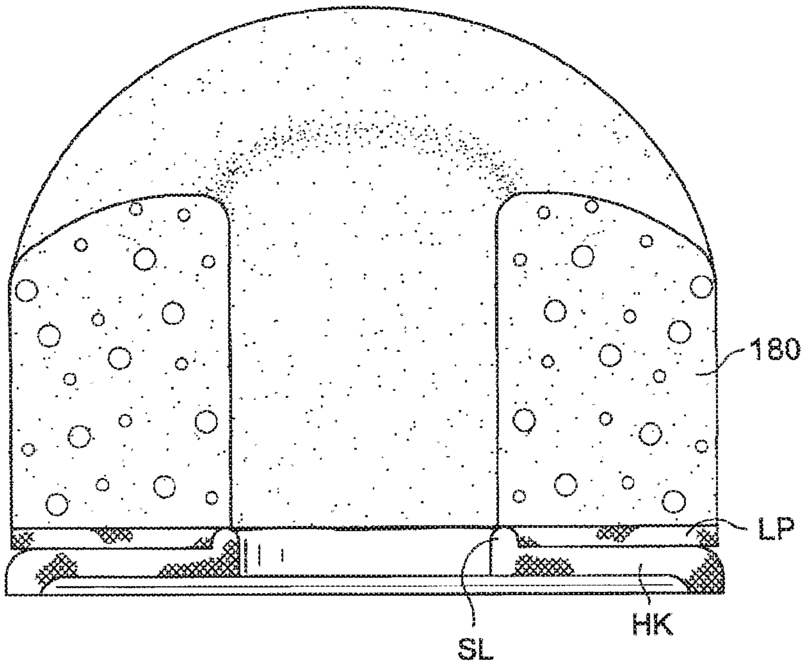

In another embodiment, the interfacing structure may include multiple layers with each layer providing a certain function. For example, FIG. 17-1 schematically illustrates an interfacing structure including four functional layers. The first layer L1 represents a skin-contacting layer that is structured to provide a comfortable seal against the skin of the patient's face and/or nose. The second layer L2 represents a conforming layer that is structured to easily conform to the patient's nasal anatomy. The third layer L3 represents a form holding layer that is structured to support the interface to hold its overall form (since the softness of the L1 and L2 layers may not be sufficiently self-supporting under loading conditions). The fourth layer L4 represents a retention/attachment layer that is structured to retain/attach the interfacing structure to the patient interface, e.g., frame, shell.

For simplicity, all functions would be provided by as few physical layers or components as possible. For example, the functionality of the skin contacting layer L1 and the conforming layer L2 may be provided by one material that includes both a comfortable feel on the skin and suitable plush compressive properties to conform around the underside of the nose. In another example, the reinforcing functionality of the L3 layer and the attachment functionality of the L4 layer may be provided by the (L4) attachment mechanism, and/or by the substrate (e.g., adhesive) used to join the functional layers together.

In an embodiment, such as that shown in FIGS. 13-1 and 13-2, the foam interface 80 with a cut cellular structure may provide the functionality of the first and second layers L1, L2, the cylindrical support 82 (e.g., made of silicone) may provide the functionality of the third layer L3, and a loop material for attachment to a frame may provide the functionality of the fourth layer L4 (described below).

In another embodiment, the L3 form holding layer may include a material that is malleable (e.g., aluminum wire) so that the interface may be manually deformed into a more effective and comfortable geometry.

In alternative embodiments, the first or skin contacting layer L1 may be flocked or covered with a textile (or other suitable breathable materials), e.g., for comfort, grip, alternative wicking properties, and/or alternative air permeability.

2.12 Attachment Mechanism

In the illustrated embodiment, the interfacing structure 20 is a separate component from the air delivery and stabilizing system 30. Therefore, an attachment mechanism is provided to secure (e.g., removably secure) the interfacing structure to the air delivery and stabilizing system. As noted above, a portion of the attachment mechanism may form a retention layer L4 of the interfacing structure.

2.12.1 General Physical Requirements

The interface component is typically a separate component to the rest of the patient interface. This is due to many reasons including: the interface geometry is usually complex and difficult to manufacture in combination with other components of the patient interface; interfaces usually need to accommodate a large anthropometric variation and as such several interchangeable interface sizes exist to cover the full range of variation; the interface may require washing many times during its life and having it removable allows for a more thorough wash and makes cleaning an easier task; and/or interface has a replacement frequency greater than that of the rest of the patient interface and needs to be removable to be replaced.

The attachment mechanism is structured such that all assembly and disassembly tasks performed by the patient should be as easy as possible, particularly considering the potentially varied ages and intellectual and physical competencies of the patient.

For ease of assembly, elements of orientation, alignment, and force are considered in the design. In an embodiment, the interface includes as little asymmetry as possible (e.g., allowing functionally correct attachment in as many different (e.g., two) orientations as possible), intuitive cues as to the method of attachment (e.g., self-aligning or self-orienting), a size, shape, and texture that is not difficult to handle (e.g., requiring minimal dexterity), tolerance to misalignment, as little force as possible to assemble, and/or as little force as possible to disassemble. A force feedback from a mechanism usually can indicate to a user that assembly has occurred and is correct. While requiring as little force as possible to assemble, a correct assembly should be evident to the patient.

If assembly force is very low, disassembly force should be higher than the assembly force to ensure that disassembly does not occur inadvertently. Disassembly force should not be too high as to risk damage to the interface component or other components of the patient interface.

The attachment of the interface to the frame of the patient interface should have no air leak (e.g., sealed) or a small, known amount of air leak over the treatment pressure range.

In an embodiment, as shown in FIG. 17-2, the foam interface 80 may be provided to a base B adapted to retain the foam interface to a frame F. As illustrated, the base B is sufficiently longer than an inlet to the frame (e.g., length D of base is longer than length d of frame inlet) such that the base B is resiliently squeezed and/or simply manipulated through the inlet and into a slot S provided in the frame F where it is retained in an operative position.

In another embodiment, as shown in FIGS. 17-3A to 17-3C, a mechanical interference type attachment mechanism may removably attach the interfacing structure to the patient interface. As illustrated, a base B (e.g. stiff laminate) may be provided on the under side of the interfacing structure (e.g., in the form of a foam interface 180) and an attachment structure AT may be provided to the frame of the patient interface.

As illustrated, a hook portion HP extends from the inner edge of the attachment structure AT. In use, the base B is resiliently stretched and/or simply manipulated over the hook portion HP where it is retained in an operative position, e.g., with a mechanical interference fit. As shown in FIG. 17-3C, the free end 185 of the hook portion HP overhangs the inner edge of the base B to prevent inadvertent removal.

Also, the free end 185 of the hook portion HP provides an internal lip that is pressed against the foam interface 180 to provide a seal. Thus, the base B and attachment structure AT provide both attachment and a circumferential seal between the interfacing structure and the frame.

In the illustrated embodiment, the base B and attachment structure AT each have a generally planar configuration and the profile of the base B and attachment structure AT is substantially similar to the profile of the under side of the interfacing structure, e.g., elongated or elliptical ring shape.

As illustrated, the outer edges of the base B and attachment structure AT substantially align with outer edges of the under side of the foam interface 180. The inner edges of the attachment structure AT may be slightly external to inner edges of the under side of the foam interface 180, e.g., due to the hook portion HP.

However, other suitable perimeter boundaries are possible. For example, the coverage of the base B and attachment structure AT on the under side of the interfacing structure may be matched, internal, or external to the inner and outer edges of the under side geometry profile. In an embodiment, the base and attachment structure may be internal to the outer edge of the under side to prevent contact of the base and attachment structure with the patient's top lip in use.

The mechanical interference type attachment mechanism may have other suitable arrangements. For example, the mechanical interference type attachment mechanism may include: an internal lip with a sleeve section; an internal lip with angle section; an external lip with a single reinforcement layer; an external lip with a double reinforcement layer; a push-in fit with a single foam layer; or a push-in fit with a double foam layer.

In yet another embodiment, an adhesive type attachment mechanism may removably attach the interfacing structure to the patient interface. For example, an adhesive (e.g. pressure sensitive adhesive (PSA)) may be provided on the under side of the interfacing structure (e.g., in the form of a foam interface) that allows the interfacing structure to be removably attached to the frame of the patient interface.

In an embodiment, the under side and adhesive (e.g., PSA) provide thereto may have a generally planar configuration. In another embodiment, the under side and adhesive may provide a curvature along a first direction. In another exemplary embodiment, the base and adhesive may provide curvature along two or more directions, e.g., saddle shape over centering action.

The coverage of the adhesive on the under side of the interfacing structure may be matched, internal, or external to the inner and outer edges of the under side geometry profile. In an embodiment, the adhesive may be matched to the edges of the profile for ease of manufacture. In another embodiment, the adhesive may be internal to the outer edge of the under side to prevent contact of the adhesive with the patient's top lip in use.

In another embodiment, the attachment mechanism may be structured to manipulate the life span of the interface, e.g., attachment mechanism fails at a predetermined time and therefore requires replacement of the interface.

In another example, an injection molded component may be provided to the foam interface which includes a biased flap portion. The flap portion is adapted to attach or grip around an opening in the frame.

In yet another example, the foam interface may include a circumferential groove with the frame edge acting as a tongue. Heat and/or pressure may be applied to the foam interface to harden the foam at the connection point.

In another embodiment, no significant attachment mechanism may be provided as the interface is sandwiched between the frame and the patient's face in use.

2.12.2 Hook and Loop Material

In an embodiment, the attachment mechanism may be in the form of a hook and loop material, e.g., Velcro™. For example, the hook material may be provided on the frame and the loop material, e.g., UnBroken Loop (UBL), may be provided on the under side or base of the interfacing structure. For example, the loop material may be provided on the underside of the cylindrical support 82, e.g., by an adhesive.

This arrangement of the hook and loop material may be reversed, but in the context of an interface that has a high replacement frequency, it is preferred that the less durable side of the hook and loop material is attached to the interfacing structure, i.e., the loop material. A hook and loop style attachment mechanism allows for an intuitive assembly that requires very little force for assembly/disassembly.

A hook and loop interface typically is not airtight. Therefore, a hook and loop interface according to an embodiment of the present invention may include a small, known amount of leak that is repeatable within a defined range between assembly actions.

In an alternative embodiment, the attachment and interface-to-frame sealing functions may be performed separately. For example, a hook and loop interface may be used to provide the attachment, and a soft deformable closed loop linear interface may be used to provide the sealing. The hook and loop interface provides attachment between the interfacing structure and the frame and in doing so provides a normal force that presses the loop material onto a soft circumferential seal on the opposing side of the interface-to-frame arrangement. The interfacing structure may lie either on or adjacent to the hook material provided to the frame.

In another embodiment, instead of the interface or seal pressing against the loop material, the loop material may have a matching smooth rubber/plastic surface for the interfacing or sealing to work against.

In an exemplary embodiment, the interfacing structure may be formed by providing a sheet of foam material (e.g., slabstock or block of foam material (e.g., 1 m×0.5 m×2 m block)), laminating or otherwise attaching hook material to the foam sheet, and die cutting the foam sheet to form the desired shape of the interfacing structure.

FIGS. 17-4A to 17-4C illustrate another embodiment of a hook and loop type attachment mechanism (e.g., Velcro™) structured to removably attach the interfacing structure to the patient interface. As illustrated, a loop material LP may be provided on the under side of the interfacing structure (e.g., in the form of a foam interface 180) and a hook material HK may be provided to the frame of the patient interface. It should be appreciated that the arrangement of the hook and loop material may be reversed.

As illustrated, a sealing lip SL extends from the inner edge of the hook material HK. In use, the hook and loop materials are removably engaged with one another, which presses the loop material LP against the sealing lip SL to provide a seal. Thus, the hook and loop type attachment mechanism provides attachment between the interfacing structure and the frame, and the sealing lip SL is deformable to provide a circumferential seal between the interfacing structure and the frame.

In the illustrated embodiment, the hook and loop material HK, LP each have a generally planar configuration and the profile of the hook and loop material HK, LP is substantially similar to the profile of the under side of the interfacing structure, e.g., elongated or elliptical ring shape.

As illustrated, the inner and outer edges of the hook and loop material substantially align with inner and outer edges of the under side of the foam interface 180. That is, the perimeter boundaries of the hook and loop material may be matched to the edges of the under side geometry profile of the interface, e.g., for ease of manufacture.

However, other suitable perimeter boundaries are possible. For example, the coverage of the hook and loop material on the under side of the interfacing structure may be matched, internal, or external to the inner and outer edges of the under side geometry profile. In an embodiment, the hook and loop material may be internal to the outer edge of the under side to prevent contact of the hook and loop material with the patient's top lip in use.

The hook and loop type attachment mechanism may have other suitable arrangements. For example, the hook and loop materials may provide a planar configuration such as that described above, but without a sealing lip. In another exemplary embodiment, the hook and loop materials may provide a curvature along a first direction. In another exemplary embodiment, the hook and loop materials may provide a curvature along a first direction and a sealing lip such as that described above. In yet another exemplary embodiment, the hook and loop materials may provide curvature along two or more directions, e.g., saddle shape over centering action.

2.12.3 Snap-Over Low Retention

Figures 3, 18:
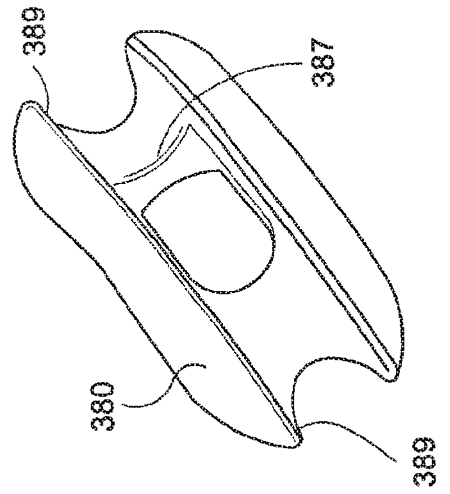
Figures 2, 18:
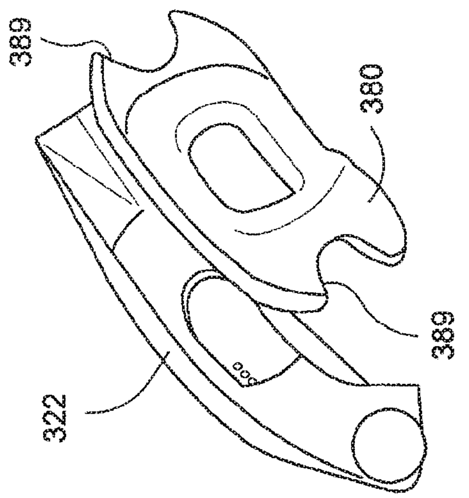
Figures 1, 18:
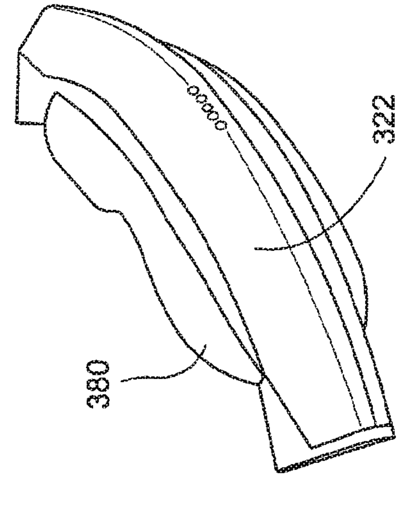

FIGS. 18-1 to 18-3 illustrate a method of joining an under-the-nose foam interface 380 to a frame 322 according to another embodiment of the present invention. In this embodiment, the under-the-nose interface 380 includes structure that allows it to be attached to the frame 322 with a snap-over fit, and the connection relies on the friction and/or mechanical interlock between the under-the-nose interface 380 and frame 322 for its strength. The resultant joint would have limited strength, however the location of the joint allows the force between the patient and the frame to assist in strengthening the joint.

As shown in FIGS. 18-1 and 18-2, the frame 322 includes a generally tubular structure that is curved along its length so that it can follow the contours and/or conform to the shape of the patient's face in use. As shown in FIGS. 18-2 and 18-3, the under-the-nose interface 380 is structured so that it can be attached to the frame 322 with a snap-over fit. Specifically, the back side of the under-the-nose interface 380 includes a groove 387 along its longitudinal axis that is adapted to receive a portion of the tubular frame 322 therein.

One or more surfaces and/or edges of the groove 387 are adapted to engage the frame 322 with a friction and/or mechanical interlock fit. Also, each end of the under-the-nose interface 380 includes an arcuate cutout 389 that is adapted to receive a respective end portion of the frame 322 as it curves along its length.

2.12.4 Snap-Over with PSA

Figures 3, 19:
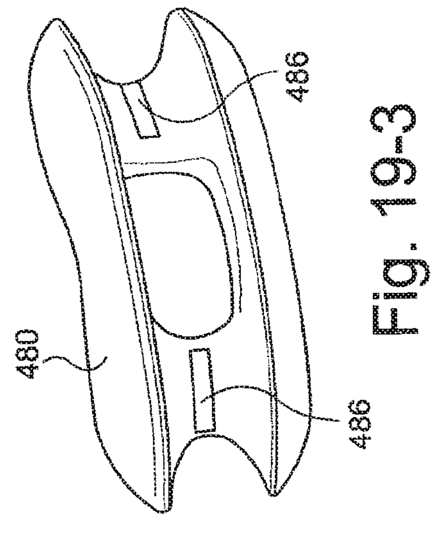
Figures 2, 19:
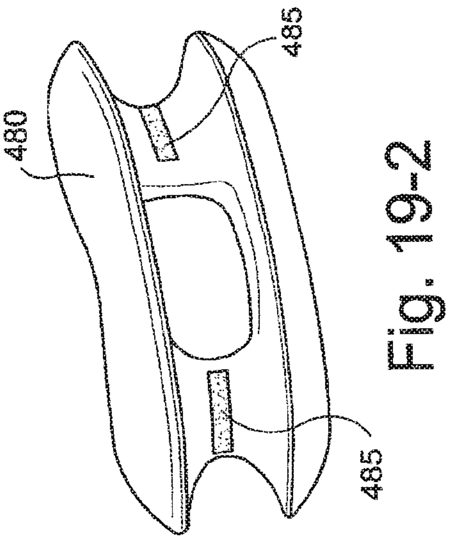
Figures 1, 19:
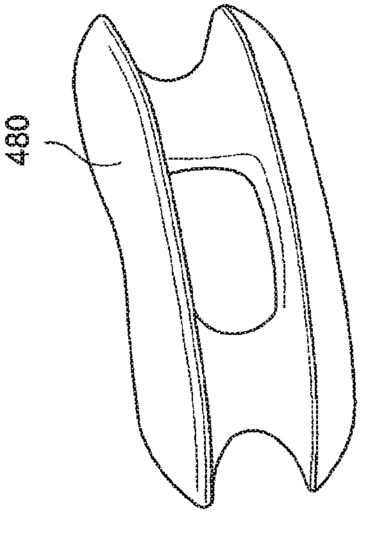

In another embodiment, an under-the-nose interface or foam interface may be joined to a frame by a pressure sensitive adhesive (PSA). FIGS. 19-1 to 19-3 are sequential views illustrating a manufacturing process for applying PSA to the back of an under-the-nose interface according to an embodiment of the present invention. FIG. 19-1 illustrates an untreated under-the-nose interface 480, FIG. 19-2 illustrates an under-the-nose interface 480 after a PSA 485 has been applied, and FIG. 19-3 illustrates the finished sub-assembly after a removable backing 486 has been applied to the PSA 485 on the under-the-nose interface 480.

The under-the-nose interface 480 would be assembled in a similar manner as that shown in FIGS. 18-1 to 18-3, e.g., snap-over fit. In contrast, the backing 486 is removed from the under-the-nose interface 480 before assembly in order to reveal the PSA 485. The resultant joint will have increased joint strength with the PSA 485. When choosing a PSA, the PSA should be configured such that it adheres better to the under-the-nose interface than to the frame. That is, the cohesive strength of the PSA is preferably higher than the adhesive strength. This arrangement allows the PSA to remain on the under-the-nose interface and not on the frame when the under-the-nose interface is pulled off from the frame, e.g., for cleaning or replacement.

2.12.5 Snap-Over with Groove or Undercut

Figures 1, 20:
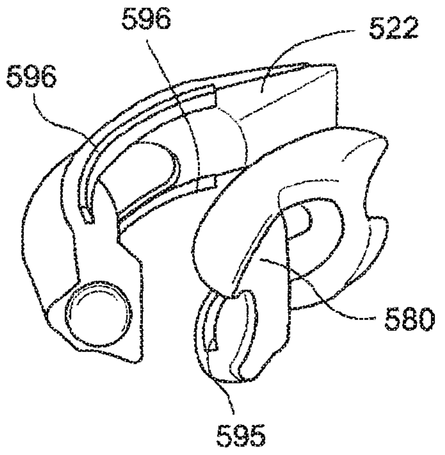
Figures 2, 20:
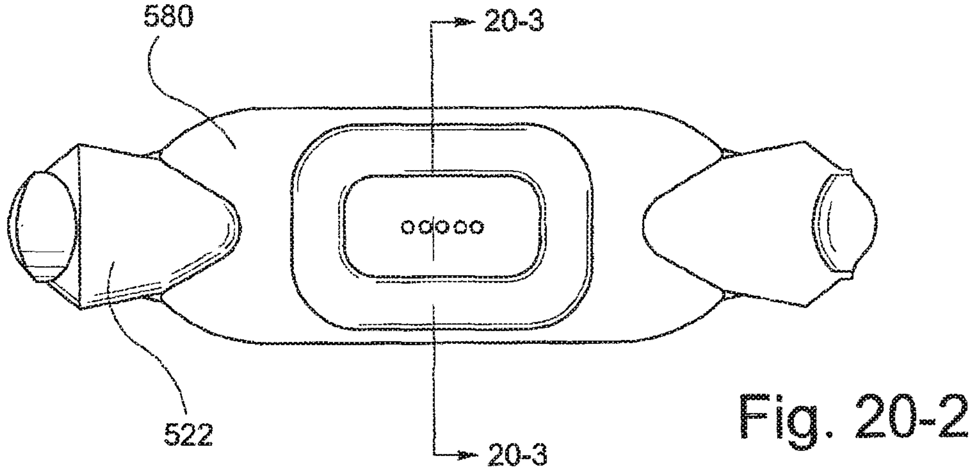
Figures 3, 20:
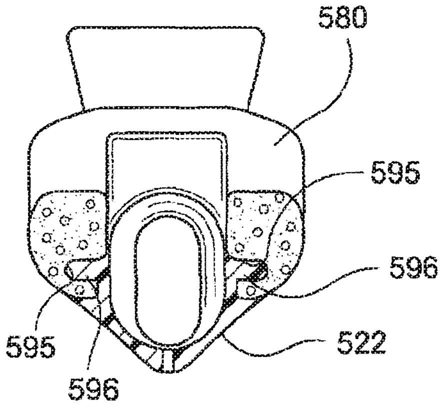
Figures 4, 20:
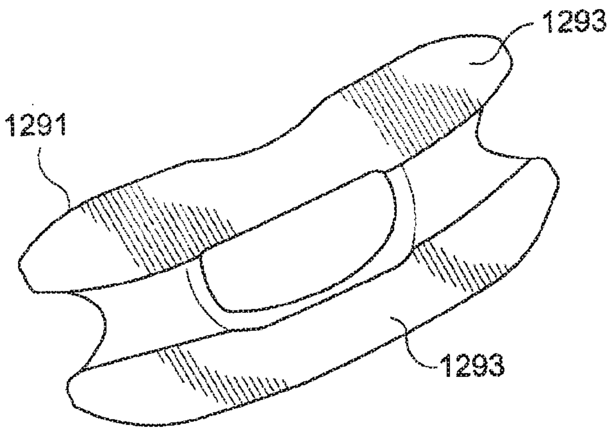
Figures 5, 20:
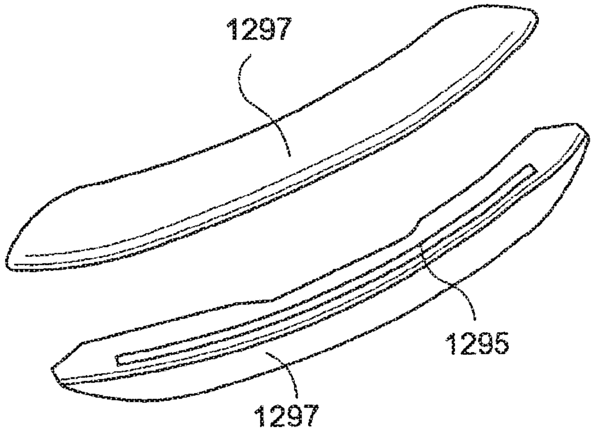
Figures 6, 20:
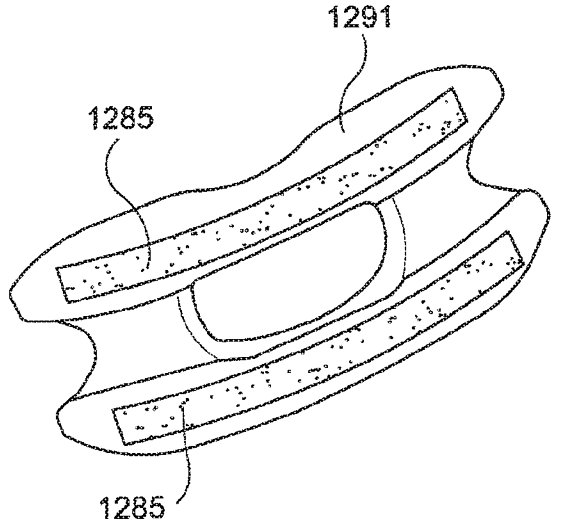
Figures 7, 20:
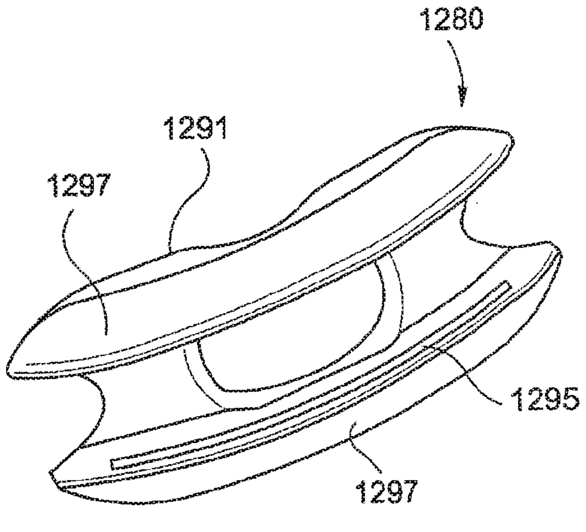

FIGS. 20-1 to 20-3 illustrate a method of joining an under-the-nose interface or foam interface 580 to a frame 522 according to another embodiment of the present invention. In this embodiment, the under-the-nose interface 580 includes a groove or undercut 595 on opposing sides thereof that is adapted to mate or interlock with respective protrusions 596 provided on the frame 522, e.g., with a snap-fit. The resultant joint will have increased joint strength with respect to that shown in FIGS. 18-1 to 18-3 for example.

In an alternative embodiment, the under-the-nose interface may provide a composite snap-over arrangement. For example, FIGS. 20-4 to 20-7 are sequential views illustrating a manufacturing process for forming a composite under-the-nose interface according to an embodiment of the present invention. In FIG. 20-4, a visco-elastic foam portion 1291 is formed having a first side that provides a patient interface and a second side that provides spaced apart platforms 1293. In FIG. 20-5, connecting portions 1297 are formed each having a groove or undercut 1295. The connecting portions 1297 are constructed from a material having a lot more resilience and structure than the visco-elastic foam portion 1291, e.g., high density foam, TPE, TP. In FIG. 20-6, an adhesive 1285, e.g., hot melt glue, is applied to each of the platforms 1293 of the foam portion 1291. Then, as shown in FIG. 20-7, the connecting portions 1297 are attached to respective platforms 1293 of the foam portion 1291 via the adhesive 1285 to assemble the composite under-the-nose interface 1280. In use, the composite under-the-nose interface 1280 may be attached to a frame such as that described in FIGS. 20-1 to 20-3, e.g., groove or undercut 1295 interlocks with respective protrusions provided on the frame. The composite under-the-nose interface 1280 provides connecting portions 1297 that are structured to provide a higher joint strength than visco-elastic foam alone.

It should be appreciated that other suitable manufacturing processes may be used to create a composite under-the-nose interface.

In yet another embodiment, the attachment mechanism may be structured to allow the foam of the interface to be received into a receiving channel in the frame or shell. The seal and retention in this case relies upon the interference fit between the foam and the channel in the frame or shell. The very soft interfacing foam is preferably laminated or otherwise joined to a harder and more dense foam (or other structure) that results in a greater interference force when engaged with the channel.

In another embodiment, the attachment mechanism can be achieved through a rigid or semi-rigid component adhered to the underside of the soft interfacing foam. The rigid/semi-rigid component may be configured to provide a number of mechanical interference fits, e.g., clipped into/onto frame.

2.12.6 Magnetic Arrangement

In an alternative embodiment, the attachment mechanism may include a magnetic arrangement to magnetically couple the frame and the interfacing structure.

2.13 Structural Compliance 2.13.1 Background

The topography around the nose has steep gradients with sharp transitions between these gradients. For an interface to be most effective, it needs to be flush with all surfaces to achieve an interface, e.g., seal. A low resilience structure would allow the greatest comfort while still achieving an interface, e.g., textile interface. However, textile interfaces are typically very thin (e.g., less then 2 mm thick) and cannot in themselves offer the required properties to add compliance. In order for a textile interface to conform to the patient's face, a support structure is required. However, a support structure is not limited to textile interfaces, i.e., foam and silicone interfaces to name a few could benefit from a support structure as well.

2.13.2 Flexible Frame

In an embodiment, the interface may be mounted on a frame made from a flexible material, e.g., injection molded silicone frame. Each end of the frame would be attached to a respective tube 42. When pulled against the patient's face, the flexible frame can conform to the patient's face, e.g., wrap around the patient's nose without pinching.

The frame may be constructed of materials having different stiffnesses. If the frame is constructed of silicone, this arrangement may be achieved by simply using silicones with different Shore Hardnesses.

Figures 1, 21:
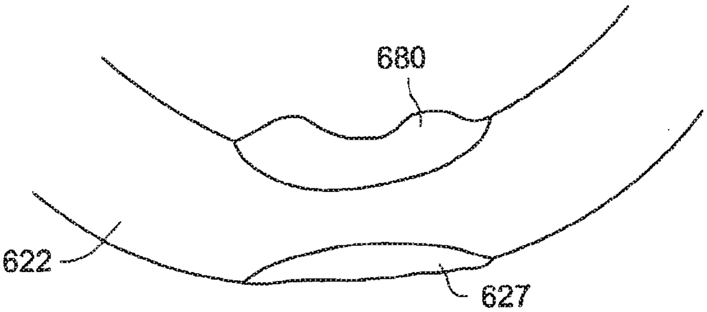
Figures 2, 21:
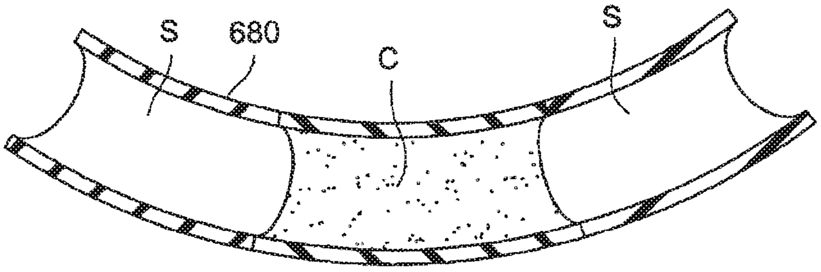
Figures 3, 21:
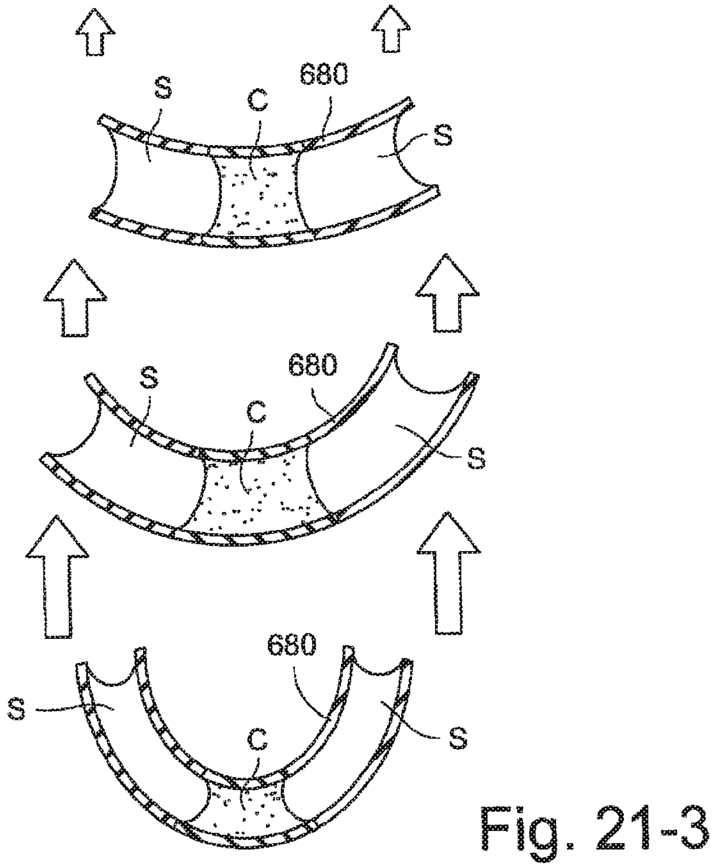

For example, FIGS. 21-1 to 21-3 illustrate a frame 622 for supporting an under-the-nose interface 680 and vent 627 according to an embodiment of the present invention. As best shown in FIGS. 21-2 and 21-3, the central portion C of the frame 622 (shown in darker shading) is stiffer than the side portions S of the frame 622.

This arrangement results in side portions S having more flexibility than the center portion C of the frame 622. As shown in FIG. 21-3, as a force applied to the frame 622 is increased, the deflection of the side portions S is more substantial than that in the center portion C. As a result, the frame 622 will not pinch the patient's nose and the center portion C will remain relatively straight to prevent the interface from occluding the nostrils. In addition, the stiffer center portion C ensures that the conduit in front on the patient's nose is maintained open in use.

Figures 1, 22:
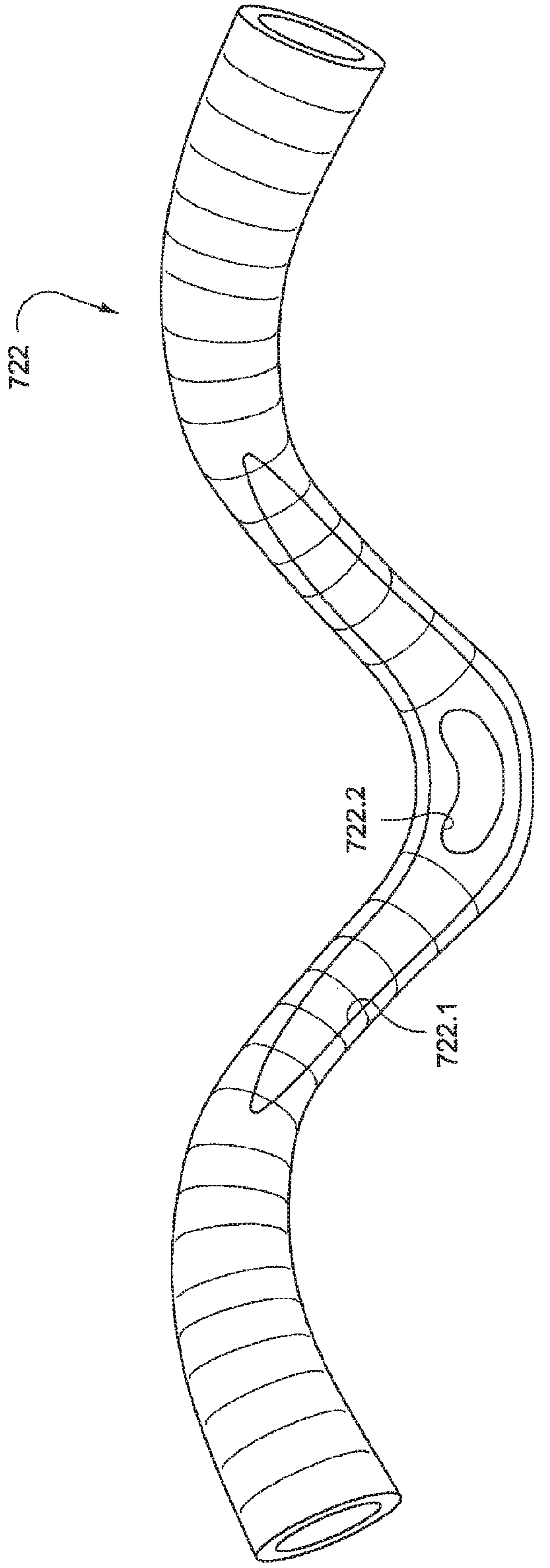
Figures 1, 23:
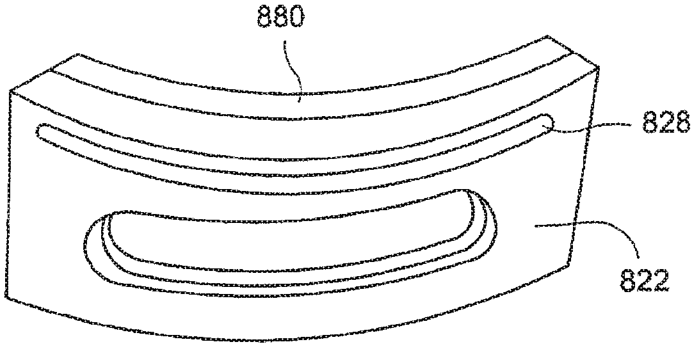
Figures 2, 23:
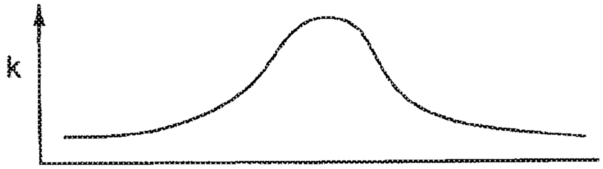
Figures 3, 23:
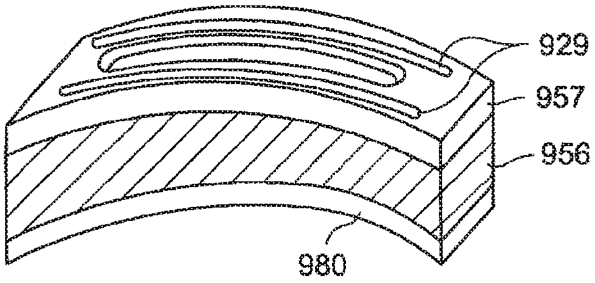

FIG. 22-1 illustrates a flexible frame 722 according to another embodiment of the present invention. In this embodiment, the frame 722 may be a molded foam conduit including openings 722.1 and 722.2 adapted to engage an under-the-nose interface, e.g., replaceable foam under-the-nose interface, and vent. The ends of the frame 722 may attach to respective tubes 42 in any suitable manner 2.13.3 Flexible Frame with Spring Element In another embodiment, a flexible frame such as those described above may include a spring element to increase comfort. For example, FIG. 23-1 illustrates a flexible frame 822 including a spring element 828 and an interface 880 provided to the frame 822. The spring element 828 may be a thermoplastic elastomer (TPE) or a metal (e.g., Polycarb, Nitinol, etc.). In the illustrated embodiment, the spring element 828 is attached horizontally along the frame 822. However, other suitable arrangements are possible. In use, the spring element 828 is structured to counteract the force provided by the air delivery and stabilizing system 30, e.g., tubes 42. The spring element will effectively increase the radius of the frame 822 when attached to the patient.

In an embodiment, the spring element may be a variable spring element that varies its k values across its length, e.g., see graph of FIG. 23-2. As illustrated, the spring element may have a k that resembles a general bell curve arrangement such that the middle of the spring element is relatively stiff and the ends of the spring element are relatively loose. This arrangement may be advantageous as the curvature of the patient could be better matched. For example, if the interface was an under the nose type interface, a relatively stiff spring may be provided in the middle of the frame and then a loosening spring may be provided as the frame moves away from the center of the nares.

To add further compliance, a low resilience foam may be added between the spring element and the interface. For example, FIG. 23-3 illustrates an interface 980 provided to a frame having a low resilience foam 956, a medium density foam 957, and spring elements 929, e.g., constructed of Nitinol.

2.14 Venting

In an embodiment, a breathable foam interface may provide the necessary volume of $CO_2$ washout or venting, which may obviate the need for separate $CO_2$ washout vents. In addition, the breathable foam interface may provide a vent silencing or diffusing feature. Thus, the breathable foam interface may provide a single component with dual purposes, e.g., sealing and venting. However, $CO_2$ vent holes may be used in conjunction with a foam interface, e.g., because condensation may block one or more breathable portions of the breathable foam interface. The air venting from the $CO_2$ vent holes may pass through the foam as a means of diffusing and reducing noise from the stream of venting air.

For example, the frame or support that supports the foam interface may include one or more vent holes for $CO_2$ washout, e.g., see FIGS. 1-8, 2-1, and 18-1.

Figures 1, 24:
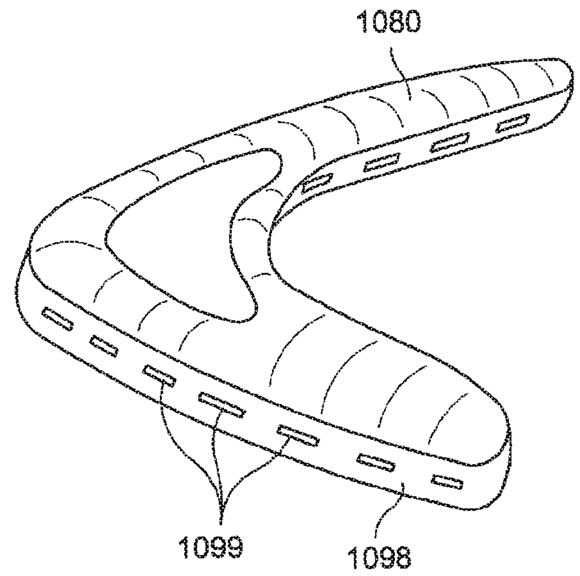

Also, FIG. 24-1 illustrates a foam interface 1080 including a rigidizer 1098 that provides venting. The rigidizer 1098 may be in the form of a rigid/semi-rigid backing piece including holes 1099 for venting. As illustrated, the foam interface 1080 includes a "boomerang" shape. The semi-porous nature of the foam and the extended arms of the "boomerang" shape allows the patient's skin to breathe under the foam, as the foam has a very small and diffuse flow of air constantly coming out of the foam from the orifice outwards.

Further, in an alternative embodiment, the frame or support that supports the foam interface may include one or more supplemental ports, e.g., to provide supplemental oxygen and/or collect pressure/humidity data.

2.15 Alternative Interfacing Arrangements

Figures 1, 25:
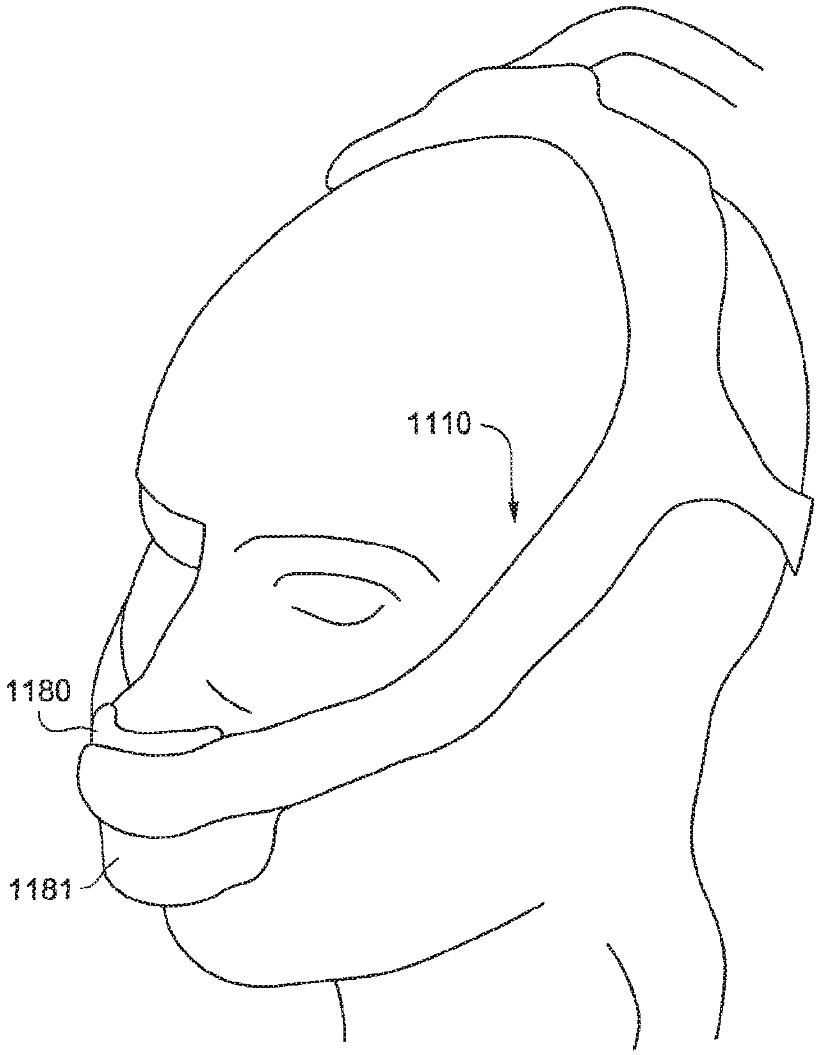

It should be appreciated that the interfacing structure may have other interfacing arrangements. That is, the foam interface type is merely exemplary, and the foam interface may be adapted for use with other suitable interface types, e.g., over-the-nose interface, nasal cushion, mouth, full-face, nasal prongs, etc. For example, FIG. 25-1 illustrates an embodiment of a patient interface 1110 including an under-the-nose interface 1180 and a mouth interface 1181, e.g., constructed of foam, to interface or seal with the patient's mouth in use.

2.16 Foamed Silicone

In lieu of and/or in addition to using visco-elastic foam (e.g., polyurethane) as discussed above, various components of the patient interface may be constructed at least in part from a silicone that is foamed, i.e. foamed silicone. That is, one or more portions of a component may be constructed from foamed silicone or an entire component may be constructed from foamed silicone.

For example, a forehead pad for a forehead support of a patient interface includes a stalk or connector adapted to connect the forehead pad to a frame and a patient-contacting pad portion adapted to contact the patient's forehead. In an embodiment, the stalk may be constructed from a non-foamed silicone (e.g., LSR) and the patient-contacting pad portion may be constructed from a foamed silicone.

In other examples, the cushion of the patient interface and/or conduits connected to the patient interface may be partly or wholly constructed from foamed silicone.

The foamed silicone can provide respective components with different "feels" and/or different connection properties.

For example, foamed silicone may provide one or more of the following properties: lighter; appealing texture, comfort; uses less material; opaque or translucent; cleanable (e.g., if there are a sufficiently high percentage of closed cells) to make the component longer lasting and with a lower replacement frequency; softer at a given thickness or durometer; lower extensibility and tear resistance; surface properties may be altered (e.g., with a skin); impermeable to air/biological matter; permanence of sealing properties with age (e.g., oil/grease absorbance); and/or surface breathable but body impermeable.

3. Application to Known Masks

One or more aspects or features of the present invention may be adapted for use and/or incorporated into embodiments and/or components of known masks, as would be apparent to those of ordinary skill in the art.

3.1 Respironics' ComfortCurve™

Figures 1, 26:
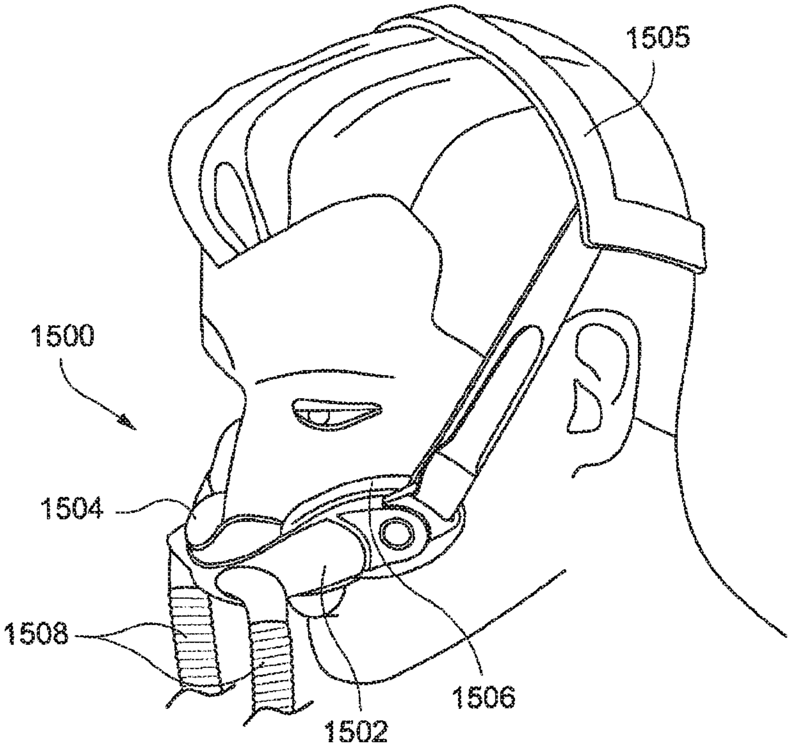
Fig. 26-1 (PRIOR ART)
Figures 2, 26:
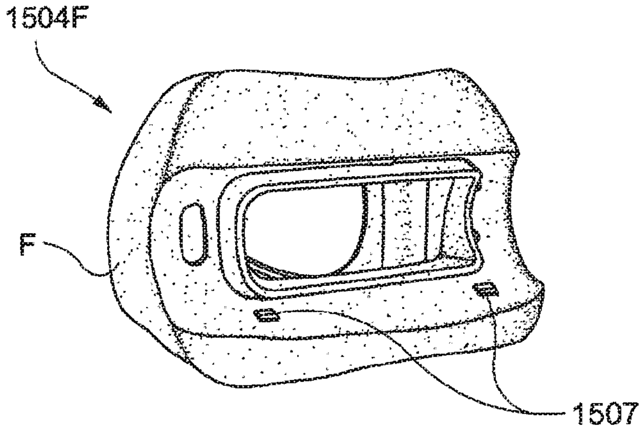
Figures 3, 26:
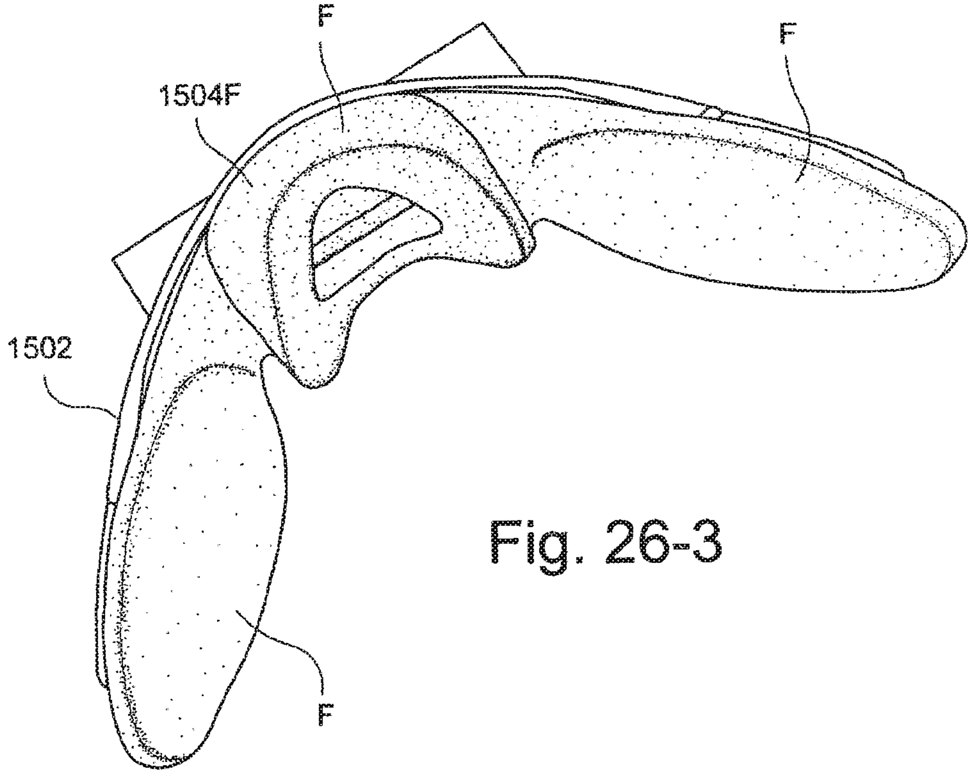
Figures 4, 26:
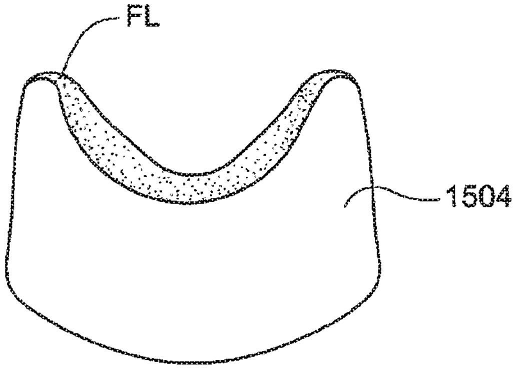
Figures 5, 26:
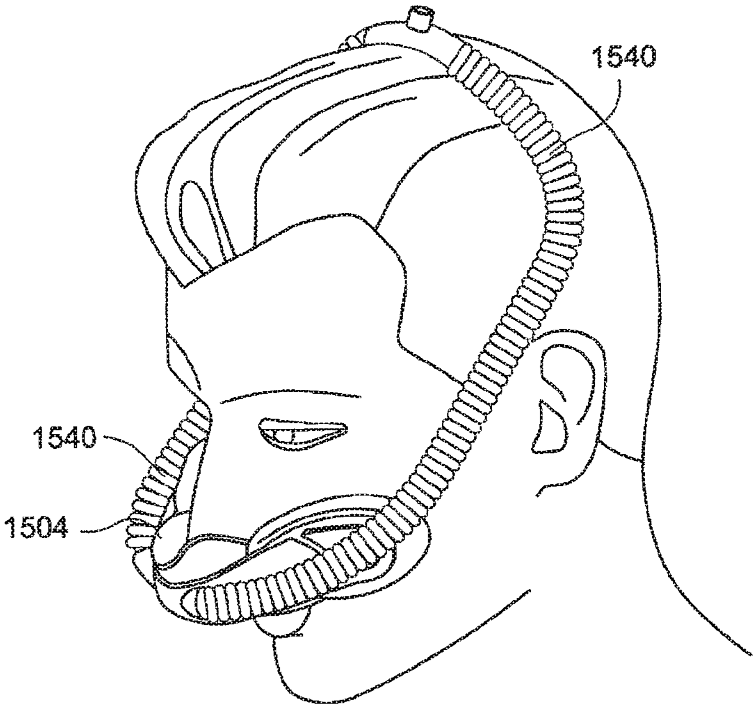
Figures 6, 26:
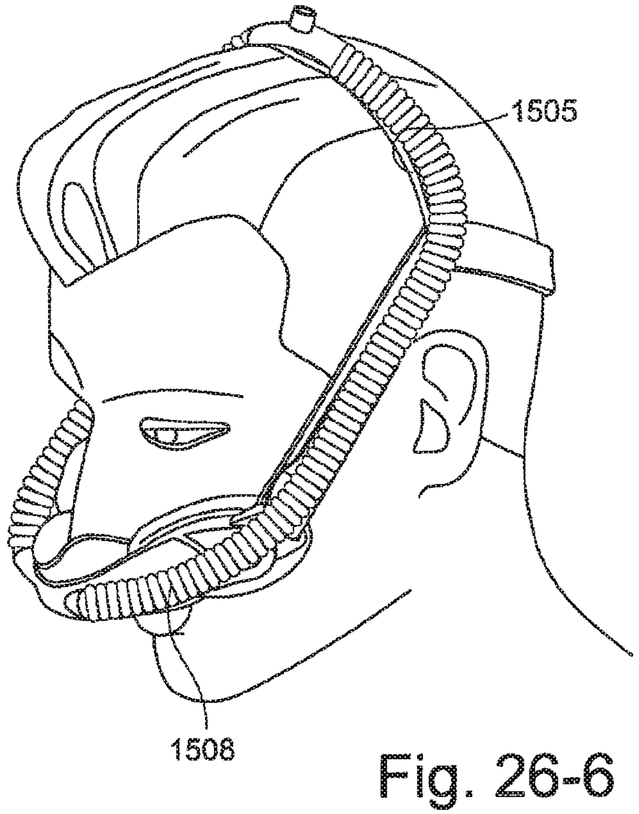
Figures 7, 26:
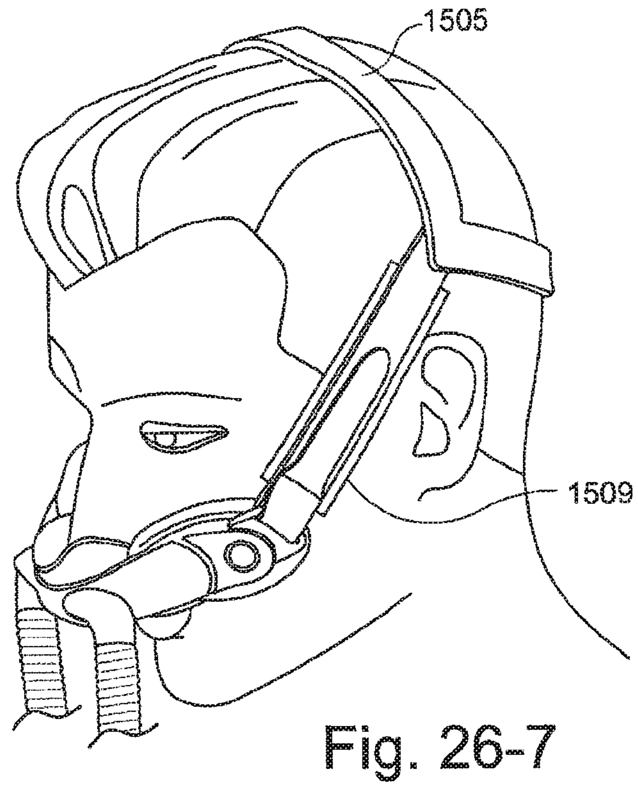
Figures 8, 26:
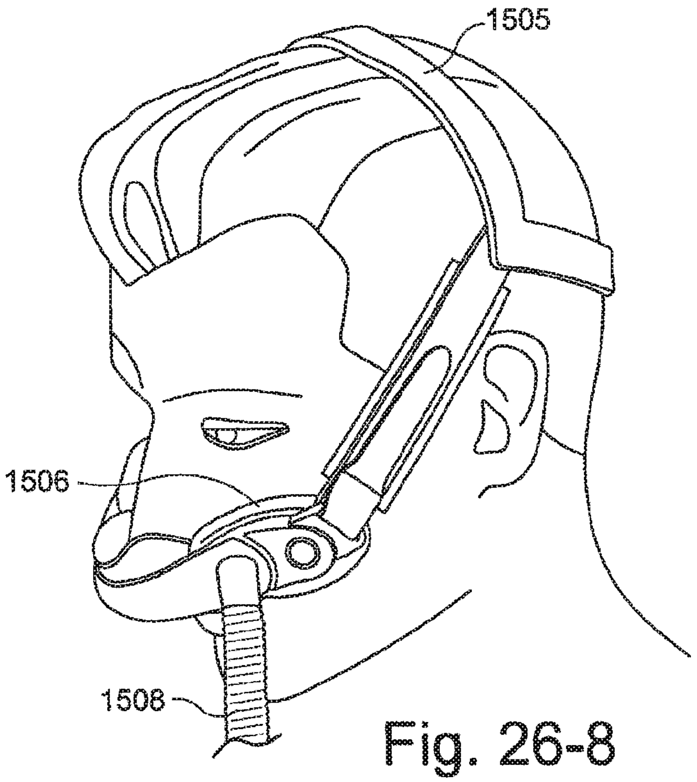
Figures 9, 26:
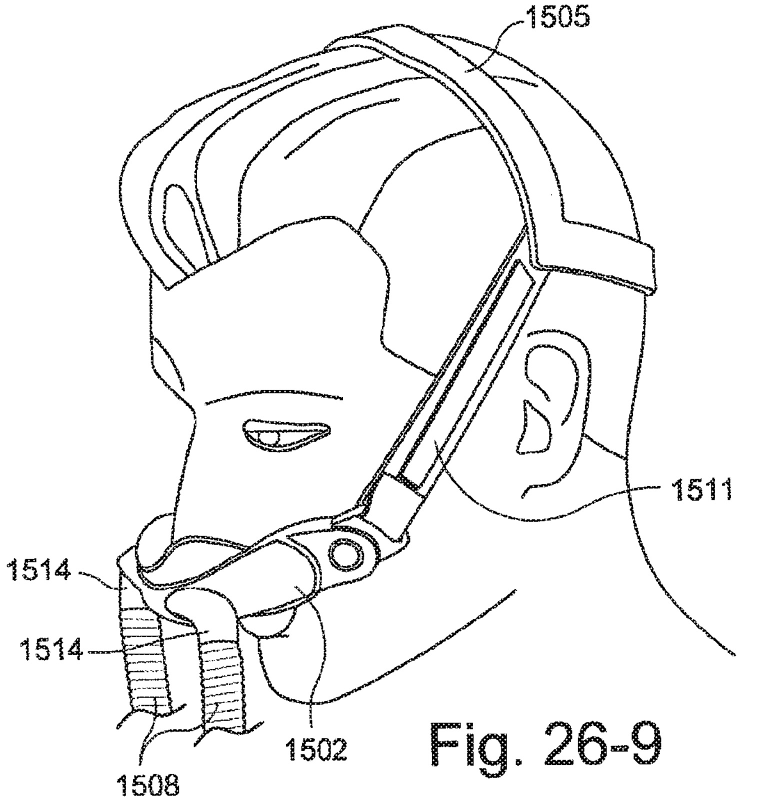
Figures 10, 26:
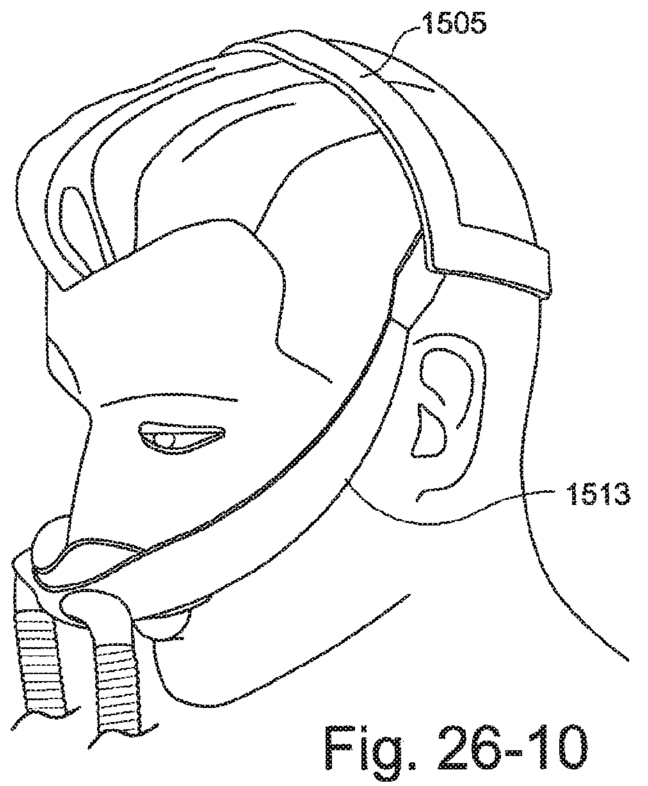

FIG. 26-1 illustrates a known mask 1500 commercially sold by Respironics Inc. under the name of ComfortCurve™ and one or more portions of the mask are described in Australian Application No. AU 2005100738, published Nov. 24, 2005. As illustrated, the mask 1500 includes a frame 1502, a cushion 1504 provided to the frame 1502 and adapted to form a seal with the patient's nose in use, cheek pads 1506 provided to the frame 1502 to support the cushion 1504 in use, inlet tubes 1508 provided to the frame 1502 and adapted to deliver breathable gas to the patient, and headgear 1505 removably attached to the frame 1502 to maintain the mask 1500 in a desired position on the patient's face.

3.1.0 Improvements/Alternative Arrangements

The following embodiments describe improvements and/or alternative arrangements of Respironics' ComfortCurve™ mask to enhance respiratory therapy.

3.1.1 Foam Seal

The ComfortCurve™ mask includes a cushion constructed of a silicone material. In an alternative embodiment, as shown in FIG. 26-2, the cushion may be a foam cushion 1504F constructed of a foam material F. The foam material F may include one or more of the foam properties described above, e.g., visco-elastic, un-skinned, etc.

In such embodiment, the frame attachment mechanism or clip 1507 may be maintained as a base substrate and the foam material F may be attached to the clip 1507. This arrangement allows removable attachment of the foam cushion to the existing frame of the ComfortCurve™ mask.

In an embodiment, as shown in FIG. 26-3, the foam cushion 1504F may extend along side portions of the frame 1502 (e.g., in place of the cheek pads 1506) so that the foam material F may wrap around the patient's nose and/or conform to the patient's face when the frame 1502 is pulled against the patient's face in use.

In an embodiment, the foam cushion 1504F may include multiple layers, e.g., a first layer constructed of a high density foam and a second layer constructed of a more compliant foam adapted to engage the patient's face.

In another embodiment, as shown in FIG. 26-4, the ComfortCurve™ cushion 1504 may be provided with a foam or fabric layer FL on a contact surface adapted to engage the patient's face. The foam or fabric layer FL may be provided to the cushion in any suitable manner, e.g., spray-on foam like flocking, fabric adhered to cushion, etc. The foam or fabric layer FL may improve comfort, feel, and/or softness, and may provide a moisture wicking feature.

3.1.2 Conduit Headgear

The ComfortCurve™ mask includes headgear constructed of a fabric-type material to maintain the mask in a desired position on the patient's face. In an alternative embodiment, as shown in FIG. 26-5, the headgear may be replaced or combined with collapsible conduits 1540 adapted to deliver breathable gas and stabilize the cushion interface on the patient's face. The conduits 1540 may include one or more of the tube properties described above, e.g., partially or fully collapsible, cross-sectional contour that blends into the patient's face, etc., and/or the conduits 1540 may include a rigidizer.

3.1.3 Tube Routing

In another embodiment, as shown in FIG. 26-6, the inlet tubes 1508 may be routed through the headgear 1505, e.g., up towards the top of the patient's head, rather than hang downwardly from the frame.

In such embodiment, a support member may be provided to the headgear to improve stability. For example, a wire member (e.g., magnesium wire) may be provided to the headgear straps that extend from the frame to top of the patient's head.

3.1.4 Soft Material on Headgear Strap

In another embodiment, as shown in FIG. 26-7, one or more straps of the headgear 1505 may include a relatively soft cover, sock, or pad 1509, e.g., constructed of foam or gel, to improve comfort.

3.1.5 Inlet Tubes Attached to Cheek Pads

In another embodiment, as shown in FIG. 26-8, the cheek pads 1506 may be inflatable and the inlet tubes 1508 may be attached or otherwise communicated to the cheek pads 1506 to inflate the cheek pads 1506 in use. Such an arrangement may be adapted for use with the conduit headgear described above.

Also, in an embodiment, the cheek pads may be in fluid communication with the cushion such that air may pass from the inlet tubes and into both the cushion cavity and cheek pads.

3.1.6 Inlet Tubing Along Inside of Frame/Headgear

In another embodiment, the inlet tubes may extend along an inner side of the frame (e.g., adjacent the patient's face) and/or the headgear, rather than along the outer side of the patient's face.

3.1.7 Accommodate Alar and Naso-Labial Angle

In another embodiment, the cushion may be structured to accommodate the alar and naso-labial angle of the patient's nose.

3.1.8 Eliminate Cheek Pads

In another embodiment, the cheek pads may be eliminated. In such embodiment, as shown in FIG. 26-9, a yoke or rigidizer 1511 may be provided one or more straps of the headgear 1505 to improve stability. For example, the rigidizer may be structured similar to that provided on ResMed's VISTA™ and SWIFT™ masks, e.g., see U.S. Pat. No. 6,907,882 and U.S. patent application Ser. No. 10/781,929, filed Feb. 20, 2004, each of which is incorporated herein by reference in its entirety.

In an embodiment, the rigidizer 1511, frame 1502, and inlet ports 1514 associated with inlet tubes 1508 may be integrally formed as a one-piece structure.

In another embodiment, the cheek pads may be eliminated and the frame may be extended to improve stability. For example, as shown in FIG. 26-10, the frame may include extended side portions 1513 that extend along the sides of the patient's head and taper/thin out towards the patient's temple. Ends of the side portions 1513 may include suitable structure for attachment to respective headgear straps.

3.2 Respironics OptiLife™

Figures 1, 27:
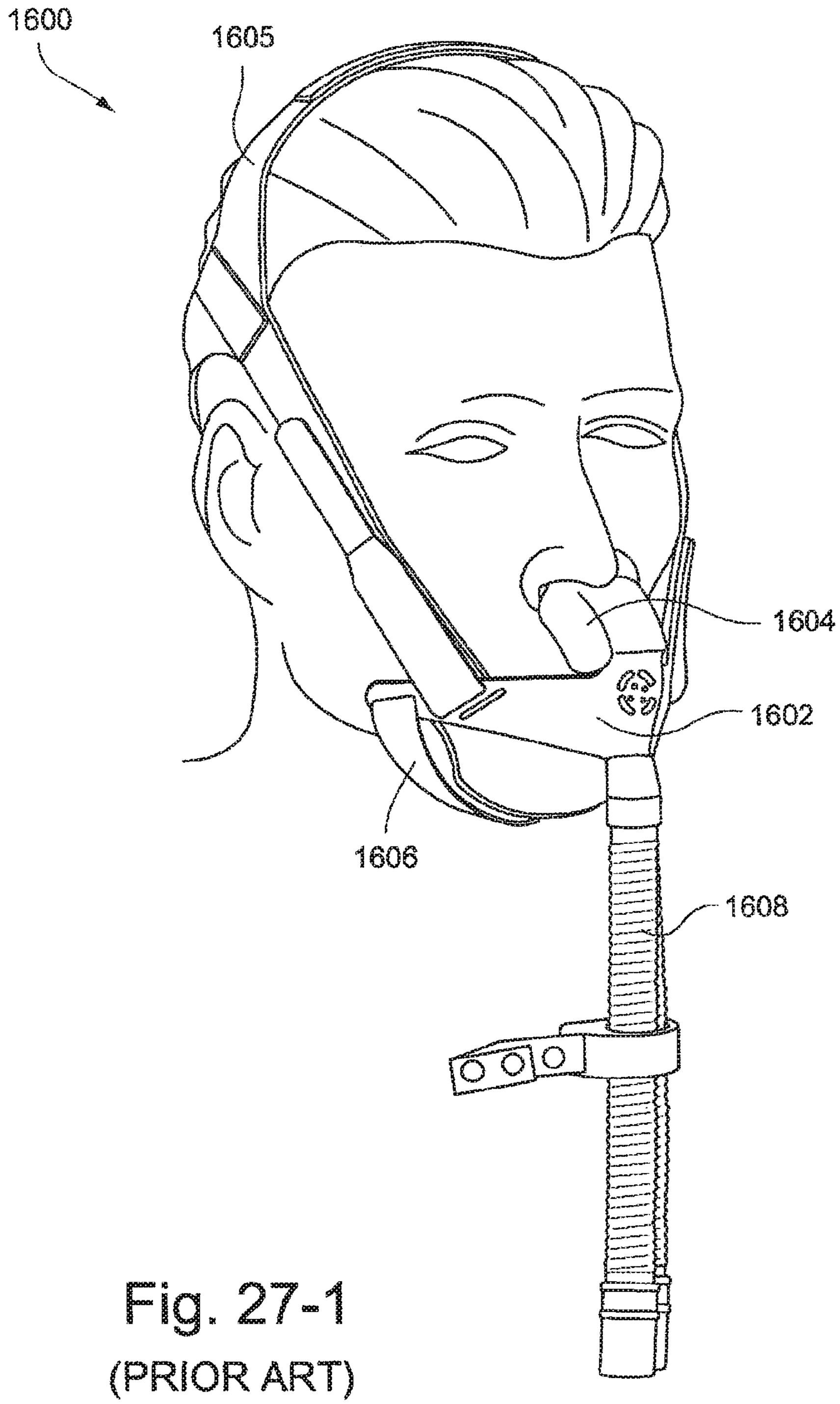
Fig. 27-1 (PRIOR ART)
Figures 2, 27:
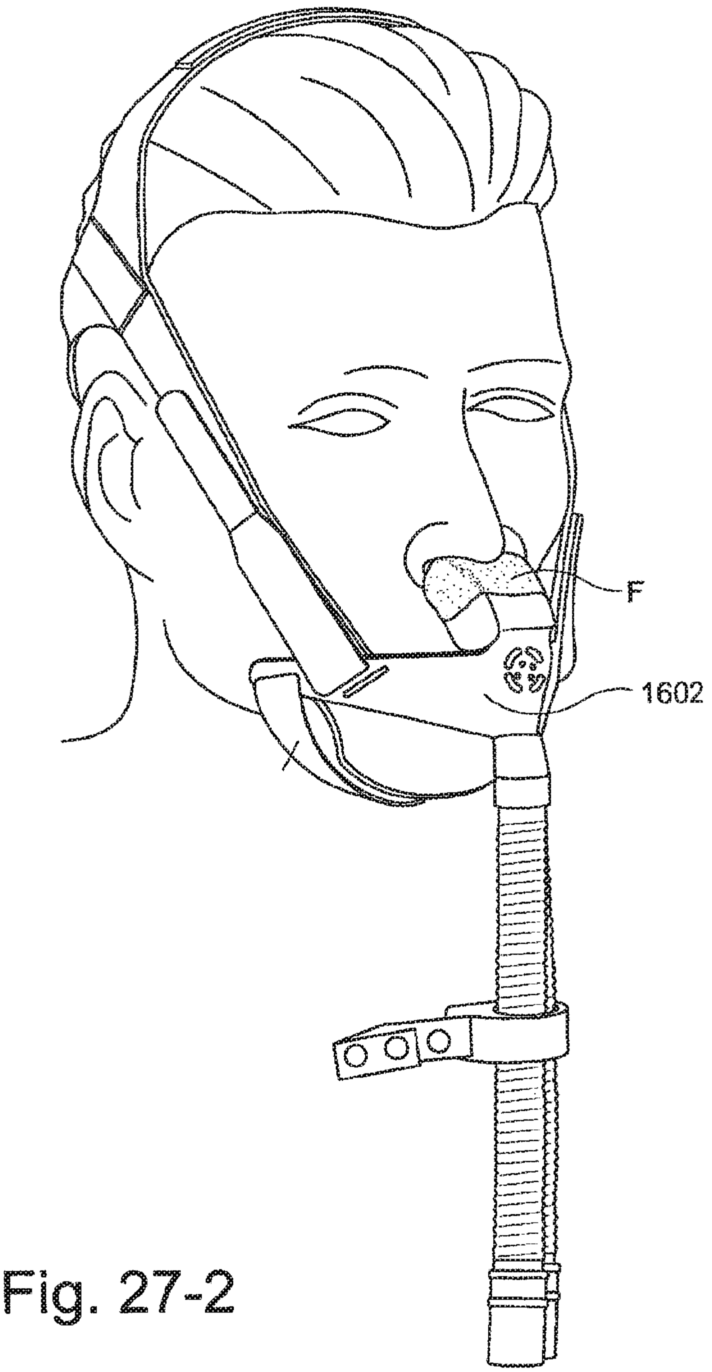
Figures 3, 27:
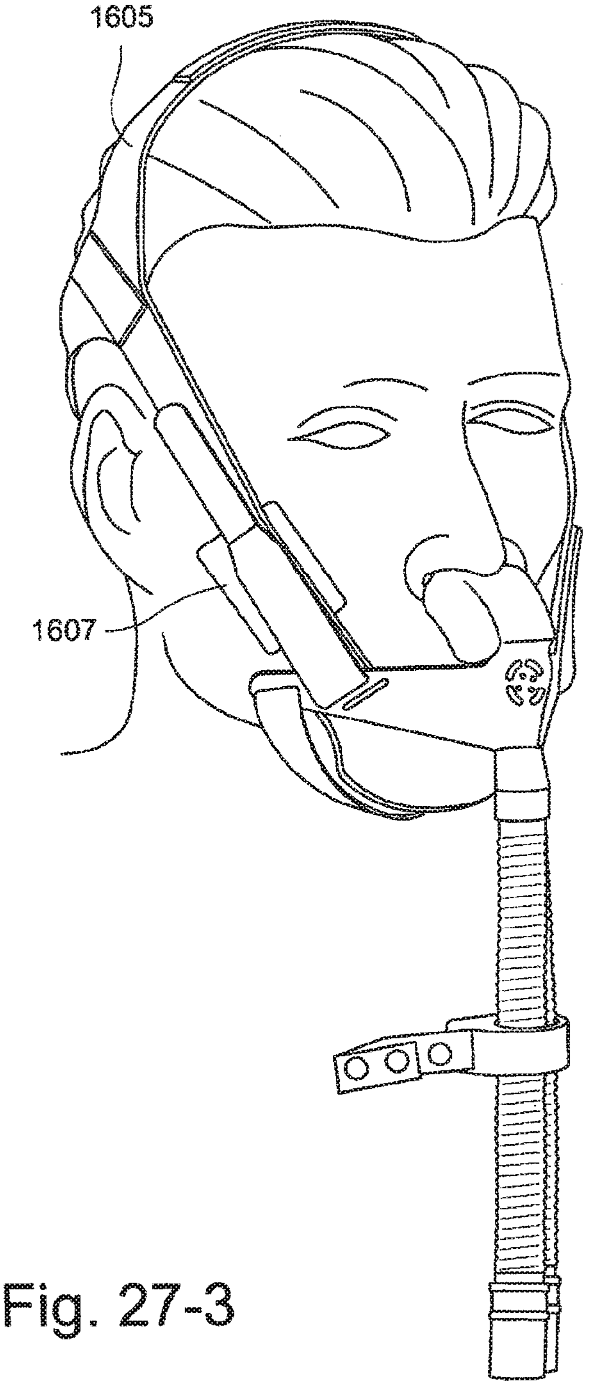
Figures 4, 27:
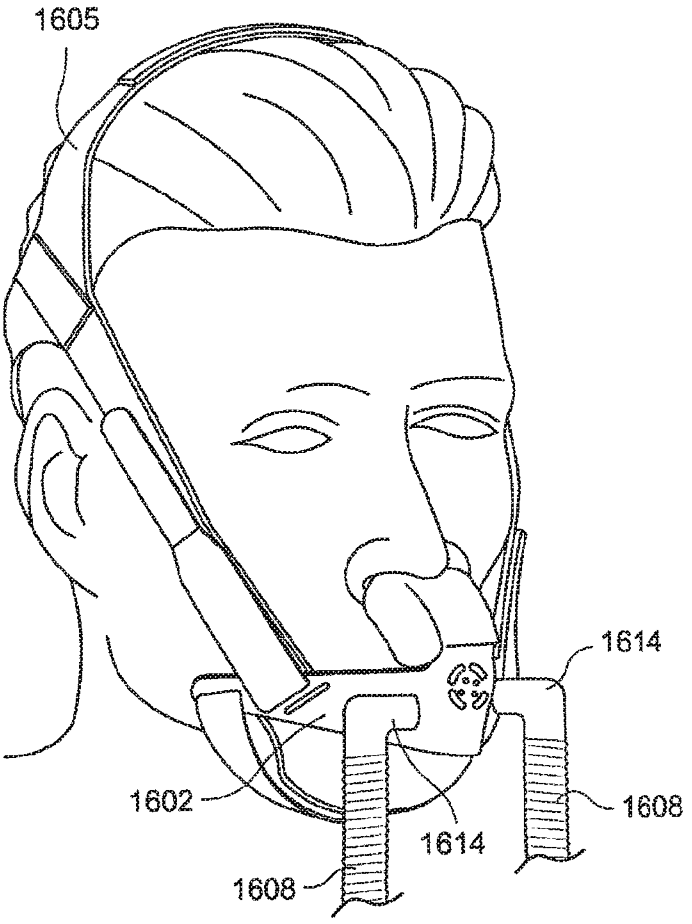
Figures 5, 27:
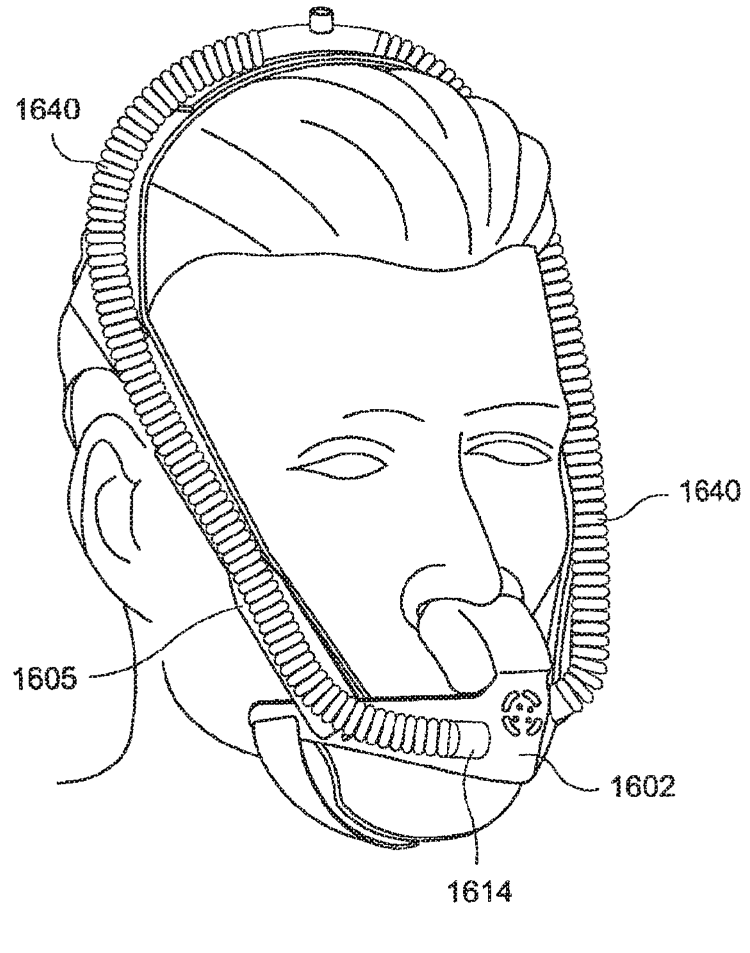
Figures 6, 27:
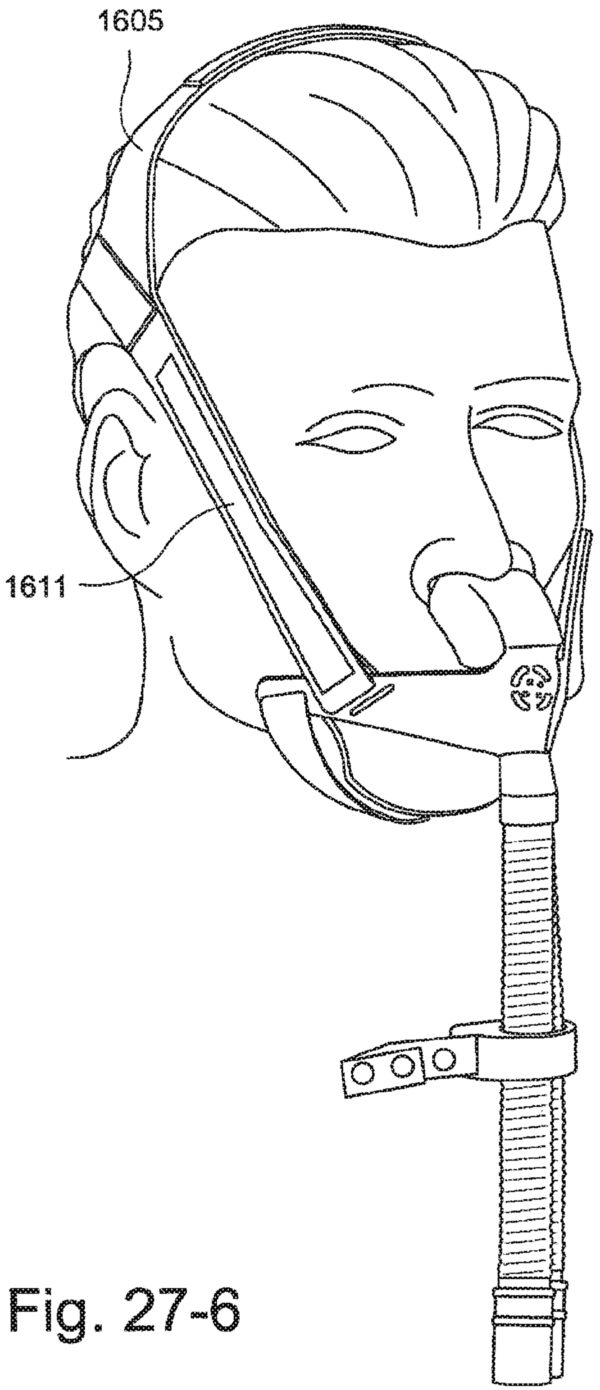
Figures 7, 27:
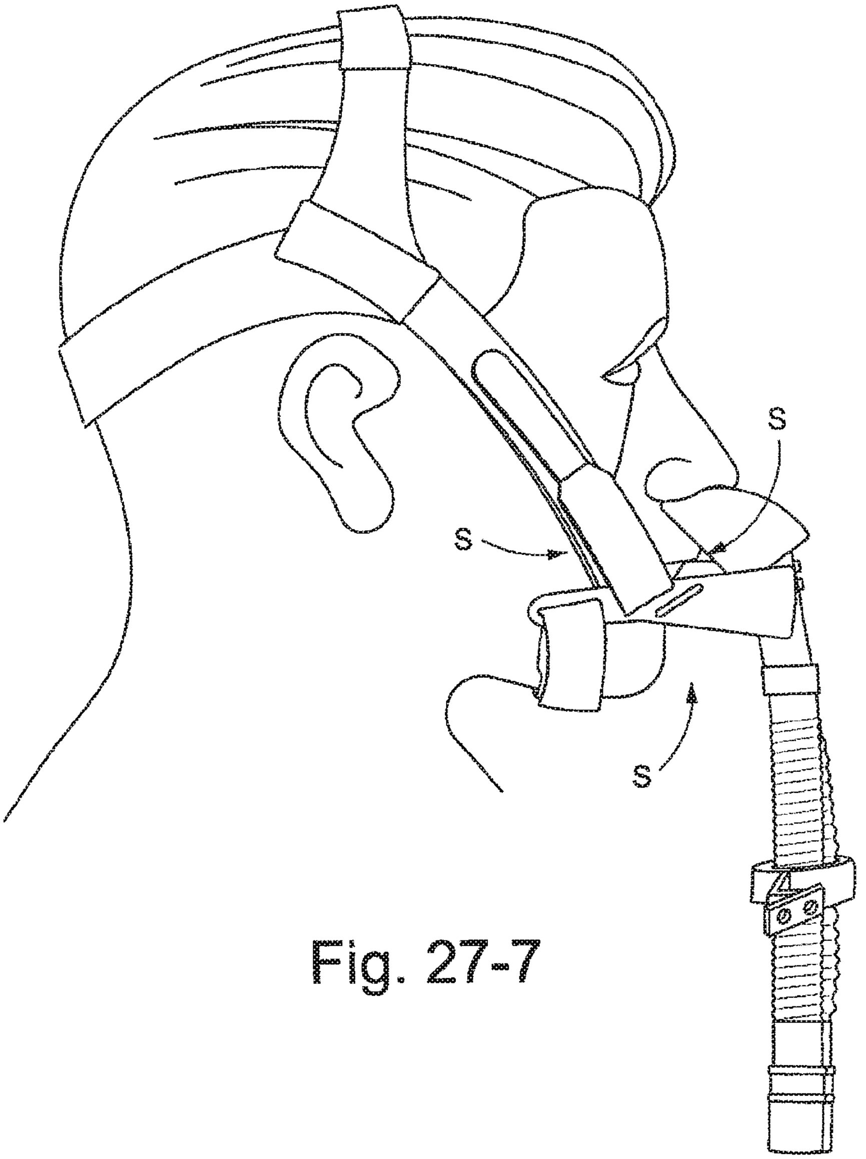

FIG. 27-1 illustrates another known mask 1600 commercially sold by Respironics under the name of OptiLife™. As illustrated, the mask 1600 includes a frame 1602, nasal pillows 1604 provided to the frame 1602 and adapted to form a seal with the patient's nasal passages in use, an inlet tube 1608 provided to the frame 1602 and adapted to deliver breathable gas to the patient, and headgear 1605 including a chin strap 1606 removably attached to the frame 1602 to maintain the mask 1600 in a desired position on the patient's face.

3.2.0 Improvements/Alternative Arrangements

The following embodiments describe improvements and/or alternative arrangements of Respironics' OptiLife™ mask to enhance respiratory therapy.

3.2.1 Foam Interface

The OptiLife™ mask includes nasal pillows. In an alternative embodiment, as shown in FIG. 27-2, the nasal pillows may be replaced with a foam interface F constructed of a foam material F. The foam interface F may include one or more of the foam properties described above, e.g., visco-elastic, de-skinned, etc.

In such embodiment, the foam interface F may be provided with an adaptor having a base that supports the foam interface F and couples the foam interface F to the existing frame 1602 of the OptiLife™ mask.

3.2.2 Foam Cheek Pads

In another embodiment, as shown in FIG. 27-3, each side strap of the headgear 1605 may include a foam cheek pad 1607 to improve comfort and/or stability.

3.2.3 Side Inlet Ports

In another embodiment, as shown in FIG. 27-4, the frame 1602 may include side inlet ports 1614 adapted to engage respective inlet tubes 1608. For example, the frame may be structured similar to that provided on Respironics' ComfortCurve™ mask.

3.2.4 Collapsible Inlet Tubes

In another embodiment, as shown in FIG. 27-5, the frame 1602 may include side inlet ports 1614 adapted to engage collapsible inlet tubes 1640 including one or more of the collapsible tube properties described above.

In an embodiment, the collapsible inlet tubes 1640 may be routed through the headgear 1605, e.g., up towards the top of the patient's head.

3.2.5 Rigidizers

In another embodiment, as shown in FIG. 27-6, a rigidizer 1611 may be provided one or more straps of the headgear 1605 to improve rigidity and/or stability.

3.2.6 Gap-Filling Structure

In another embodiment, the mask may include structure (e.g., provided to the headgear, frame, etc.) that is adapted to fill gaps or spaces provided between the patient's face and the mask/headgear. The gap-filling structure may improve comfort and/or stability in use. For example, as shown in FIG. 27-7, the mask may include structure to fill gaps or spaces S provided between the patient's face and the mask/headgear.

3.3 Respironics' ComfortLite™ and ComfortLite™ 2

Figures 1A, 28:
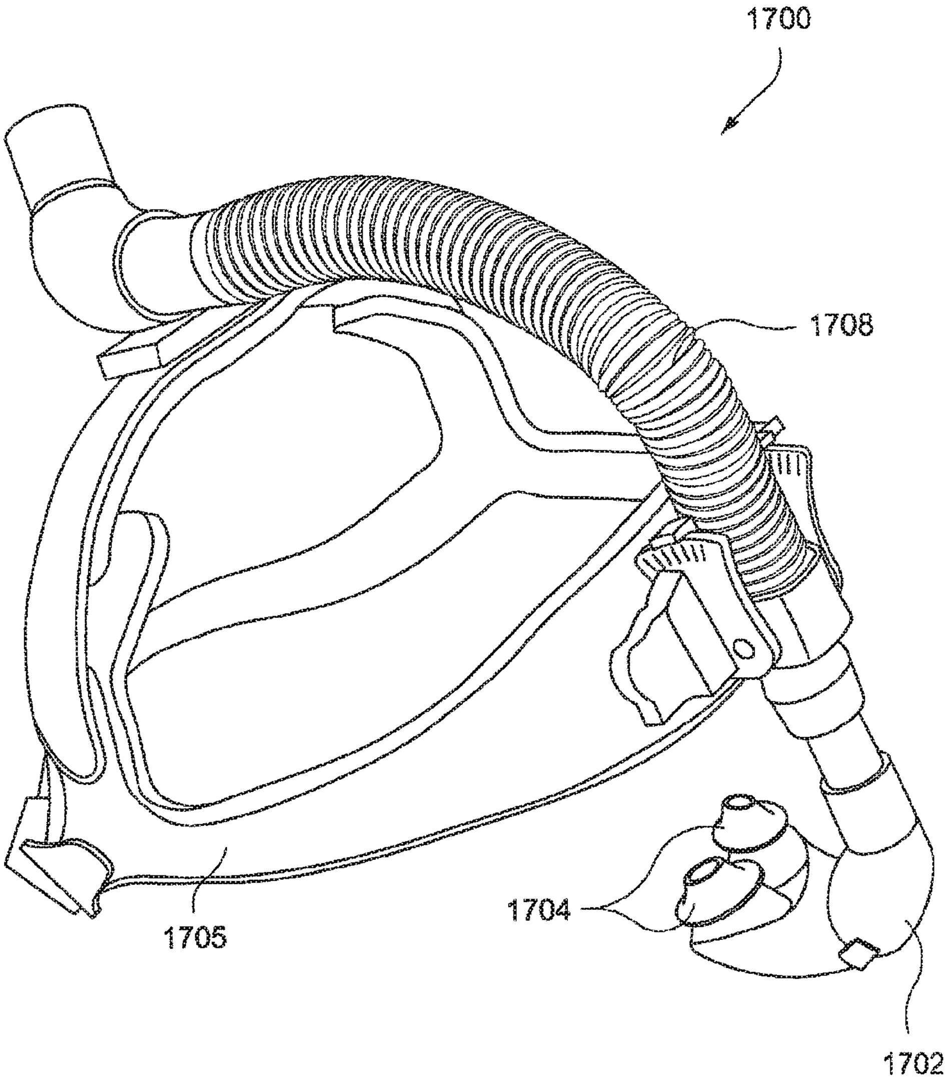
Fig. 28-1A (PRIOR ART)
FIG. 28-1A is a perspective view of a known mask commercially sold by Respironics' under the name of ComfortLite™.
Figures 2A, 28:
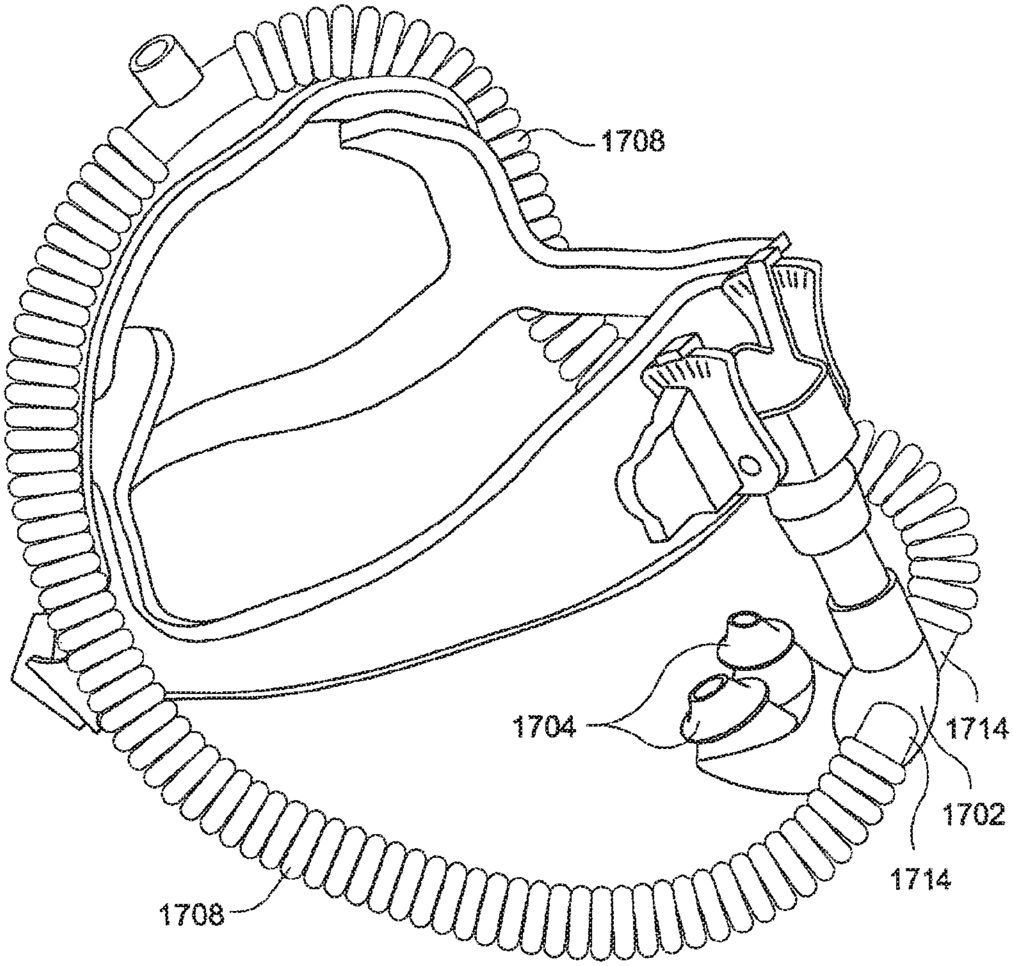
Figures 1B, 28:
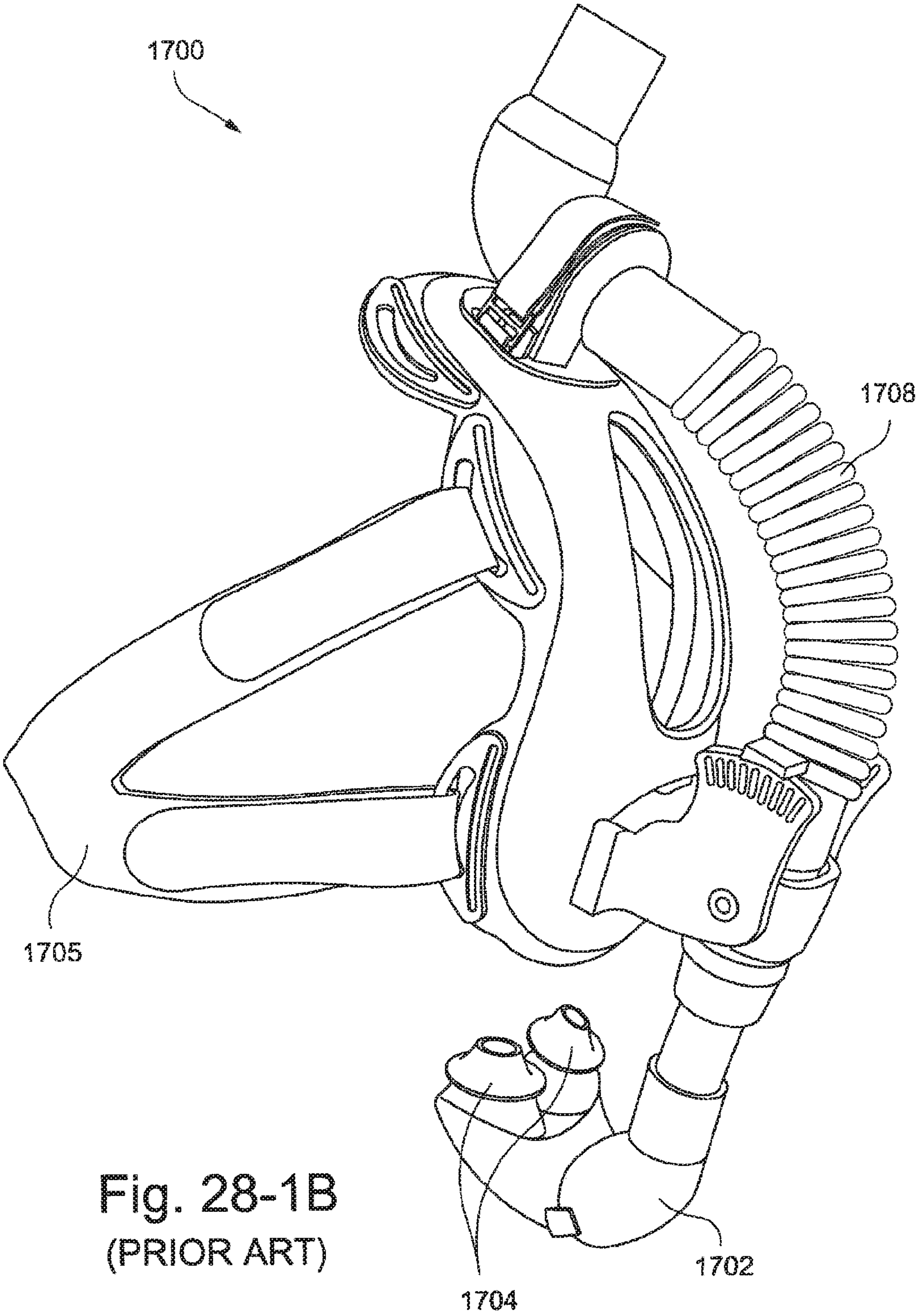
Fig. 28-1B (PRIOR ART)
Figures 2B, 28:
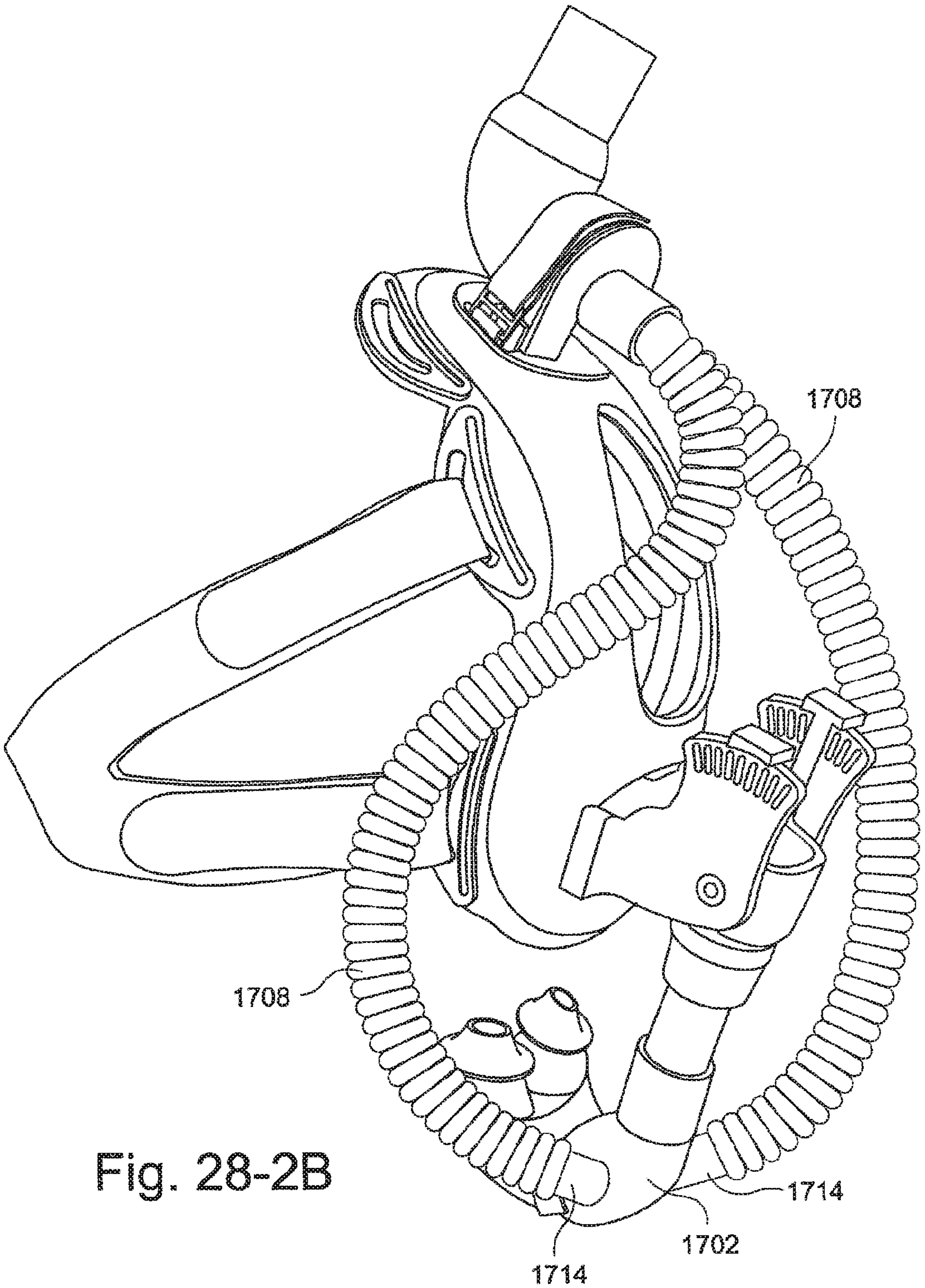

FIG. 28-1A illustrates a known mask commercially sold by Respironics' under the name of ComfortLite™ and FIG. 28-1B illustrates a known mask commercially sold by Respironics' under the name of ComfortLite™ 2. As illustrated, the ComfortLite™ and ComfortLite™ 2 masks 1700 each include a frame 1702, nasal pillows 1704 provided to the frame 1702 and adapted to form a seal with the patient's nasal passages in use, an inlet tube 1708 provided to the frame 1702 and adapted to deliver breathable gas to the patient, and headgear 1705 to maintain the mask 1700 in a desired position on the patient's face.

3.3.0 Improvements/Alternative Arrangements

The following embodiments describe improvements and/or alternative arrangements of Respironics' ComfortLite™ and ComfortLite™ 2 masks to enhance respiratory therapy.

3.3.1 Two Tube Arrangement

In another embodiment, each mask may include two inlet tubes rather than a single inlet tube that extends over the patient's nose to the top of the patient's head. For example, as shown in FIGS. 28-2A and 28-2B, the frame 1702 may include side inlet ports 1714 adapted to engage respective inlet tubes 1708 routed towards the top of the patient's head.

In such embodiment, one or more portions of the headgear may be eliminated such as the forehead support.

3.4 Fisher & Paykel's Opus™

Figures 1, 29:
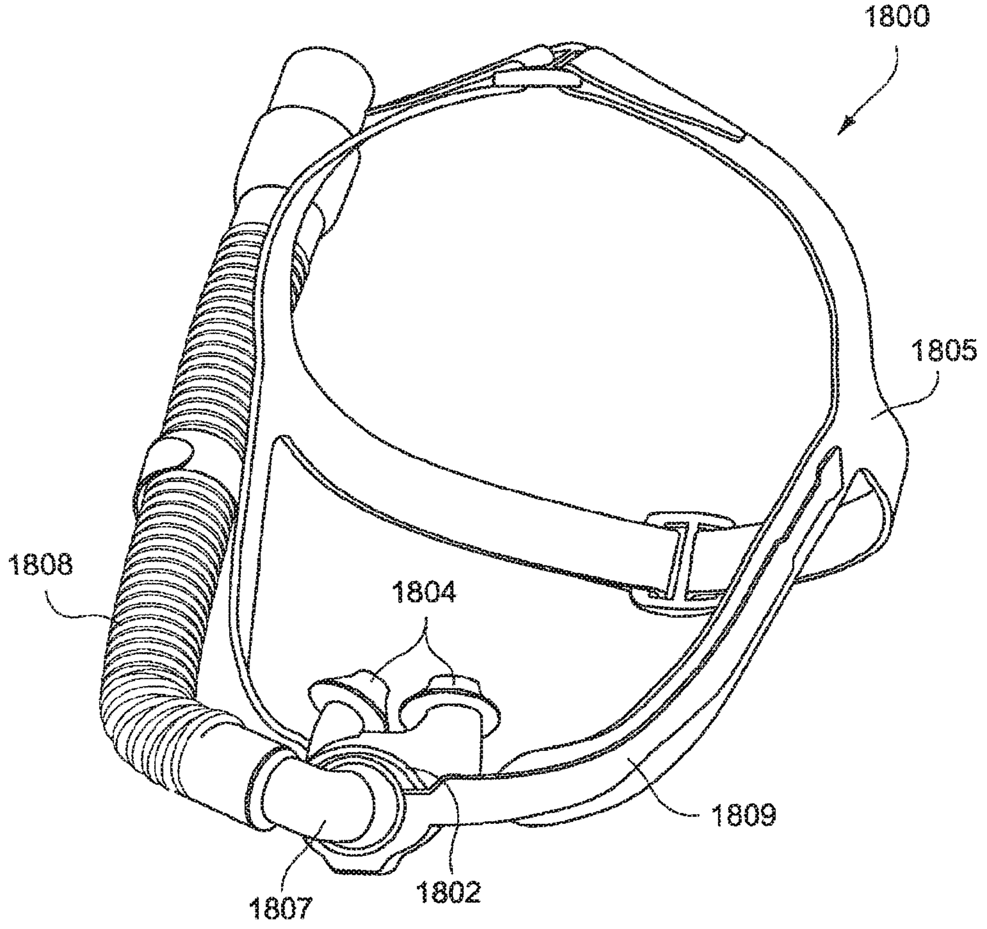
Fig. 29-1 (PRIOR ART)
Figures 2, 29:
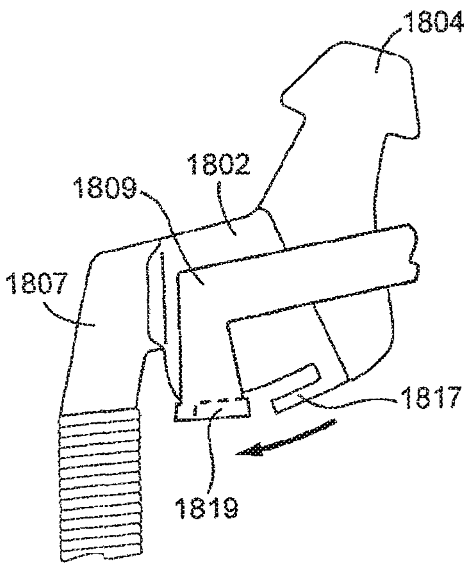
Fig. 29-2 (Prior Art)
Figures 3, 29:
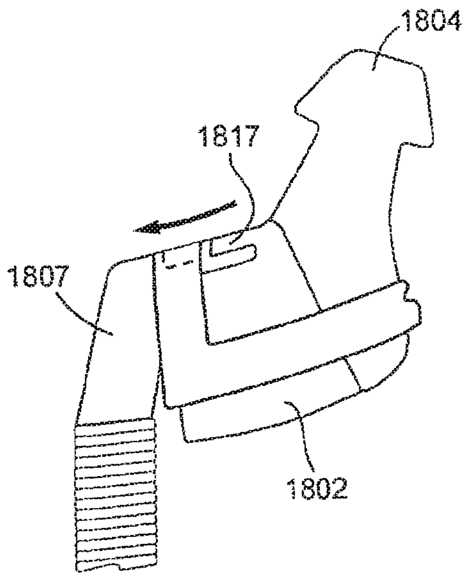
Figures 4, 29:
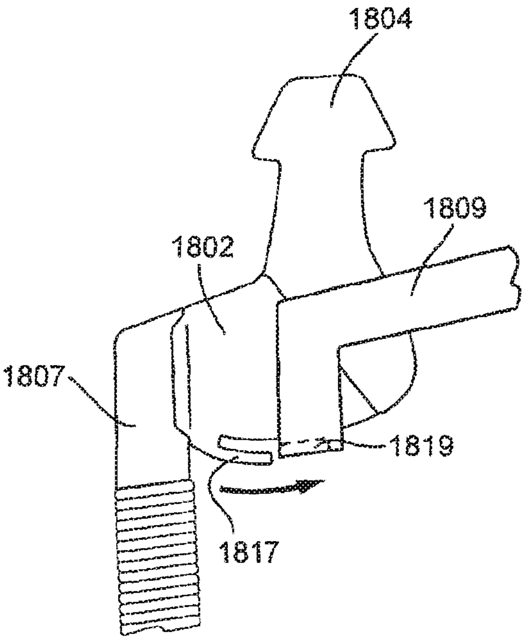
Figures 5, 29:
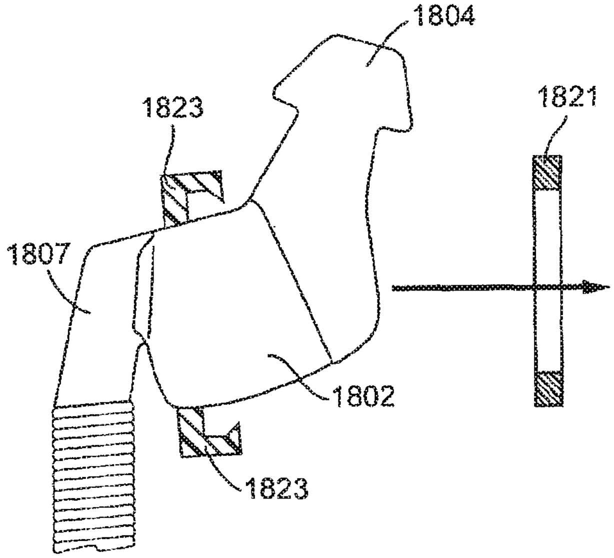
Figures 6, 29:
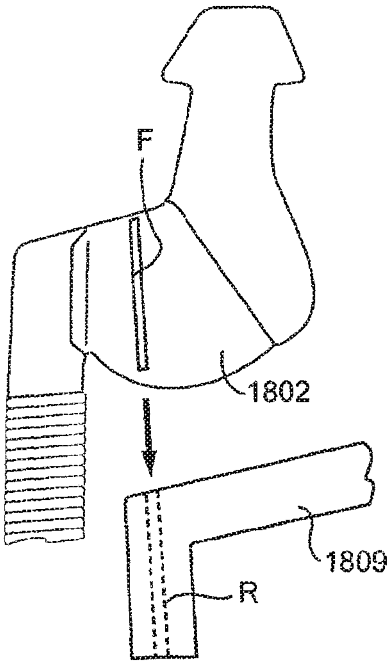
Figures 7, 29:
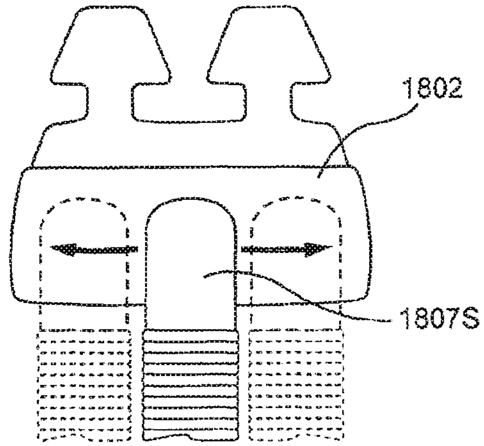
Figures 8, 29:
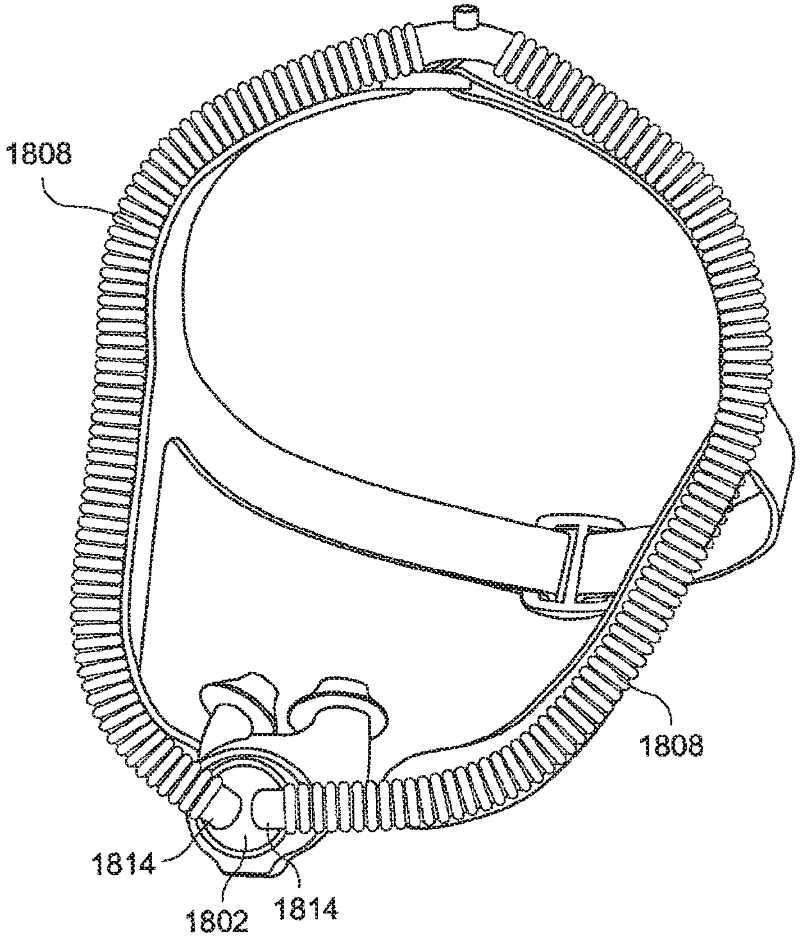
Figures 9, 29:
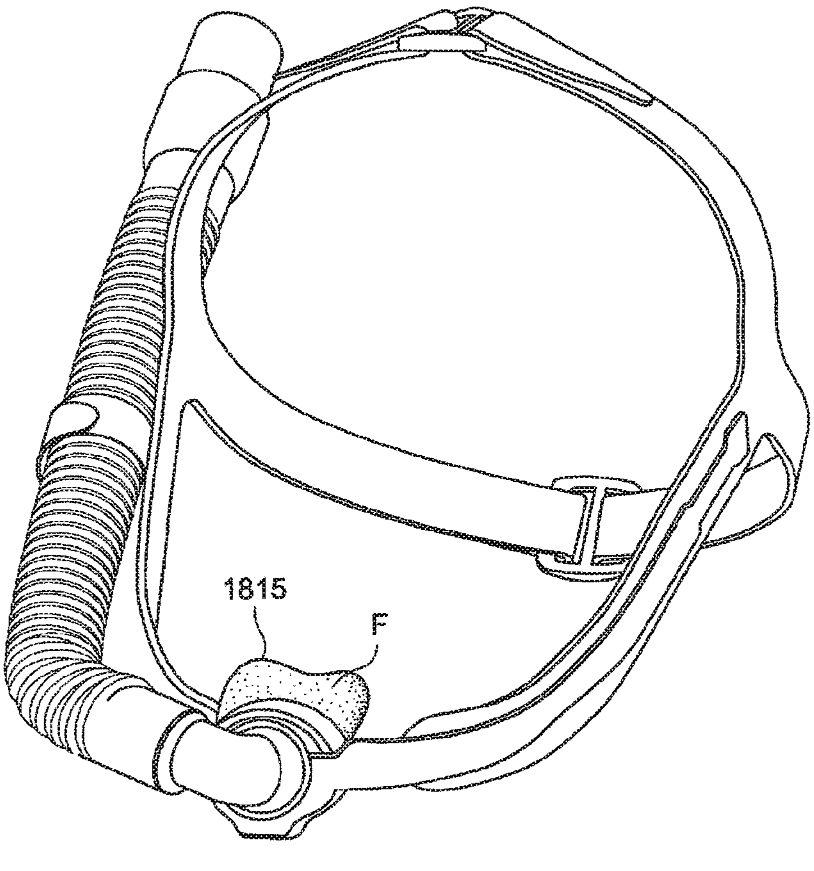

FIG. 29-1 illustrates another known mask 1800 commercially sold by Fisher & Paykel under the name of Opus™. As illustrated, the mask 1800 includes a frame 1802, nasal pillows 1804 provided to the frame 1802 and adapted to form a seal with the patient's nasal passages in use, an elbow 1807 provided to the frame 1802 and connected to an inlet tube 1808 adapted to deliver breathable gas to the patient, and headgear 1805 including a support structure or rigidizer 1809 to maintain the mask 1800 in a desired position on the patient's face.

3.4.0 Improvements/Alternative Arrangements

The following embodiments describe improvements and/or alternative arrangements of Fisher & Paykel's Opus™ mask to enhance respiratory therapy.

3.4.1 Quick Release

The frame 1802, nasal pillows 1804, and elbow 1807 of the Opus™ mask form a sub-assembly that is coupled to the support structure 1809 via a clip arrangement. In an alternative embodiment, quick release arrangements may be provided to releasably connect the sub-assembly to the support structure. For example, the sub-assembly may be coupled to the support structure via a magnet arrangement.

In another embodiment, the sub-assembly may be coupled to the support structure in a manner that allows removal of the sub-assembly while the headgear is maintained on the patient's head.

In another embodiment, the joint between the elbow and the frame can be structured in a quick-release design, e.g., where the ball joint of the elbow can be resiliently attached/detached from the frame. This arrangement allows the frame/nasal pillows to be maintained along with the headgear on the patient's head.

As shown in FIG. 29-2, the clip arrangement of the Opus™ mask includes a clip 1817 on the bottom portion of the frame 1802 that is adapted to engage a clip receptacle 1819 provided to the support structure 1809. In an alternative embodiment, as shown in FIG. 29-3, the clip arrangement may have a reverse position, e.g., clip 1817 provided to a top portion of the frame 1802. This arrangement may allow a more continuous form across the front of the mask.

In another embodiment, as shown in FIG. 29-4, the clip arrangement may be arranged to allow the sub-assembly to engage the support structure 1809 from the front of the support structure, rather than from the rear of the support structure (e.g. see FIG. 29-2).

In another embodiment, as shown in FIG. 29-5, the support structure may provide an annular ring 1821 that is adapted to engage a resilient mating portion or snap-fit connector 1823 provided to the frame 1802. The snap-fit arrangement may be similar to the elbow connection arrangement of ResMed's VISTA™ mask, e.g., see U.S. Pat. No. 6,907,882 which is incorporated herein by reference in its entirety.

In yet another embodiment, as shown in FIG. 29-6, one of the frame 1802 and support structure 1809 may include a flange (e.g., flange F on frame as shown in FIG. 29-6) and the other of the frame 1802 and support structure 1809 may include a recess (e.g., recess R on support structure as shown in FIG. 29-6) adapted to receive the flange to retain the frame to the support structure.

3.4.2 Adjustment Mechanism

In another embodiment, an adjustment mechanism may be provided to the frame and/or nasal pillows to allow adjustment of the nasal pillows to accommodate the alar and naso-labial angle of the patient's nose.

3.4.3 Slidable Elbow/Inlet Tube

In another embodiment, the elbow and/or tube may be arranged for sliding movement relative to the frame to isolate the seal from tube drag. For example, FIG. 29-7 illustrates a slidable elbow 1807S that is slidable with respect to the frame 1802 into multiple operative positions, e.g., 2 or more operative positions.

3.4.4 Low Profile Elbow

In another embodiment, a portion of the elbow may have a substantially oval-shaped cross-section (rather than a round cross-section) to provide the elbow with a lower profile.

3.4.5 Tube Routing

In another embodiment, the mask may include two inlet tubes rather than a single inlet tube. For example, as shown in FIG. 29-8 the frame 1802 may include side inlet ports 1814 adapted to engage respective inlet tubes 1808 routed towards the top of the patient's head.

In such embodiments, the headgear may be eliminated or integrated with the tubes, e.g., two inlet tubes adapted to deliver breathable gas and stabilize the nasal pillows on the patient's face.

Also, the inlet tubes may be collapsible and may include one or more of the collapsible tube properties described above.

3.4.6 Foam Seal

In an alternative embodiment, as shown in FIG. 29-9, the silicone nasal pillows of the Opus™ mask may be replaced with a foam interface 1815 constructed of foam F and including one or more of the foam properties described above.

In an embodiment, the foam interface may be a block of foam (e.g., reticulated foam) wherein the perimeter of the interface is sealed or relatively less permeable and the center of the interface is breathable to act as diffusing mechanism. In such embodiment, the center of the interface may have two discrete areas for each nostril.

Other foam alternatives include edible packaging foams, fibrous filter material, and foam prongs. The foam prongs may have a bell shape with a cylindrical outlet hole, and optional reinforcement may be provided to one or more portions of the foam prongs, e.g., inner walls, outer walls, etc.

In another embodiment, the silicone nasal pillows may be provided with a foam layer on a contact surface adapted to engage the patient's nose. The foam layer may be provided to the nasal pillows in any suitable manner, e.g., spray-on micro diffuse layer (e.g., HC405). The foam layer may improve comfort, feel, and/or softness, and may provide a moisture wicking feature.

3.5 Puritan Bennett's Breeze® SleepGear® DreamSeal®

FIGS. 30-1 and 30-2 illustrate another known mask 1900 commercially sold by Puritan Bennett under the name of Breeze® SleepGear® DreamSeal®. As illustrated, the mask 1900 includes a frame 1902, a cushion 1904 provided to the frame 1902 and adapted to form a seal with the patient's nose in use, an inlet tube 1908 provided to the frame 1902 and adapted to deliver breathable gas to the patient, and a head support 1905 provided to the frame 1902 to maintain the mask 1900 in a desired position on the patient's face.

3.5.0 Improvements/Alternative Arrangements

The following embodiments describe improvements and/or alternative arrangements of Puritan Bennett's Breeze® SleepGear® DreamSeal® mask to enhance respiratory therapy.

3.5.1 Foam Seal

The Breeze® SleepGear® DreamSeal® mask includes a cushion constructed of a silicone material. In an alternative embodiment, as shown in FIG. 30-3, the cushion may be a foam cushion 1904F constructed of a foam material F. The foam material F may include one or more of the foam properties described above, e.g., visco-elastic, un-skinned, etc.

3.5.2 One-Piece Tube/Head Support

The head support 1905 of the Breeze® SleepGear® DreamSeal® mask includes a metal spring 1911 that supports a cradle 1913 adapted to engage the rear the patient's head (e.g., see FIG. 30-1). In an alternative embodiment, the metal spring 1911 may be replaced with a plastic component that may be molded in one-piece with the remainder of the head support. In addition, the one-piece head support may be overmolded with the inlet tube 1908, e.g., to reduce the number of parts, facilitate assembly, etc.

3.5.3 Lower Profile

As shown in FIG. 30-2, the Breeze® SleepGear® DreamSeal® mask includes a gap G between the inlet tube 1908 and the nose/forehead of the patient's face. In an alternative embodiment, the gap G may be reduced by changing the contour and/or routing of the inlet tube 1908. For example, as shown in FIG. 30-4, the inlet tube 1908 may be flatter towards the top of the patient's head (e.g., more oval-shaped cross-section 1917 as opposed to round-shaped cross-section 1919) and have a configuration such that it provides narrower portion 1921 as it passes between the patient's eyes (e.g., hourglass-shaped).

3.5.4 Two Tube Arrangement

In another embodiment, the mask may include two inlet tubes rather than a single inlet tube. For example, as shown in FIG. 30-5, the frame 1902 may include side inlet ports 1914 adapted to engage respective inlet tubes 1908 routed towards the top of the patient's head.

In such arrangement, a manifold 1916 may be provided at the top of the patient's head to interconnect the tubes 1908.

3.5.5 Cover or Sock

In another embodiment, one or more portions of the frame, inlet tube, and/or head support may include a cover or sock to improve aesthetics and/or comfort.

3.6 InnoMed Technologies' Nasal-Aire™

Figures 1, 31:
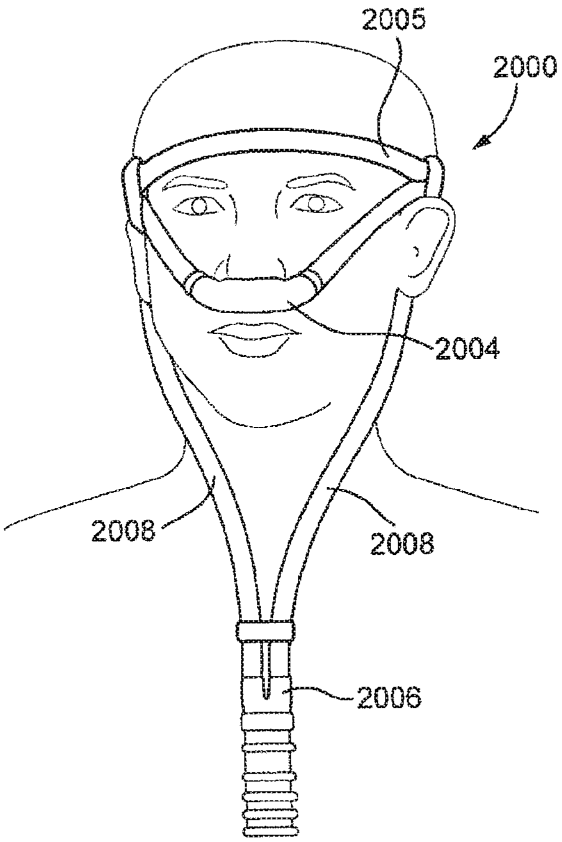
Fig. 31-1 (Prior Art)
Figures 2, 31:
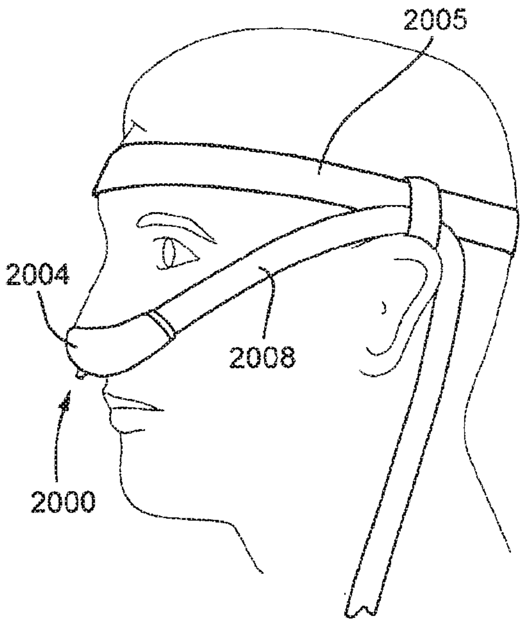
Fig. 31-2 (Prior Art)
Figures 3, 31:
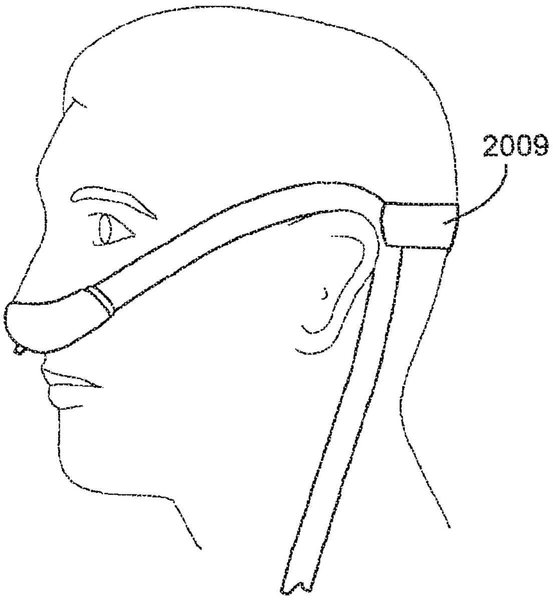
Figures 4, 31:
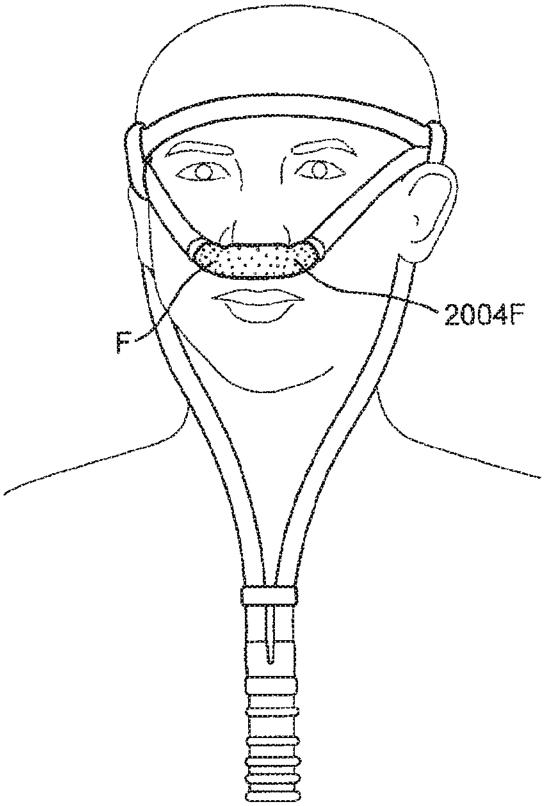

FIGS. 31-1 and 31-2 illustrate another known mask 2000 commercially sold by InnoMed Technologies under the name of Nasal-Aire™. As illustrated, the mask 2000 includes a nasal interface 2004 provided to the patient's nose in use, inlet tubes 2008 provided to the respective sides of the nasal interface 2004 to deliver breathable gas to the patient, a manifold 2006 to interconnect the inlet tubes 2008, and a head strap 2005 to maintain the mask 2000 in a desired position on the patient's face.

3.6.0 Improvements/Alternative Arrangements

The following embodiments describe improvements and/or alternative arrangements of InnoMed Technologies' Nasal-Aire™ mask to enhance respiratory therapy.

3.6.1 Collapsible Tubes

The inlet tubes of the Nasal-Aire™ mask are substantially non-collapsible and/or crush-resistant. In an alternative embodiment, the inlet tubes may be replaced with collapsible conduits adapted to deliver breathable gas and stabilize the nasal interface on the patient's face. The collapsible conduits may include one or more of the collapsible tube properties described above. For example, each conduit may be provided with a rigidizer and/or each conduit may have a general D-shaped cross-section.

3.6.2 Back Strap

In an embodiment, as shown in FIG. 31-3, the mask may include a back strap 2009 rather than a full head strap to maintain the mask in a desired position on the patient's face. The back strap 209 may include one or more of the back strap properties described above.

3.6.3 Foam Seal

The Nasal-Aire™ mask includes a nasal interface constructed of a silicone material. In an alternative embodiment, as shown in FIG. 31-4, the nasal interface may be a foam nasal interface 2004F constructed of a foam material F. The foam material F may include one or more of the foam properties described above, e.g., visco-elastic, un-skinned, etc.

3.6.4 Manifold

The manifold of the Nasal-Aire™ mask includes a relatively rigid, one-piece, plastic structure. In an alternative embodiment, the manifold may be constructed of more than one material, e.g., rigid portion and semi-rigid portion, to improve comfort and/or aesthetics.

In another embodiment, the manifold may be positioned on the patient's head, rather than hang downwardly from the patient's head.

A preferred interfacing structure according to an embodiment of the invention utilizes foam having properties as set forth in FIG. 14-1. Known sealing interfaces have quite different bulk properties, for example, a typical silicone has a density in the range of 1050 to 1150 kg/m^3, a tear strength of 20 to 40 N/mm, a tensile strength of approximately 10 Mpa, an elongation at break of 600%, a 40 Shore A hardness, hysteresis of less than about 5%, a resilience of approximately 40 to 50%, and an air permeability of 0.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

For example, as an alternative to polyurethane foam, the interfacing structure may be made from one of more of TPE foam, silicone foam, latex foam and polyolefin foam.

Whilst the interfacing structure is configured to form a gasket or compression-type seal, it may be configured alternatively or additionally as a flap-type seal. In another form, the interfacing structure may be configured as an adhesive seal.

Preferably an unskinned foam is used, however, a partially skinned, or pierced skinned foam may be used. Furthermore, a porous skinned foam may also be used. An integral, or a non-integral skin may also be used for part or all of the foam.

Whilst a foam is preferably used in the interfacing structure, possible alternative materials include high pile textiles, rubber, chamois, non-woven textiles or fibre arrangements and spacer fabric.

In the illustrative embodiments of the invention, a single layer of foam has been shown as the interfacing structure. In other forms, multiple layers may be used. Furthermore, foam may be combined with flaps, bladders, or rigid backing material. A layer of foam may be arranged over a gusset configuration. A layer of foam may be used over a flap, or a solid section. For an example of a suitable gusset, see U.S. Provisional application 60/935,179 filed 30 Jul. 2007, the contents of which are hereby expressly incorporated by cross-reference. In other forms, foam may be reinforced with other materials, for example a wire.

Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The interfacing structure described in the present application may have other applications. For example, headphones, headgear and other equipment where a soft, conforming layer against the skin or body may be advantageous. Headphones may use the foam described in the present application to surround or cover the ear, to insert into the ear, to lie on the head or other parts of the face or body. Helmets or masks used in other respiratory or non-respiratory applications may also benefit from an interfacing structure as described. Other devices, such as devices to deliver drugs transdermally, or prostheses may also benefit from the present interfacing structure

What is claimed is:

1. A mask assembly for delivering breathable gas at positive pressure to a patient for treatment of sleep disordered breathing, comprising:

an interfacing structure configured to sealingly engage the patient's face in use;

an air delivery and stabilizing system configured to deliver the breathable gas to the interfacing structure and support the interfacing structure on the patient's face during use; and an adjustment mechanism configured to be positioned on top of the patient's head at or near the crown of the patient's head during use;

the air delivery and stabilizing system, the adjustment mechanism and the interfacing structure together forming a ring shape, the air delivery and stabilizing system including two tubes that form respective sections of the ring shape, wherein the ring shape is formed by only the interfacing structure, the two tubes and the adjustment mechanism, wherein the adjustment mechanism is configured to allow lengthwise adjustment of the ring shape, the adjustment mechanism including a pair of bellows structures, wherein each tube is configured to, in use, pass along a respective side of the patient's face between the patient's eye and the patient's ear, and wherein each tube includes a cheek portion configured to, in use, extend along a respective cheek region of the patient, the adjustment mechanism being configured to, in use, adjust a distance between the cheek portions that extends along the ring shape across the top of the patient's head so as to provide lengthwise adjustment of the ring shape.

2. The mask assembly of claim 1, wherein, in use, the ring shape is configured to move relative to the top of the patient's head for lengthwise adjustment of the ring shape.

3. The mask assembly of claim 1, wherein the adjustment mechanism is configured to, in use, adjust a distance between two points along the ring shape, the two points configured to be positioned on top of the patient's head during use.

4. The mask assembly of claim 3, wherein the bellows structures are positioned, respectively, along the ring shape superiorly to each cheek portion in use.

5. The mask assembly of claim 1, wherein the adjustment mechanism allows lengthwise adjustment of the ring shape by moving points of the air delivery and stabilizing system closer together or farther apart.

6. The mask assembly of claim 1, wherein the two tubes are connected respectively, to opposing sides of the interfacing structure to deliver the breathable gas to the interfacing structure.

7. The mask assembly of claim 1, wherein each tube has a D-shaped cross-sectional shape.

8. The mask assembly of claim 1, wherein the two tubes are configured to directly engage the patient's skin in use.

9. The mask assembly of claim 1, wherein the interfacing structure comprises textile configured to sealingly engage the patient's face.

10. The mask assembly of claim 9, wherein the interfacing structure is an under-the-nose interface configured to sealingly engage an underside of the patient's nose in use.

11. The mask assembly of claim 1, wherein the adjustment mechanism includes a rack and pinion arrangement.

12. The mask assembly of claim 11, wherein the adjustment mechanism allows lengthwise adjustment of the ring shape by moving points of the air delivery and stabilizing system closer together or farther apart, wherein the adjustment mechanism includes a rotatable dial whereby rotational motion of the dial is configured to provide the lengthwise adjustment, wherein rotation of the dial is configured to cause corresponding rotation of a pinion which provides lengthening or shortening of the ring shape via a toothed-engagement of the pinion with first and second racks of the rack and pinion arrangement.

13. The mask assembly of claim 12, wherein the rack and pinion arrangement includes a first housing and a second housing supporting the pinion and the dial with respect to the first and second racks.

14. The mask assembly of claim 13, wherein the first and second racks comprise respective first and second rack portions, each rack portion including a slot and a series of teeth along one side of the slot.

15. The mask assembly of claim 14, wherein the first and second rack portions are overlapped with one another to align the slots and to provide opposed teeth by situating the series of teeth of the first rack portion in opposed relation to the series of teeth of the second rack portion, the pinion including pinion teeth, wherein the pinion is positioned within the aligned slots and the pinion teeth are engaged with the opposed teeth.

16. The mask assembly of claim 14, wherein each rack includes a tube connector portion that is connected between a respective one of the two tubes and a conduit, and wherein the tubes are respectively movably mounted to the first and second rack portions so that lengthwise adjustment of the ring shape also adjusts the routing of the tubes and the conduits.

17. The mask assembly of claim 16, wherein the tubes are respectively rotatably mounted to the first and second rack portions.

18. A mask assembly for delivering breathable gas at positive pressure to a patient for treatment of sleep disordered breathing, comprising:

an interfacing structure configured to sealingly engage the patient's face in use;

an air delivery and stabilizing system configured to deliver the breathable gas to the interfacing structure and support the interfacing structure on the patient's face during use; and adjustment mechanism configured to be positioned on top of the patient's head during use;

the air delivery and stabilizing system, the adjustment mechanism and the interfacing structure together forming a ring shape, the air delivery and stabilizing system including two tube portions that form respective sections of the ring shape, wherein the ring shape is formed by only the interfacing structure, the two tube portions and the adjustment mechanism, wherein the adjustment mechanism is configured to allow lengthwise adjustment of the ring shape, the adjustment mechanism including a pair of bellows structures, wherein each tube portion is configured to, in use, pass along a respective side of the patient's face between the patient's eye and the patient's ear, and wherein each tube portion has a terminal end formed as part of the respective section of the ring shape, the adjustment mechanism being configured to adjust a distance between the terminal ends that extends along the ring shape across the top of the patient's head so as to provide lengthwise adjustment of the ring shape.

19. The mask assembly of claim 18, wherein the two tube portions are connected respectively, to opposing sides of the interfacing structure to deliver the breathable gas to the interfacing structure.

20. The mask assembly of claim 18, wherein the interfacing structure comprises textile configured to sealingly engage the patient's face in use.

21. The mask assembly of claim 18, wherein the adjustment mechanism includes a rack and pinion arrangement.

22. The mask assembly of claim 18, wherein the two tube portions are configured to directly engage the patient's skin in use.

* * * * *